US011033520B2

(12) United States Patent
Nikoulin et al.

(10) Patent No.: US 11,033,520 B2
(45) Date of Patent: Jun. 15, 2021

(54) LIPOSOMAL ANTICANCER COMPOSITIONS

(71) Applicant: IriSys, LLC, San Diego, CA (US)

(72) Inventors: Igor Nikoulin, San Diego, CA (US); Gerald Yakatan, San Diego, CA (US); Yevgeniya Plekhov, San Diego, CA (US); Robert Giannini, San Diego, CA (US)

(73) Assignee: IRISYS, INC., San Diego, CA (US)

( * ) Notice: Subject to any disclaimer, the term of this patent is extended or adjusted under 35 U.S.C. 154(b) by 3 days.

(21) Appl. No.: 16/331,258

(22) PCT Filed: Sep. 1, 2017

(86) PCT No.: PCT/US2017/049968
§ 371 (c)(1),
(2) Date: Mar. 7, 2019

(87) PCT Pub. No.: WO2018/048752
PCT Pub. Date: Mar. 15, 2018

(65) Prior Publication Data
US 2019/0269635 A1  Sep. 5, 2019

Related U.S. Application Data

(60) Provisional application No. 62/385,763, filed on Sep. 9, 2016.

(51) Int. Cl.
| *A61K 31/194* | (2006.01) |
| *A61P 35/00* | (2006.01) |
| *A61K 9/00* | (2006.01) |
| *A61K 9/127* | (2006.01) |
| *A61K 9/19* | (2006.01) |
| *A61K 31/122* | (2006.01) |
| *A61K 31/136* | (2006.01) |
| *A61K 31/198* | (2006.01) |
| *A61K 31/375* | (2006.01) |
| *A61K 31/4745* | (2006.01) |
| *A61K 31/704* | (2006.01) |
| *A61K 47/10* | (2017.01) |
| *A61K 47/24* | (2006.01) |
| *A61K 47/28* | (2006.01) |
| *A61K 9/10* | (2006.01) |

(52) U.S. Cl.
CPC .......... *A61K 31/194* (2013.01); *A61K 9/0019* (2013.01); *A61K 9/10* (2013.01); *A61K 9/127* (2013.01); *A61K 9/19* (2013.01); *A61K 31/122* (2013.01); *A61K 31/136* (2013.01); *A61K 31/198* (2013.01); *A61K 31/375* (2013.01); *A61K 31/4745* (2013.01); *A61K 31/704* (2013.01); *A61K 47/10* (2013.01); *A61K 47/24* (2013.01); *A61K 47/28* (2013.01); *A61P 35/00* (2018.01)

(58) Field of Classification Search
CPC ....... A61K 31/194; A61K 9/0019; A61K 9/10
See application file for complete search history.

(56) References Cited

U.S. PATENT DOCUMENTS

| 5,008,380 | A | 4/1991 | Palladino et al. |
| 5,616,341 | A * | 4/1997 | Mayer .................. A61K 9/127 264/4.3 |
| 5,736,155 | A | 4/1998 | Bally et al. |
| 6,083,530 | A | 7/2000 | Mayer et al. |
| 6,133,318 | A | 10/2000 | Hart |
| 7,964,219 | B2 | 6/2011 | Li et al. |
| 8,138,191 | B2 | 3/2012 | Danter |
| 8,580,792 | B2 | 11/2013 | Danter |
| 9,072,776 | B2 | 7/2015 | Kritiansen |
| 2004/0156889 | A1 | 8/2004 | Hu et al. |
| 2005/0025709 | A1 | 2/2005 | McBride et al. |
| 2005/0129753 | A1 | 6/2005 | Gabizon et al. |
| 2005/0158375 | A1 * | 7/2005 | Kimura .............. A61K 47/6911 424/450 |
| 2006/0128638 | A1 | 6/2006 | Magda et al. |
| 2006/0165744 | A1 | 7/2006 | Jamil et al. |
| 2009/0017105 | A1 | 1/2009 | Khattar et al. |
| 2009/0181048 | A1 | 7/2009 | Kamei et al. |
| 2011/0177156 | A1 | 7/2011 | Szoka, Jr. et al. |
| 2011/0288023 | A1 | 11/2011 | Kamei et al. |
| 2012/0121692 | A1 | 5/2012 | Xu et al. |
| 2014/0121367 | A1 | 5/2014 | Dugar et al. |
| 2015/0182460 | A1 | 7/2015 | Hong et al. |
| 2015/0306095 | A1 | 10/2015 | Lo et al. |

FOREIGN PATENT DOCUMENTS

| CN | 1186011 C | 1/2005 |
| CN | 1593437 A | 3/2005 |
| CN | 1602844 A | 4/2005 |
| CN | 1994279 A | 7/2007 |
| CN | 102935068 A | 2/2013 |
| EP | 2508170 A1 | 10/2012 |
| JP | 60-152417 | 8/1985 |
| WO | WO-98/17256 A1 | 4/1998 |
| WO | WO-2005/002546 A1 | 1/2005 |
| WO | WO-2005/107712 A1 | 11/2005 |
| WO | WO-2007/018272 A1 | 2/2007 |
| WO | WO-2011/062420 A2 | 5/2011 |
| WO | WO-2011/062420 A3 | 5/2011 |
| WO | WO-2013/114377 A1 | 8/2013 |

OTHER PUBLICATIONS

Kurbacher (cancer letters; 103, 1996, 183-189).*
Extended European Search Report dated Apr. 24, 2020, for EP Patent Application No. 17849367.2, 11 pages.
(Continued)

*Primary Examiner* — Pancham Bakshi
(74) *Attorney, Agent, or Firm* — Mintz, Levin, Cohn, Ferris, Glovsky and Popeo, P.C.

(57) ABSTRACT

Provided herein includes methods and compositions for the treatment of cancer. Described herein are liposome encapsulated chemotherapeutic agents, encompassing a weakly basic anticancer compound and an acid or salt thereof, wherein the acid is oxalic acid or tartaric acid and methods for preparing and utilizing the same.

32 Claims, 20 Drawing Sheets

(56) References Cited

OTHER PUBLICATIONS

Swenson, C.E. et al. ((Jun. 1, 2001). "Liposome technology and the development of Myocett™ (liposomal doxorubicin citrate)," *The Breast* Supplemental 2:1-7.
International Search Report dated Dec. 27, 2017, for PCT Application No. PCT/US2017/049968, filed Sep. 1, 2017, 5 pages.
Written Opinion dated Dec. 27, 2017, for PCT Application No. PCT/US2017/049968, filed Sep. 1, 2017, 5 pages.

* cited by examiner

E. Desirable release profile

LIPOSOMAL ANTICANCER COMPOSITIONS

CROSS-REFERENCES TO RELATED APPLICATIONS

This application is a Section 371 US national phase of International Application No. PCT/US2017/049968 filed Sep. 1, 2017, which claims the benefit of U.S. Provisional Application No. 62/385,763 filed Sep. 9, 2016, the content of which is incorporated herein in its entirety and for all purposes.

BACKGROUND

The lack of an adequate drug concentration at the tumor site as a result of dose limiting toxicity and poor local accumulation is often the reason why an in vitro promising anticancer agent fails when applied in vivo. Over the years many strategies have been developed to improve intratumoral drug delivery including passive drug targeting, active targeting to tumor cells and triggered drug release by nanocarriers [2-12]. However, incorporating drugs in a nanocarrier may greatly change their kinetics and interaction characteristics with cells. The anthracycline antibiotic doxorubicin is an effective anticancer agent for various malignancies but its application is severely limited due to its cardiotoxic side effects. Encapsulating doxorubicin into pegylated liposomal nanocarriers lowers the typical doxorubicin related side-effects [4, 5, 7-8]. Also, the circulation time is prolonged [2] and tumor specific delivery is improved due to the enhanced permeability and retention effect [3].

Stability of liposomes containing anticancer compounds depends on both the stability of liposomes in blood and the stability of drugs inside liposomes. The stable form of drugs inside liposomes would attribute to the prolongation of liposomes containing anti-tumor drugs in blood and lower toxicity. It has been demonstrated that doxorubicin can form aggregates with several counter ions, such as sulfate [1, 13-15], phosphate [13-14], and citrate [1, 10, 13-15]. The leakage behavior of doxorubicin from liposomes containing different doxorubicin salts confirms that doxorubicin-salt aggregate determines rate of the free doxorubicin release from the liposomes.

Doxorubicin is a chemotherapy drug. In liposomal doxorubicin, the molecules of the drug are enclosed (encapsulated) in a fatty coating known as a liposome. The liposome allows the doxorubicin to remain in the body for longer [2]. This means more of the chemotherapy is delivered to the cancer cells while having fewer side effects on healthy tissue [4, 5, 7-8]. Two liposomal formulations of doxorubicin approved for human use are currently on the market, Myocet® and Caelyx® (EU) respectively Doxil® (US). These two liposomal doxorubicin drugs currently work in slightly different ways and are used to treat different types of cancer.

The nanodrug Doxil® has been approved for the treatment of AIDS-related Kaposi sarcoma, advanced ovarian and breast cancer and multiple myeloma [4] Doxil® is composed of PEGylated phospholipids and Cholesterol and is loaded via an ammonium sulfate gradient. Encapsulating doxorubicin into pegylated liposomal nanocarriers lowers the typical doxorubicin related side-effects [4-7]. Although encapsulation decreases cardiotoxicity and increases circulation time [2] and intratumoral delivery [3], therapeutic efficacy compared to the free formulation is rather modest [6-9, 11-12]. To create a longer circulation time and high stability, the carrier is composed of a robust bilayer of phospholipids and PEG-coating. Subsequently, after entering the tumor interstitium most of the drug remains encapsulated and the intracellular bioavailability (i.e. the presence of drug at its intracellular target site) is limited [9]. Thus, the liposomal Doxil® formulation delivers more doxorubicin to the tumor but does not release the active doxorubicin molecule effectively. This perpetual state with very slow drug release can account for the unsatisfactory tumor responses compared to free drug administration and the need for repeated administration. Indeed, the antitumor efficacy of Doxil® is hindered by the poor release of the active drug from the liposome at the tumor sites [11]. Numerous published reports demonstrate that although a significant increase in intratumoral doxorubicin delivered by Doxil® is observed compared to free doxorubicin administration, this significant increase does not necessarily correlate with an increase in intracellular bioavailability and therefore therapeutic doxorubicin levels [9, 11-12]. Investigation of the kinetics of free doxorubicin versus liposomal doxorubicin (Doxil®) in vitro as well as in vivo demonstrated that within 8 h after administration of free doxorubicin, 26% of the drug translocated to the nucleus and when reaching a specific concentration killed the cell. Unlike free doxorubicin, only 0.4% of the doxorubicin added as liposomal formulation entered the nucleus [12]. It has been also demonstrated that sequestering of liposomal doxorubicin in the lysosomal compartment resulting in limited delivery to the nucleus. This entrapment makes the bioavailable concentration of Doxil®-delivered doxorubicin significantly lower and therefore ineffective as compared to free doxorubicin in killing tumor cells [12]. Additionally, this drug is associated with a local inflammatory tissue reaction, called palmoplantar erythrodysesthesia (PPE) [10] which is a drawback of PEGylated doxorubicin-loaded liposomes. The major side effects of Doxil® were stomatitis and skin toxicity [7, 10]. In fact, although the cardiotoxicity is reduced by PEGylation, the long circulation time often results in skin toxicity referred as Palmar Plantar Erythrodysthesia (PPE) [7, 10, 38-39], which is a drawback of PEGylated doxorubicin-loaded liposomes and remains to be overcome.

Myocet® includes egg phosphatidylcholine/cholesterol, and is loaded with doxorubicin via a citrate gradient. Although formation of doxorubicin-citrate aggregates results in relatively high drug release rate at pH 4.5-5.5 (desirable outcome in the acidic lysosomal environment) [1, 13-15], this also results in extra leakage of doxorubicin from the liposomes at physiological pH and 37° C. [14]. Such release profile will lead to loss of doxorubicin from the liposomes while liposomes are circulating in the blood, and decrease of the efficacious concentration of incorporated Dox [14]. In a long run (depending on administration regimen) this might result in higher toxicity and lower efficacy of formulated doxorubicin and shorter product shelf life as liposomal suspension. To overcome the stability issue Myocet® is supplied as a three vials system that requires compounding pharmacy to follow multistep protocol for preparation of doxorubicin loaded liposomes prior to administration to patients. Indeed, the procedure involves heating and vigorous shaking, and consists of multiple steps that include separate reconstitution of the liposomal material and doxorubicin in different medias, adjusting pH of the empty liposomes, heating material to 55-60° C., loading of doxorubicin into liposomes, and cooling material to RT before use. This is a very inconvenient formulation to prepare at the bedside.

Thus, existing therapies have room for improvement. Although Doxil® has excellent stability as liposomal suspension, and is therefore in an attractive one vial presentation format, the antitumor efficacy of Doxil® is hindered by its decreased or limited release of active drug from the liposome at the tumor site. Compared to Doxil®, Myocet® demonstrates markedly higher release of doxorubicin at acidic pH (tumor site) but exhibits leakage of doxorubicin from the liposomes at physiological pH resulting in decreased safety and efficacy of the drug. The Myocet® product also requires the pharmacy to follow a difficult multistep protocol for preparation of doxorubicin loaded liposomes prior to administration to patients.

Thus, there is a need for development of novel liposomal nanocarriers with improved drug release profiles relative to the known marketed products (for example, Myocet® and Doxil®) and with a simple, efficient, and attractive formulation preparation system. Provided here are solutions to these and other needs in the art.

SUMMARY

The disclosure herewith provides, inter alia, anticancer compositions and methods for their production. In certain aspects, the composition is a pharmaceutical composition including a liposome. The liposome encompasses a weakly basic anticancer compound and an acid or salt thereof. In embodiments, the acid is oxalic acid or tartaric acid. In embodiments, the weakly basic anticancer compound is doxorubicin, irinotecan, mitoxantrone or a combination thereof.

In embodiments, the liposome comprises a poloxamer. In embodiments, the poloxamer is poloxamer 188.

In embodiments, the liposome includes a plurality of lipid compounds. The weight ratio of the plurality of lipids to the weakly basic anticancer agent may be at least 20/1. In embodiments, liposome includes a plurality of lipid compounds and the weight ratio of the plurality of lipids to the weakly basic anticancer agent is about 20/1 to about 100/1. In embodiments, the liposome includes a plurality of lipid compounds and the weight ratio of the plurality of lipids to the weakly basic anticancer agent is 20/1 to about 50/1.

In embodiments, the weakly basic anticancer compound is substantially released from the liposome only at acidic pH. In embodiments, at least 10-100% of the weakly basic anticancer compound is released from the liposome at pH 5.0 to 6.7 under standard assay conditions. In embodiment, less than 5% of the weakly basic anticancer compound is released from the liposome at pH 7.4 under standard assay conditions. In embodiments, the standard assay conditions include 20× and/or 50× dilution in PBS buffer pH 5.0 or higher, e.g. pH 5.0, pH 5.5, pH 6.0, pH 6.5, pH 6.7, pH 7.0, or pH 7.4 or any intervening numbers of the foregoing pHs or human serum, or human blood and incubation at 37° C. for 2, 4, or 8 hours. In embodiments, the standard assay conditions include 20× and/or 50× dilution in PBS buffer. In embodiments, the standard assay conditions include incubation in PBS buffer having about pH 5.0. In embodiments, the standard assay conditions include incubation in PBS buffer having about pH 5.5. In embodiments, the standard assay conditions include incubation in PBS buffer having about pH 6.0. In embodiments, the standard assay conditions include incubation in PBS buffer having about pH 6.5. In embodiments, the standard assay conditions include incubation in PBS buffer having about pH 6.7. In embodiments, the standard assay conditions include incubation in PBS buffer having about pH 7.0. In embodiments, the standard assay conditions include incubation in PBS buffer having about pH 7.4. In embodiments, the standard assay conditions include incubation in human serum or human blood. In embodiments, the standard assay conditions include incubation at 37° C. for about 2 hours. In embodiments, the standard assay conditions include incubation at 37° C. for about 4 hours. In embodiments, the standard assay conditions include incubation at 37° C. for about 6 hours.

In embodiments, the liposome is substantially spherical. In embodiments, the pharmaceutical composition includes a plurality of liposomes with a mean longest dimension of about 60-80 nm determined by the intensity-averaged particle diameters (Z-average) measured by Dynamic Light Scattering. In embodiments, the pharmaceutical composition includes a plurality of liposomes with a mean longest dimension of about 10-30 nm determined by the number-based particle diameters measured by Dynamic Light Scattering. In embodiments, the pharmaceutical composition includes s a plurality of liposomes having a mean longest dimension from 10-30 nm determined by Cryo-Transmission Electron Microscopy.

In embodiments, the liposome comprises about 500-1000 µg/mL of the weakly basic anticancer compound and optionally an acid or salt thereof. In embodiments, the liposome includes about 700-850 µg/mL of the weakly basic anticancer compound and, as applicable, an acid or salt thereof. In embodiments, the liposome includes a plurality of the weakly basic anticancer compounds forming an aggregate. The aggregate may be non-crystalline. The non-crystalline aggregate may be partially or fully disorganized (non-ordered). In embodiments, the liposome includes a plurality of the weakly basic anticancer compound and retains greater than 90% of the plurality of weakly basic anticancer compound after 40 days when stored at 2-8° C. under standard storage conditions.

In embodiments, the liposome does not includes a cholesterol or a poloxamer 188. In embodiments, the liposome does not include an acidic organic compound other than oxalic acid, tartaric acid, or salts thereof. In embodiments, the liposome does not include an active agent other than the weakly basic anticancer compound. In embodiments, the liposome does not include a drug other than the weakly basic anticancer compound. In embodiments, the liposome does not include a pharmaceutically active compound other than the weakly basic anticancer compound. In embodiments, the liposome does not include any anticancer compound other than the weakly basic anticancer compound (e.g. the liposome includes a weakly basic anticancer compound of only one chemical structure including salts thereof).

In embodiments, the liposome is formed by loading the weakly basic anticancer compound into an unloaded liposome followed by incubation at a room temperature. In some embodiments, the unloaded liposomes are stored for about 30 days. In embodiments, the unloaded liposomes are stored for about 60 days. In embodiments, the unloaded liposomes are stored for about 90 days. In embodiments, the unloaded liposomes are stored for about 120 days. In embodiments, the unloaded liposomes are stored for about 150 days. In embodiments, the unloaded liposomes are stored for about 180. In embodiments, the unloaded liposomes are stored for about 210 days. In embodiments, the unloaded liposomes are stored for about 240 days. In embodiments, the unloaded liposomes are stored for about 270 days. In embodiments, the unloaded liposomes are stored for about 300 days. In embodiments, the unloaded liposomes are stored for about 330 days. In embodiments, the unloaded liposomes are stored for about 360 days. In embodiments, the unloaded liposomes are stored for about 390 days. In embodiments, the unloaded liposomes are stored for about 420 days. In embodiments, the unloaded liposomes are stored for about 450 days. In embodiments, the unloaded liposomes are stored for about 480 days. In embodiments, the unloaded liposomes are stored for about 510 days. In embodiments, the unloaded liposomes are stored for about 540 days. In embodiments, the unloaded liposomes are stored at 2-8° C. under standard storage conditions. In embodiments, the unloaded liposomes, stored in any conditions above, retain greater than 90% of the weakly basic anticancer compound upon loading of the weakly basic anticancer compound. In embodiments, at least 40-80% of the weakly basic anticancer compound is released from the liposome at pH 5.0 under standard assay conditions. In embodiments, at least 20-60% of the weakly basic anticancer compound is released from the liposome at pH 6.0. In embodiments, at least 7-30% of the weakly basic anticancer compound is released from the liposome at pH 6.7 under standard assay conditions. In some embodiments, less than 5% of the weakly basic anticancer compound is released from the liposome at pH 7.4 under standard assay conditions.

In further aspects, the disclosures provided herewith include a method for preparing a liposome encompassing (i.e. comprising or encapsulating) the weakly basic anticancer compound a weakly basic anticancer compound and an acid or salt thereof. In embodiments, the acid is oxalic acid or tartaric acid. The method includes: mixing a solution of the weakly basic anticancer compound thereof with a suspension including the liposomes containing an encapsulated acid or salt; and incubating the solution of the weakly basic anticancer compound thereof with the suspension including the liposomes containing an encapsulated acid or salt. In embodiments, about 85-100% of the weakly basic anticancer compound thereof used in mixing with the suspension of liposomes containing an encapsulated acid or salt is retained within the liposomes. In embodiments, about 90-100% of the weakly basic anticancer compound thereof used in mixing with the suspension of liposomes containing an encapsulated acid or salt is retained within the liposomes. In embodiments, the incubating step occurs at room temperature. In the incubating step is about 10-30 minutes. In embodiments, the incubating step is about 5-25 minutes.

In further aspects, the disclosures provided herewith include a kit comprising a first vial including a weakly basic anticancer compound thereof, and a second vial including a suspension of liposomes containing an encapsulated acid or salt. In embodiments, the weakly basic anticancer compound thereof of the first vial is a lyophilized weakly basic anticancer compound a thereof. In embodiments, the suspension of liposomes containing an encapsulated acid or salt of the second vial is an aqueous liposome suspension.

In further aspects, the disclosures provided herewith include a method of using the kit described above, the method including mixing the contents of the first vial with the contents of the second vial. In embodiments, the mixing is at room temperature.

In an embodiment, the disclosures provided herewith include a method for preparing a liposome encompassing a weakly basic anticancer compound and an acid or salt thereof. In embodiments, the acid is citric acid. The method includes mixing a solution of the weakly basic anticancer compound and an acid or salt thereof with a suspension including the liposomes containing an encapsulated acid or salt thereof; and incubating the solution of the weakly basic anticancer compound and an acid or salt thereof with the suspension including the liposomes containing an encapsulated acid or salt thereof.

In an embodiment, the disclosures provided herewith include a pharmaceutical composition including a liposome, the liposome encompassing a weakly basic anticancer compound and an acid or salt thereof. In embodiments, the acid is citric acid. In embodiments, the liposome includes a plurality of lipid compounds and the weight ratio of the plurality of lipids to the weakly basic anticancer agent is at least 20/1.

In further aspects, the disclosures herewith provide a method of treating a cancer in a subject. The method includes administering an effective amount of a pharmaceutical composition to the subject in need of the treatment. The pharmaceutical composition contains a liposome encompassing a weakly basic anticancer compound and an acid or salt thereof. In embodiments, the acid is oxalic acid or tartaric acid. The weakly basic anticancer compound has anticancer activity to the cancer.

Each of the aspects and embodiments described herein are capable of being used together, unless excluded either explicitly or clearly from the context of the embodiment or aspect.

BRIEF DESCRIPTION OF THE DRAWINGS

FIG. 7A has a magnification of 27K and FIGS. 7B and 7C have magnification of 50K.

FIG. 23A shows the solution at time 0. FIG. 23B shows the solution at time 24 hours. Mitoxantrone loading into liposomes was performed at 2-8° C.

DETAILED DESCRIPTION OF THE DISCLOSURES

Figure 1:
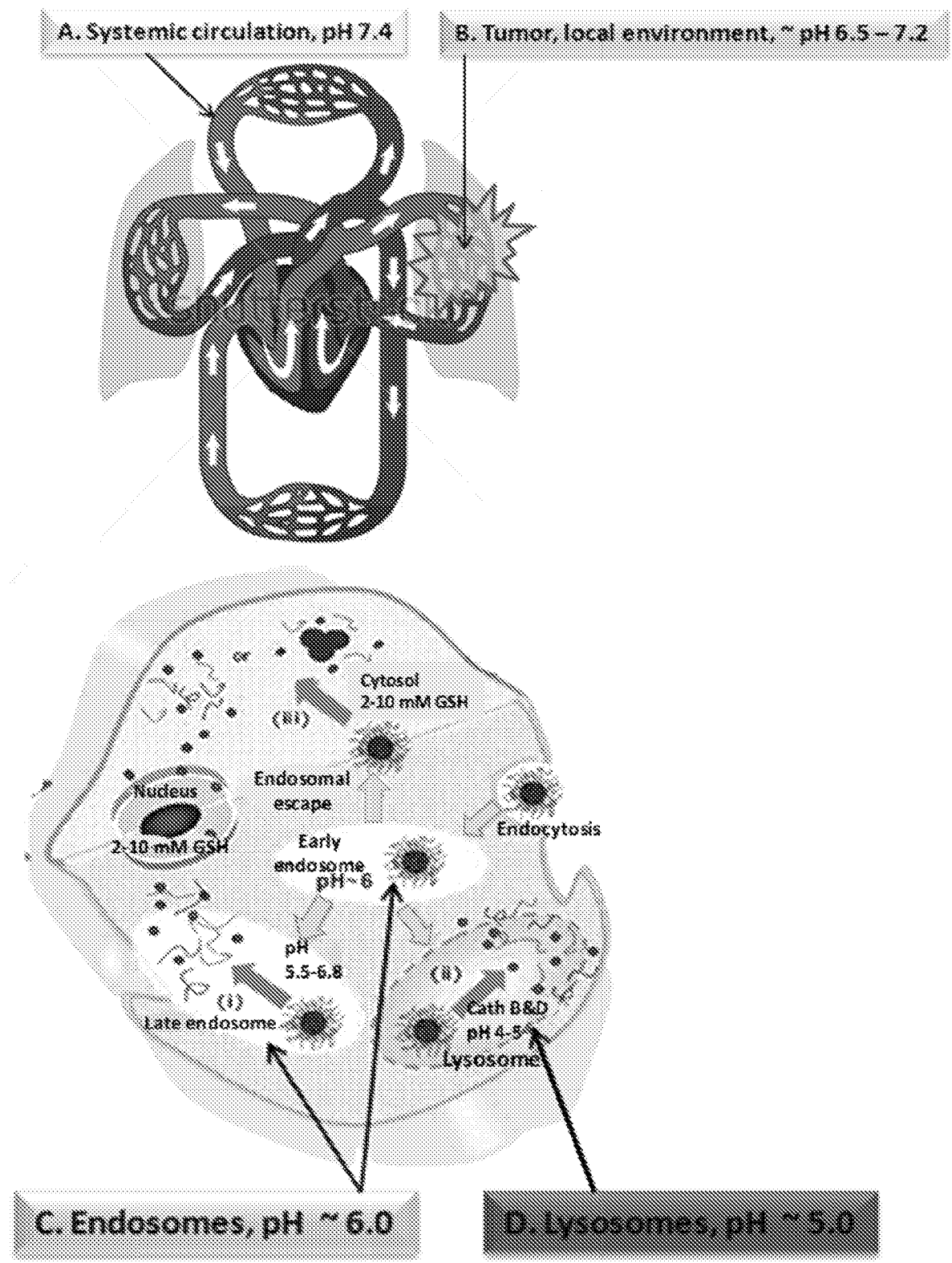
FIG. 1 is a schematic drawing showing pH gradients in (A) systematic circulation, (B) tumoral and local environment and (C and D) intracellular environment. (E) shows a desirable release profiles over the range of pH 8.0-5.0.
Figure 1:
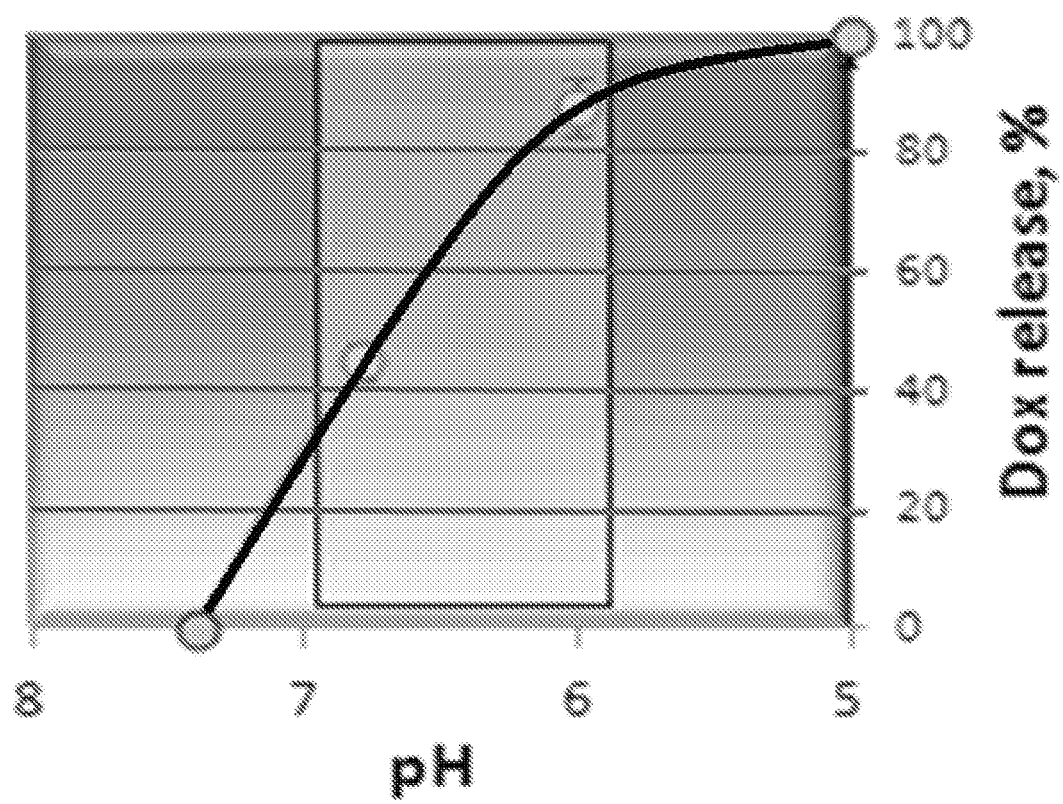

The present disclosures describe compositions and processes used to create stable anticancer compounds and acids or salts thereof and lipid rich submicron particles (nanoparticles with liposomes) suitable for drug delivery. Compositions and methods of the present disclosures can be similarly applied to other drug salts in liposomes. The composition of the doxorubicin salt and structure of the liposomes prepared according to the methods disclosed herein results in desirable biological and physicochemical performance (pH dependent drug release profile).

In embodiments of the present disclosures utilizing the anticancer compound doxorubicin, the therapeutic utility of the present disclosures are improved compared to known liposome encapsulated doxorubicin therapies in their more desirable release profile which includes: low rate of doxorubicin release from the liposomes at physiological pH-7.4 (while in circulation), and significantly higher release rate at more acidic pH 5.0-6.7 (e.g. after exposure to local tumor environment or to endosomal/lysosomal environment upon internalization of the doxorubicin loaded liposomes by the cancer cells).

There are numerous published reports indicating the existence and importance of the pH gradient between normal tissues and the tumor site, as well as the effect of pH dependent drug release from liposomes for not just delivery but for making the free drug available (via efficient release) to the cancer cells [1, 10, 13-15, 25, 40-42]. One major difference between many solid tumors and surrounding normal tissue is the nutritional and metabolic environment. The functional vasculature of tumors is often inadequate to supply the nutritional needs of the expanding population of tumor cells, leading to deficiency of oxygen and many other nutrients. The production of lactic acid under anaerobic conditions and the hydrolysis of ATP in an energy-deficient environment contribute to the acidic microenvironment found in many tumor types [35]. The pH in human and rodent normal tissues ranges from 7.00 to 8.06, whereas a wider range of pH values was determined in malignant tissue, from about pH 5.8 to pH 7.6 in both human and rodent tumors [1, 41-42]

Thus, the desirable release profile of doxorubicin from the liposomes would be the following: maximized release rate at acidic pH 5.0-6.7 (i.e. after exposure to local tumor environment or to endosomal/lysosomal environment upon internalization of liposomes by the cancer cells), while suppressing release from the liposomes at physiological pH-7.4 (while in circulation).

Definitions

As used herein "liposomes" are largely spherical nanoparticles made up of a lipid bilayer. In embodiments, liposomes can encapsulate therapeutic agents for delivery. The lipid content of liposomes can vary altering liposome size, stability, solubility, curvature, etc. Examples of lipids include, but are not limited to, cholesterol, phosphatidylcholine (PC) products/derivatives (various carbon chain length fatty acids, saturated, multi-unsaturated and mixed acid PC's); 1,2-dioleoyl-sn-glycero-3-phosphoethanolamine (DOPE); 1,2-dimyristoyl-sn-glycero-3-phosphate (DMPA); 1,2-dipalmitoyl-sn-glycero-3-phosphate (DPPA); 1,2-dioleoyl-sn-glycero-3-phosphate (DOPA); 1,2-dimyristoyl-sn-glycero-3-phospho-(1'-rac-glycerol) (DMPG); 1,2-dipalmitoyl-sn-glycero-3-phospho-(1'-rac-glycerol) (DPPG); 1,2-dioleoyl-sn-glycero-3-phospho-(1'-rac-glycerol) (DOPG); 1,2-dimyristoyl-sn-glycero-3-phosphocholine (DMPC); 1,2-dimyristoyl-sn-glycero-3-phospho-L-serine (DMPS); 1,2-dipalmitoyl-sn-glycero-3-phospho-L-serine (DPPS); 1,2-dioleoyl-sn-glycero-3-phospho-L-serine (DOPC); 1,2-distearoyl-sn-glycero-3-phosphoethanolamine-N-[methoxy (polyethylene glycol)-2000] (DSPE-mPEG-2000); 1,2-distearoyl-sn-glycero-3-phosphoethanol-amine-N-[folate (polyethylene glycol)-5000] (DSPE-mPEG-5000); 1,2-distearoyl-sn-glycero-3-phosphoethanolamine-N-[amino (polyethylene glycol)-2000] (DSPE-PEG-2000); 1,2-stearoyl-3-trimethylammonium-propane (DOTAP); L-α-phosphatidylcholine, hydrogenated (Hydro Soy PC); and 2-stearoyl-sn-glycero-3-phosphocholine (Lyso PC).

The term "encompassing," "encapsulating" or "retaining" as used herein means to include within, for example, a liposome. This may also be referred to as "comprising" in the context of a claim herein. For example, a liposome may encompass a therapeutic agent such as an anticancer compound, or acid or salt thereof. In embodiments, when encompassed, a therapeutic agent may dissipate from, or diffuse out of, a liposome over time.

The term "weakly basic anticancer compound" as used herein includes any therapeutic agent useful in the treatment of a cancer or neoplastic disease with a weakly basic pKa. In embodiments, a weakly basic pH is indicated by a pKa of about pH 7.0-10.0. In embodiments, a weakly basic pH is indicated by a pKa of about pH 7.0 to 9.0. In embodiments, a weakly basic pH is indicated by a pKa of about pH 7.5 to 9.0. In embodiments, a weakly basic pH is indicated by a pKa of about pH 8.0 to 9.0. In embodiments, an anticancer agent has more than one pKa, any one of which can fall within the ranges of weakly basis as described above.

The term "doxorubicin" is used according to its plain and ordinary meaning, doxorubicin is an anticancer compound originally obtained from *Streptomyces peucetius*. doxorubicin may also be referred to as Adriamycin, Doxil, Rubex, Adriablastin, and doxorubicine. In embodiments, doxorubicin is a weakly basic anticancer compound. The structure of doxorubicin is shown herein.

The term "irinotecan" is used according to its plain and ordinary meaning. Irinotecan is an anticancer compound that may be used for colorectal cancer that has metastasized (spread to other parts of the body), including metastatic cancer that has recurred (come back) or has not gotten better with other chemotherapy and for the treatment of patients with metastatic adenocarcinoma of the pancreas after disease progression following gemcitabine-based therapy. Irinotecan may also be referred to as Camptosar; 97682-44-5; (+)-Irinotecan; Irinotecanum; and Irinotecanum. In embodiments, irinotecan is a weakly basic anticancer compound. The structure of irinotecan is shown herein.

The term "mitoxantrone" is used according to its plain and ordinary meaning. Mitoxantrone is an anticancer compound that may be used for acute myeloid leukemia (AML)

and prostate cancer. It also may be used as palliative treatment in advanced disease that is hormone-refractory (does not respond to hormone treatment). Mitoxantrone may also be referred to as 65271-80-9; Mitoxantrone; Mitozantrone; DHAQ; and Mitoxantron. In embodiments, mitoxantrone is a weakly basic anticancer compound. The structure of mitoxantrone is shown herein.

As used herein, the term "an acid or salt thereof" refers to any pharmaceutically acceptable acid or salt of a stated compound. Example acids or salts suitable for use with anticancer compounds include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L)malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid As used herein, the term "disorganized" or "non-crystalline" refers to the disordered polymorphic state of a compound. This disorganized state may resemble an amorphous state. In disorganized, non-crystalline aggregates the molecules do not form an ordered crystal lattice. In embodiments, a disorganized aggregate may also include any non-crystalline structures, and colloids. In embodiments, some disorganized and non-crystalline aggregates may contain some fibroid structures.

As used herein, the term "substantially released" indicates that a majority of contents are released, e.g., from a liposome. In embodiments, substantially released means greater than about 5% or more of encompassed contents are released. In embodiments, substantially released means greater than about 10% or more of encompassed contents are released. In embodiments, substantially released means greater than about 20% or more of encompassed contents are released. In embodiments, substantially released means greater than about 30% or more of encompassed contents are released. In embodiments, substantially released means greater than about 40% or more of encompassed contents are released. In embodiments, substantially released means greater than about 50% or more of encompassed contents are released. In embodiments, substantially released means greater than about 60% or more of encompassed contents are released. In embodiments, substantially released means greater than about 70% or more of encompassed contents are released. In embodiments, substantially released means greater than about 80% or more of encompassed contents are released. In embodiments, substantially released means greater than about 90% or more of encompassed contents are released. In embodiments, substantially released means greater than about 95% or more of encompassed contents are released. In embodiments, substantially released means greater than about 97% or more of encompassed contents are released. In embodiments, substantially released means greater than about 98% or more of encompassed contents are released. In embodiments, substantially released means greater than about 99% or more of encompassed contents are released. In embodiments, substantial release is pH drive, e.g., an anticancer agent is substantially released only at acidic pH.

As used herein, the terms "a standard assay condition" or "standard assay conditions" refer to controlled set of assay conditions, including standard measures of time, temperature, pH, etc. In embodiments, the standard assay conditions include 20× and/or 50× dilution in PBS. In embodiments, the standard assay conditions include 20× and/or 50× dilution in serum or blood. In embodiments, standard assay conditions for release assays described herein are at about 25° C. In embodiments, standard assay conditions for release assays described herein are at about 37° C. In embodiments, standard assay conditions for release assays described herein include incubations of about 2, 4, 8 hours or any intervening period of the foregoing or more than about 8 hours. In embodiments, standard assay conditions for release assays described herein include incubations of about 2 hours. In embodiments, standard assay conditions for release assays described herein include incubations of about 4 hours. In embodiments, standard assay conditions for release assays described herein include incubations of about 8 hours. In embodiments, standard assay conditions for release assays described herein include incubations of more than 8 hours. In embodiments, standard assay conditions for release assays described herein include incubation at about pH 7.4. In embodiments, standard assay conditions for release assays described herein include incubation at about pH 6.7. In embodiments, standard assay conditions for release assays described herein include incubation at about pH 6.0. In embodiments, standard assay conditions for release assays described herein include incubation at about pH 5.0.

Therefore, in some embodiments, standard assay conditions for release assay are at 25° C. or at about 25° C. and include incubation in 20× dilution in PBS having about pH 7.4 for about 2 hours. In some embodiments, standard assay conditions for release assay are at 25° C. or at about 25° C. and include incubation in 20× dilution in PBS having about pH 7.4 for about 4 hours. In some embodiments, standard assay conditions for release assay are at 25° C. or at about 25° C. and include incubation in 20× dilution in PBS having about pH 7.4 for about 8 hours. In some embodiments, standard assay conditions for release assay are at 25° C. or at about 25° C. and include incubation in 20× dilution in PBS having about pH 7.4 for more than 8 hours.

Therefore, in some embodiments, standard assay conditions for release assay are at 25° C. or at about 25° C. and include incubation in 20× dilution in PBS having about pH 6.7 for about 2 hours. In some embodiments, standard assay conditions for release assay are at 25° C. or at about 25° C. and include incubation in 20× dilution in PBS having about pH 6.7 for about 4 hours. In some embodiments, standard assay conditions for release assay are at 25° C. or at about 25° C. and include incubation in 20× dilution in PBS having about pH 6.7 for about 8 hours. In some embodiments, standard assay conditions for release assay are at 25° C. or at about 25° C. and include incubation in 20× dilution in PBS having about pH 6.7 for more than 8 hours.

Therefore, in some embodiments, standard assay conditions for release assay are at 25° C. or at about 25° C. and include incubation in 20× dilution in PBS having about pH 6.0 for about 2 hours. In some embodiments, standard assay conditions for release assay are at 25° C. or at about 25° C. and include incubation in 20× dilution in PBS having about pH 6.0 for about 4 hours. In some embodiments, standard assay conditions for release assay are at 25° C. or at about 25° C. and include incubation in 20× dilution in PBS having about pH 6.0 for about 8 hours. In some embodiments, standard assay conditions for release assay are at 25° C. or at about 25° C. and include incubation in 20× dilution in PBS having about pH 6.0 for more than 8 hours.

Therefore, in some embodiments, standard assay conditions for release assay are at 25° C. or at about 25° C. and include incubation in 20× dilution in PBS having about pH 5.0 for about 2 hours. In some embodiments, standard assay conditions for release assay are at 25° C. or at about 25° C. and include incubation in 20× dilution in PBS having about pH 5.0 for about 4 hours. In some embodiments, standard assay conditions for release assay are at 25° C. or at about 25° C. and include incubation in 20× dilution in PBS having about pH 5.0 for about 8 hours. In some embodiments, standard assay conditions for release assay are at 25° C. or at about 25° C. and include incubation in 20× dilution in PBS having about pH 5.0 for more than 8 hours.

Therefore, in some embodiments, standard assay conditions for release assay are at 25° C. or at about 25° C. and include incubation in 50× dilution in PBS having about pH 7.4 for about 2 hours. In some embodiments, standard assay conditions for release assay are at 25° C. or at about 25° C. and include incubation in 50× dilution in PBS having about pH 7.4 for about 4 hours. In some embodiments, standard assay conditions for release assay are at 25° C. or at about 25° C. and include incubation in 50× dilution in PBS having about pH 7.4 for about 8 hours. In some embodiments, standard assay conditions for release assay are at 25° C. or at about 25° C. and include incubation in 50× dilution in PBS having about pH 7.4 for more than 8 hours.

Therefore, in some embodiments, standard assay conditions for release assay are at 25° C. or at about 25° C. and include incubation in 50× dilution in PBS having about pH 6.7 for about 2 hours. In some embodiments, standard assay conditions for release assay are at 25° C. or at about 25° C. and include incubation in 50× dilution in PBS having about pH 6.7 for about 4 hours. In some embodiments, standard assay conditions for release assay are at 25° C. or at about 25° C. and include incubation in 50× dilution in PBS having about pH 6.7 for about 8 hours. In some embodiments, standard assay conditions for release assay are at 25° C. or at about 25° C. and include incubation in 50× dilution in PBS having about pH 6.7 for more than 8 hours.

Therefore, in some embodiments, standard assay conditions for release assay are at 25° C. or at about 25° C. and include incubation in 50× dilution in PBS having about pH 6.0 for about 2 hours. In some embodiments, standard assay conditions for release assay are at 25° C. or at about 25° C. and include incubation in 50× dilution in PBS having about pH 6.0 for about 4 hours. In some embodiments, standard assay conditions for release assay are at 25° C. or at about 25° C. and include incubation in 50× dilution in PBS having about pH 6.0 for about 8 hours. In some embodiments, standard assay conditions for release assay are at 25° C. or at about 25° C. and include incubation in 50× dilution in PBS having about pH 6.0 for more than 8 hours.

Therefore, in some embodiments, standard assay conditions for release assay are at 25° C. or at about 25° C. and include incubation in 50× dilution in PBS having about pH 5.0 for about 2 hours. In some embodiments, standard assay conditions for release assay are at 25° C. or at about 25° C. and include incubation in 50× dilution in PBS having about pH 5.0 for about 4 hours. In some embodiments, standard assay conditions for release assay are at 25° C. or at about 25° C. and include incubation in 50× dilution in PBS having about pH 5.0 for about 8 hours. In some embodiments, standard assay conditions for release assay are at 25° C. or at about 25° C. and include incubation in 50× dilution in PBS having about pH 5.0 for more than 8 hours.

Therefore, in some embodiments, standard assay conditions for release assay are at 37° C. or at about 37° C. and include incubation in 20× dilution in PBS having about pH 7.4 for about 2 hours. In some embodiments, standard assay conditions for release assay are at 37° C. or at about 37° C. and include incubation in 20× dilution in PBS having about pH 7.4 for about 4 hours. In some embodiments, standard assay conditions for release assay are at 37° C. or at about 37° C. and include incubation in 20× dilution in PBS having about pH 7.4 for about 8 hours. In some embodiments, standard assay conditions for release assay are at 37° C. or at about 37° C. and include incubation in 20× dilution in PBS having about pH 7.4 for more than 8 hours.

Therefore, in some embodiments, standard assay conditions for release assay are at 37° C. or at about 37° C. and include incubation in 20× dilution in PBS having about pH 6.7 for about 2 hours. In some embodiments, standard assay conditions for release assay are at 37° C. or at about 37° C. and include incubation in 20× dilution in PBS having about pH 6.7 for about 4 hours. In some embodiments, standard assay conditions for release assay are at 37° C. or at about 37° C. and include incubation in 20× dilution in PBS having about pH 6.7 for about 8 hours. In some embodiments, standard assay conditions for release assay are at 37° C. or at about 37° C. and include incubation in 20× dilution in PBS having about pH 6.7 for more than 8 hours.

Therefore, in some embodiments, standard assay conditions for release assay are at 37° C. or at about 37° C. and include incubation in 20× dilution in PBS having about pH 6.0 for about 2 hours. In some embodiments, standard assay conditions for release assay are at 37° C. or at about 37° C. and include incubation in 20× dilution in PBS having about pH 6.0 for about 4 hours. In some embodiments, standard assay conditions for release assay are at 37° C. or at about 37° C. and include incubation in 20× dilution in PBS having about pH 6.0 for about 8 hours. In some embodiments, standard assay conditions for release assay are at 37° C. or at about 37° C. and include incubation in 20× dilution in PBS having about pH 6.0 for more than 8 hours.

Therefore, in some embodiments, standard assay conditions for release assay are at 37° C. or at about 37° C. and include incubation in 20× dilution in PBS having about pH 5.0 for about 2 hours. In some embodiments, standard assay conditions for release assay are at 37° C. or at about 37° C. and include incubation in 20× dilution in PBS having about pH 5.0 for about 4 hours. In some embodiments, standard assay conditions for release assay are at 37° C. or at about 37° C. and include incubation in 20× dilution in PBS having about pH 5.0 for about 8 hours. In some embodiments, standard assay conditions for release assay are at 37° C. or at about 37° C. and include incubation in 20× dilution in PBS having about pH 5.0 for more than 8 hours.

Therefore, in some embodiments, standard assay conditions for release assay are at 37° C. or at about 37° C. and include incubation in 50× dilution in PBS having about pH 7.4 for about 2 hours. In some embodiments, standard assay conditions for release assay are at 37° C. or at about 37° C. and include incubation in 50× dilution in PBS having about pH 7.4 for about 4 hours. In some embodiments, standard assay conditions for release assay are at 37° C. or at about 37° C. and include incubation in 50× dilution in PBS having about pH 7.4 for about 8 hours. In some embodiments, standard assay conditions for release assay are at 37° C. or at about 37° C. and include incubation in 50× dilution in PBS having about pH 7.4 for more than 8 hours.

Therefore, in some embodiments, standard assay conditions for release assay are at 37° C. or at about 37° C. and include incubation in 50× dilution in PBS having about pH 6.7 for about 2 hours. In some embodiments, standard assay conditions for release assay are at 37° C. or at about 37° C. and include incubation in 50× dilution in PBS having about pH 6.7 for about 4 hours. In some embodiments, standard assay conditions for release assay are at 37° C. or at about 37° C. and include incubation in 50× dilution in PBS having about pH 6.7 for about 8 hours. In some embodiments, standard assay conditions for release assay are at 37° C. or at about 37° C. and include incubation in 50× dilution in PBS having about pH 6.7 for more than 8 hours.

Therefore, in some embodiments, standard assay conditions for release assay are at 37° C. or at about 37° C. and include incubation in 50× dilution in PBS having about pH 6.0 for about 2 hours. In some embodiments, standard assay conditions for release assay are at 37° C. or at about 37° C. and include incubation in 50× dilution in PBS having about pH 6.0 for about 4 hours. In some embodiments, standard assay conditions for release assay are at 37° C. or at about 37° C. and include incubation in 50× dilution in PBS having about pH 6.0 for about 8 hours. In some embodiments, standard assay conditions for release assay are at 37° C. or at about 37° C. and include incubation in 50× dilution in PBS having about pH 6.0 for more than 8 hours.

Therefore, in some embodiments, standard assay conditions for release assay are at 37° C. or at about 37° C. and include incubation in 50× dilution in PBS having about pH 5.0 for about 2 hours. In some embodiments, standard assay conditions for release assay are at 37° C. or at about 37° C. and include incubation in 50× dilution in PBS having about pH 5.0 for about 4 hours. In some embodiments, standard assay conditions for release assay are at 37° C. or at about 37° C. and include incubation in 50× dilution in PBS having about pH 5.0 for about 8 hours. In some embodiments, standard assay conditions for release assay are at 37° C. or at about 37° C. and include incubation in 50× dilution in PBS having about pH 5.0 for more than 8 hours.

Therefore, in some embodiments, standard assay conditions for release assay are at 25° C. or at about 25° C. and include incubation in 20× dilution in serum or blood having about pH 7.4 for about 2 hours. In some embodiments, standard assay conditions for release assay are at 25° C. or at about 25° C. and include incubation in 20× dilution in serum or blood having about pH 7.4 for about 4 hours. In some embodiments, standard assay conditions for release assay are at 25° C. or at about 25° C. and include incubation in 20× dilution in serum or blood having about pH 7.4 for about 8 hours. In some embodiments, standard assay conditions for release assay are at 25° C. or at about 25° C. and include incubation in 20× dilution in serum or blood having about pH 7.4 for more than 8 hours.

Therefore, in some embodiments, standard assay conditions for release assay are at 25° C. or at about 25° C. and include incubation in 20× dilution in serum or blood having about pH 6.7 for about 2 hours. In some embodiments, standard assay conditions for release assay are at 25° C. or at about 25° C. and include incubation in 20× dilution in serum or blood having about pH 6.7 for about 4 hours. In some embodiments, standard assay conditions for release assay are at 25° C. or at about 25° C. and include incubation in 20× dilution in serum or blood having about pH 6.7 for about 8 hours. In some embodiments, standard assay conditions for release assay are at 25° C. or at about 25° C. and include incubation in 20× dilution in serum or blood having about pH 6.7 for more than 8 hours.

Therefore, in some embodiments, standard assay conditions for release assay are at 25° C. or at about 25° C. and include incubation in 20× dilution in serum or blood having about pH 6.0 for about 2 hours. In some embodiments, standard assay conditions for release assay are at 25° C. or at about 25° C. and include incubation in 20× dilution in serum or blood having about pH 6.0 for about 4 hours. In some embodiments, standard assay conditions for release assay are at 25° C. or at about 25° C. and include incubation in 20× dilution in serum or blood having about pH 6.0 for about 8 hours. In some embodiments, standard assay conditions for release assay are at 25° C. or at about 25° C. and include incubation in 20× dilution in serum or blood having about pH 6.0 for more than 8 hours.

Therefore, in some embodiments, standard assay conditions for release assay are at 25° C. or at about 25° C. and include incubation in 20× dilution in serum or blood having about pH 5.0 for about 2 hours. In some embodiments, standard assay conditions for release assay are at 25° C. or at about 25° C. and include incubation in 20× dilution in serum or blood having about pH 5.0 for about 4 hours. In some embodiments, standard assay conditions for release assay are at 25° C. or at about 25° C. and include incubation in 20× dilution in serum or blood having about pH 5.0 for about 8 hours. In some embodiments, standard assay conditions for release assay are at 25° C. or at about 25° C. and include incubation in 20× dilution in serum or blood having about pH 5.0 for more than 8 hours.

Therefore, in some embodiments, standard assay conditions for release assay are at 25° C. or at about 25° C. and include incubation in 50× dilution in serum or blood having about pH 7.4 for about 2 hours. In some embodiments, standard assay conditions for release assay are at 25° C. or at about 25° C. and include incubation in 50× dilution in serum or blood having about pH 7.4 for about 4 hours. In some embodiments, standard assay conditions for release assay are at 25° C. or at about 25° C. and include incubation in 50× dilution in serum or blood having about pH 7.4 for about 8 hours. In some embodiments, standard assay conditions for release assay are at 25° C. or at about 25° C. and include incubation in 50× dilution in serum or blood having about pH 7.4 for more than 8 hours.

Therefore, in some embodiments, standard assay conditions for release assay are at 25° C. or at about 25° C. and include incubation in 50× dilution in serum or blood having about pH 6.7 for about 2 hours. In some embodiments, standard assay conditions for release assay are at 25° C. or at about 25° C. and include incubation in 50× dilution in serum or blood having about pH 6.7 for about 4 hours. In some embodiments, standard assay conditions for release assay are at 25° C. or at about 25° C. and include incubation in 50× dilution in serum or blood having about pH 6.7 for about 8 hours. In some embodiments, standard assay conditions for release assay are at 25° C. or at about 25° C. and include incubation in 50× dilution in serum or blood having about pH 6.7 for more than 8 hours.

Therefore, in some embodiments, standard assay conditions for release assay are at 25° C. or at about 25° C. and include incubation in 50× dilution in serum or blood having about pH 6.0 for about 2 hours. In some embodiments, standard assay conditions for release assay are at 25° C. or at about 25° C. and include incubation in 50× dilution in serum or blood having about pH 6.0 for about 4 hours. In some embodiments, standard assay conditions for release assay are at 25° C. or at about 25° C. and include incubation in 50× dilution in serum or blood having about pH 6.0 for about 8 hours. In some embodiments, standard assay conditions for release assay are at 25° C. or at about 25° C. and include incubation in 50× dilution in serum or blood having about pH 6.0 for more than 8 hours.

Therefore, in some embodiments, standard assay conditions for release assay are at 25° C. or at about 25° C. and include incubation in 50× dilution in serum or blood having about pH 5.0 for about 2 hours. In some embodiments, standard assay conditions for release assay are at 25° C. or at about 25° C. and include incubation in 50× dilution in serum or blood having about pH 5.0 for about 4 hours. In some embodiments, standard assay conditions for release assay are at 25° C. or at about 25° C. and include incubation in 50× dilution in serum or blood having about pH 5.0 for about 8 hours. In some embodiments, standard assay conditions for release assay are at 25° C. or at about 25° C. and include incubation in 50× dilution in serum or blood having about pH 5.0 for more than 8 hours.

Therefore, in some embodiments, standard assay conditions for release assay are at 37° C. or at about 37° C. and include incubation in 20× dilution in serum or blood having about pH 7.4 for about 2 hours. In some embodiments, standard assay conditions for release assay are at 37° C. or at about 37° C. and include incubation in 20× dilution in serum or blood having about pH 7.4 for about 4 hours. In some embodiments, standard assay conditions for release assay are at 37° C. or at about 37° C. and include incubation in 20× dilution in serum or blood having about pH 7.4 for about 8 hours. In some embodiments, standard assay conditions for release assay are at 37° C. or at about 37° C. and include incubation in 20× dilution in serum or blood having about pH 7.4 for more than 8 hours.

Therefore, in some embodiments, standard assay conditions for release assay are at 37° C. or at about 37° C. and include incubation in 20× dilution in serum or blood having about pH 6.7 for about 2 hours. In some embodiments, standard assay conditions for release assay are at 37° C. or at about 37° C. and include incubation in 20× dilution in serum or blood having about pH 6.7 for about 4 hours. In some embodiments, standard assay conditions for release assay are at 37° C. or at about 37° C. and include incubation in 20× dilution in serum or blood having about pH 6.7 for about 8 hours. In some embodiments, standard assay conditions for release assay are at 37° C. or at about 37° C. and include incubation in 20× dilution in serum or blood having about pH 6.7 for more than 8 hours.

Therefore, in some embodiments, standard assay conditions for release assay are at 37° C. or at about 37° C. and include incubation in 20× dilution in serum or blood having about pH 6.0 for about 2 hours. In some embodiments, standard assay conditions for release assay are at 37° C. or at about 37° C. and include incubation in 20× dilution in serum or blood having about pH 6.0 for about 4 hours. In some embodiments, standard assay conditions for release assay are at 37° C. or at about 37° C. and include incubation in 20× dilution in serum or blood having about pH 6.0 for about 8 hours. In some embodiments, standard assay conditions for release assay are at 37° C. or at about 37° C. and include incubation in 20× dilution in serum or blood having about pH 6.0 for more than 8 hours.

Therefore, in some embodiments, standard assay conditions for release assay are at 37° C. or at about 37° C. and include incubation in 20× dilution in serum or blood having about pH 5.0 for about 2 hours. In some embodiments, standard assay conditions for release assay are at 37° C. or at about 37° C. and include incubation in 20× dilution in serum or blood having about pH 5.0 for about 4 hours. In some embodiments, standard assay conditions for release assay are at 37° C. or at about 37° C. and include incubation in 20× dilution in serum or blood having about pH 5.0 for about 8 hours. In some embodiments, standard assay conditions for release assay are at 37° C. or at about 37° C. and include incubation in 20× dilution in serum or blood having about pH 5.0 for more than 8 hours.

Therefore, in some embodiments, standard assay conditions for release assay are at 37° C. or at about 37° C. and include incubation in 50× dilution in serum or blood having about pH 7.4 for about 2 hours. In some embodiments, standard assay conditions for release assay are at 37° C. or at about 37° C. and include incubation in 50× dilution in serum or blood having about pH 7.4 for about 4 hours. In some embodiments, standard assay conditions for release assay are at 37° C. or at about 37° C. and include incubation in 50× dilution in serum or blood having about pH 7.4 for about 8 hours. In some embodiments, standard assay conditions for release assay are at 37° C. or at about 37° C. and include incubation in 50× dilution in serum or blood having about pH 7.4 for more than 8 hours.

Therefore, in some embodiments, standard assay conditions for release assay are at 37° C. or at about 37° C. and include incubation in 50× dilution in serum or blood having about pH 6.7 for about 2 hours. In some embodiments, standard assay conditions for release assay are at 37° C. or at about 37° C. and include incubation in 50× dilution in serum or blood having about pH 6.7 for about 4 hours. In some embodiments, standard assay conditions for release assay are at 37° C. or at about 37° C. and include incubation in 50× dilution in serum or blood having about pH 6.7 for about 8 hours. In some embodiments, standard assay conditions for release assay are at 37° C. or at about 37° C. and include incubation in 50× dilution in serum or blood having about pH 6.7 for more than 8 hours.

Therefore, in some embodiments, standard assay conditions for release assay are at 37° C. or at about 37° C. and include incubation in 50× dilution in serum or blood having about pH 6.0 for about 2 hours. In some embodiments, standard assay conditions for release assay are at 37° C. or at about 37° C. and include incubation in 50× dilution in serum or blood having about pH 6.0 for about 4 hours. In some embodiments, standard assay conditions for release assay are at 37° C. or at about 37° C. and include incubation in 50× dilution in serum or blood having about pH 6.0 for about 8 hours. In some embodiments, standard assay conditions for release assay are at 37° C. or at about 37° C. and include incubation in 50× dilution in serum or blood having about pH 6.0 for more than 8 hours.

Therefore, in some embodiments, standard assay conditions for release assay are at 37° C. or at about 37° C. and include incubation in 50× dilution in serum or blood having about pH 5.0 for about 2 hours. In some embodiments, standard assay conditions for release assay are at 37° C. or at about 37° C. and include incubation in 50× dilution in serum or blood having about pH 5.0 for about 4 hours. In some embodiments, standard assay conditions for release assay are at 37° C. or at about 37° C. and include incubation in 50× dilution in serum or blood having about pH 5.0 for about 8 hours. In some embodiments, standard assay conditions for release assay are at 37° C. or at about 37° C. and include incubation in 50× dilution in serum or blood having about pH 5.0 for more than 8 hours.

As used herein, the terms "a standard storage condition" or "standard storage conditions" refer to a condition controlled for proper storage of compound, e.g. a pharmaceutical compound. In embodiments, certain standard measures such as time, temperature, humidity and others can be controlled. In embodiments, the standard storage conditions include storage under 2-8° C., ambient relative humidity. In embodiments, the ambient relative humidity includes any range between about 10% to about 90% relative humidity. In embodiments, the ambient relative humidity includes about 10% relative humidity. In embodiments, the ambient relative humidity includes about 20% relative humidity. In embodiments, the ambient relative humidity includes about 30% relative humidity. In embodiments, the ambient relative humidity includes about 40% relative humidity. In embodiments, the ambient relative humidity includes about 50% relative humidity. In embodiments, the ambient relative humidity includes about 60% relative humidity. In embodiments, the ambient relative humidity includes about 70% relative humidity. In embodiments, the ambient relative humidity includes about 80% relative humidity. In embodiments, the ambient relative humidity includes about 90% relative humidity.

As used herein "substantially spherical" means an average tendency towards a spherical shape, e.g., a diameter through any axis is roughly equivalent. In embodiments, no diameter differs in length. In embodiments, no diameter differs in length more than about 20% or less from a diameter at any other axis. In embodiments, no diameter differs in length more than about 20% or less from a diameter at any other axis within a substantially spherical shape. In embodiments, no diameter differs in length more than about 15% or less from a diameter at any other axis within a substantially spherical shape. In embodiments, no diameter differs in length more than about 10% or less from a diameter at any other axis within a substantially spherical shape. In embodiments, no diameter differs in length more than about 9% or less from a diameter at any other axis within a substantially spherical shape. In embodiments, no diameter differs in length more than about 8% or less from a diameter at any other axis within a substantially spherical shape. In embodiments, no diameter differs in length more than about 7% or less from a diameter at any other axis within a substantially spherical shape. In embodiments, no diameter differs in length more than about 6% or less from a diameter at any other axis within a substantially spherical shape. In embodiments, no diameter differs in length more than about 5% or less from a diameter at any other axis within a substantially spherical shape. In embodiments, no diameter differs in length more than about 4% or less from a diameter at any other axis within a substantially spherical shape. In embodiments, no diameter differs in length more than about 3% or less from a diameter at any other axis within a substantially spherical shape. In embodiments, no diameter differs in length more than about 3% or less from a diameter at any other axis within a substantially spherical shape. In embodiments, no diameter differs in length more than about 1% or less from a diameter at any other axis within a substantially spherical shape.

As used herein, the term "mean longest dimension" refers to an average of the longest dimension of a substantially spherical object. In some embodiments, the mean longest dimension can be measured by the intensity-averaged particle diameters (Z-average). In some embodiments, the intensity-averaged particle diameters (Z-average) are calculated from the cumulants analysis as defined in ISO 13321 (International Organization for Standardization 1996). In some embodiments, the mean longest dimension can be measured by the number-based particle diameters. In some embodiments, particle size distribution by number is computed from the intensity distribution and the optical properties of the material. There is first-power relationship between particle size and contribution to the distribution.

As used herein, the term "room temperature" or "RT" refers to the temperature of an assay conducted at standard indoor temperature. In embodiments, room temperature refers to an assay conduct without any additional heating or cooling. In embodiments, room temperature is a controlled temperature of about 22-25° C. In embodiments, room temperature is 25° C.

As used herein, "liposome solution," "an aqueous solution of liposomes," "liposome suspension" or "an aqueous suspension of liposomes" refer to a liquid solution or suspension of liposomes. Liposomes may be suspended in a variety of solvents, buffers or solutions. In embodiments, liposomes are suspended in aqueous phase. In embodiments, liposomes are suspended in a physiological buffer having pH 7.0-7.4.

As used herein, the term "poloxamer" is a nonionic copolymer. Poloxamers include a central hydrophobic chain of polyoxypropylene and two flanking chains of polyoxyethylene. In embodiments, a poloxamer is Poloxamer 188. Additional names for poloxamer 188 are Lutrol® F68, P188, Kolliphor® P188, and Poly(ethylene glycol)-block-poly(propylene glycol)-block-poly(ethylene glycol). The CAS Number for P188 is 9003-11-6. P188 has the following structure wherein X is 80, Z is 80 and Y is 27:

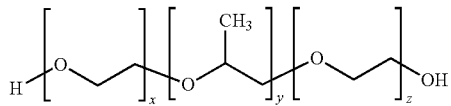

As used herein, the term "cholesterol" or "cholesterol compound" refers to a sterols or a modified steroids. Non-limiting examples include: cholesterol, hydroxycholesterols, cholestans, cholestanes, ketocholestanols, campesterol, cholesterol epoxides, cholesterol-peg, lanosterol, esterified cholesterols. The term "free cholesterol" refers to unesterified cholesterol with the following general formula $C_{27}H_{46}O$ and structure:

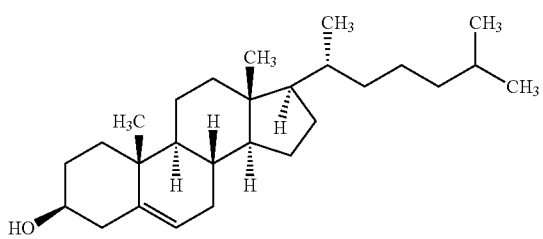

As used herein, the term "phospholipid" or "phospholipids", also called phosphatide or phosphatides, refer to an member of a class of phosphorous- and/or fatty acid-containing substances. In general, phospholipids are composed of a phosphate group, two alcohols, and one or two fatty acids. On one end of the molecule are the phosphate group and one alcohol; this end is polar, i.e., has an electric charge, and is attracted to water (hydrophilic). The other end, which consists of the fatty acids, is neutral; it is hydrophobic and water-insoluble but is fat-soluble. Some non-limiting and illustrative examples of phospholipids include, but not limited to, phosphatidic acid (phosphatidate), phosphatidylcholine (pc) products/derivatives (various carbon chain length fatty acids, saturated, multi-unsaturated and mixed acid PC's); 1,2-dioleoyl-sn-glycero-3-phosphoethanolamine (DOPE); 1,2-dimyristoyl-sn-glycero-3-phosphate (DMPA); 1,2-dipalmitoyl-sn-glycero-3-phosphate (DPPA); 1,2-dioleoyl-sn-glycero-3-phosphate (DOPA); 1,2-dimyristoyl-sn-glycero-3-phospho-(1'-rac-glycerol) (DMPG); 1,2-dipalmitoyl-sn-glycero-3-phospho-(1'-rac-glycerol) (DPPG); 1,2-dioleoyl-sn-glycero-3-phospho-(1'-rac-glycerol) (DOPG); 1,2-dimyristoyl-sn-glycero-3-phosphocholine (DMPC); 1,2-dimyristoyl-sn-glycero-3-phospho-L-serine (DMPS); 1,2-dipalmitoyl-sn-glycero-3-phospho-L-serine (DPPS); 1,2-dioleoyl-sn-glycero-3-phospho-L-serine (DOPC); 1,2-distearoyl-sn-glycero-3-phosphoethanolamine-N-[methoxy (polyethylene glycol)-2000] (DSPE-mPEG-2000); 1,2-distearoyl-sn-glycero-3-phosphoethanol-amine-N-[folate (polyethylene glycol)-5000] (DSPE-mPEG-5000); 1,2-distearoyl-sn-glycero-3-phosphoethanolamine-N-[amino (polyethylene glycol)-2000] (DSPE-PEG-2000); 1,2-stearoyl-3-trimethylammonium-propane (DOTAP); L-α-phosphatidylcholine, hydrogenated (Hydro Soy PC); and 2-stearoyl-sn-glycero-3-phosphocholine (Lyso PC), phosphatidylethanolamine, phosphatidylinositol, phosphatidylserine, phosphatidylinositol (PI) phosphatidylinositol phosphate (PIP) phosphatidylinositol bisphosphate (PIP2), phosphosphingolipids and any derivatives thereof.

As used herein, the terms "lyophilize," "lyophilizing," "lyophilized" or "lyophilization", also know as freeze-drying or cryodesiccation, refer to a dehydration process that can be used to preserve a material or compound. Lyophilization can involve freezing the material or compound and then reducing the surrounding pressure to allow the frozen water or liquid component in the freezed material or compound to the gas phase.

"Treatment," "treating," and "treat" are defined as acting upon a disease, disorder, or condition with an agent to reduce or ameliorate harmful or any other undesired effects of the disease, disorder, or condition and/or its symptoms. "Treating" or "treatment of" a condition or subject in need thereof refers to (1) taking steps to obtain beneficial or desired results, including clinical results such as the reduction of symptoms; (2) inhibiting the disease, for example, arresting or reducing the development of the disease or its clinical symptoms; (3) relieving the disease, for example, causing regression of the disease or its clinical symptoms; or (4) delaying the disease. For example, beneficial or desired clinical results include, but are not limited to, reduction and/or elimination of cancer cells and prevention and/or reduction of metastasis of cancer cells.

As used herein, "administering" refers to the physical introduction of a composition to a subject, using any of the various methods and delivery systems known to those skilled in the art. Routes of administration for the composition described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, the composition described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

An "anticancer agent" or "anticancer compound" is a therapeutic having an anticancer activity that can be used in the treatment or prevention of cancer. An anticancer agent can be a large or small molecule. Example anti-cancer agents include antibodies, small molecules, and large molecules or combinations thereof. Examples of "anticancer activity" include, but are not limited to, reduction of cancer cell number, reduction of cancer size, killing of cancer cells, reductions and/or inhibition of metastasis and reduction of cancer cell growth and/or proliferation.

The term "subject" or "subject in need thereof" refers to a living organism suffering from a disease or condition or having a possibility to have a disease or condition in the future. A term "patient" refers to a living organism that already has a disease or condition, e.g. a patient who has been diagnosed with a disease or condition or has one or more symptoms associated with a disease or condition. Non-limiting examples include humans, other mammals, bovines, rats, mice, dogs, monkeys, goat, sheep, cows, deer, and other non-mammalian animals. In some embodiments, a patient is human.

According to the methods provided herein, the subject can be administered an effective amount of one or more of agents, compositions or complexes, all of which are interchangeably used herein, (e.g. a pharmaceutical composition comprising a liposome, the liposome encompassing an anticancer compound and an acid or salt thereof) provided herein. The terms "effective amount" and "effective dosage" are used interchangeably. The term "effective amount" is defined as any amount necessary to produce a desired effect (e.g., treatment of a disease such as cancer). Effective amounts and schedules for administering the agent can be determined empirically by one skilled in the art. The dosage ranges for administration are those large enough to produce the desired effects. The dosage should not be so large as to cause substantial adverse side effects, such as unwanted cross-reactions, anaphylactic reactions, and the like. Generally, the dosage can vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount can show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation can depend on the purpose of the treatment, and can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

Liposomal Compositions

In embodiments, the compositions of the present disclosures are chemically and physically stable in a manufactured drug product to allow a commercially adequate shelf life.

In embodiments, particle size reduction can result in significant increases in drug solubility. Materials in a nanoparticle have a much higher tendency to leave the particle and go into the surrounding solution than those in a larger particle of the same composition. This phenomenon can increase the availability of drug for transport across a biological membrane, but it can also create physical instability of the nanoparticle itself. The physical stability of nanoparticles may be improved by the use of appropriate surface active agents and excipients at the right levels to reduce the interfacial energy, controlling the surface charge of the particles to maintain the dispersion, and manufacturing the particles in a narrow size distribution.

In embodiments, the advantageous disposition of the compositions of the present disclosures may be attributed to the particle's size, shape, composition and charge. In embodiments, the particles may be substantially spherical to move smoothly through the capillaries. In embodiments, the size distribution range is about 10 to 160 nm. In embodiments, the size distribution range is about 20 to 150 nm. In embodiments, the size distribution range is about 30 to 140 nm. In embodiments, the size distribution range is about 40 to 130 nm. In embodiments, the size distribution range is about 50 to 120 nm. In embodiments, the size distribution range is about 60 to 110 nm. In embodiments, the size distribution range is about 70 to 100 nm. In embodiments, the size distribution range is a mean of about 10 nm. In embodiments, the size distribution range is a mean of about 20 nm. In embodiments, the size distribution range is a mean of about 30 nm. In embodiments, the size distribution range is a mean of about 40 nm. In embodiments, the size distribution range is a mean of about 50 nm. In embodiments, the size distribution range is a mean of about 60 nm. In embodiments, the size distribution range is a mean of about 70 nm. In embodiments, the size distribution range is a mean of about 80 nm. In embodiments, the size distribution range is a mean of about 90 nm. In embodiments, the size distribution range is a mean of about 100 nm. In embodiments, the size distribution range is a mean of about 110 nm. In embodiments, the size distribution range is a mean of about 120 nm. In embodiments, the size distribution range is a mean of about 130 nm. In embodiments, the size distribution range is a mean of about 140 nm. In embodiments, the size distribution range is a mean of about 150 nm. In embodiments, the size distribution range is a mean of about 160 nm. The composition may include cholesterol, other lipids and surface-active agents with or without the addition of polymers used to define particle structure.

Particle size can be determined by multiple techniques. Example techniques include dynamic light scattering (DLS) and cryo-transmission electron microscopy. DLS can be used to assess particle size by measuring of intensity, e.g., the intensity-averaged particle diameters (Z-average) are calculated from the cumulants analysis as defined in ISO 13321 (International Organization for Standardization 1996). In embodiments, a mean longest dimension of a liposome when measured by DLS by intensity is in the range of about 40-100 nm, 50-90 nm, or 60-80 nm.

DLS can also be used to assess particle size by measurement by number, e.g., there is first-power relationship between particle size and contribution to the distribution. Particle size distribution by number is computed from the intensity distribution and the optical properties of the material. In embodiments, a mean longest dimension of a liposomal particle when measured by DLS by number is in the range of about 1-50 nm, 5-40 nm, or 10-30 nm Cryotransmission electron microscopy can also be used to assess a liposome size. In embodiments, the mean longest dimension of a liposome as measured by cryotransmission electron microscopy is in the range of about 1-50 nm, 5-40 nm, or 10-30 nm.

In embodiments, liposomes of the present disclosures are unilamellar. Examples lipids that can be included within the bilayer of a liposome include, but are not limited to, cholesterol, phosphatidylcholine (PC) products/derivatives (various carbon chain length fatty acids, saturated, multi-unsaturated and mixed acid PC's); 1,2-dioleoyl-sn-glycero-3-phosphoethanolamine (DOPE); 1,2-dimyristoyl-sn-glycero-3-phosphate (DMPA); 1,2-dipalmitoyl-sn-glycero-3-phosphate (DPPA); 1,2-dioleoyl-sn-glycero-3-phosphate (DOPA); 1,2-dimyristoyl-sn-glycero-3-phospho-(1'-rac-glycerol) (DMPG); 1,2-dimyristoyl-sn-glycero-3-phosphocholine (DMPC); 1,2-dipalmitoyl-sn-glycero-3-phospho-(1'-rac-glycerol) (DPPG); 1,2-dioleoyl-sn-glycero-3-phospho-(1'-rac-glycerol) (DOPG); 1,2-dimyristoyl-sn-glycero-3-phospho-L-serine (DMPS); 1,2-dipalmitoyl-sn-glycero-3-phospho-L-serine (DPPS); 1,2-dioleoyl-sn-glycero-3-phospho-L-serine (DOPC); 1,2-distearoyl-sn-glycero-3-phosphoethanolamine-N-[methoxy(polyethylene glycol)-2000] (DSPE-mPEG-2000); 1,2-distearoyl-sn-glycero-3-phosphoethanol-amine-N-[folate(polyethylene glycol)-5000] (DSPE-mPEG-5000); 1,2-distearoyl-sn-glycero-3-phosphoethanolamine-N-[amino(polyethylene glycol)-2000] (DSPE-PEG-2000); 1,2-stearoyl-3-trimethylammonium-propane (DOTAP); L-α-phosphatidylcholine, hydrogenated (Hydro Soy PC); and 2-stearoyl-sn-glycero-3-phosphocholine (Lyso PC).

Salts and Counterions

The present disclosures include compositions of anticancer compounds and salts thereof encapsulated in liposomes. Physicochemical properties of the counter ions that determine performance and physical state of the salt aggregates include pKa, valence, size, stereochemistry, dipole moment, polarizability. The present disclosures provides optimal lipid to drug ratio(s) along with proper counter ion(s) to take full advantage of both pKa properties of the counter ion and physical state of anticancer compounds aggregates to achieve target release properties (e.g. highest possible ΔpH 7.4 to 5.0 release differential).

Tables 1 provides example salts including applicable pKa's. Table 2 provides example weakly basic anticancer compounds, an in particular those that form salts or aggregates with oxalate or tartrate.

TABLE 1

Pharmaceutical salts and counter ions.

| Reagents | Counter Ion | pKa 1 | pKa 2 | pKa 3 |
|---|---|---|---|---|
| Sulfate | 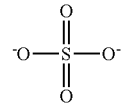 | −3 | 1.92 | NA |
| Picolinate | 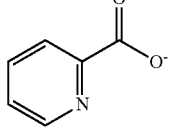 | 1.07 | NA | NA |
| Oxalate | 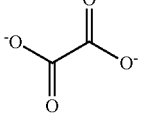 | 1.27 | 4.27 | NA |
| Maleate | 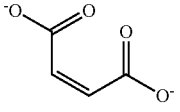 | 1.92 | 6.23 | NA |
| Phosphate | 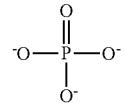 | 1.96 | 7.12 | 12.32 |

TABLE 1-continued

Pharmaceutical salts and counter ions.

| Reagents | Counter Ion | pKa 1 | pKa 2 | pKa 3 |
|---|---|---|---|---|
| Cysteinate | 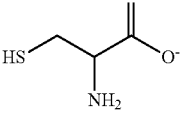 | 1.96 | 8.18 | NA |
| Malonate | 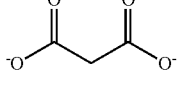 | 2.83 | 5.70 | NA |
| Tartrate | 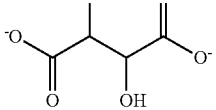 | 3.03 | 4.36 | NA |
| Fumarate | 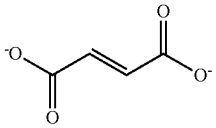 | 3.03 | 4.38 | NA |
| Citrate | 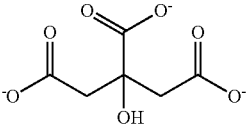 | 3.13 | 4.76 | 6.40 |
| Formate |  | 3.75 | NA | NA |
| N-Acetyl-L-cysteine | 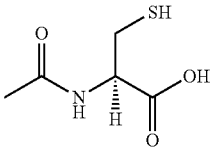 | 3.82 | 9.52 | NA |
| Succinate | 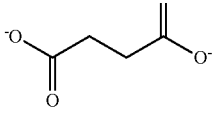 | 4.21 | 5.64 | NA |
| Ascorbate | 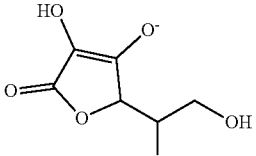 | 4.17 | 11.57 | NA |
| Acetate | 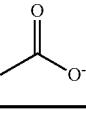 | 4.76 | NA | NA |

TABLE 2

Examples of weak bases chemotherapeutic agents that form salts/aggregates with Oxalate or Tartrate and demonstrate desirable pH discriminative drug release profile.

Doxorubicin hydrochloride

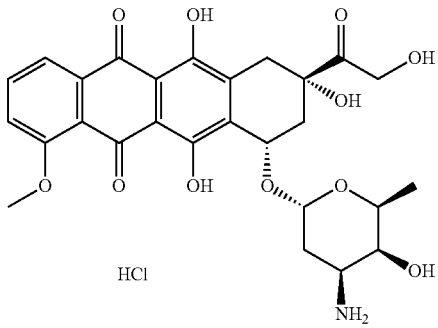 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1 ; Cl]

Approved for:
Acute lymphoblastic leukemia (ALL).
Acute myeloid leukemia (AML).
Breast cancer. It is also used as adjuvant therapy for breast cancer that has spread to the lymph nodes after surgery.
Gastric (stomach) cancer.
Hodgkin lymphoma.
Neuroblastoma.
Non-Hodgkin lymphoma.
Ovarian cancer.
Small cell lung cancer.
Soft tissue and bone sarcomas.
Thyroid cancer.
Transitional cell bladder cancer.
Wilms tumor Irinotecan hydrochloride

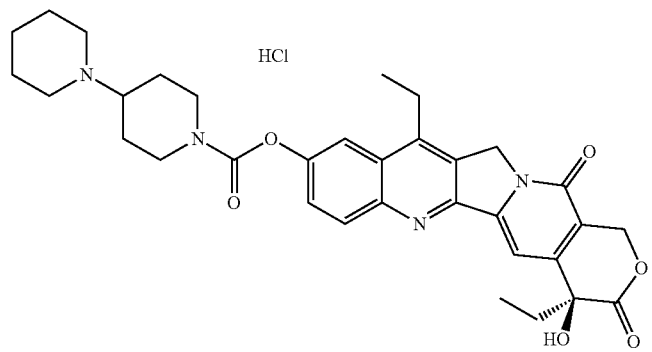 [SMILES: CCc1c2c(nc3ccc(OC(=O)N4CCC(N5CCCCC5)CC4)cc13)-c1cc3c(c(=O)n1C2)COC(=O)[C@]3(O)CC ; Cl]

Approved for:
Colorectal cancer that has metastasized (spread to other parts of the body), including metastatic cancer that has recurred (come back) or has not gotten better with other chemotherapy Mitoxantrone hydrochloride

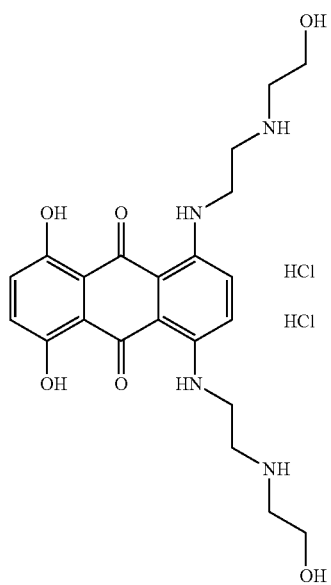 [SMILES: O=C1c2c(O)ccc(O)c2C(=O)c2c(NCCNCCO)ccc(NCCNCCO)c21 ; Cl ; Cl]

Approved for:
Acute myeloid leukemia (AML).
Prostate cancer. It is used as palliative treatment in advanced disease that is hormone-refractory (does not respond to hormone treatment).

In embodiments, a composition of the present disclosures include a doxorubicin salt. In embodiments, the doxorubicin salt is present in a liposome. In embodiments, the doxorubicin salt may be formed within a liposome upon encapsulation of doxorubicin. In embodiments, the composition provided herein exhibits desirable physical performance and optimal pH-dependent drug release profile which may be extremely effective in tumor tissues while exhibiting low off target toxicity. In embodiments, without being bound by any particular theory, at physiological pH, while circulating in the blood, doxorubicin is mostly retained by the liposomes, whereas strikingly higher drug release is achieved at lower pH (~5.0-6.7) that occurs in intracellular lysosomal compartment and local extracellular space of the tumor site that due to poor vasculature tends to retain liposomes.

In embodiments, the composition of doxorubicin salt is determined by the selection of the physical-chemical properties of the anions and corresponding acids, and of the processing steps used to create liposomes incorporated doxorubicin salt aggregates with desirable physicochemical properties.

In embodiments, the optimal lipid to drug ratio(s) within a proper counter ion(s) containing liposome encapsulating an anticancer compound functions to take advantage of both pKa properties of the counter ion and physical state of doxorubicin aggregates to achieve target release properties (e.g. highest possible $\Delta$pH 7.4/6.7/6.0/5.0 release differential—$\Delta$pH 7.4/5.0). In embodiments, doxorubicin is stabilized with suitable counter ions inside of the liposomes at the proper lipid/drug ratio to maximize safety and efficacy.

When a ratio between two parts, i.e. ratio between A and B, is mentioned, it can be referred to A/B, A:B or A to B. For instance, if the value referenced to each part A and B is 1 and 10, respectively, it can be indicated that the A/B ratio (or the ratio of A to B or the ratio A:B) is 1:10, 1/10 or 1 to 10.

For example, the pKa1 of sulfuric acid is −3 (doxorubicin-sulfate—Doxil®), while the pKa1 of citric acid is +3.13 (doxorubicin-citrate—Myocet®) (Table 1). Sulfate can form a strong salt with doxorubicin that may result in lower doxorubicin release in Doxil® liposomes at pH 7 to 5.0 range. In contrast, doxorubicin-citrate is a weaker salt that may result in higher doxorubicin release from the Myocet® liposomes at pH 7 to 5.0 range.

Thus, provided herein are embodiments in which doxorubicin optimum release from liposomes is achieved via selection of the appropriate counter ions with pKa (e.g. pKa1) values higher than −3 (sulfuric acid) and less than +3.13 (citric acid). Thus, in embodiments, the acid employed herein has a pKa (e.g. pKa1) higher than −3 and less than 3. In embodiments, the acid employed herein has a pKa (e.g. pKa1) higher than −2.9 and less than 2.9. In embodiments, the acid employed herein has a pKa (e.g. pKa1) higher than −2.8 and less than 2.8. In embodiments, the acid employed herein has a pKa (e.g. pKa1) higher than −2.5 and less than 2.5.

A variety of counter ions were tested (Table 1) with different pKa values for their ability to facilitate doxorubicin loading into liposomes and to provide pH dependent doxorubicin release from the liposomes. A counter ion(s) that provides the highest differential between doxorubicin release at pH 7.4 to pH 5.0 ($\Delta$pH 7.4/5.0) has a preferred release profile.

In embodiments, an example release profile assay liposomal samples are diluted 20× (i.e. 100 µL of sample+1.9 mL of diluent) or 50× (i.e. 50 µL of sample+2.45 mL of diluent) in PBS pH 7.4 buffers at 25° C. or pre-warmed to 37° C. (to simulate in vivo temperature) and incubated for 2, 4, and 8 hrs at 25° C. or 37° C., respectively. In embodiments, an example release profile assay liposomal samples are diluted 20× (i.e. 100 µL of sample+1.9 mL of diluent) or 50× (i.e. 50 µL of sample+2.45 mL of diluent) in PBS pH 6.7 buffers at 25° C. or pre-warmed to 37° C. (to simulate in vivo temperature) and incubated for 2, 4, and 8 hrs at 25° C. or 37° C., respectively. In embodiments, an example release profile assay liposomal samples are diluted 20× (i.e. 100 µL of sample+1.9 mL of diluent) or 50× (i.e. 50 µL of sample+2.45 mL of diluent) in PBS pH 6.0 buffers at 25° C. or pre-warmed to 37° C. (to simulate in vivo temperature) and incubated for 2, 4, and 8 hrs at 25° C. or 37° C., respectively. In embodiments, an example release profile assay liposomal samples are diluted 20× (i.e. 100 µL of sample+1.9 mL of diluent) or 50× (i.e. 50 µL of sample+2.45 mL of diluent) in PBS pH 5.0 buffers at 25° C. or pre-warmed to 37° C. (to simulate in vivo temperature) and incubated for 2, 4, and 8 hrs at 25° C. or 37° C., respectively.

In embodiments, for T0 time point determination, liposomal formulations were diluted in PBS pH 7.4 at ~25° C. In embodiments, for T0 time point determination, liposomal formulations were diluted in PBS pH 6.7 at ~25° C. In embodiments, for T0 time point determination, liposomal formulations were diluted in PBS pH 6.0 at ~25° C. In embodiments, for T0 time point determination, liposomal formulations were diluted in PBS pH 5.0 at ~25° C. The plate reader temperature may be set to 25° C. and excitation and emission wavelengths were set at 478 nm and 594 nm, respectively. At each time point fluorescence of intact liposomes (Fi) and total fluorescence of liposomes ruptured with Triton X-100 (Ft) was measured. The percent of drug release was quantified as $[(Fi\_n-Fi\_t)/Ft\_avrg)]*100\%$, where $Fi\_n$—Fi measured at 2, 4, or 8 hrs, $Fi\_t0$—Fi measured at T0, and $Ft\_avrg$—average of Ft values determined for all time points.

In embodiments, and not to be bound by theory, the crystalline state of various anticancer compound salts may be selected for favorable properties. For example, cryotransmission electron microscopy (cTEM) reveals doxorubicin precipitates as fibrous-bundle aggregates in both citrate- and sulfate-containing liposomes [1, 13-14]. The planar aromatic anthracycline rings are thought to stack longitudinally to form linear fibers. These fibers are aligned in a hexagonal arrangement to form bundles, with approximately 12-60 fibers per bundle [25]. Doxorubicin aggregates in the presence of sulfate typically have rigid linear fiber bundles (interfiber spacing is approximately 27 A°) compared with the doxorubicin-citrate aggregates in the presence of citrate, which appear mostly linear or curved (interfiber spacing is approximately 30-35 A°) [15, 25]. In embodiments, the sulfate anion, being smaller than the citrate anion, may allow a tighter packing arrangement, resulting in a decreased flexibility of fiber bundles. In embodiments, doxorubicin-sulfate (e.g. doxorubicin-sulfate aggregates) results in slower drug release at physiological and acidic pH compare to doxorubicin-phosphate [13-14], and citrate (e.g. citrate aggregates) [1, 13-15].

In embodiments, compositions of the present disclosures are designed to take an advantage of tumor biology by employing proper counter ions (oxalate and tartrate), optimized lipid/drug ratio and optimized anticancer compound (e.g. doxorubicin) loading conditions, strong pH dependence of drug release and preferential targeting of chemotherapeutic agent(s) to the tumor site. In embodiments, chelators are employed to complement counter ion(s) and/or antioxidants.

In embodiment, using Oxalate or Tartrate as counter ions, lipid/drug ratio in the optimized range, and proper loading conditions will allow achieving targeted (pH dependent) drug release, and therefore improve safety and efficacy of number weak bases chemotherapeutic agents with various molecular targets (DNA intercalating/damaging agents, topoisomerase inhibitors, kinase inhibitors, etc.; Table 3).

TABLE 3

Other examples of weak bases chemotherapeutic agents anticipated to form salts/aggregates with Oxalate or Tartrate.

| | | |
|---|---|---|
| Daunorubicin hydrochloride | 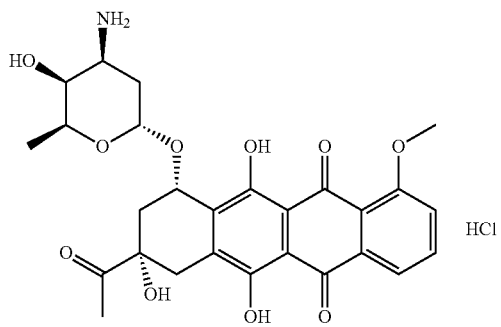 [SMILES: COc1cccc2c1C(=O)c1c(O)c3c(c(O)c1C2=O)C[C@@](O)(C(C)=O)C[C@@H]3O[C@H]1C[C@H](N)[C@H](O)[C@H](C)O1 ; Cl] | Approved for: Acute lymphoblastic leukemia in adults and children. Acute myeloid leukemia in adults |
| Epirubicin hydrochloride | 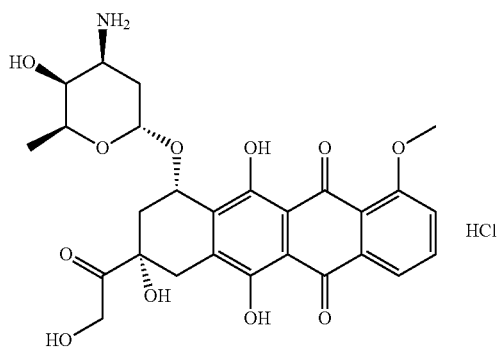 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1 ; Cl] | Approved for: Breast cancer. It is used after surgery in patients with early-stage breast cancer that has spread to the lymph nodes under the arm. |
| Idarubicin hydrochloride | 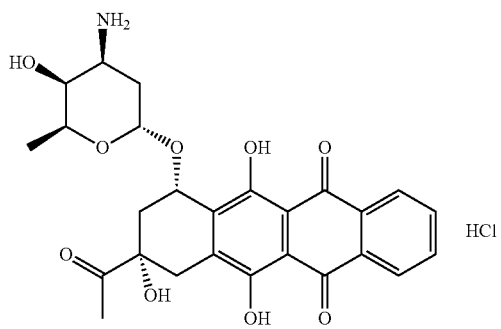 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O ; Cl] | Approved for: Acute myeloid leukemia (AML). |
| Bendamustine hydrochloride | 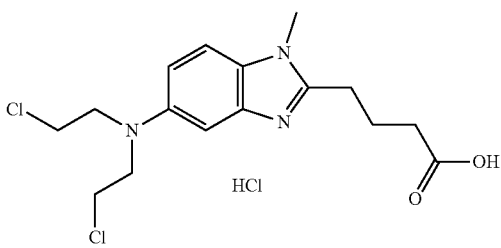 [SMILES: Cn1c(CCCC(=O)O)nc2cc(N(CCCl)CCCl)ccc21 ; Cl] | Approved for: B-cell non-Hodgkin lymphoma (NHL) in patients whose disease has not gotten better with other chemotherapy or has recurred (come back). Chronic lymphocytic leukemia (CLL) |
| Indimitecan hydrochloride | 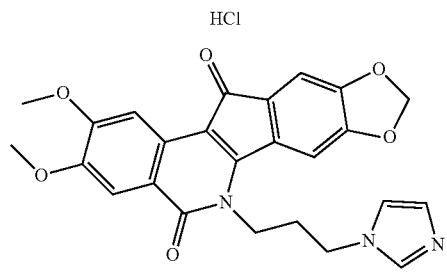 [SMILES: Cl ; COc1cc2c3c(n(CCCn4ccnc4)c(=O)c2cc1OC)-c1cc2c(cc1C3=O)OCO2] | Clinical trials. Solid tumors and lymphomas. |

TABLE 3-continued

Other examples of weak bases chemotherapeutic agents anticipated to form salts/aggregates with Oxalate or Tartrate.

| | | |
|---|---|---|
| Indotecan hydrochloride | 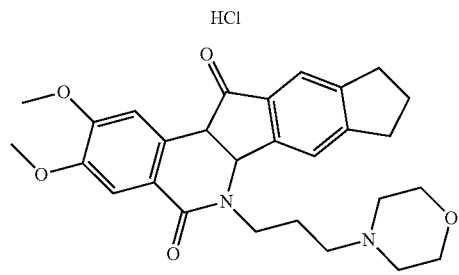 [SMILES: Cl ; COc1cc2c(cc1OC)C1C(=O)c3cc4c(cc3C1N(CCCN1CCOCC1)C2=O)CCC4] HCl | Clinical trials. Solid tumors and lymphomas. |
| Erlotinib hydrochloride | 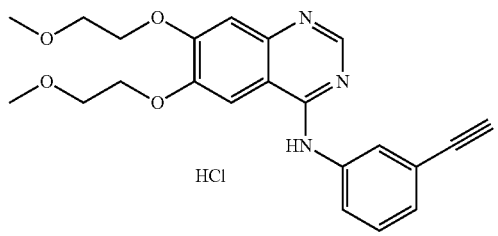 [SMILES: C#Cc1cccc(Nc2ncnc3cc(OCCOC)c(OCCOC)cc23)c1 ; Cl] HCl | Approved for: Non-small cell lung cancer (NSCLC). It is used as first-line treatment for metastatic NSCLC in patients with tumors that have certain epidermal growth factor receptor (EGFR) mutations. It is used for locally advanced or metastatic NSCLC in patients who have already been treated with chemotherapy. Pancreatic cancer. It is used with gemcitabine hydrochloride in patients whose disease cannot be removed by surgery or has metastasized. |
| Raloxifene hydrochloride | 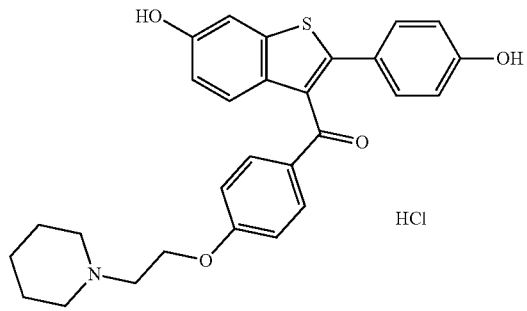 [SMILES: O=C(c1ccc(OCCN2CCCCC2)cc1)c1c(-c2ccc(O)cc2)sc2cc(O)ccc12 ; Cl] HCl | Approved for: Breast cancer. It is used to decrease the chance of invasive breast cancer in postmenopausal women who have a high risk for developing the disease or who have osteoporosis. Raloxifene hydrochloride is also approved to prevent and treat: Osteoporosis in postmenopausal women |
| Topotecan hydrochloride | 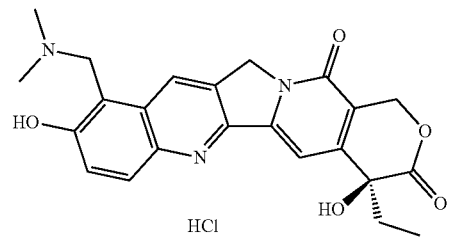 [SMILES: CC[C@@]1(O)C(=O)OCc2c1cc1n(c2=O)Cc2cc3c(CN(C)C)c(O)ccc3nc2-1 ; Cl] HCl | Approved for: Cervial cancer that has not gotten better with other treatment or has recurred (come back). It is used with another drug, called cisplatin. Ovarian cancer in patients whose disease has not gotten better with other chemotherapy. Small cell lung cancer in patients whose disease has not gotten better with other chemotherapy. |

TABLE 3-continued

Other examples of weak bases chemotherapeutic agents anticipated to form salts/aggregates with Oxalate or Tartrate.

| | | |
|---|---|---|
| Ponatinib hydrochloride | 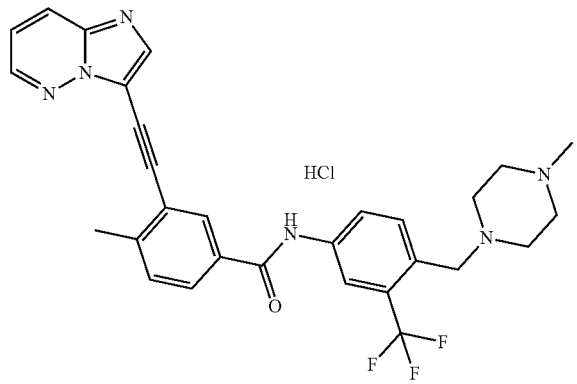 [SMILES: Cc1ccc(C(=O)Nc2ccc(CN3CCN(C)CC3)c(C(F)(F)F)c2)cc1C#Cc1cnc2cccnn12 ; Cl] | Approved for: Acute lymphoblastic leukemia that is Philadelphia chromosome positive and has the T315I mutation. Chronic myelogenous leukemia that has the T315I mutation. For these types of leukemia without the T315I mutation, ponatinib hydrochloride is used when other tyrosine kinase inhibitors cannot be used. |
| Tipiracil hydrochloride | 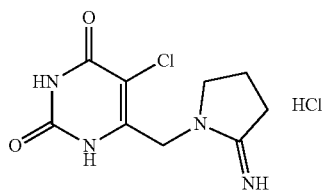 [SMILES: N=C1CCCN1Cc1[nH]c(=O)[nH]c(=O)c1Cl ; Cl] | Approved for: Colorectal cancer that has metastasized (spread to other parts of the body). It is used in patients who have already been treated with certain chemotherapy and biologic therapy. |
| Procarbazine hydrochloride | 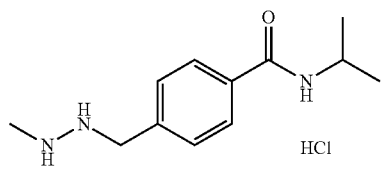 [SMILES: CNNCc1ccc(C(=O)NC(C)C)cc1 ; Cl] | Approved for: Hodgkin lymphoma that is advanced. |
| Mechlorethamine hydrochloride | 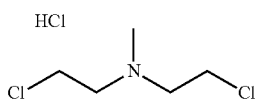 | Approved for: Bronchogenic carcinoma. Chronic lymphocytic leukemia (CLL). Chronic myelogenous leukemia (CML). Hodgkin lymphoma that is advanced. Malignant pleural effusion, malignant pericardial effusion, and malignant peritoneal effusion. Mycosis fungoides. Non-Hodgkin lymphoma (NHL). |
| Pazopanib hydrochloride | 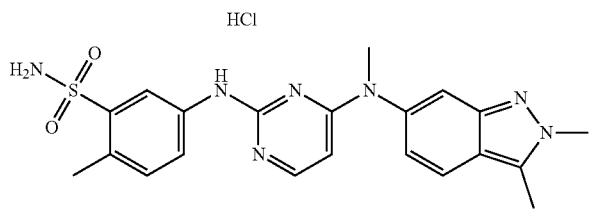 [SMILES: Cl ; Cc1ccc(Nc2nccc(N(C)c3ccc4c(C)n(C)nc4c3)n2)cc1S(N)(=O)=O] | Approved for: Renal cell carcinoma (a type of kidney cancer) that is advanced. Soft tissue sarcoma that is advanced. It is used in patients who have already been treated with chemotherapy. |

TABLE 3-continued

Other examples of weak bases chemotherapeutic agents anticipated to form salts/aggregates with Oxalate or Tartrate.

| | | |
|---|---|---|
| Ponatinib hydrochloride | 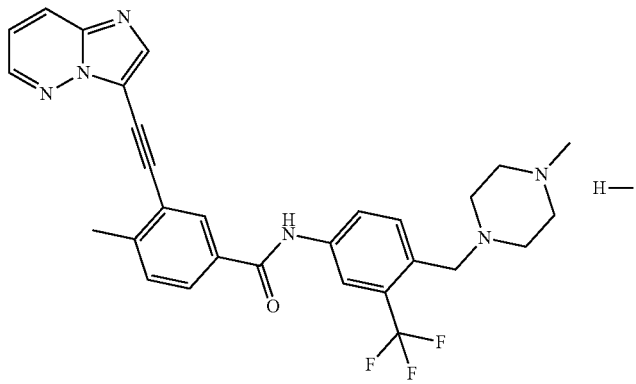 | Approved for:<br>Acute lymphoblastic leukemia that is Philadelphia chromosome positive and has the T315I mutation.<br>Chronic myelogenous leukemia that has the T315I mutation. |
| Gemcitabine hydrochloride | 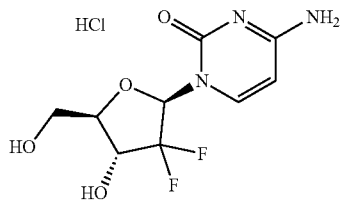 [SMILES: Nc1ccn([C@@H]2O[C@H](CO)[C@@H](O)C2(F)F)c(=O)n1 ; Cl] | Approved for:<br>Breast cancer that has metastasized (spread to other parts of the body) and has not gotten better with other chemotherapy. It is used with paclitaxel.<br>Non-small cell lung cancer that is advanced or has metastasized. It is used in patients whose disease cannot be removed by surgery. It is used with cisplatin.<br>Ovarian cancer that is advanced and has not gotten better with other chemotherapy. It is used with carboplatin.<br>Pancreatic cancer that is advanced or has metastaszied. It is used in patients whose disease cannot be removed by surgery and who have already been treated with other chemotherapy. It is used with paclitaxel albumin-stabilized nanoparticle formulation. |
| AZD7762 | 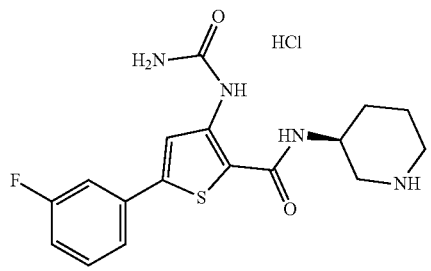 [SMILES: NC(=O)Nc1cc(-c2cccc(F)c2)sc1C(=O)N[C@H]1CCCNC1 ; Cl] | Approved for:<br>AZD7762 is a Chk1 kinase inhibitor which increases sensitivity to DNA-damaging agents, including gemcitabine. Development discontinued due to unpredictable cardiac toxicity.<br>Chk1 kinase remains an important therapeutic target. |

TABLE 3-continued

Other examples of weak bases chemotherapeutic agents anticipated to form salts/aggregates with Oxalate or Tartrate.

Vincristine sulfate

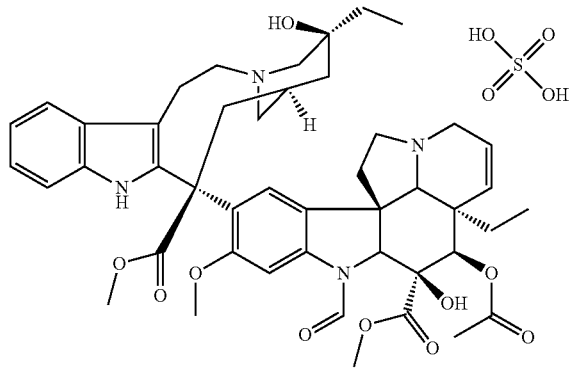

Approved for:
Acute lymphoblastic leukemia that is Philadelphia chromosome negative. It is used in patients whose disease has relapsed two or more times or has not gotten better with two or more types of treatment.

Vinblastine sulfate

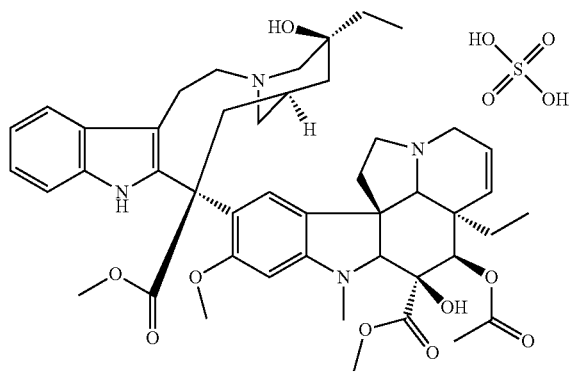

Approved for:
Breast cancer that has not gotten better with other treatment.
Choriocarcinoma that has not gotten better with other chemotherapy. Choriocarcinoma is a type of gestational trophoblastic disease.
Hodgkin lymphoma.
Kaposi sarcoma.
Mycosis fungoides.
Non-Hodgkin lymphoma (NHL).
Testicular cancer.

Sunitinib malate

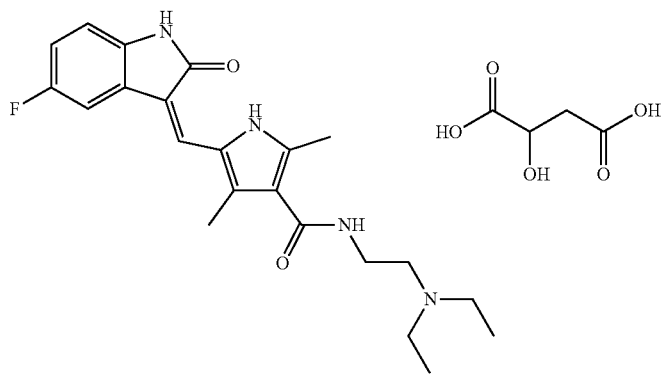 [SMILES: CCN(CC)CCNC(=O)c1c(C)[nH]c(/C=C2\C(=O)Nc3ccc(F)cc32)c1C ; O=C(O)CC(O)C(=O)O]

Approved for:
Gastrointestinal stromal tumor (a type of stomach cancer). It is used in patients whose condition has become worse while taking another drug called imatinib mesylate or who are not able to take imatinib mesylate.
Pancreatic cancer. It is used in patients with progressive neuroendocrine tumors that cannot be removed by surgery, are locally advanced, or have metastasized (spread to other parts of the body).
Renal cell carcinoma (a type of kidney cancer) that has metastasized.

Lanreotide acetate

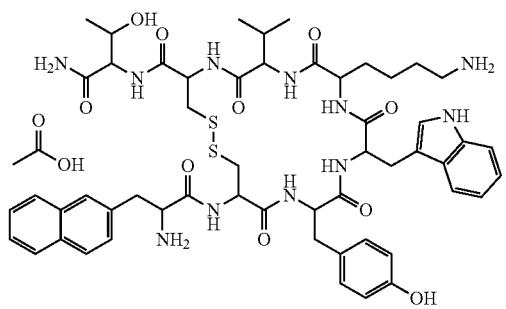

Approed for:
Gastroenteropancreatic neuroendocrine tumors. It is used for some tumors that cannot be removed by surgery, are locally advanced, or have metastasized (spread to other parts of the body).

TABLE 3-continued

Other examples of weak bases chemotherapeutic agents anticipated to form salts/aggregates with Oxalate or Tartrate.

Tamoxifen citrate

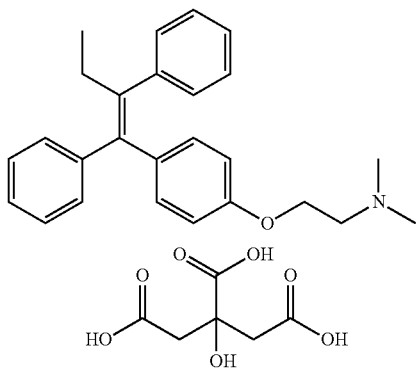

Approved for:
Breast cancer in women and men.
Tamoxifen citrate is also approved to prevent:
Breast cancer in women who are at high risk for the disease.

Leuprolide acetate

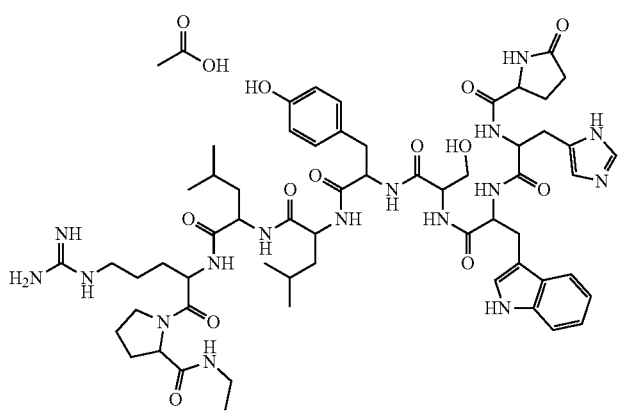

Approved for:
Prostate cancer that is advanced.

In embodiments, targeting the liposomal drug release according to the blood—tumor site—lysosomes pH gradient improves the safety and efficacy of weak bases chemotherapeutic agents compare to their non- or less-pH, discriminative liposomal and/or free forms.

Lipid to Drug (i.e. Lipid/Drug) and Phospholipid to Free Cholesterol (i.e. PL/FC) Ratios In embodiments, the optimal drug load in the particles of the present application is achieved with the proper counter ion selection. In addition, lipophilic inactive components and surface active agents may be selected. In addition, proper drug to lipid ratio may be selected. In embodiments, selections are made in order to decrease release neutral pH while in circulation and increase extracellular/intracellular release at more acidic pH at the target site.

In embodiments, the lipid to drug (lipid/drug) and PL/FC ratio is related to desirable physicochemical and biological performance.

In embodiments, the structure of the particles is determined by the selection of the formulation components and lipid/drug and PL/FC ratio, and of the processing steps used to create the particles. Structural and quantitative elements that determine particle performance include lipid/drug and PL/FC ratio, counter ions, particle size (and size distribution in the population), particle shape, particle charge and the distribution of individual components in the particle, especially those at the particle surface.

In embodiments, the structured lipid rich nanoparticles/liposomes of the present application are designed to carry a useful drug load in a parenterally administered drug product. Drugs of interest with respect to this delivery system includes those drugs/salts complexes which have low solubility at physiological pH and significantly higher solubility at more acidic (local tumor extracellular and endosomal/lysosomal environment) pH. The liposomes included in the present application may have unique physical-chemical performance. In embodiments, high lipid/drug and ≤4.0 but ≥1.0 PL/FC ratios may result in a stable lipid layer that restricts release of liposomal content via concentration gradient and in serum or blood but allow discriminative drug release in response to change of the outside pH, and therefore to take the advantage of the particular counter ions and pKa(s) of the corresponding acid(s).

In embodiments, the doxorubicin may be a pegylated liposomal doxorubicin, such as that used in Doxil®. In embodiments the doxorubicin is substituted with amphiphilic block copolymer rather than polyethylene glycol.

In embodiments, the lipids used in the liposome formulation herein are pegylated lipids. In embodiments, rather than pegylated lipids, poloxamer lipids are used (e.g. P188 lipids). Poloxamers are non-ionic poly (ethylene oxide) (PEO)—poly (propylene oxide) (PPO) copolymers. They may be used in pharmaceutical formulations as surfactants. Their surfactant property has been useful for detergency, dispersion, stabilization, foaming, and emulsification. Poloxamers are broadly used in clinical applications [16]. In embodiments, liposomes coated (e.g. intercalated) with p188 are formed by dissolving lipids and P188 in DCM, evaporating DCM—forming lipid film, and hydration of lipid film. This example process results in intercalation (insertion) of p188 hydrophobic hydrocarbon chain between the lipid hydrocarbon chain) and exposure of more hydrophilic part in aqueous phase, and in modified lipid surface of the liposomes that prevents their opsonization and recognition by the macrophage system.

In embodiments, the compositions used herein having liposomes coated with poloxamer (e.g. p188) are used to treat diseases requiring the active (e.g. the weakly basic anticancer compound) to cross the blood brain barrier. In embodiments, the compositions used herein having liposomes coated with poloxamer (e.g p188) are used to treat diseases requiring the active (e.g. the weakly basic anticancer compound) are used where Apolipoprotein E interference is not desired.

In embodiments, lower lipid/drug ratios lead are used to increased surface tension and compromised lipid layer integrity that upon dilution could result in increased leakage of liposomal content into dissolution media at neutral pH due to concentration gradient, and could offset the pH driven release of drug. In embodiments, higher lipid to drug ratios are used to lower surface tension and achieve higher integrity lipid layer(s) that are capable of preventing "off target" leakage of intraliposomal material into dissolution media, and release the drug only in response to pH transition.

In embodiments, liposomes include a plurality of lipids and the ratio of the plurality of lipids to a drug (e.g. a weakly basic anticancer agent and/or an acid or salt thereof) can be considered. In embodiments, lipid to drug (lipid to drug) ratio represents a weight to weight (w to w) ratio of total lipids to a drug (e.g. doxorubicin free base) in final suspension of drug-loaded liposomes and has a mean of about 0.5 to 1 (weight to weight), about 1 to 1, about 5 to 1, about 10 to 1, about 20 to 1, about 30 to 1, about 40 to 1, about 50 to 1, about 60 to 1, about 70 to 1, about 80 to 1, about 90 to 1, about 100 to 1 or any intervening number of the foregoing or higher than about 100 to 1. In embodiments, lipid to drug (lipid to drug) ratio represents a mole to mole (mol to mol) ratio of total lipids to a drug in final suspension of drug-loaded liposomes and has a mean of 0.5 to 1 (mol to mol), about 1 to 1, about 5 to 1, about 10 to 1, about 20 to 1, about 30 to 1, about 40 to 1, about 50 to 1, about 60 to 1, about 70 to 1, about 80 to 1, about 90 to 1 or about 100 to 1 or any intervening number of the foregoing or higher than about 100 to 1.

In embodiments, lipid to drug (i.e. lipid/drug) ratio (mol to mol or weight to weight) has a mean in a range of about 0.5 to 1 to 1 to 1, about 0.5 to 1 to 5 to 1, about 0.5 to 1 to 10 to 1, about 0.5 to 1 to 20 to 1, about 0.5 to 1 to 30 to 1, about 0.5 to 1 to 40 to 1, about 0.5 to 1 to 50 to 1, about 0.5 to 1 to 60 to 1, about 0.5 to 1 to 70 to 1, about 0.5 to 1 to 80 to 1, about 0.5 to 1 to 90 to 1 or about 0.5 to 1 to 100 to 1. In embodiments, lipid to drug ratio (mol to mol or weight to weight) has a mean in a range of about 1 to 1 to 5 to 1, about 1 to 1 to 10 to 1, about 1 to 1 to 20 to 1, about 1 to 1 to 30 to 1, about 1 to 1 to 40 to 1, about 1 to 1 to 50 to 1, about 1 to 1 to 60 to 1, about 1 to 1 to 70 to 1, about 1 to 1 to 80 to 1, about 1 to 1 to 90 to 1 or about 1 to 1 to 100 to 1. In embodiments, lipid to drug ratio (mol to mol or weight to weight) has a mean in a range of about 5 to 1 to 10 to 1, about 5 to 1 to 20 to 1, about 5 to 1 to 30 to 1, about 5 to 1 to 40 to 1, about 5 to 1 to 50 to 1, about 5 to 1 to 60 to 1, about 5 to 1 to 70 to 1, about 5 to 1 to 80 to 1, about 5 to 1 to 90 to 1 or about 5 to 1 to 100 to 1. In embodiments, lipid to drug ratio (mol to mol or weight to weight) has a mean in a range of about 10 to 1 to 20 to 1, about 10 to 1 to 30 to 1, about 10 to 1 to 40 to 1, about 10 to 1 to 50 to 1, about 10 to 1 to 60 to 1, about 10 to 1 to 70 to 1, about 10 to 1 to 80 to 1, about 10 to 1 to 90 to 1 or about 10 to 1 to 100 to 1. In embodiments, lipid to drug ratio (mol to mol or weight to weight) has a mean in a range of about 20 to 1 to 30 to 1, about 20 to 1 to 40 to 1, about 20 to 1 to 50 to 1, about 20 to 1 to 60 to 1, about 20 to 1 to 70 to 1, about 20 to 1 to 80 to 1, about 20 to 1 to 90 to 1 or about 20 to 1 to 100 to 1. In embodiments, lipid to drug ratio (mol to mol or weight to weight) has a mean in a range of about 30 to 1 to 40 to 1, about 30 to 1 to 50 to 1, about 30 to 1 to 60 to 1, about 30 to 1 to 70 to 1, about 30 to 1 to 80 to 1, about 30 to 1 to 90 to 1 or about 30 to 1 to 100 to 1. In embodiments, lipid to drug ratio (mol to mol or weight to weight) has a mean in a range of about 40 to 1 to 50 to 1, about 40 to 1 to 60 to 1, about 40 to 1 to 70 to 1, about 40 to 1 to 80 to 1, about 40 to 1 to 90 to 1 or about 40 to 1 to 100 to 1. In embodiments, lipid to drug ratio (mol to mol or weight to weight) has a mean in a range of about 50 to 1 to 60 to 1, about 50 to 1 to 70 to 1, about 50 to 1 to 80 to 1, about 50 to 1 to 90 to 1 or about 50 to 1 to 100 to 1. In embodiments, lipid to drug ratio (mol to mol or weight to weight) has a mean in a range of about 60 to 1 to 70 to 1, about 60 to 1 to 80 to 1, about 60 to 1 to 90 to 1 or about 60 to 1 to 100 to 1. In embodiments, lipid to drug ratio (mol to mol or weight to weight) has a mean in a range of about 70 to 1 to 80 to 1, about 70 to 1 to 90 to 1 or about 70 to 1 to 100 to 1. In embodiments, lipid to drug ratio (mol to mol or weight to weight) has a mean in a range of about 80 to 1 to 90 to 1 or about 80 to 1 to 100 to 1. In embodiments, lipid to drug ratio (mol to mol or weight to weight) has a mean in a range of about 90 to 1 to 100 to 1.

In embodiments, drug mol % (e.g. the number of moles of drug relative to total number of moles of all formulation constitutions including phospholipids, cholesterol, poloxamers, anticancer drug, salts, etc.) has a mean of about 0.5%, about 1%, about 2%, about 3%, about 4%, about 5%, about 6%, about 7%, about 8%, about 9%, about 10%, about 15%, about 20%, about 30% or any intervening number of the foregoing or higher than about 30%.

In embodiments, drug mol % has a range of about 0.5-1%, about 0.5-2%, about 0.5-3%, about 0.5-4%, about 0.5-5%, about 0.5-6%, about 0.5-7%, about 0.5-8%, about 0.5-9%, about 0.5-10%, about 0.5-15%, about 0.5-20% or about 0.5-30%. In some embodiments, drug mol % has a range of about 1-2%, about 1-3%, about 1-4%, about 1-5%, about 1-6%, about 1-7%, about 1-8%, about 1-9%, about 1-10%, about 1-15%, about 1-20% or about 1-30%. In some embodiments, drug mol % has a range of about 2-3%, about 2-4%, about 2-5%, about 2-6%, about 2-7%, about 2-8%, about 2-9%, about 2-10%, about 2-15%, about 2-20% or about 2-30%. In some embodiments, drug mol % has a range of about 3-4%, about 3-5%, about 3-6%, about 3-7%, about 3-8%, about 3-9%, about 3-10%, about 3-15%, about 3-20% or about 3-30%. In some embodiments, drug mol % has a range of about 4-5%, about 4-6%, about 4-7%, about 4-8%, about 4-9%, about 4-10%, about 4-15%, about 4-20% or about 4-30%. In some embodiments, drug mol % has a range of about 5-6%, about 5-7%, about 5-8%, about 5-9%, about 5-10%, about 5-15%, about 5-20% or about 5-30%. In some embodiments, drug mol % has a range of about 6-7%, about 6-8%, about 6-9%, about 6-10%, about 6-15%, about 6-20% or about 6-30%. In some embodiments, drug mol % has a range of about 7-8%, about 7-9%, about 7-10%, about 7-15%, about 7-20% or about 7-30%. In some embodiments, drug mol % has a range of about 8-9%, about 8-10%, about 8-15%, about 8-20% or about 8-30%. In some embodiments, drug mol % has a range of about 9-10%, about 9-15%, about 9-20% or about 9-30%. In some embodiments, drug mol % has a range of about 10-15%, about 10-20% or about 10-30%. In some embodiments, drug mol % has a range of about 15-20% or about 15-30%. In some embodiments, drug mol % has a range of about 20-30%.

In embodiments, liposomes include a plurality of free cholesterol (FC). In embodiments, unloaded liposomes and/or drug loaded into the liposomes have a plurality of phospholipids (PL). Therefore, in certain embodiments, liposomes loaded with a drug have free cholesterol (FC) and phospholipids (PL). In embodiments, a ratio of PL to FC (i.e. "PL to FC" or "PL/FC" ratio) represents a weight to weight (w to w) ratio of phospholipids to free cholesterols in final suspension of drug-loaded liposomes and has a mean of 0.5 to 1 (w to w), about 1 to 1, about 2 to 1, about 3 to 1, about 4 to 1, about 5 to 1, about 10 to 1, about 20 to 1, about 30 to 1, about 40 to 1, about 50 to 1, about 60 to 1, about 70 to 1, about 80 to 1, about 90 to 1, about 100 to 1 or any intervening number of the foregoing or higher than about 100 to 1. In embodiments, a ratio of PL to FC (i.e. "PL to FC" ratio) represents a mole to mole (mol to mol) ratio of phospholipids to free cholesterols in final suspension of drug-loaded liposomes and has a mean of about 0.5 to 1 (mol to mol), about 1 to 1, about 2 to 1, about 3 to 1, about 4 to 1, or about 5 to 1, about 10 to 1, about 20 to 1, about 30 to 1, about 40 to 1, about 50 to 1, about 60 to 1, about 70 to 1, about 80 to 1, about 90 to 1, about 100 to 1 or any intervening number of the foregoing or higher than about 100 to 1.

In embodiments, "PL to FC (i.e. PL/FC)" ratio (mol to mol or w to w) has a mean in a range of about 0.5 to 1, about 0.55 to 1, about 0.6 to 1, about 0.65 to 1, about 0.7 to 1, about 0.75 to 1, about 0.8 to 1, about 0.85 to 1, about 0.9 to 1, about 0.95 to 1, about 1 to 1, about 1.05 to 1, about 1.1 to 1, about 1.15 to 1, about 1.2 to 1, about 1.25 to 1, about 1.3 to 1, about 1.35 to 1, about 1.4 to 1, about 1.45 to 1, about 1.5 to 1, about 1.55 to 1, about 1.6 to 1, about 1.65 to 1, about 1.7 to 1, about 1.75 to 1, about 1.8 to 1, about 1.85 to 1, about 1.9 to 1, about 2 to 1, about 2.05 to 1, about 2.1 to 1, about 2.15 to 1, about 2.2 to 1, about 2.25 to 1, about 2.3 to 1, about 2.35 to 1, about 2.4 to 1, about 2.45 to 1, about 2.5 to 1, about 2.55 to 1, about 2.6 to 1, about 2.65 to 1, about 2.7 to 1, about 2.75 to 1, about 2.8 to 1, about 2.85 to 1, about 2.9 to 1, about 3 to 1, about 3.05 to 1, about 3.1 to 1, about 3.15 to 1, about 3.2 to 1, about 3.25 to 1, about 3.3 to 1, about 3.35 to 1, about 3.4 to 1, about 3.45 to 1, about 3.5 to 1, about 3.55 to 1, about 3.6 to 1, about 3.65 to 1, about 3.7 to 1, about 3.75 to 1, about 3.8 to 1, about 3.85 to 1, about 3.9 to 1, about 4 to 1, about 4.05 to 1, about 4.1 to 1, about 4.15 to 1, about 4.2 to 1, about 4.25 to 1, about 4.3 to 1, about 4.35 to 1, about 4.4 to 1, about 4.45 to 1, about 4.5 to 1, about 4.55 to 1, about 4.6 to 1, about 4.65 to 1, about 4.7 to 1, about 4.75 to 1, about 4.8 to 1, about 4.85 to 1, about 4.9 to 1, about 5 to 1 or any intervening number of the foregoing.

In embodiments, "PL to FC (i.e. PL/FC)" ratio (mol to mol or w to w) has a mean in a range of about 0.86 to 1, about 1.22 to 1, about 1.29 to 1, about 1.62 to 1, about 1.72 to 1, about 3.68 to 1 or any intervening number of the foregoing. In embodiments, "PL to FC" ratio (mol to mol or w to w) has a mean in a range of about 0.86 to 1. In embodiments, "PL to FC" ratio (mol to mol or w to w) has a mean in a range of about 1.22 to 1. In embodiments, "PL to FC" ratio (mol to mol or w to w) has a mean in a range of about 1.29 to 1. In embodiments, "PL to FC" ratio (mol to mol or w to w) has a mean in a range of about 1.62 to 1. In embodiments, "PL to FC" ratio (mol to mol or w to w) has a mean in a range of about 1.72 to 1. In embodiments, "PL to FC" ratio (mol to mol or w to w) has a mean in a range of about 3.68 to 1. In embodiments, "PL to FC" ratio (mol to mol or w to w) has a mean in a range of about 0.86 to 1 to 1.22 to 1, about 0.86 to 1 to 1.29 to 1, about 0.86 to 1 to 1.62 to 1, about 0.86 to 1 to 1.72 to 1 or about 0.86 to 1 to 3.68 to 1. In embodiments, "PL to FC" ratio (mol to mol or w to w) has a mean in a range of about 1.22 to 1 to 1.29 to 1, about 1.22 to 1 to 1.62 to 1, about 1.22 to 1 to 1.72 to 1 or about 1.22 to 1 to 3.68 to 1. In embodiments, "PL to FC" ratio (mol to mol or w to w) has a mean in a range of about 1.29 to 1 to 1.62 to 1, about 1.29 to 1 to 1.72 to 1 or about 1.29 to 1 to 3.68 to 1. In embodiments, "PL to FC" ratio (mol to mol or w to w) has a mean in a range of about 1.62 to 1 to 1.72 to 1 or about 1.62 to 1 to 3.68 to 1. In embodiments, "PL to FC" ratio (mol to mol or w to w) has a mean in a range of about 1.72 to 1 to 3.68 to 1.

In embodiments, "PL to FC (i.e. PL/FC)" ratio (mol to mol or w to w) has a mean in a range of about 0.5 to 1 to 1 to 1, about 0.5 to 1 to 2 to 1, about 0.5 to 1 to 3 to 1, about 0.5 to 1 to 4 to 1, about 0.5 to 1 to 5 to 1, about 0.5 to 1 to 10 to 1, about 0.5 to 1 to 20 to 1, about 0.5 to 1 to 30 to 1, about 0.5 to 1 to 40 to 1, about 0.5 to 1 to 50 to 1, about 0.5 to 1 to 60 to 1, about 0.5 to 1 to 70 to 1, about 0.5 to 1 to 80 to 1, about 0.5 to 1 to 90 to 1 or about 0.5 to 1 to 100 to 1. In embodiments, lipid to drug ratio (mol to mol or w to w) has a mean in a range of about 1 to 1 to 2 to 1, about 1 to 1 to 3 to 1, about 1 to 1 to 4 to 1, about 1 to 1 to 5 to 1, about 1 to 1 to 10 to 1, about 1 to 1 to 20 to 1, about 1 to 1 to 30 to 1, about 1 to 1 to 40 to 1, about 1 to 1 to 50 to 1, about 1 to 1 to 60 to 1, about 1 to 1 to 70 to 1, about 1 to 1 to 80 to 1, about 1 to 1 to 90 to 1 or about 1 to 1 to 100 to 1. In embodiments, lipid to drug ratio (mol to mol or w to w) has a mean in a range of about 2 to 1 to 3 to 1, about 2 to 1 to 4 to 1, about 2 to 1 to 5 to 1, about 2 to 1 to 10 to 1, about 2 to 1 to 20 to 1, about 2 to 1 to 30 to 1, about 2 to 1 to 40 to 1, about 2 to 1 to 50 to 1, about 2 to 1 to 60 to 1, about 2 to 1 to 70 to 1, about 2 to 1 to 80 to 1, about 2 to 1 to 90 to 1 or about 1 to 1 to 100 to 1. In embodiments, lipid to drug ratio (mol to mol or w to w) has a mean in a range of about 3 to 1 to 4 to 1, about 3 to 1 to 5 to 1, about 3 to 1 to 10 to 1, about 3 to 1 to 20 to 1, about 3 to 1 to 30 to 1, about 3 to 1 to 40 to 1, about 3 to 1 to 50 to 1, about 3 to 1 to 60 to 1, about 3 to 1 to 70 to 1, about 3 to 1 to 80 to 1, about 3 to 1 to 90 to 1 or about 3 to 1 to 100 to 1. In embodiments, lipid to drug ratio (mol to mol or w to w) has a mean in a range of about 4 to 1 to 5 to 1, about 4 to 1 to 10 to 1, about 4 to 1 to 20 to 1, about 4 to 1 to 30 to 1, about 4 to 1 to 40 to 1, about 4 to 1 to 50 to 1, about 4 to 1 to 60 to 1, about 4 to 1 to 70 to 1, about 4 to 1 to 80 to 1, about 4 to 1 to 90 to 1 or about 4 to 1 to 100 to 1. In embodiments, lipid to drug ratio (mol to mol or w to w) has a mean in a range of about 5 to 1 to 10 to 1, about 5 to 1 to 20 to 1, about 5 to 1 to 30 to 1, about 5 to 1 to 40 to 1, about 5 to 1 to 50 to 1, about 5 to 1 to 60 to 1, about 5 to 1 to 70 to 1, about 5 to 1 to 80 to 1, about 5 to 1 to 90 to 1 or about 5 to 1 to 100 to 1. In embodiments, lipid to drug ratio (mol to mol or w to w) has a mean in a range of about 10 to 1 to 20 to 1, about 10 to 1 to 30 to 1, about 10 to 1 to 40 to 1, about 10 to 1 to 50 to 1, about 10 to 1 to 60 to 1, about 10 to 1 to 70 to 1, about 10 to 1 to 80 to 1, about 10 to 1 to 90 to 1 or about 10 to 1 to 100 to 1. In embodiments, lipid to drug ratio (mol to mol or w to w) has a mean in a range of about 20 to 1 to 30 to 1, about 20 to 1 to 40 to 1, about 20 to 1 to 50 to 1, about 20 to 1 to 60 to 1, about 20 to 1 to 70 to 1, about 20 to 1 to 80 to 1, about 20 to 1 to 90 to 1 or about 20 to 1 to 100 to 1. In embodiments, lipid to drug ratio (mol to mol or w to w) has a mean in a range of about 30 to 1 to 40 to 1, about 30 to 1 to 50 to 1, about 30 to 1 to 60 to 1, about 30 to 1 to 70 to 1, about 30 to 1 to 80 to 1, about 30 to 1 to 90 to 1 or about 30 to 1 to 100 to 1. In embodiments, lipid to drug ratio (mol to mol or w tow) has a mean in a range of about 40 to 1 to 50 to 1, about 40 to 1 to 60 to 1, about 40 to 1 to 70 to 1, about 40 to 1 to 80 to 1, about 40 to 1 to 90 to 1 or about 40 to 1 to 100 to 1. In embodiments, lipid to drug ratio (mol to mol or w to w) has a mean in a range of about 50 to 1 to 60 to 1, about 50 to 1 to 70 to 1, about 50 to 1 to 80 to 1, about 50 to 1 to 90 to 1 or about 50 to 1 to 100 to 1. In embodiments, lipid to drug ratio (mol to mol or w to w) has a mean in a range of about 60 to 1 to 70 to 1, about 60 to 1 to 80 to 1, about 60 to 1 to 90 to 1 or about 60 to 1 to 100 to 1. In embodiments, lipid to drug ratio (mol to mol or w to w) has a mean in a range of about 70 to 1 to 80 to 1, about 70 to 1 to 90 to 1 or about 70 to 1 to 100 to 1. In embodiments, lipid to drug ratio (mol to mol or w to w) has a mean in a range of about 80 to 1 to 90 to 1 or about 80 to 1 to 100 to 1. In embodiments, lipid to drug ratio (mol to mol or w to w) has a mean in a range of about 90 to 1 to 100 to 1.

In embodiments, phospholipid mol % (e.g. the number of moles of phospholipid relative to total number of moles of all formulation constitutions including phospholipids, cholesterol, poloxamers, anticancer drug, salts, etc.) has a mean of about 10%, about 20%, about 30%, about 40%, about 50%, about 60%, about 70%, about 80%, about 90% or any intervening number of the foregoing or higher that about 90%.

In embodiments, free cholesterol (FC) mol % (e.g. the number of moles of FC relative to total number of moles of all formulation constitutions including phospholipids, cholesterol, poloxamers, anticancer drug, salts, etc.) has a mean of about 5%, about 10%, about 20%, about 30%, about 40%, about 50%, about 60% or any intervening number of the foregoing or higher that about 60%.

In embodiments, lower PL/FC ratios (w/w or mol/mol) lead to increased lipid bilayer rigidity that in its turn negatively impacts pH dependent drug release. In embodiments, higher PL/FC ratios (w/w or mol/mol) compromise the stability of the liposomes in serum or blood. Thus, in some embodiments, optimal range of PL/FC is determined to lie in 1/1 to 4/1 range.

Obtained data on Irinotecan containing liposomes are in a good agreement with results obtained for doxorubicin and support the effect of oxalate and tartrate counter ions and preferred lipid/drug ratio.

Method of Loading Anticancer Compounds within Liposomes

In embodiments, the effect of the loading conditions can alter the volume of drug contained within a liposome, release kinetics, liposome size, etc. In embodiments, loading the liposomes under cold (e.g. without a heated step, or at room temperature) conditions produces favorable release kinetics.

In embodiments, an anticancer compound and its paired liposomes containing encapsulated counter ion can be stored in separate container (e.g. vials) for mixing in a medical setting prior to use. In embodiments, weakly basic anticancer compound of the present disclosures is lyophilized and readily reconstitutable in sterile water for injection. In embodiments, lyophilized and reconstituted anticancer compound—can be mixed with a liposome suspension. In embodiments, this mixing occurs at room temperature. The compositions of the present disclosures allow for a short incubation time upon mixing. In embodiments, an incubation time is about 0-60 minutes. In embodiments, an incubation time is about 0-45 minutes. In embodiments, an incubation time is about 0-30 minutes. In embodiments, an incubation time is about 0-25 minutes. In embodiments, an incubation time is about 0-20 minutes. In embodiments, an incubation time is about 0-15 minutes. In embodiments, an incubation time is about 0-10 minutes. In embodiments, an incubation time is about 10-30 minutes. In embodiments, an incubation time is about 5-25 minutes. In embodiments, liposomes are suspended in aqueous buffer, pH ~7.4

Lyophilization of water solution of doxorubicin in presence of lactose and/or mannitol resulted in lyophilized material that is readily reconstitutable in sterile water for injection at room temperature to the final concentration 6 mg/mL. Mixing of lyophilized and reconstituted doxorubicin of the present disclosures with oxalate and -tartrate containing liposomes results in efficient and rapid encapsulation of the doxorubicin.

EXAMPLES

In embodiments, the liposomal compositions of the present disclosures have unique biological performance. Upon administration, these particles may not be recognized as foreign, e.g., they are not labeled with proteins which trigger clearance processes in the tissues of the reticulo-endothelial system. In embodiments, the liposomal compositions are coated with a component that inhibits opsonization and phagocytosis. Furthermore, the liposomal compositions may allow for optimized drug release under certain conditions, e.g., pH dependent release.

In embodiments, pH dependent drug release profile may be optimized via selection of proper counter ions, lipid composition, and fine tuning lipid/drug ratio in consideration of systemic and tumor biology (FIG. 1). For example, the following principles may be considered during parameter optimization:

While in systemic circulation—restricting drug release at neutral pH (pH of blood is 7.4) (FIG. 1A).

Upon accumulation at the tumor site—propelling drug release at more acidic local extracellular space (FIG. 1B). Tumors may have an acidic local environment (~pH 6.5-7.2) compare to the blood [1, 40-42]. Moreover, poor vasculature of the tumor may result in preferred accumulation of liposomal carrier of the drug. Thus, both accumulation of liposomes and more acidic local environment may propel local drug release in extracellular space of the tumor site.

Upon internalization by the cancerous cells—maximal release of the drug during liposome residency at more acidic pH (e.g. 6-6.5) of the endosomal environment (FIG. 1C) thereby requiring less drug to be trapped in lysosomes (FIG. 1D) [50-51]. Local accumulation/entrapment of liposomal drug carrier at the tumor site may also result in enhanced internalization of the liposomes by the cancerous cells. Upon internalization and entering acidic endosomal environment (~pH 6.0-6.5) liposomes may readily release the drug, and therefore significantly improve its cytoplasmic bioavailability.

Thus the desirable drug release profile (FIG. 1E) would facilitate release of the majority of encapsulated drug at pH range from 6.9 to 6.0 representing the local tumor and endosomal environment at least in some embodiments.

Example 1: Materials and Methods: Doxorubicin

HPLC Quantification of Doxorubicin

All HPLC was performed using an Agilent 1260 Infinity system, equipped with a G13110B pump, 01329B autosampler, G1316A column compartment, and a G1315D diode-array detector. OpenLab CDS (EZChrom edition) software controlled all modules and was used for analysis and reporting of chromatography. A Phenomenex Luna C18 column (5μ, 150×4.6 mm; part #00G-4252-E0) was used for all analyses.

Sodium acetate was cGMP grade from Macco Organiques Inc. (Valleyfield, P.Q., Canada) and hydrochloric acid (used to adjust pH) was ACS grade from EMD Millipore (Billerica, Mass.). All water used was purified.

Chromatographic analysis of doxorubicin (DOX) was performed on the Agilent 1260 Infinity system using a C18 column (see above) with a column temperature of 40° C. and sample temperature at ambient conditions (~25° C.). All mobile phase reagents were filtered with a 0.45 μm filter membrane prior to use. HPLC grade acetonitrile was from EMD Millipore. An isocratic mobile phase containing 0.05 M sodium acetate (pH 4.0) and acetonitrile (72:28, v/v) was used. Mobile phase flow rate was set to 1.0 mL/min with a run time of 15 minutes. The diode array detector was operated at 487 nm with a bandwidth of 4 nm. Injection volume was set to 10 μL.

Standard stock solution of doxorubicin was prepared in a 0.9% saline, or methanol, or water solution (1 mg/mL). Calibration standards were prepared by diluting the stock solution in anhydrous methanol to bracket the target concentration for analysis. For this study, the doxorubicin solution was diluted with anhydrous methanol or IPA to the final concentration 50 μg/mL, 100 μg/mL and 200 μg/mL; respectively. Samples of liposomal suspension were also diluted with anhydrous methanol or IPA by a factor of 8 or 10 times prior to analysis.

Fluorometry

All analyses were performed using a Molecular Devices SpectraMax Gemini EM Fluorescence Plate Reader. SoftMax Pro software controlled the device and was used for analysis and reporting of values.

Standard stock solution of doxorubicin hydrochloride was prepared in a 0.9% saline solution (6 mg/mL). Calibration standards were prepared by diluting the stock solution in phosphate buffered saline, pH 7.4 and 5.0 to bracket the target concentration for analysis. The plate reader temperature was set to 25° C., and excitation and emission wavelengths were set at 478 nm and 594 nm, respectively. The linear response range was determined to be 0.5-4 μg/mL of doxorubicin hydrochloride. To remain in the linear response range, the doxorubicin hydrochloride calibration standards and samples were diluted accordingly.

To determine total content of doxorubicin in liposomal formulation (Ft), the liposomes were ruptured by addition of Triton X-100 to the final concentration 1%, mixed by inversion, and incubated for prior to quantification.

To determine free doxorubicin the liposomal formulation was loaded into an ultrafiltration unit (Pierce concentrator, ThermoScientific, Rockford, Ill.) with a molecular weight cutoff of 100,000 D. After centrifugation at 2500 rpm for 1 to 2 hours, the filtrate was analyzed using the SpectraMax Gemini EM Fluorescence plate reader and quantified.

To determine fluorescence of intraliposomal content of doxorubicin the liposomal formulation was subjected to fluorometric analysis without pretreatment with Triton X-100.

Quantification of Doxorubicin Release from Liposomal Formulations

The method of Lee et al. [20], which employs a fluorescence dequenching technique and relays it to 100% fluorescence (liposomes ruptured with Triton X-100) has been used for determination of doxorubicin release. This approach is based on the fact that fluorescence of doxorubicin is quenched upon encapsulation into liposomes and markedly increases upon doxorubicin release from liposomes. Therefore, increase of fluorescence of intact liposomes (Fi) during the incubation of sample in dissolution media represents release of doxorubicin into the media. The difference between Fi values at different time points and T0 relayed to Ft (100% fluorescence of ruptured liposomes), and represents percent of released drug.

The study was carried out at 25° C. and 37° C. (to mimic in vivo conditions) at the following time points: T0, T2 hrs, T4 hrs, and T8 hrs. Individual samples were diluted in up to 4 separate diluents/dissolution medias; PBS pH 7.4, and/or PBS/pH 6.7, and/or PBS pH6.0, and/or PBS pH 5.0 by a factor of 20 times (e.g. 100 μL of sample+1.9 mL of diluent), or 50× (e.g. 50 μL of sample+2.45 mL of diluent). For T0 time point determination, liposomal formulations were diluted in PBS pH 7.4, and/or pH 6.7, and/or pH 6.0, and/or pH 5.0 buffers at ~25° C. The fluorescence of intact liposomes (Fi) and total fluorescence of liposomes ruptured with Triton X-100 (Ft) were measured immediately. The plate reader temperature was set to 25° C. and excitation and emission wavelengths were set at 478 nm and 594 nm, respectively.

Other liposomal samples were diluted 20× or 50× in PBS pH 7.4, 6.7, 6.0, and pH 5.0 buffers pre-warmed to 37° C. (to simulate in vivo temperature) and incubated for 2, 4, and 8 hrs at 37° C.

Other liposomal samples were diluted 20× or 50× in Human serum or human blood pre-warmed to 37° C. (to simulate in vivo temperature) and incubated for 2, 4, and 8 hrs at 37° C. At each time point fluorescence of intact liposomes (Fi) and total fluorescence of liposomes ruptured with Triton X-100 (Ft) was measured. The percent of drug release was quantified as $[(Fi\_n-Fi\_t0)/Ft\_avrg]*100\%$, where $Fi\_n$—Fi measured at 2, 4, or 8 hrs, $Fi\_t0$—Fi measured at T0, and $Ft\_avrg$—average of Ft values determined for all time points. It is worth mentioning that there was no significant change of Ft values observed at different time points and pH.

Particle Size Determination

All analyses were performed using a Malvern Zetasizer Nano ZS with 4 mW He—Ne laser operating at a wavelength of 633 nm and a detection angle of 173°. Zetasizer software controlled the device and was used for analysis and reporting of values.

Particle size distribution by Intensity. The intensity-averaged particle diameters (Z-average) were calculated from the cumulants analysis as defined in ISO 13321 (International Organization for Standardization 1996).

Particle size distribution by Number. In this distribution, there is first-power relationship between particle size and contribution to the distribution. Particle size distribution by Number is computed from the intensity distribution and the optical properties of the material. Typical, high-quality DLS results usually see a decrease in diameter when going from Intensity Mean to Number Mean values [35].

In general, the intensity based Z-Average and Intensity values are larger than a diameters obtained from transmission electron microscopy (TEM) because of a) sixth power relationship between light scattering intensity and particle diameter, the larger particles dominate the signal, and b) DLS measures the hydrodynamic diameter (i.e. diameter of the particle plus ligands, ions or molecules that are associated with the surface of the particle) so the particle appear larger to the instrument in comparison to TEM Samples are prepared using 30 μL of liposomal formulation in 1.5 mL of phosphate buffered saline (pH 7.4) and were equilibrated to 25° C. prior to analysis. Size measurements were done in triplicates for each sample.

Cryo-Transmission Electron Microscopy Analysis of Doxorubicin Containing Liposomes.

Copper 400 mesh+carbon film" grids (EMS) were glow discharged using an EMS100× glow discharge unit. Three microliter of a sample diluted 1.5× in the provided buffer were applied on a glow discharged grid and subsequently plunge-frozen in liquid ethane using a Vitrobot™ Mark II (FEI) and then stored in liquid nitrogen. The grids were imaged using a FEI CM200 field emission gun transmission electron microscope at an accelerating voltage of 200 kV. The grid was thoughtfully observed and representative images were acquired at magnification of 15kx, 27.5kx, 381a, 50kx and 66kx using a TVIPS F224 2kx2k detector.

pH Measurements.

All analyses were performed using a Mettler Toledo SevenCompact pH meter with a Mettler Toledo InLab pH microelectrode.

Coarse Suspension Preparation.

Coarse suspension was prepared by dissolving PC, DMPC, FC, and P188 in 10 mL of DCM at the ratios indicated in Table 6. The mixture was dried under the stream of nitrogen until viscous film was formed. The film was further dried in vacuum oven overnight. Next day dried lipid film was hydrated with 300 mM solution of the following ammonium salts: ammonium-oxalate, or ammonium-sulfate, or ammonium-picolinate, or ammonium-phosphate, or ammonium-citrate, or ammonium-acetate, or ammonium-formate pre-warmed to 65° C., and immediately homogenized with a hand-held homogenizer for 2-3 min. Particle size of coarse suspension was determined and always was in the range of 800-1200 nm. Maleic acid, cysteine, NAC, ascorbic acid, malonic acid, tartaric acid, fumaric acid, or succinic acid were first titrated with ammonium hydroxide to pH 4.8-5.0 and then used as hydration media.

Mf Processing.

MF processing volume was always 100 ml unless specified differently. MF processing pressure was always 10 KPSI. Microfluidization of coarse suspension was performed in recycling mode (return of the material into the feed reservoir) at controlled (≤65° C.) temperature. Processing time was in 10-16 min range. The target particle size (Z-average) was 60-70 nm.

Tangential Flow Filtration

Translucent nanosuspension was harvested from microfluidizer and subjected to tangential flow filtration (TFF) with 15-20× volumes of PBS, pH 7.4. The purpose of TFF was to replace external buffers encompassing ammonium-oxalate, or ammonium-sulfate, or ammonium-phosphate, or ammonium-tartrate, or ammonium-citrate, or maleic acid, cysteine, NAC, ascorbic acid, malonic acid, tartaric acid, fumaric acid, or succinic acid titrated with ammonium hydroxide to pH 4.8-5.0 with PBS, and to majorly remove ammonium from external buffer and intraliposomal space. Ammonium in external buffer was measured by using ammonium specific electrode. TFF was stopped when ammonium concentration in external buffer was ≤3 mM.

Remote Loading of Doxorubicin doxorubicin hydrochloride was dissolved in saline to the final concentration 6 mg/mL. Saline solution of doxorubicin was added to the liposomal nanosuspension in PBS, pH 7.4 to the final concentration 1 mg/mL. The mixture was heated to 70° C. After 30 min of incubation at 70° C. the mixture was allowed to cool down to ambient temperature (~25° C.) and subjected to another TFF 5× cycle with PBS pH 7.4 containing 6% of sucrose.

The cold loading of doxorubicin into liposomes was performed as follows: saline solution of doxorubicin was added to the liposomal nanosuspension at room temperature to final concentration 1 mg/mL, gently inverted (2-3 times) and incubated at room temperature for 10 min. After 10 min of incubation at room temperature the mixture was: a) subjected to another TFF 5× cycle with PBS pH 7.4 containing 6% of Sucrose, and/or b) placed in 2-8° C. refrigerator for 16 hrs, and then was sterile filtered or subjected to another TFF 5× cycle with PBS pH 7.4 containing 6% of Sucrose.

Following cold loading, liposomal nanosuspension was sterile filtered into sterile Nalgene flask via 0.22 um filter. Particle size, pH, HPLC content of doxorubicin, Fi, Ft, free doxorubicin, and doxorubicin release profile were determined. The sterile nanosuspension was aseptically dispensed into 2 mL pre-sterilized vials, stoppered, and sealed. The vials were stored at 2-8° C.

In Vitro Cell-Based Cytotoxicity Assay.

Daudi cells (ATCC, CCL-213). Cells were plated in 96 well plates at the density 100K cells per well. Doxorubicin hydrochloride, Doxil®, or doxorubicin oxalate liposomes were appropriately diluted in Growth medium (RPMI-1640, 10% FBS) and added to the cells. After 1 hr of incubation at 37° C. plates were centrifuged, supernatant was removed via aspiration, 100 μL of fresh media were added into each well, and cells were cultured for 48 hrs.

Hela cells (HeLa (ATCC CCL-2). Cells were plated in 96 well plates at the density 25K cells per well. Doxorubicin hydrochloride, Doxil®, or doxorubicin oxalate liposomes were appropriately diluted in Growth medium (DMEM, 5% FBS, 1% antibiotic, 1% HEPES) and added to the cells. After 1 hr of incubation at 37° C. plates were centrifuged, supernatant was removed via aspiration, 100 μL of fresh media were added into each well, and cells were cultured for 48 hrs.

On the day 3 to assess cell viability, Alamar Blue solution was prepared in Growth medium (RPMI-1640, 10% FBS) at 1:250 dilution and added directly into cell media. After 6 hrs of incubation at 37° C. the resulting fluorescence was read on a plate reader. The fluorescence of cells that have not received any drug treatment was defined as maximum viability. The fluorescence of cell free media was defined as complete cell death. Data analysis was performed by using Prism nonlinear regression software (GraphPad Software) for the curve-fitting and determination of IC50 values.

In Vivo Study

Human B lymphoma cell line Ramos (RA 1) (ATCC CRL-1596) were cultured in RPMI-1640 medium containing 20 mM HEPES, 10% Fetal bovine serum, 2 mM L-glutamine, and 1 mM sodium pyruvate. Cell density was maintained in $3\times10^5$-$1.5\times10^6$ range, and viability in 90-95% range. On the same day prior to administration into animals cell were counted, centrifuged at 12000 rpm, washed with sterile PBS, centrifuged again at 1200 rpm, resuspended in sterile PBS to the final cell count 35×10-per mL. Suspension of cells was administered into animals intravenously via single bolus injection to deliver $5\times10^6$ cells per mouse.

Figure 2:
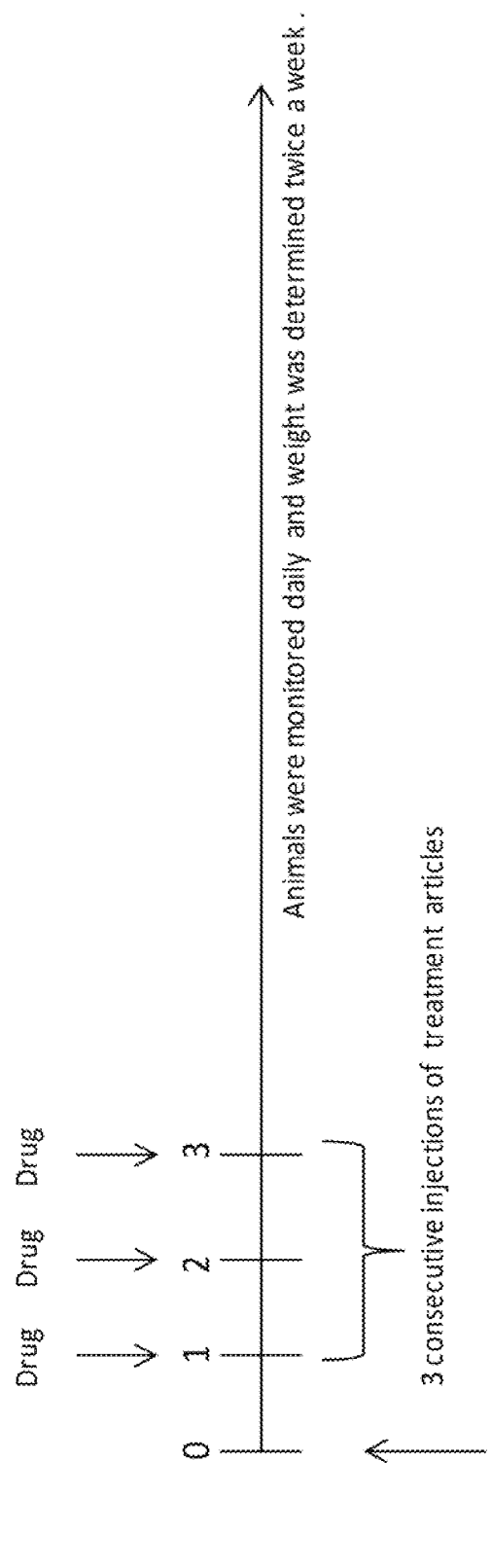
FIG. 2 is a schematic of the experimental design for the in vivo study.

Four weeks old immune deficient SCID Beige, (Line—CB17.Cg-Prkdc$^{scid}$Lyst$^{bg-J}$/Crl) mice were maintained on Chow diet. At the age of 8 weeks mice were subdivided in 3 groups. On the day 1, $5\times10^6$ B lymphoma cells were intravenously injected into each mouse (FIG. 2). On the day 2 one group received placebo (doxorubicin free liposomes), and another two received treatment with Doxil® (lot #FAZSR00) or doxorubicin Oxalate liposomes, respectively. On the day 2 and 3 all treatments were repeated (FIG. 2). Animals were monitored daily and weighed twice a week.

Prior to injection Doxil® liposomes, or doxorubicin Oxalate liposomes were diluted appropriately with PBS to final concentration 0.5 mg/mL. Treatment articles were administered intravenously in 120 μL via single bolus injection to deliver 60 μg of doxorubicin per mouse or ~3 mg/kg dose.

Materials used are shown in Table 4.

TABLE 4

List of Materials

| Reagents | MW | Catalog # | Vendor/Manufacturer |
|---|---|---|---|
| Phosphatidyl choline (PC) egg lecithin (LIPOID E PC S) | 770 | 510800-KG-1 | Lipoid |
| 1,2-dimyristoyl-sn-glycero-3-phosphocholine (DMPC) | 678 | 850345P | Avanti Polar Lipids |
| DSPE-PEG (2000) Amine 1,2-distearoyl-sn-glycero-3-phosphoethanolamine-N-[amino(polyethylene glycol)-2000] (ammonium salt) | 2790 | 880128P | Avanti Polar Lipids |
| Kolliphor P 188 (Poloxamer P188) | 7680-9510 | WPCH537B | Mutchler |
| P188/Synperonic PE/F68 | 7680-9510 | ETK1229 | Croda |
| Free Cholesterol (FC) | 387 | A11470 | Alfa Aesar |
| doxorubicin hydrochloride | 579.98 | 7000AO02113 | Sicor, TEVA* API Division |
| Doxil ® (Caelyx) | N/A | FAZSR00 | TTY Biopharm Company Ltd, |
| Doxil ® (Caelyx) | N/A | L01DB01 | Ben Venue, Ohio, USA |
| Irinotecan hydrochloride trihydrate | 677.18 | I-4122 | LC Labs |
| Irinotecan hydrochloride | 623.14 | I1406 | Sigma-Aldrich |
| Mitoxantrone dihydrochloride | 516.70 | 14842 | Cayman Chemicals |
| Ammonium Sulfate | 132.14 | A4418 | Sigma-Aldrich |
| Oxalic acid | 90.03 | 241172 | Sigma-Aldrich |
| Ammonium oxalate monohydrate | 142 | 09898 | Sigma-Aldrich |
| Ammonium Phosphate monobasic | 115.03 | 216003 | Sigma-Aldrich |
| Ammonium Phosphate dibasic | 132.06 | 215996 | Sigma-Aldrich |
| Ammonium Citrate dibasic | 226.18 | 25102 | Sigma-Aldrich |
| Ammonium Citrate tribasic | 243.22 | A1332 | Sigma-Aldrich |
| L - (+) Tartaric acid | 150.09 | 251380 | Sigma-Aldrich |
| Cysteine | 121.16 | C 7352 | Sigma-Aldrich |
| Ammonium Acetate | 77.08 | AX 1222-5 | EMD |
| Picolinic acid | 123.11 | P 42800 | Sigma-Aldrich |
| Malonic acid | 104.06 | M 1296 | Sigma-Aldrich |
| Maleic acid | 116.07 | M0375 | Sigma-Aldrich |
| Fumaric acid | 116.07 | 47910 | Sigma-Aldrich |
| Ammonium Formate solution, 10M | 63.06 | 78314 | Sigma-Aldrich |
| Succinic acid | 118.09 | S3674 | Sigma-Aldrich |
| L-Ascorbic acid | 176.12 | A5960 | Sigma-Aldrich |
| Butylated hydroxytoluene (BHT) | 220.36 | B1196 | Spectrum |
| N-acetyl L cysteine | 163.19 | A7250 | Sigma-Aldrich |
| Ammonium Hydroxide | 35.04 | AX1303-6 | EMD |
| HCl | 36.5 | HX0603 | EMD Millipore |
| Dichloromethane (DCM) | 85 | P3813 | Sigma-Aldrich |
| Phosphate buffered saline | NA | P5368-10PAK | Sigma-Aldrich |
| Triton X-100 | 625 | 9400 | OmniPur |
| Low endotoxin Sucrose | 342 | 1.00892.1003 | EMD Millipore |
| Lactose | 360.31 | Tabletose 80 | MEGGE Pharma |
| Mannitol | 182.17 | Pearlitol 160C | Roquette |
| Ethylenediaminetetraacetic acid (EDTA) | 292.25 | PN: 0322 | Amresco |
| Sodium Chloride | 58 | M-11619 | Fisher Scientific |
| L-Ascorbic acid 6-palmitate | 414.53 | A1968 | Sigma-Aldrich |
| CoenzymeQ10 | 863.34 | C9538 | Sigma-Aldrich |
| Resazurin Sodium Salt (Alamar Blue) | 251.17 | R7017 | Sigma Aldrich |
| Water for Irrigation | NA | PN: BMGR5007 | B. Braun |
| Water for Injection | NA | PN: 2B0309 | Baxter |
| 2 mL vials | N/A | RTF8409 | Afton Scientific |
| Pooled normal Human Serum | N/A | IPLA-SER | Innovative Research |
| Single Donor Human Whole Blood- Na EDTA anticoagulant | N/A | IPLA-WB1 | Innovative Research |
| Mice Serum Wild Type | N/A | IGMS-C57-SER | Innovative Research |

*Drug Master File holder.

Equipment used is shown in Table 5.

TABLE 5

List of Equipment

| Instrument | Model | Vendor/Manufacturer |
|---|---|---|
| High shear lab mixer | Silverson L5M-A | Silverson |
| Microfluidizer | M 110P | Microfluidics |
| Zetasizer | Nano ZSP | Malvern |
| Microplate Reader | SpectraMax Gemini EM | Molecular devices |
| Tangential Flow Filtration Unit | Labscale TFF System w/ Pellicon XL cassette | MD Millipore |
| Repeater Pump | BAXA | Baxter |
| VWR recirculating water bath | 1160 A | VWR Scientific |
| Lyophilizer | VirTis Genesis SQ25EL | VirTis |
| Analytical balance | XS 6002S | Mettler Toledo |
| pH meter | SevenCompact | Mettler Toledo |

TABLE 5-continued

List of Equipment

| Instrument | Model | Vendor/Manufacturer |
|---|---|---|
| Eppendorf centrifuge | 5417 | Eppendorf |
| Handheld pH meter w/ ammonium specific electrode | SP21 | VWR |
| Beckman Coulter Centrifuge | Allegra 6R | Beckman Coulter |
| HPLC Agilent Technologies | 1220 Infinity LC | Agilent |
| Vacuum Oven | 1430 D | VWR Scientific |
| Microscope | Olympus BHA | Olympus |

Summary of Abbreviations Used: HPLC—high pressure liquid chromatography; MFD—manufacturing date; DCM—Dichloromethane; PC—phosphatidylcholine; FC—free cholesterol; P188—Poloxamer 188; DMPC—1,2-Dimyristoyl-sn-glycero-3-phosphorylcholine; MF—microfluidizer; WN—weight to volume; mfg—manufacturing; ND—not determined; Fi—fluorescence of intact liposomes loaded with fluorescent drug; Ft—total fluorescence of the drug derived from the ruptured liposomes; TFF—tangential flow filtration; W/W—weight to weight ratio; Lipid to Drug Ratio—W/W Ratio of (PC+DMPC+FC)/doxorubicin, or irinotecan, or mitoxantrone.

Example 2: Doxorubicin Loading at 70° C.: Comparison of Different Counter Ions at Fixed 50:1 (i.e. 50 to 1 or 50/1) Lipid/Drug (i.e. Lipid to Drug) Ratio Hydration media used:

a) 300 mM solution of the following ammonium salts: ammonium-oxalate, or ammonium-sulfate, or ammonium-picolinate, or ammonium-phosphate, or ammonium-citrate, or ammonium-acetate, or ammonium-formate.

b) oxalic acid, maleic acid, cysteine, malonic acid, tartaric acid, fumaric acid, succinic acid, ascorbic acid, or N-acetyl L cysteine (NAC) were first titrated with ammonium hydroxide to pH 4.8-5.0 and then used as hydration media.

Remote loading was carried out at 70° C. with 1 mg/mL of doxorubicin hydrochloride (e.g. 0.936 mg of doxorubicin free base per mL). Hydrochloride. Formulation composition is shown in Table 6. All formulations were prepared at 50:1 lipid/drug ratio (Table 6). Lipid/Drug ratio represents weight/weight (w/w) ratio of total lipids to doxorubicin free base in final suspension of doxorubicin loaded liposomes.

The data for picolinate, maleate, cysteinate, malonate, fumarate, formate, succinate, acetate, ascorbic acid, or NAC are not shown since no doxorubicin loading was observed and liposomal material precipitated after overnight storage at 2-8° C.

TABLE 6

Formulation Composition.

| | | Amounts of solids used in formulations, W/W, % | | | | | |
|---|---|---|---|---|---|---|---|
| Lot # | Hydration Media | PC | DMPC | FC | P188 | Doxorubicin Hydrochloride | Lipid/Drug |
| 647-2-106 | Ammonium-Sulfate | 65.50 | 16.38 | 11.46 | 4.91 | 1.75 | 50 |
| 647-2-121 A | Ammonium-Oxalate | 65.50 | 16.38 | 11.46 | 4.91 | 1.75 | 50 |
| 647-2-145 B | Oxalic acid + NH$_4$OH to pH 4.8-5.0 | 65.50 | 16.38 | 11.46 | 4.91 | 1.75 | 50 |
| 647-2-144 B | Ammonium-Phosphate | 65.50 | 16.38 | 11.46 | 4.91 | 1.75 | 50 |
| 647-2-151 B | Tartaric acid + NH$_4$OH to pH 4.8-5.0 | 65.50 | 16.38 | 11.46 | 4.91 | 1.75 | 50 |
| 647-2-105 B | Ammonium-Citrate | 65.50 | 16.38 | 11.46 | 4.91 | 1.75 | 50 |

Coarse suspension was prepared and MF processed. After 9-12 min of MF processing the particle size (Z-average) reached ~60-75 nm. A sample was collected and sterile filtered into Nalgene flask. The particle size of filtered nanosuspension was determined (Table 7).

TABLE 7

Summary of MF processing and resultant emulsion parameters.

| Lot # | Counter Ion | MFD | Processing Pressure, KPSI | Particle size Z avrg, nm |
|---|---|---|---|---|
| 647-2-106 | Sulfate | 28 MAR 16 | 10 | 60 |
| 647-2-121 A | Oxalate | 12 APR 16 | 10 | 59 |
| 647-2-145 B | Oxalate | 09 MAY 16 | 10 | 63 |
| 647-2-144 B | Phosphate | 06 MAY 16 | 10 | 60 |
| 647-2-151 B | Tartrate | 05 MAY 16 | 10 | 65 |
| 647-2-105 B | Citrate | 03 MAY 16 | 10 | 60 |

The liposomes were subjected to TFF followed by remote loading with doxorubicin, and another TFF cycle with PBS sucrose. Doxorubicin hydrochloride concentration used for remote loading: 1.0 mg/mL (doxorubicin free base concentration: 0.936 mg/mL).

The particle size of doxorubicin loaded liposomes is presented in Table 8.

TABLE 8

Particle size of doxorubicin loaded liposomes.

| Lot # | Counter Ion | Loading Date | Particle size Z avrg, nm |
|---|---|---|---|
| 647-2-106 | Sulfate | 31 MAR 16 | 66 |
| 647-2-121 A | Oxalate | 12 APR 16 | 68 |
| 647-2-145 B | Oxalate | 09 MAY 16 | 72 |
| 647-2-144 B | Phosphate | 06 May 16 | 70 |
| 647-2-151 B | Tartrate | 18 MAY 16 | 70 |
| 647-2-105 B | Citrate | 03 MAY 16 | 72 |

Determination of doxorubicin in liposomal suspension. Followed doxorubicin loading liposomal suspension was subjected to 5× TFF to majorly remove free (not encapsulated) doxorubicin. To determine total doxorubicin concentration at T0 (within one week of MFD) TFF washed liposomes were diluted with methanol or IPA and subjected to HPLC analysis. Doxorubicin content, percent of recovery (doxorubicin content in liposomal suspension relative to doxorubicin free base concentration used for remote loading), and encapsulation efficiency (%) are presented in the Table 9. Encapsulation efficiency (%) represents the difference between doxorubicin recovery (%) and free doxorubicin (%).

TABLE 9

Total doxorubicin content and Encapsulation efficiency.

| Lot # | Counter Ion | Doxorubicin free base used for loading, µg/mL | Assay, HPLC Doxorubicin content (Liposomal Suspesion) µg/mL | Recovery, % | Encapsulated doxorubicin, % [Recovery, %]-[Free, %] |
|---|---|---|---|---|---|
| 647-2-106 | Sulfate | 936 | 936 | 100 | 100 |
| 647-2-121 A | Oxalate | 936 | 841 | 90 | 100 |
| 647-2-145 B | Oxalate | 936 | 792 | 85 | 100 |
| 647-2-144 B | Phosphate | 936 | 795 | 85 | 84 |
| 647-2-151 B | Tartrate | 936 | 814 | 87 | 87 |
| 647-2-105 B | Citrate | 936 | 750 | 80 | 79 |

The amount of free (not encapsulated) doxorubicin was determined within one week of manufacturing (Table 10).

TABLE 10

Free doxorubicin content.

| Lot# | Counter Ion | % of Total |
|---|---|---|
| 647-2-106 | Sulfate | 0.02 |
| 647-2-121 A | Oxalate | 0.13 |
| 647-2-145 B | Oxalate | 0.01 |
| 647-2-144 B | Phosphate | 0.46 |
| 647-2-151 B | Tartrate | 0.03 |
| 647-2-105 B | Citrate | 0.90 |

The change of free (not encapsulated) doxorubicin content during the storage at 2-8° C. is presented in the Table 11.

TABLE 11

Change of Free doxorubicin content during the storage at 2-8° C.

| Lot# | Counter Ion | Days past T0 | % of Total |
|---|---|---|---|
| 647-2-106 | Sulfate | 0 | 0.02 |
|  |  | 62 | 0.03 |
| 647-2-121 A | Oxalate | 0 | 0.13 |
|  |  | 45 | 0.3 |
| 647-2-145 B | Oxalate | 0 | 0.01 |
|  |  | 36 | 0.19 |
| 647-2-144 B | Phosphate | 0 | 0.46 |
|  |  | 26 | 0.25 |
| 647-2-151 B | Tartrate | 0 | 0.03 |
|  |  | 26 | 0.1 |
| 647-2-105 B | Citrate | 0 | 0.90 |
|  |  | 34 | 1.10 |

Liposomal doxorubicin release studies were carried out at 25° C. (Table 12) and 37° C. (Table 13). For each sample doxorubicin release was determined at 2, 4 and 8 hrs time points.

TABLE 12

Doxorubicin release rate determined at 25° C.

| Lot# | Counter Ion | Pka1 | pH 5, Release, % | | | pH 7.4, Release, % | | |
|---|---|---|---|---|---|---|---|---|
| | | | 2 hrs | 4 hrs | 8 hrs | 2 hrs | 4 hrs | 8 hrs |
| 647-2-106 | Sulfate | −3 | 1 | 0 | 1 | 0 | 0 | 1 |
| 647-2-121 A | Oxalate | 1.27 | 2 | 5 | 7 | 0 | 0 | 0 |
| 647-2-144 B | Phosphate | 1.96 | 2 | 3 | 4 | 0 | 1 | 0 |

TABLE 12-continued

Doxorubicin release rate determined at 25° C.

| Lot# | Counter Ion | Pka1 | pH 5, Release, % | | | pH 7.4, Release, % | | |
|---|---|---|---|---|---|---|---|---|
| | | | 2 hrs | 4 hrs | 8 hrs | 2 hrs | 4 hrs | 8 hrs |
| 647-2-151 B | Tartrate | 3.03 | 0 | 4 | 4 | 0 | 0 | 0 |
| 647-2-105 B | Citrate | 3.13 | 3 | 4 | 6 | 0 | 0 | 0 |

TABLE 13

Doxorubicin release rate determined at 37° C.

| Lot# | Counter Ion | Pka1 | pH 5, Release, % | | | pH 7.4, Release, % | | |
|---|---|---|---|---|---|---|---|---|
| | | | 2 hrs | 4 hrs | 8 hrs | 2 hrs | 4 hrs | 8 hrs |
| DOXIL ® | Sulfate | −3 | 0.9 | 1.1 | 1.4 | 0.9 | 1.1 | 1.1 |
| 647-2-106 | Sulfate | −3 | 0.1 | 2.7 | 2.4 | 0.01 | 0.6 | 0.1 |
| 647-2-121 A | Oxalate | 1.27 | 47 | 55 | 73 | 2 | 2 | 5 |
| 647-2-145 B | Oxalate | 1.27 | 41 | 58 | 70 | 1 | 4 | 5 |
| 647-2-144 B | Phosphate | 1.96 | 18 | 20 | 22 | 0 | 0 | 1 |
| 647-2-151 B | Tartrate | 3.03 | 14 | 27 | 39 | 0 | 1 | 1 |
| 647-2-105 B | Citrate | 3.13 | 14 | 19 | 24 | 0 | 0 | 0 |

Doxorubicin release rate (at 37° C.) was also monitored during storage of samples at 2-8° C. conditions (Table 14).

TABLE 14

Doxorubicin release rate at 37° C. Effect of the storage at 2-8° C.

| Lot# | Counter Ion | Days past T0 | pH 5, Release, % | | | pH 7.4, Release, % | | |
|---|---|---|---|---|---|---|---|---|
| | | | 2 hrs | 4 hrs | 8 hrs | 2 hrs | 4 hrs | 8 hrs |
| 647-2-106 | Sulfate | 0 | 0.1 | 2.7 | 2.4 | 0 | 0.6 | 0.1 |
| | | 62 | 1 | 2 | 2 | 0 | 0 | 1 |
| 647-2-121 A | Oxalate | 0 | 47 | 55 | 73 | 2 | 2 | 4 |
| | | 45 | 41 | 56 | 72 | 4 | 6 | 5 |
| 647-2-145 B | Oxalate | 0 | 41 | 58 | 70 | 1 | 4 | 5 |
| | | 36 | 30 | 50 | 68 | 1 | 4 | 6 |
| 647-2-144 B | Phosphate | 0 | 18 | 20 | 22 | 0 | 0 | 1 |
| | | 38 | 16 | 17 | 19 | 1 | 1 | 3 |
| 647-2-151 B | Tartrate | 0 | 14 | 27 | 39 | 0 | 1 | 1 |
| | | 26 | 15 | 24 | 35 | 1 | 1 | 2 |
| 647-2-105 B | Citrate | 0 | 14 | 19 | 24 | 0 | 0 | 0 |
| | | 59 | 22 | 27 | 31 | 0 | 0 | 0 |

Particle size. It can be seen from the Tables 7 that microfluidization of different liposomal formulation resulted in similar particle sizes. Doxorubicin loading resulted in slight increase of particle size of all formulations (Table 8).

Efficiency of doxorubicin encapsulation varied from 79% to 100%. The highest encapsulation 100% was observed when sulfate was used as a counter ion (Table 9).

Free doxorubicin reflects concentration of not encapsulated drug determined (within one week after manufacturing (T0), and during the storage of liposomal material at 2-8° C. It can be seen from the Table 10 that free doxorubicin content- at T0 was in the range from 0.02-0.9%. There was no significant change in concentration of free doxorubicin observed over at least one month of storage at 2-8° C. (Table 11).

Liposomal doxorubicin release rate. Drug release studies were carried out at 25° C. and 37° C.

At 25° C. all formulations (e.g. with sulfate, oxalate, phosphate, tartrate, and citrate) demonstrated very low and similar release rate (Table 12) with ΔpH7.4/5.0 release differential close to zero.

Figure 3:
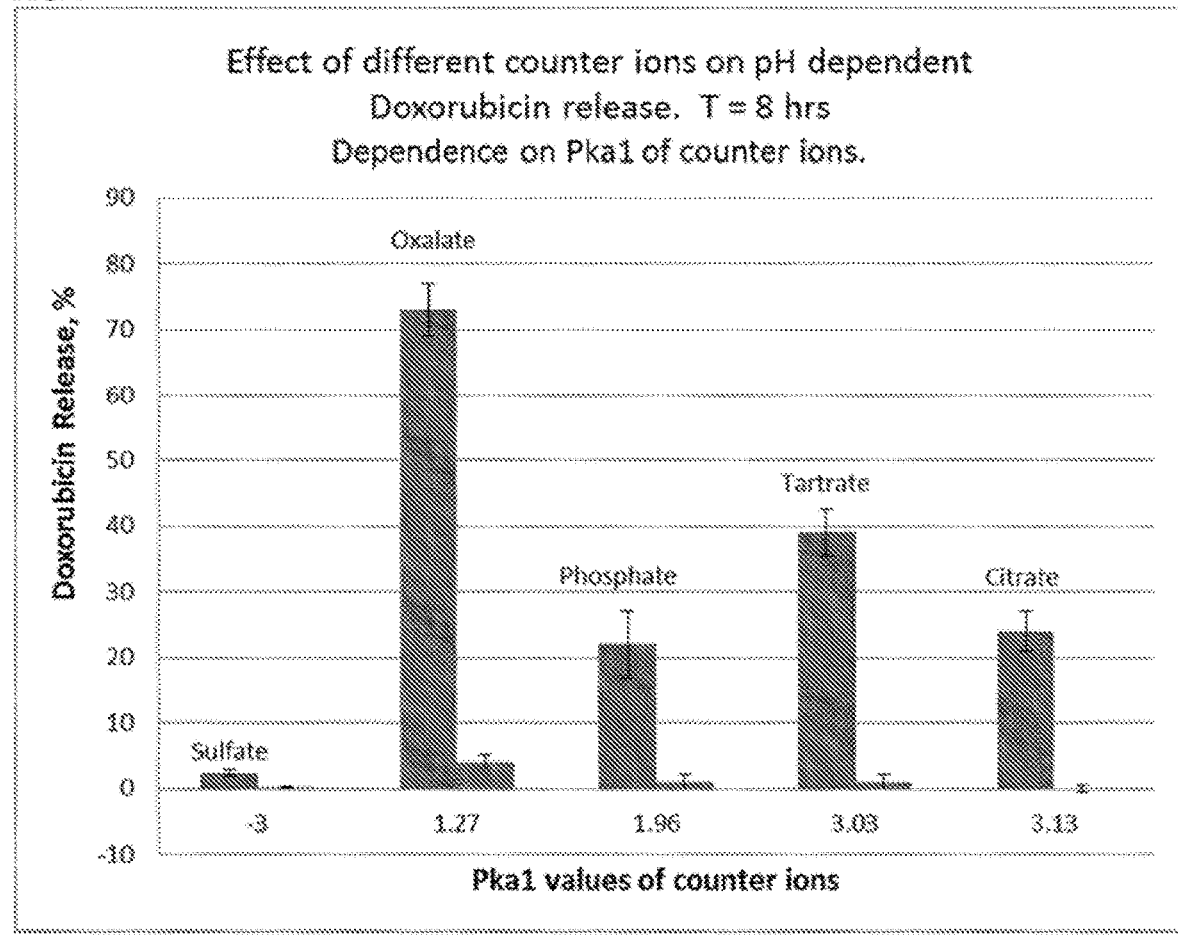
FIG. 3 is a bar graph showing the percent of intraliposomal doxorubicin release into dissolution media after 8 hrs incubation at 37° C. Doxorubicin loading into liposomes was performed at 70° C. Left-side bars on each pair—release at pH 5; right-side bars on each pair-release at pH 7.4. Each point on the curves represents mean±STD of data obtained in 2-6 independent experiments. For each experiment all the measurements were performed in sixtiplicate.

At 37° C., when oxalate or tartrate were used as a counter ions the difference between doxorubicin release at pH7.4 and pH 5.0 (ΔpH7.4/5.0 release differential) was markedly higher compare to other used counter ions (Table 13 and FIG. 3).

It is worth mentioning that regardless of whether ammonium-oxalate salt or oxalic acid (titrated to pH 4.8-5.0 with NH$_4$OH) were used to prepare hydration media, the particle size of empty or doxorubicin loaded liposomes (Tables 7-8), efficiency of doxorubicin encapsulation (Table 9), and release profile (Tables 13-14) were essentially the same.

The 37° C. release rate and extent of ΔpH7.4/5.0 differential observed at T0 (within one week after MFD) were sustained during the storage at 2-8° C. for at least ~two months (Table 14).

The poor doxorubicin release rates observed for all tested counter ions at 25° C. (Table 12) and dramatic increase of doxorubicin release at 37° C. observed with oxalate or tartrate compared to sulfate, phosphate, and citrate (Table 13) suggests uniqueness of physical state(s) of doxorubicin-oxalate or -tartrate aggregates at 37° C. that may facilitate their dissolution, and therefore doxorubicin release. The observed difference in ΔpH7.4/5.0 release differential determined for specified counter ions at 25° C. and 37° C. might also indicates on more profound temperature dependent transition of the physical state of doxorubicin-oxalate or -tartrate intraliposomal aggregates compared to -sulfate or -phosphate in some embodiments.

In embodiments, doxorubicin forms aggregates when encapsulated in liposomes in response to a pH gradient and counter-ions, an observation that has been confirmed by several research groups [1, 13, 15, 23-25]. The physicochemical properties of the counter ions (e.g., oxalate, sulfate, phosphate, tartrate, and citrate) such as size, pKa values, stereochemistry, dipole moment, polarizability, etc. may interplay to generate different precipitated structures, and therefore control release of doxorubicin from the liposomes.

Figure 4:
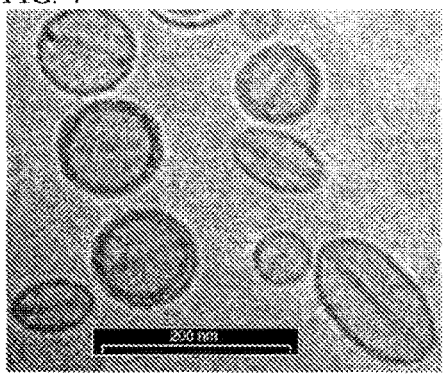
FIG. 4 is a (C-TEM) micrograph of EPC/Chol liposomes loaded with doxorubicin via a $(NH_4)_2HPO_4$ gradient [13].

Andreas Fritze, et all [13] used Cryotransmission electron microscopy (C-TEM) to visualize doxorubicin loaded liposomes prepared in 300 mM (NH$_4$)$_2$HPO$_4$ solution. As shown in FIG. 4, entrapped and precipitated doxorubicin forms bundles appear as linear structures and induce a change in liposomal shape, resulting in a characteristic "coffee bean"—structure. It was demonstrated that doxorubicin release into pH 7.4 buffer from liposomes containing doxorubicin phosphate bundles was <2-3% at 1 hr and at 25° C. [13].

Figure 5:
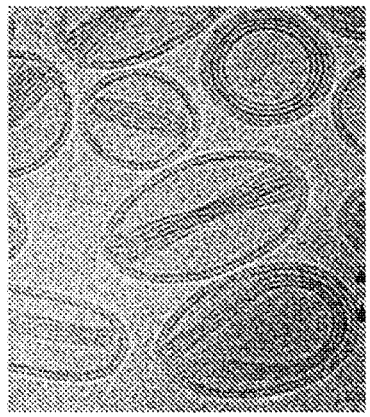
FIG. 5 is a (C-TEM) image of doxorubicin loaded into liposomes buffered by citrate [15].

Xingong Li, et all [15] have examined doxorubicin's (DOX) physical state in solution and inside EPC/cholesterol liposomes that were loaded via a transmembrane pH gradient. Using cryogenic electron microscopy (cryo-EM) they noted that doxorubicin loaded to 200-300 mM internal concentrations in citrate containing liposomes formed linear, curved, and circular bundles of fibers with no significant interaction/perturbation of the vesicle membrane [15] (FIG. 5). It was also demonstrated that doxorubicin release into pH 7.6 buffer from liposomes containing doxorubicin citrate fibers was relatively slow (~4% at 1 hr).

Figure 6:
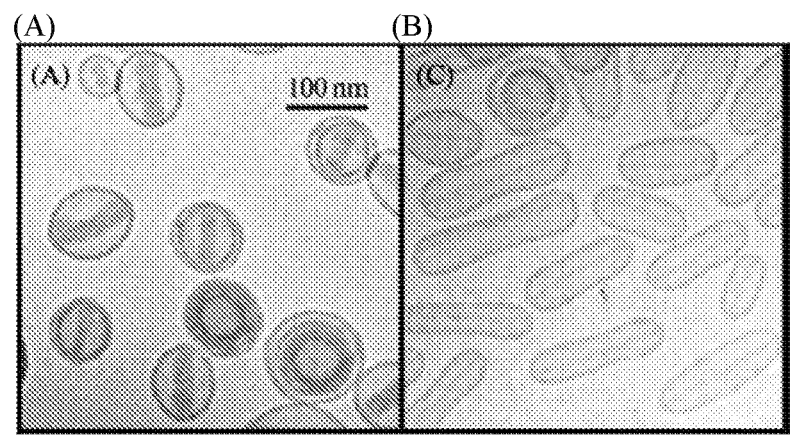
FIG. 6A and FIG. 6B show cryo-transmission electron microscopy (cTEM) images of (FIG. 6A) liposomes prepared in citrate [15], and (FIG. 6B) liposomes prepared in $(NH_4)_2SO_4$ [15, 25].

Doxorubicin aggregates in the presence of sulfate typically have rigid linear fiber bundles (interfiber spacing is approximately 27 A°) compared with the doxorubicin-citrate aggregates in the presence of citrate, which appear mostly linear or curved (interfiber spacing is approximately 30-35A°) [1, 15, 23-25] (FIG. 6). These results suggest that the sulfate anion, being smaller than the citrate anion, may allow a tighter packing arrangement, resulting in a decreased flexibility of fiber bundles and therefore lower rate of drug release from liposomes.

Cryo-TEM analysis of doxorubicin-oxalate-containing liposomes (lot #647-2-157). The doxorubicin-oxalate-containing liposomes (lot #647-2-157) were characterized by cryo transmission electron microscopy (cryo-TEM). Cryo-TEM analysis revealed well-defined dense liposomal particles of spherical morphology (FIGS. 7A, 7B, and 7C) with a well-define bilayer membrane (5-6 nm thickness, FIG. 7C) and a minute internal density of the liposomes that is in line with high (50:1) drug to lipid ratio. It is also worth mentioning that free (not encapsulated) doxorubicin determined by ultrafiltration method was ~0.3% (Table 21).

Figure 7:
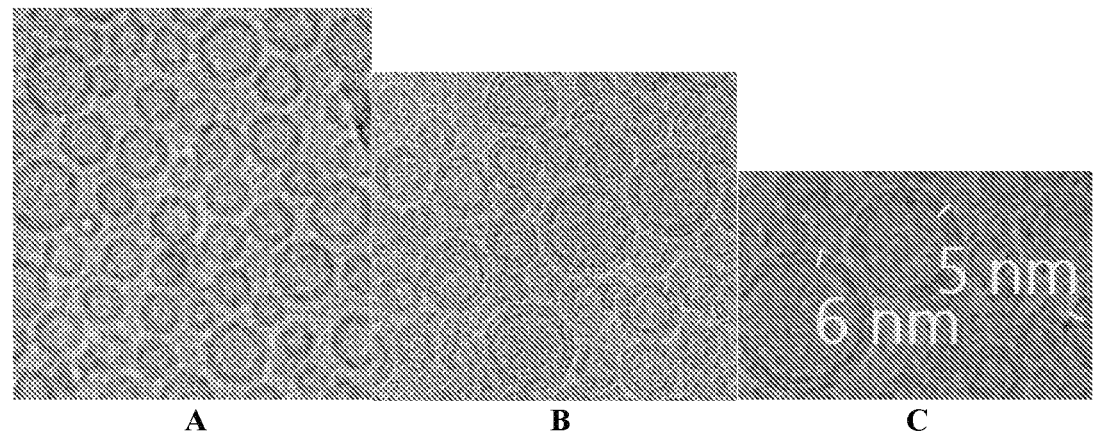
FIGS. 7A, 7B and 7C show cryotransmission electron microscopy characterization of doxorubicin-Oxalate-containing liposomes (lot #647-2-157).

Even though the particles appear densely packed on the support, the on-grid spreading of the sample was relatively even and no particle clustering, nor aggregation was observed. At higher magnification, the membrane bilayer can be clearly distinguished (FIGS. 7B and 7C). The vast majority (97%) of the particles was unilamellar.

In embodiments, doxorubicin-oxalate aggregates appeared to have non-crystalline nature (FIGS. 7A-7C) and did not form tightly packed bundles observed when sulfate or phosphate was used as a counter ions (FIGS. 4-6). This finding signifies unique physical state of the intraliposomal doxorubicin-oxalate aggregates compared to doxorubicin-sulfate and -phosphate aggregates, and is in a good agreement with observed difference in drug release profiles (FIG. 3, Tables 13-14).

Overall obtained data demonstrate efficient loading of doxorubicin and formation of stable liposomal formulations when sulfate, oxalate, phosphate, tartrate, and citrate were used as counter ions. Although all formulations similarly released doxorubicin at 25° C., oxalate and tartrate showed desirable ΔpH 7.4/5.0 release differential when doxorubicin release rate was determined at 37° C. This data indicate that temperature dependent physical state transition of doxorubicin-oxalate or -tartrate aggregates may be more extensive compared to doxorubicin-sulfate or -phosphate aggregates.

In embodiments, not to be bound by theory, although pKa values of the counter-ions determine response to the change of external pH, pKa may be important not just for liposomal doxorubicin release on molecular level (when in solution), but combined with other physical-chemical properties of the counter-ions (e.g. size, stereochemistry, dipole moment, polarizability, etc.) are also important in controlling intraliposomal doxorubicin packaging, physical state of formed aggregates, and therefore their dissolution rate.

Thus, the effect of counter ion for optimal pH dependent drug release was demonstrated, and performed studies strongly suggest that optimal counter ions are oxalate and tartrate at least in some embodiments.

In some alternative embodiments, citrate can be used as a counter ion.

Example 3: Further Characterization of Doxorubicin-Oxalate Containing Liposomes. Variable Lipid/Drug Ratios Hydration Media: 300 mM Ammonium-Oxalate.

Liposomes were prepared at different lipid/drug ratios (5:1-100:1) and various concentrations of P188 (Table 15). Final doxorubicin hydrochloride concentrations used for remote loading were 0.5 or 1.0 mg/mL Remote loading was performed at 70° C.

TABLE 15

Formulation composition.

| | Amounts of solids used in formulations, W/W, % | | | | | Ratios |
|---|---|---|---|---|---|---|
| Lot # | PC | DMPC | FC | P188 | Doxorubicin Hydrochloride | Lipid/Drug |
| 647-1-175 | 65.50 | 16.38 | 11.46 | 4.91 | 1.75 | 50 |
| 647-1-174 | 66.05 | 16.51 | 11.56 | 4.95 | 0.88 | 100 |
| 647-2-13 | 63.94 | 15.98 | 11.19 | 7.99 | 0.85 | 100 |
| 647-2-48 | 65.50 | 16.38 | 11.46 | 4.91 | 1.75 | 50 |
| 647-2-121 A | 65.50 | 16.38 | 11.46 | 4.91 | 1.75 | 50 |
| 647-2-157 | 65.50 | 16.38 | 11.46 | 4.91 | 1.75 | 50 |
| 647-2-159 B | 68.89 | 17.22 | 12.06 | 0.00 | 1.84 | 50 |
| 647-2-99 A | 61.72 | 15.43 | 10.80 | 7.71 | 4.34 | 20 |
| 647-2-99 B | 54.61 | 13.65 | 9.56 | 6.83 | 15.35 | 5 |

Coarse suspension was prepared and MF processed at 10 KPSI processing pressure. After 9-15 min of MF processing the particle size (Z-average) reached ~60-65 nm. A sample was collected and sterile filtered into Nalgene flask. The particle size of filtered nanosuspension was determined (Table 16).

TABLE 16

Summary of MF processing and resultant emulsion parameters.

| Lot# | MFD | Particle size Z avrg, nm |
|---|---|---|
| 647-1-175 | 15 JUL 15 | 62 |
| 647-1-174 | 15 JUL 15 | 62 |
| 647-2-13 | 08 OCT 15 | 63 |
| 647-2-48 | 20 JAN 16 | 63 |
| 647-2-121 A | 12 APR 16 | 60 |
| 647-2-157 | 24 MAY 16 | 65 |
| 647-2-159 B | 02 JUN 16 | 65 |
| 647-2-99 A | 22 MAR 16 | 64 |
| 647-2-99 B | 23 MAR 16 | 61 |

The liposomes were subjected to TFF followed by remote loading with doxorubicin, and another TFF cycle with PBS sucrose. Doxorubicin hydrochloride concentration used for remote loading: 0.5 or 1.0 mg/mL.

The particle size of doxorubicin loaded liposomes is presented in Table 17.

TABLE 17

Particle size of doxorubicin loaded liposomes.

| Lot # | Lipid/Drug | Loading Date | Particle size Z avrg, nm |
|---|---|---|---|
| 647-1-175 | 50 | 21 JUL 15 | 66 |
| 647-1-174 | 100 | 22 JUL 15 | 66 |
| 647-2-13 | 100 | 09 OCT 15 | 70 |

TABLE 17-continued

Particle size of doxorubicin loaded liposomes.

| Lot # | Lipid/Drug | Loading Date | Particle size Z avrg, nm |
|---|---|---|---|
| 647-2-48 | 50 | 21 JAN 16 | 73 |
| 647-2-121 A | 50 | 12 APR 16 | 68 |
| 647-2-157 | 50 | 24 MAY 16 | 73 |
| 647-2-159 B | 50 | 02 JUN 16 | 67 |

TABLE 17-continued

Particle size of doxorubicin loaded liposomes.

| Lot # | Lipid/Drug | Loading Date | Particle size Z avrg, nm |
|---|---|---|---|
| 647-2-99 A | 20 | 22 MAR 16 | 81 |
| 647-2-99 B | 5 | 23 MAR 16 | 80 |

Particle size stability data are presented in Tables 18.

TABLE 18

Particle size of doxorubicin loaded liposomes. Stability at 2-8° C.

| Lot# | Lipid/Drug | Stability Days past T0 | Particle size Z avrg, nm |
|---|---|---|---|
| 647-1-175 | 50 | 0 | 66 |
|  |  | 41 | 67 |
|  |  | 113 | 67 |
| 647-1-174 | 100 | 0 | 66 |
|  |  | 42 | 67 |
|  |  | 114 | 68 |
| 647-2-13 | 100 | 0 | 70 |
|  |  | 34 | 71 |
|  |  | 114 | 72 |
| 647-2-48 | 50 | 0 | 73 |
|  |  | 82 | 74 |
| 647-2-121 A | 50 | 0 | 68 |
|  |  | 45 | 69 |
| 647-2-99 A | 20 | 0 | 81 |
|  |  | 7 | 81 |
|  |  | 65 | 83 |
| 647-2-99 B | 5 | 0 | 80 |
|  |  | 7 | 80 |
|  |  | 65 | 84 |

Determination of doxorubicin in liposomal suspension. Followed doxorubicin loading liposomal suspension was subjected to 5× TFF to majorly remove free (not encapsulated) doxorubicin. To determine total doxorubicin concentration at T0 (within one week of MFD) TFF washed liposomes were diluted with methanol or IPA and subjected to HPLC analysis. Doxorubicin content, percent of recovery (doxorubicin content in liposomal suspension relative to doxorubicin free base concentration used for remote loading), and encapsulation efficiency (%) are presented in the Table 19. Encapsulation efficiency (%) represents the difference between doxorubicin recovery (%) and free doxorubicin (%).

TABLE 19

Total doxorubicin content and Encapsulation efficiency.

| Lot # | Lipid/Drug | Doxorubicin free base used for loading, µg/mL | Assay, HPLC Doxorubicin content (Liposomal Suspesion) µg/mL | Recovery, % | Encapsulated doxorubicin, % [Recovery, %]-[Free, %] |
|---|---|---|---|---|---|
| 647-1-175 | 50 | 936 | 839 | 90 | 90 |
| 647-1-174 | 100 | 468 | 436 | 93 | 93 |
| 647-2-13 | 100 | 468 | 461 | 98 | 98 |
| 647-2-48 | 50 | 936 | 899 | 95 | 95 |
| 647-2-121A | 50 | 936 | 841 | 90 | 90 |
| 647-2-157 | 50 | 936 | 861 | 92 | 92 |
| 647-2-159 B | 50 | 936 | 920 | 98 | 98 |
| 647-2-99 A | 20 | 936 | 526 | 56 | 52 |
| 647-2-99 B | 5 | 936 | 384 | 41 | 31 |

Stability of liposomal doxorubicin was assessed during the storage at 2-8° C. The percent of recovery during the storage relative to initial doxorubicin content determined at T0 is shown in the Table 20.

TABLE 20

Stability of Encapsulated doxorubicin. Storage conditions: 2-8° C.

| Lot# | Lipid/Drug | Days past T0 | Content, µg/m | Recovery, % |
|---|---|---|---|---|
| 647-1-175 | 50 | 41 | 861 | 102 |
| 647-1-174 | 100 | 42 | 452 | 103 |
| 647-2-13 | 100 | 118 | 461 | 100 |
| 647-2-48 | 50 | 84 | 812 | 91 |
| 647-2-121 A | 50 | 45 | 799 | 95 |

The amount of free doxorubicin was determined within one week of manufacturing (Table 21).

TABLE 21

Free doxorubicin content.

| Lot# | Lipid/Drug | % of Total |
|---|---|---|
| 647-1-175 | 50 | 0.38 |
| 647-1-174 | 100 | 0.20 |
| 647-2-13 | 100 | 0.35 |
| 647-2-48 | 50 | 0.41 |
| 647-2-121 A | 50 | 0.13 |
| 647-2-157 | 50 | 0.29 |
| 647-2-159 B | 50 | 0.02 |
| 647-2-99 A | 20 | 4 |
| 647-2-99 B | 5 | 10 |

The change of free doxorubicin content during the storage at 2-8° C. is presented in the Table 22.

TABLE 22

Change of Free doxorubicin content during the storage at 2-8° C.

| Lot# | Lipid/Drug | Days past T0 | % of Total |
|---|---|---|---|
| 647-1-175 | 50 | 0 | 0.38 |
| | | 41 | 0.49 |
| | | 114 | 0.74 |
| 647-1-174 | 100 | 0 | 0.20 |
| | | 41 | 0.34 |
| | | 114 | 0.64 |
| 647-2-13 | 100 | 0 | 0.35 |
| | | 38 | 0.5 |
| | | 124 | 0.5 |
| 647-2-48 | 50 | 0 | 0.41 |
| | | 82 | 0.9 |
| 647-2-121 A | 50 | 0 | 0.13 |
| | | 45 | 0.69 |
| 647-2-99 A | 20 | 0 | 4 |
| | | 7 | 5 |
| 647-2-99 B | 5 | 0 | 10 |
| | | 7 | 15 |

Liposomal doxorubicin release studies were carried out at 37° C. within one week after manufacturing (Table 23). For each sample doxorubicin release was determined at 2, 4 and 8 hrs time points.

TABLE 23

Doxorubicin release rate determined at T0 (within one week after manufacturing).

| | Lipid/ | pH 5, Release, % | | | pH 7.4, Release, % | | |
|---|---|---|---|---|---|---|---|
| Lot# | Drug | 2 hrs | 4 hrs | 8 hrs | 2 hrs | 4 hrs | 8 hrs |
| 647-1-175 | 50 | 55 | 65 | 81 | 2 | 1 | 5 |
| 647-1-174 | 100 | 38 | 57 | 81 | 2 | 3 | 7 |
| 647-2-13 | 100 | ND* | ND* | ND* | ND* | ND* | ND* |
| 647-2-48 | 50 | 50 | 56 | 75 | 0 | 0 | 0 |
| 647-2-121 A | 50 | 47 | 55 | 73 | 2 | 2 | 5 |
| 647-2-157 | 50 | 43 | 56 | 73 | 0 | 3 | 5 |
| 647-2-159 B | 50 | 50 | 65 | 78 | 2 | 7 | 7 |
| 647-2-99 A | 20 | 22 | 35 | 53 | 14 | 27 | 35 |
| 647-2-99 B | 5 | 27 | 43 | 64 | 12 | 20 | 42 |

ND* - not done

Liposomal doxorubicin release rate (at 37° C.) was also monitored during the further storage of samples at 2-8° C. conditions (Table 23a).

TABLE 23a

Change of doxorubicin release rate during the storage at 2-8° C.

| Lot# | Lipid/ Drug | Days past T0 | pH 5, Release, % | | | pH 7.4, Release, % | | |
|---|---|---|---|---|---|---|---|---|
| | | | 2 hrs | 4 hrs | 8 hrs | 2 hrs | 4 hrs | 8 hrs |
| 647-1-175 | 50 | 0 | 55 | 65 | 81 | 2 | 1 | 5 |
| | | 41 | 66 | 75 | 96 | 4 | 5 | 7 |
| | | 114 | 65 | 72 | 84 | 1 | 3 | 3 |
| 647-1-174 | 100 | 0 | 38 | 57 | 81 | 2 | 3 | 7 |
| | | 41 | 42 | 60 | 75 | 3 | 5 | 10 |
| | | 114 | 28 | 45 | 62 | 0 | 2 | 5 |
| 647-2-13 | 100 | 0 | ND* | ND* | ND* | ND* | ND* | ND* |
| | | 38 | 29 | 34 | 54 | 0 | 0 | 3 |
| | | 119 | 40 | 42 | 71 | 4 | 7 | 8 |
| 647-2-48 | 50 | 0 | 50 | 56 | 75 | 0 | 0 | 0 |
| | | 82 | 40 | 54 | 74 | 0 | 0 | 2 |
| 647-2-121 A | 50 | 0 | 47 | 55 | 73 | 2 | 2 | 5 |
| | | 45 | 41 | 56 | 72 | 4 | 6 | 8 |
| 647-2-99 A | 20 | 0 | 22 | 35 | 53 | 14 | 27 | 35 |
| 647-2-99 B | 5 | 0 | 27 | 43 | 64 | 12 | 20 | 42 |

ND* - not done

Particle size. It can be seen from the Tables 15 and 16 that microfluidization of all specified liposomal formulations resulted in similar particle size. Doxorubicin loading resulted in only slight increase of particle size of formulations with lipid/drug ratios from 50:1 to 100:1 (Table 17), whereas marked increase was observed for formulations with lipid/drug ratios 20:1 and 5:1 (Table 17). Particle size of doxorubicin loaded liposomes with lipid/drug ratios from 50:1 to 100:1 remains stable for at least four months (Table 18), whereas particle size of liposomes with lipid/drug ratios 20:1 and 5:1 was unstable and showed significant increase.

Efficiency of doxorubicin encapsulation. Efficiency of doxorubicin encapsulation into liposomes with lipid/drug ratios from 50:1 to 100:1 varied from 90 to 98% (Table 19), and there was no significant change of liposomal doxorubicin content observed during storage at 2-8° C. (Table 20). In contrast, markedly lower encapsulation efficiency (31%-52%) was observed for liposomes with lipid/drug ratios 20:1 and 5:1 (Table 19).

Free (not encapsulated) doxorubicin. Free doxorubicin reflects concentration of drug that did not get encapsulated into liposomes during loading step or leaked from the liposome during the storage. It can be seen from the Table 21 that free doxorubicin content in formulations with lipid/drug ratios 50:1 and 100:1 was in the range from 0.2-0.41%. There was no significant change in concentration of free doxorubicin observed up to ~4 months of storage at 2-8° C. (Table 22).

Free doxorubicin content determined in formulations with 20:1 and 5:1 lipid/drug ratios was markedly higher (Table 21), and markedly increased after 7 day of storage at 2-8° C. (Table 22). These data indicate on evident leakage of doxorubicin from the liposomes made at lower than 50:1 lipid/drug ratios and stored at 2-8° C. and pH 7.4.

Liposomal doxorubicin release rate. It can be seen from the Table 23 that doxorubicin release rate at pH 5 was markedly higher compare to that at pH 7.4 for the formulations with lipid/drug ratios 50:1 and 100:1 (Table 23 and FIG. 3). The ΔpH 7.4/5.0 release differential observed at T0 (within one week of MFD) was sustained during the storage at 2-8° C. for up to 114 days (Table 23a).

Figure 8:
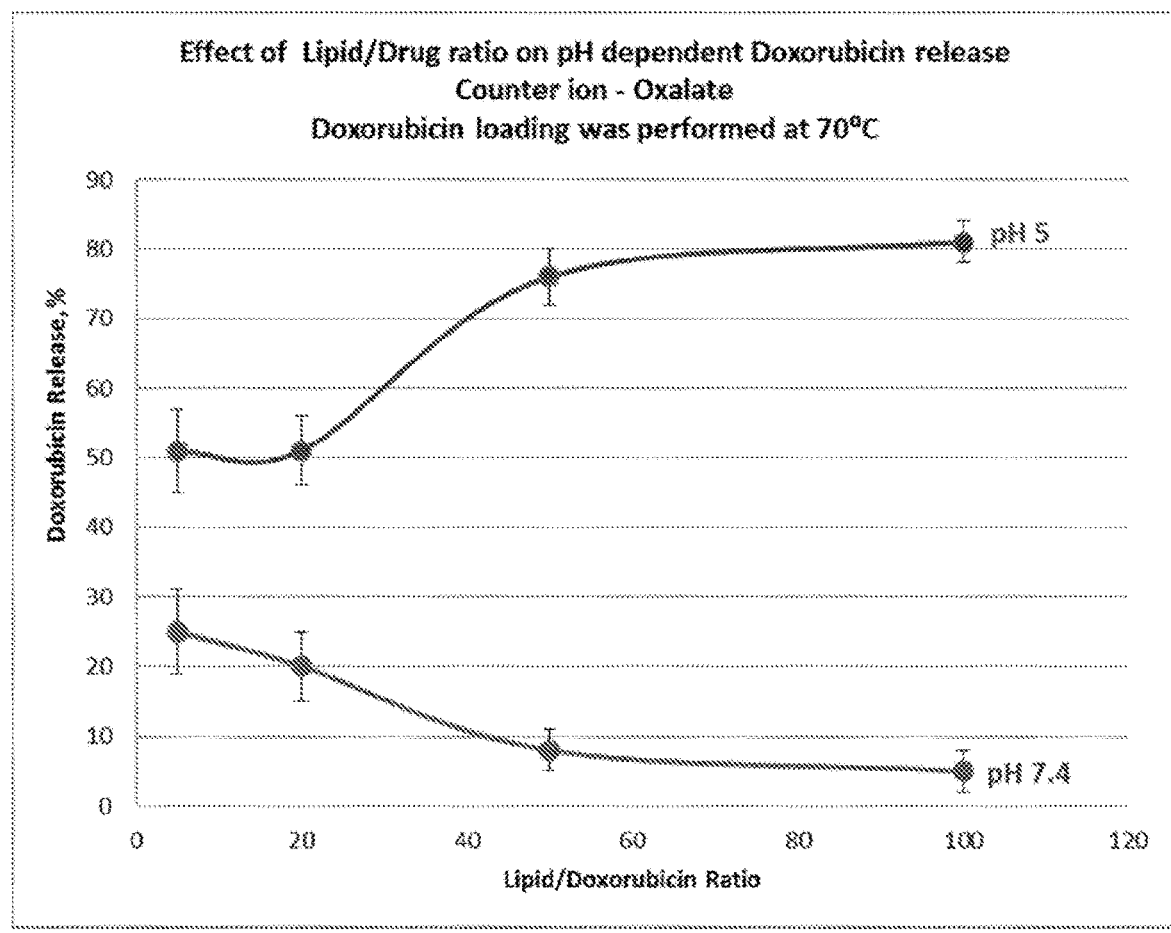
FIG. 8 is a graph showing effect of lipid to drug (or equally referred to lipid/drug or lipid:drug) ratio on percent of release of intraliposomal doxorubicin into dissolution media at 8 hrs. Doxorubicin loading into Oxalate-containing liposomes was performed at 70° C. Release experiment was carried out at 37° C. Release at pH 5.0—the top line. Release at pH 7.4—the bottom line. Each point on the curves represents mean f STD of data obtained in two to three independent experiments. For each experiment all the measurements were performed in sixtiplicate.

In contrast, the formulations with lower lipid/drug ratios (20:1 and 5:1) demonstrated poor ΔpH 7.4/5.0 release differential (Table 23 and FIG. 8) and marked leakage of the doxorubicin at pH 7.4 (Tables 22-23a).

In embodiments, not to be bound by theory, lower lipid/drug ratios may lead to increased surface tension and compromised lipid layer integrity that upon dilution could result in increased not pH dependent leakage of liposomal content into dissolution media due to concentration gradient, and could offset the pH driven release of drug. In contrast, higher lipid to drug ratios may result in formation of the liposomes with lower surface tension and higher integrity lipid layer(s) that are capable of preventing "off target"

leakage of intraliposomal material into dissolution media, and release the drug only in response to pH transition.

Thus, the effect of lipid/drug ratio for both pH dependent drug release and stable performance of liposomes was demonstrated. Performed studies suggest that optimal lipid/drug ratios are in the range from 20:1 to 50:1 in some embodiments. Other ratios that can be used include 20:1 to 100:1 in some other embodiments.

It is also worth mentioning that addition of P188 to the liposomal formulation did not have any significant impact on particle size (Tables 15-17), efficiency of doxorubicin encapsulation (Tables 19 and 21), and doxorubicin release profile (Table 23) compared to liposomal formulation prepared with no P188 (lot #647-2-159 B.). However, P188 was elected for use in liposomal formulations due to its possible advantageous impact on biological performance of drug-loaded liposomes [10-11, 16-19].

Example 4: In Vitro Cell-Based Cytotoxicity Assay

The human lymphoma Daudi B-cell line, commonly used for evaluating drugs for treatment of B-cell lymphomas [21, 22] was next used to test the B-cell cytotoxicity of the doxorubicin-oxalate loaded liposomes vs free doxorubicin, and Doxil®. It can be seen from the Table 24 that three different lots of doxorubicin-oxalate loaded liposomes demonstrated cell cytotoxicity similar to free doxorubicin and were ~50-70 fold more potent relative to Doxil® (Lot #L01DB01), a difference predictive of increased efficacy in vivo.

Hela cells, the human cell line derived from cervical cancer was also used for evaluating drugs cytotoxicity. It can be seen from the Table 24 that doxorubicin-oxalate loaded liposomes demonstrated cell cytotoxicity 2-3 fold lower than free doxorubicin but were 4-6 fold higher more potent relative to Doxil® (Table 24).

TABLE 24

$CC_{50}$ (µM) values obtained for doxorubicin and liposomal doxorubicin formulations.

| Lot # | Name | Lipid/Drug | Storage T° C. | Daudi, $CC_{50}$, µM | Hela, $CC_{50}$, µM |
|---|---|---|---|---|---|
| 7000AO02113 | Doxorubicin Hydrochloride | N/A | N/A | 0.4 | 7 |
| L01DB01 | Doxil ® (Liposomal Doxorubicin Sulfate) | 8 | 2-8 | 29 | 100 |
| 647-1-175 | Liposomal Doxorubicin Oxalate | 50 | 2-8 | 0.4 | 26 |
| 647-1-174 | Liposomal Doxorubicin Oxalate | 100 | 2-8 | 0.4 | 20 |
| 647-2-13 | Liposomal doxorubicin Oxalate | 100 | 2-8 | 0.2 | 15 |

Obtained cytotoxicity data demonstrated markedly increased potency of doxorubicin-oxalate containing liposomes compared to Doxil® that is in a good agreement with markedly higher ΔpH 7.4/5.0 release differential of doxorubicin-oxalate compared to doxorubicin-sulfate containing liposomes.

Example 5: In Vivo Study

The efficacy of doxorubicin-oxalate loaded liposomes (Lot #647-2-13) vs Doxil® (Lot #FAZSR00) was evaluated in a standard lymphoma model in Beige, (Line—CB17.Cg-Prkdc$^{scid}$Lyst$^{bg-J}$/Crl) mice. As illustrated by the timeline in FIG. 2, B lymphoma cells (5×10$^6$) were injected intravenously on day 0 and allowed to disseminate for 24 hours, followed by dosing mice on days 1, 2, and 3 with drug-free lipid formulation (Placebo), or doxorubicin-oxalate containing liposomes (3 mg doxorubicin/kg), or Doxil® (3 mg doxorubicin/kg).

Animals treated with Placebo (doxorubicin free liposomes) reached a median survival time (MST) in 21 days, whereas the doxorubicin-oxalate loaded liposomes increased the MTS to 33 days (FIG. 5). In contrast, Doxil® liposomes exhibited a MST of 15 days (FIG. 5). The shorter MST observed with Doxil® compared to Placebo (FIG. 5) treated mice indicate potential Doxil® toxicity, whereas no such toxicity was observed with doxorubicin-Oxalate containing liposomes. Group of untreated mice (not injected with any material) showed survival rate identical to Placebo (not shown in the graph). Approximately 8% maximum group average weight loss was observed on the day 11 in doxorubicin-oxalate treated animals with complete recovery on the day 17, whereas in Doxil® treated mice ~30% weight loss was observed on day 14 resulting in death of 4 from 8 animals. High toxicity was also observed in a group of mice treated with free doxorubicin (50% death rate on day 13), although survivors demonstrated longest MST that validates the model. The lower toxicity observed for doxorubicin-oxalate containing liposomes could be in part due to their faster clearance. The lower toxicity and higher efficacy of the tested liposomes in accordance with the disclosure compared to Doxil® is a highly desirable and encouraging outcome. Thus, under the same experimental protocol, the treatment with doxorubicin-oxalate containing liposomes demonstrated no obvious toxicity and significant improvement of survival rates compared to Placebo control, whereas treatment with Doxil® at the same doses and regimen demonstrated noticeable toxicity and did not result in any significant improvement of MST compared to Placebo.

Better performance of doxorubicin-oxalate liposomes was in line with the optimized ΔpH release differential and overall resulted in improved safety and efficacy compared to Doxil® (doxorubicin-sulfate) liposomes.

Figure 9:
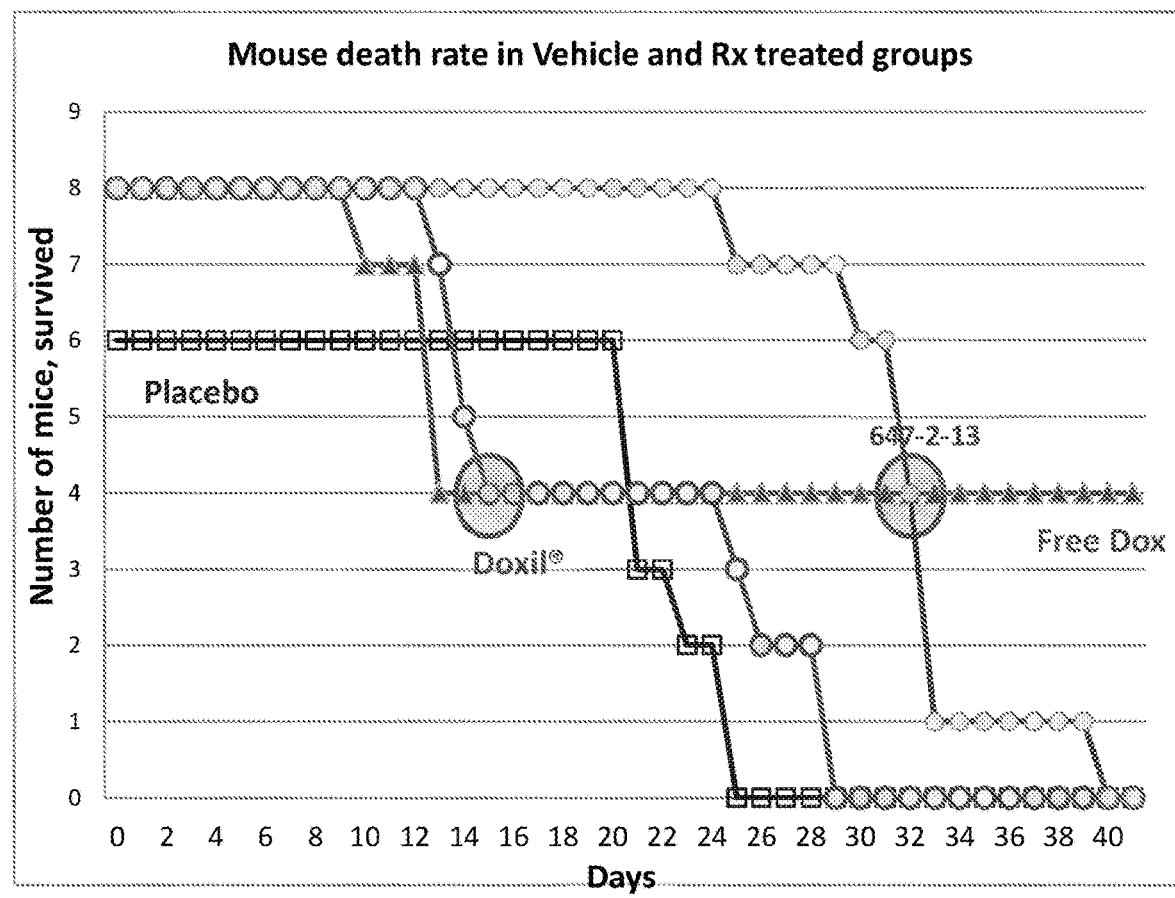
FIG. 9 is a graph showing effect of placebo, free doxorubicin, Doxil®, and doxorubicin-Oxalate containing liposomes on mouse death rate. Mice were divided in 4 groups (8 mice in each Rx group; 6 mice in Placebo group). All test articles were administered to mice for three consecutive days via intravenous (iv) injections. Each Rx treated group received 3 mg/kg of doxorubicin per injection. Group #1 (Placebo) received drug free lipid formulation. Group 2 received doxorubicin oxalate liposomes (lot #647-2-13). Group 3 received Doxil®. Group 4 received free doxorubicin. The treatment is also indicated in the graph. In the graph the Day of B-lymphoma cells administration is defined as Day 0

Thus, under the same experimental protocol, the treatment with doxorubicin-oxalate containing liposomes demonstrated no obvious toxicity and significant improvement of survival rates compared to Placebo control, whereas treatment with Doxil® at the same doses and regimen demonstrated noticeable toxicity and did not result in any significant improvement of MST compared to Placebo (FIG. 9). Better performance of doxorubicin-oxalate containing liposomes was in line with the optimized ΔpH 7.4/5.0 release differential and overall resulted in improved safety and efficacy compared to Doxil® (doxorubicin-sulfate) liposomes.

Example 6: Further Characterization of Doxorubicin-Tartrate Containing Liposomes: Variable Lipid to Drug Ratios Preparation and further characterization of doxorubicin-tartrate containing liposomes. Liposomes were prepared at different lipid/drug ratios (5:1, which is equally referred to 5 to 1 or 5/1-100:1, which is equally referred to 100 to 1 or 100/1) (Table 25). Doxorubicin hydrochloride concentrations used for remote loading were 0.5 or 1.0 mg/mL (i.e. 0.468 and 0.936 mg of doxorubicin free base per mL). Remote loading was performed with doxorubicin Hydrochloride at 70° C. Tartaric acid was first titrated with ammonium hydroxide to pH 4.8-5.0 and then used as hydration media.

TABLE 25

Formulation Composition.

| | Amounts of solids used in formulations, W/W, % | | | | | Ratios |
|---|---|---|---|---|---|---|
| Lot # | PC | DMPC | FC | P188 | Doxorubicin Hydrochloride | Lipid/ Drug |
| 647-2-186 B | 66.0.5 | 16.51 | 11.56 | 4.95 | 0.88 | 100 |
| 647-2-151 B | 65.50 | 16.38 | 11.46 | 4.91 | 1.75 | 50 |
| 647-2-178 B | 63.68 | 15.92 | 11.14 | 4.78 | 4.48 | 20 |
| 647-2-178 D | 56.15 | 14.04 | 9.83 | 4.21 | 15.78 | 5 |

Coarse suspension was prepared and MF processed at 10 KPSI processing pressure. After 9-15 min of MF processing the particle size (Z-average) reached ~0.60-65 nm. A sample was collected and sterile filtered into Nalgene flask. The particle size of filtered nanosuspension was determined (Table 25a).

TABLE 25a

Summary of MF processing and resultant emulsion parameters.

| Lot# | MFD | Particle size Z avrg, nm |
|---|---|---|
| 647-2-186 B | 18 JUL 16 | 62 |
| 647-2-151 B | 05 MAY 16 | 65 |
| 647-2-178 B | 11 LUL 16 | 61 |
| 647-2-178 D | 11 LUL 16 | 61 |

The liposomes were subjected to TFF followed by remote loading with doxorubicin, and another TFF cycle with PBS sucrose. Doxorubicin hydrochloride concentration used for remote loading: 0.5 or 1.0 mg/mL.

The particle size of doxorubicin loaded liposomes is presented in Table 25b.

TABLE 25b

Particle size of doxorubicin loaded liposomes.

| Lot # | Lipid/ Drug | Loading Date | Particle size Z avrg, nm |
|---|---|---|---|
| 647-2-186 B | 100 | 19 JUL 16 | 64 |
| 647-2-151 B | 50 | 18 MAY 16 | 68 |
| 647-2-178 B | 20 | 11 LUL 16 | 67 |
| 647-2-178 D | 5 | 11 LUL 16 | 66 |

Determination of doxorubicin in liposomal suspension. Followed doxorubicin loading liposomal suspension was subjected to 5×TFF to majorly remove free (not encapsulated) doxorubicin. To determine total doxorubicin concentration at T0 (within one week of MFD) TFF washed liposomes were diluted with methanol or IPA and subjected to HPLC analysis. Doxorubicin content, percent of recovery (doxorubicin content in liposomal suspension relative to doxorubicin free base concentration used for remote loading), and encapsulation efficiency (%) are presented in the Table 25c. Encapsulation efficiency (%) represents the difference between doxorubicin recovery (%) and free doxorubicin (%).

TABLE 25c

Total doxorubicin content and Encapsulation efficiency.

| | | Doxorubicin free base used for loading, μg/mL | Assay, HPLC | | Encapsulated doxorubicin, % [Recovery, %]- [Free, %] |
|---|---|---|---|---|---|
| Lot # | Lipid/Drug | | Doxorubicin content (Liposomal Suspesion) μg/mL | Recovery, % | |
| 647-2-186 B | 100 | 468 | 354 | 76 | 76 |
| 647-2-151 B | 50 | 936 | 814 | 87 | 87 |
| 647-2-178 B | 20 | 936 | 897 | 96 | 96 |
| 647-2-178 D | 5 | 936 | 413 | 44 | 41 |

The amount of free (not encapsulated) doxorubicin was determined within one week of manufacturing (Table 25d).

TABLE 25d

Free doxorubicin content.

| Lot # | Lipid/Drug | % of Total |
|---|---|---|
| 647-2-186 B | 100 | 0.01 |
| 647-2-151 B | 50 | 0.03 |
| 647-2-178 B | 20 | 0.01 |
| 647-2-178 D | 5 | 3.20 |

Liposomal doxorubicin release studies were carried out at 37° C. within one week after manufacturing (Table 25e). For each sample doxorubicin release was determined at 2, 4 and 8 hrs time points.

TABLE 25e

Doxorubicin release rate determined at T0
(within one week after manufacturing).

| Lot# | Lipid/Drug | pH 5, Release, % | | | pH 7.4, Release, % | | |
|---|---|---|---|---|---|---|---|
| | | 2 hrs | 4 hrs | 8 hrs | 2 hrs | 4 hrs | 8 hrs |
| 647-2-186 B | 100 | 18 | 35 | 56 | 2 | 1 | 0 |
| 647-2-151 B | 50 | 14 | 27 | 39 | 0 | 1 | 1 |
| 647-2-178 B | 20 | 9 | 15 | 21 | 1 | 2 | 3 |
| 647-2-178 D | 5 | 17 | 23 | 27 | 1 | 4 | 5 |

Particle size. It can be seen from the Tables 25 and 25a that microfluidization of all specified liposomal formulations resulted in similar particle size. Doxorubicin loading resulted in only slight increase of particle size (Table 25b).

Efficiency of doxorubicin encapsulation. Efficiency of doxorubicin encapsulation into liposomes with lipid/drug ratios from 5:1 to 100:1 varied from 76 to 96% (Table 25c). In contrast, markedly lower encapsulation efficiency (41%) was observed for liposomes with lipid/drug ratios 5:1 (Table 25c).

Free (not encapsulated) doxorubicin. Free doxorubicin reflects concentration of not encapsulated drug that did not get encapsulated into liposomes during loading step or leaked from the liposome during the storage. It can be seen from the Table 25d that free doxorubicin content in formulations with lipid/drug ratios 20:1 to 100:1 was in the range from 0.01-0.03%, whereas increased levels of free doxorubicin (3.2%) were observed at 5:1 lipid/drug ratio. These data are in agreement with results obtained for Oxalate containing liposomes (Table 21) and indicate on evident leakage of doxorubicin at neutral pH from the liposomes made at lower than 20:1 lipid/drug ratios.

Figure 10:
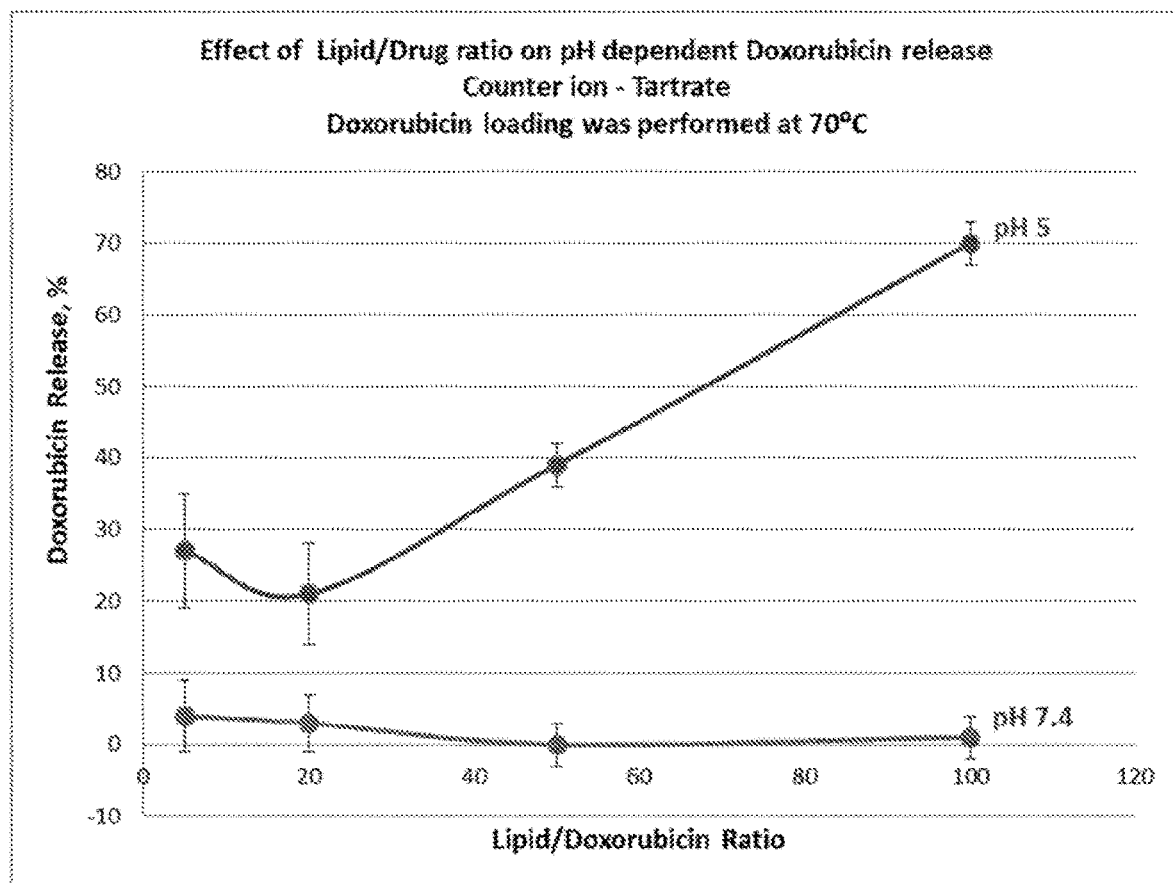
FIG. 10 is a graph showing effect of lipid/drug ratio on percent of release of intraliposomal doxorubicin into dissolution media at 8 hrs. Doxorubicin loading into tartrate-containing liposomes was performed at 70° C. Release experiment was carried out at 37° C. Release at pH 5.0—the top line. Release at pH 7.4—the bottom line. Each point on the curves represents mean±STD of data obtained in two to three independent experiments. For each experiment all the measurements were performed in sixtiplicate.

Liposomal doxorubicin release rate. Although doxorubicin release rate at pH 5 was higher compare to that at pH 7.4 for all formulations (Table 25e), the extra leakage at neutral pH was observed for formulations with lipid/drug ratios below 50:1. It is worth mentioning, however, that doxorubicin leakage at pH 7.4 was markedly less for Tartrate containing liposomes compared to that of oxalate containing liposomes (Table 21, 23, FIGS. 8 and 10).

Thus, the effect of lipid/drug ratio for both counter ions oxalate and tartrate was demonstrated. Performed studies suggest that optimal lipid/drug ratios are in the range from 20:1 to 50:1 in some embodiments. Other ratios that can be used include 20:1 to 100:1 in some other embodiments.

Example 7: Cold Loading of Doxorubicin into Oxalate- and Tartrate-Containing Liposomes: Variable Lipid/Drug Ratio The cold loading of doxorubicin into liposomes was performed as follows: saline solution of doxorubicin Hydrochloride was added to the liposomal nanosuspension at room temperature to the final concentration 0.5 or 1 mg/mL (i.e. 0.468 and 0.936 mg of doxorubicin free base per mL), gently inverted (2-3 times) and incubated at room temperature for 10-20 min. After 10-20 min of incubation at room temperature the mixture was: a) subjected to another TFF 5× cycle with PBS pH 7.4 containing 6% of Sucrose, and/or b) placed in 2-8° C. refrigerator for 16 hrs, and then subjected to another TFF 5× cycle with PBS pH 7.4 containing 6% of Sucrose. There was no notable difference observed between doxorubicin release profiles of the liposomes loaded at RT, or RT followed by 2-8° C. overnight incubation Data for RT followed by 2-8° C. overnight incubation not shown.

Formulation composition is shown in the Table 26.

TABLE 26

Formulation Composition.

Amounts of solids used in formulations, W/W, %

| Lot # | Counter Ion | PC | DMPC | FC | P 188 | Doxorubicin Hydrochloride | Ratios Lipid/Drug |
|---|---|---|---|---|---|---|---|
| 647-2-181 A | Oxalate | 66.0.5 | 16.51 | 11.56 | 4.95 | 0.88 | 100 |
| 647-2-163 B | Oxalate | 65.57 | 16.38 | 11.46 | 4.91 | 1.75 | 50 |
| 647-2-185 A | Oxalate | 63.68 | 15.92 | 11.14 | 4.78 | 4.48 | 20 |
| 647-2-185 C | Oxalate | 56.15 | 14.04 | 9.83 | 4.21 | 15.78 | 5 |
| 647-2-186 A | Tartrate | 66.0.5 | 16.51 | 11.56 | 4.95 | 0.88 | 100 |
| 647-2-170 B | Tartrate | 65.50 | 16.38 | 11.46 | 4.91 | 1.75 | 50 |
| 647-2-178 A | Tartrate | 63.68 | 15.92 | 11.14 | 4.78 | 4.48 | 20 |
| 647-2-178 C | Tartrate | 56.15 | 14.04 | 9.83 | 4.21 | 15.78 | 5 |

Coarse suspension was prepared and MF processed at 10 KPSI processing pressure. After 9-15 min of MF processing the particle size (Z-average) reached ~60-66 nm. A sample was collected and sterile filtered into Nalgene flask. The particle size of filtered nanosuspension was determined (Table 26a).

TABLE 26a

Summary of MF processing and resultant emulsion parameters.

| Lot # | Counter Ion | MFD | Lipid/Drug | Particle size Z avrg, nm |
|---|---|---|---|---|
| 647-2-181 A | Oxalate | 24 MAY 16 | 100 | 66 |
| 647-2-163 B | Oxalate | 24 MAY 16 | 50 | 66 |
| 647-2-185 A | Oxalate | 19 JUL 16 | 20 | 62 |
| 647-2-185 C | Oxalate | 19 JUL 16 | 5 | 63 |
| 647-2-186 A | Tartrate | 19 JUL 16 | 100 | 62 |
| 647-2-170 B | Tartrate | 23 JUN 16 | 50 | 63 |
| 647-2-178 A | Tartrate | 11 LUL 16 | 20 | 61 |
| 647-2-178 C | Tartrate | 11 LUL 16 | 5 | 61 |

The liposomes were subjected to TFF followed by remote loading with doxorubicin, and another TFF cycle with PBS sucrose. The particle size of doxorubicin loaded liposomes is presented in Table 26b.

TABLE 26b

Particle size of doxorubicin loaded liposomes.

| Lot # | Counter Ion | Loading Date | Lipid/Drug | Particle size Z avrg, nm |
|---|---|---|---|---|
| 647-2-181 A | Oxalate | 14 JUL 16 | 100 | 67 |
| 647-2-163 B | Oxalate | 10 JUN 16 | 50 | 67 |
| 647-2-185 A | Oxalate | 19 JUL 16 | 20 | 62 |
| 647-2-185 C | Oxalate | 19 JUL 16 | 5 | 62 |
| 647-2-186 A | Tartrate | 19 JUL 16 | 100 | 62 |
| 647-2-170 B | Tartrate | 23 JUN 16 | 50 | 63 |
| 647-2-178 A | Tartrate | 11 JUL 16 | 20 | 60 |
| 647-2-178 C | Tartrate | 11 JUL 16 | 5 | 65 |

Determination of doxorubicin in liposomal suspension. Followed doxorubicin loading liposomal suspension was subjected to 5×TFF to majorly remove free (not encapsulated) doxorubicin. To determine total doxorubicin concentration at T0 (within one week of MFD) TFF washed liposomes were diluted with methanol or IPA and subjected to HPLC analysis. Doxorubicin content, percent of recovery (doxorubicin content in liposomal suspension relative to doxorubicin free base concentration used for remote loading), and encapsulation efficiency (%) are presented in the Table 26c. Encapsulation efficiency (%) represents the difference between doxorubicin recovery (%) and free doxorubicin (%).

TABLE 26c

Total doxorubicin content and Encapsulation efficiency.

| | | | Doxorubicin | Assay, HPLC | | |
| Lot # | Counter Ion | Lipid/Drug | free base used for loading, μg/mL | Doxorubicin content (Liposomal Suspension) μg/mL | Recovery % | Encapsulated Doxorubicin, % [Recovery, %]-[Free, %] |
|---|---|---|---|---|---|---|
| 647-2-181 A | Oxalate | 100 | 468 | 425 | 91 | 91 |
| 647-2-163 B | Oxalate | 50 | 936 | 909 | 97 | 97 |
| 647-2-185 A | Oxalate | 20 | 936 | 892 | 95 | 95 |
| 647-2-185 C | Oxalate | 5 | 936 | 252 | 27 | 22 |
| 647-2-186 A | Tartrate | 100 | 468 | 388 | 83 | 83 |
| 647-2-170 B | Tartrate | 50 | 936 | 850 | 91 | 91 |
| 647-2-178 A | Tartrate | 20 | 936 | 850 | 91 | 91 |
| 647-2-178 C | Tartrate | 5 | 936 | 645 | 69 | 67 |

The amount of free doxorubicin was determined within one week of manufacturing (Table 26d).

TABLE 26d

Free doxorubicin content.

| Lot # | Counter Ion | Lipid/Drug | % of Total |
|---|---|---|---|
| 647-2-181 A | Oxalate | 100 | 0.07 |
| 647-2-163 B | Oxalate | 50 | 0.08 |
| 647-2-185 A | Oxalate | 20 | 0.01 |
| 647-2-185 C | Oxalate | 5 | 4.96 |
| 647-2-186 A | Tartrate | 100 | 0.01 |
| 647-2-170 B | Tartrate | 50 | 0.04 |
| 647-2-178 A | Tartrate | 20 | 0.01 |
| 647-2-178 C | Tartrate | 5 | 2.51 |

Liposomal doxorubicin release studies were carried out at 37° C. within one week after manufacturing (Table 26e). For each sample doxorubicin release was determined at 2, 4 and 8 hrs time points.

TABLE 26e

Doxorubicin release rate determined at 37° C.

| Lot # | Counter Ion | Lipid/Drug | pH 5, Release, % | | | pH 6.7, Release, % | | |
|---|---|---|---|---|---|---|---|---|
| | | | 2 hrs | 4 hrs | 8 hrs | 2 hrs | 4 hrs | 8 hrs |
| 647-2-181 A | Oxalate | 100 | 93 | 100 | 100 | 0 | 0 | 0 |
| 647-2-163 B | Oxalate | 50 | 92 | 100 | 100 | 0 | 0 | 0 |
| 647-2-185 A | Oxalate | 20 | 51 | 66 | 84 | 3 | 8 | 4 |
| 647-2-185 C | Oxalate | 5 | 40 | 49 | 60 | 3 | 8 | 11 |
| 647-2-186 A | Tartrate | 100 | 56 | 72 | 81 | 0 | 0 | 0 |
| 647-2-170 B | Tartrate | 50 | 63 | 89 | 100 | 0 | 0 | 0 |
| 647-2-178 A | Tartrate | 20 | 20 | 32 | 42 | 0 | 1 | 2 |
| 647-2-178 C | Tartrate | 5 | 13 | 18 | 24 | 0 | 2 | 4 |

Particle size. It can be seen from the Tables 26 and 26a that microfluidization of all specified liposomal formulations resulted in similar particle size. Doxorubicin loading resulted in only slight increase of particle size of some formulations.

Efficiency of doxorubicin encapsulation. Efficiency of doxorubicin encapsulation into Oxalate containing liposomes with lipid/drug ratios from 20:1 to 100:1 varied from 91 to 97% (Table 26c). In contrast, markedly lower encapsulation efficiency (22%) was observed for liposomes with lipid/drug ratio 5:1(Table 26c).

When tartrate was used as counter ion efficiency of doxorubicin encapsulation into liposomes with lipid/drug ratios from 20:1 to 100:1 varied from 83 to 91% (Table 26c), while lower encapsulation efficiency (67%) was observed for liposomes with lipid/drug ratio 5:1(Table 26c).

Free (not encapsulated) doxorubicin. Free doxorubicin reflects concentration of the drug that did not get encapsulated into liposomes during loading step or leaked from the liposome during the storage. It can be seen from the Table 26d that free doxorubicin content in oxalate containing liposomes with lipid/drug ratios 20:1 and 100:1 was in the range from 0.01-0.08%. Free doxorubicin content determined in formulations with 5:1 lipid/drug ratio was 4.96% (Table 26d).

When tartrate was used as counter ion free doxorubicin content of liposomes with lipid/drug ratios from 20:1 to 100:1 varied from 0.01 to 0.04% (Table 26d), while lower encapsulation efficiency and higher free doxorubicin content (2.51%) was observed for liposomes with lipid/drug ratio 5:1(Table 26d).

Liposomal Doxorubicin Release Rate.

Effect of the lipid/drug ratio. It can be seen from the Table 26e that for both counter ions doxorubicin release at pH 5 was dramatically higher compare to that at pH 7.4 for the formulations with lipid/drug ratios 50:1 and 100:1 (Table 26e, FIGS. 11-12). Moreover, doxorubicin leakage at pH 7.4 was fully suppressed (Table 26e, FIGS. 11-12).

At pH 5 doxorubicin release from the cold loaded oxalate-containing liposomes achieved ~100% at 2 hrs time point, and was doubled that of liposomes loaded at 70° C. (FIG. 13).

At pH 5 doxorubicin release from the cold loaded tartrate-containing liposomes achieved ~90-100% at 4 hrs time point, and was tripled that of liposomes loaded at 70° C. (FIG. 14).

Figure 13:
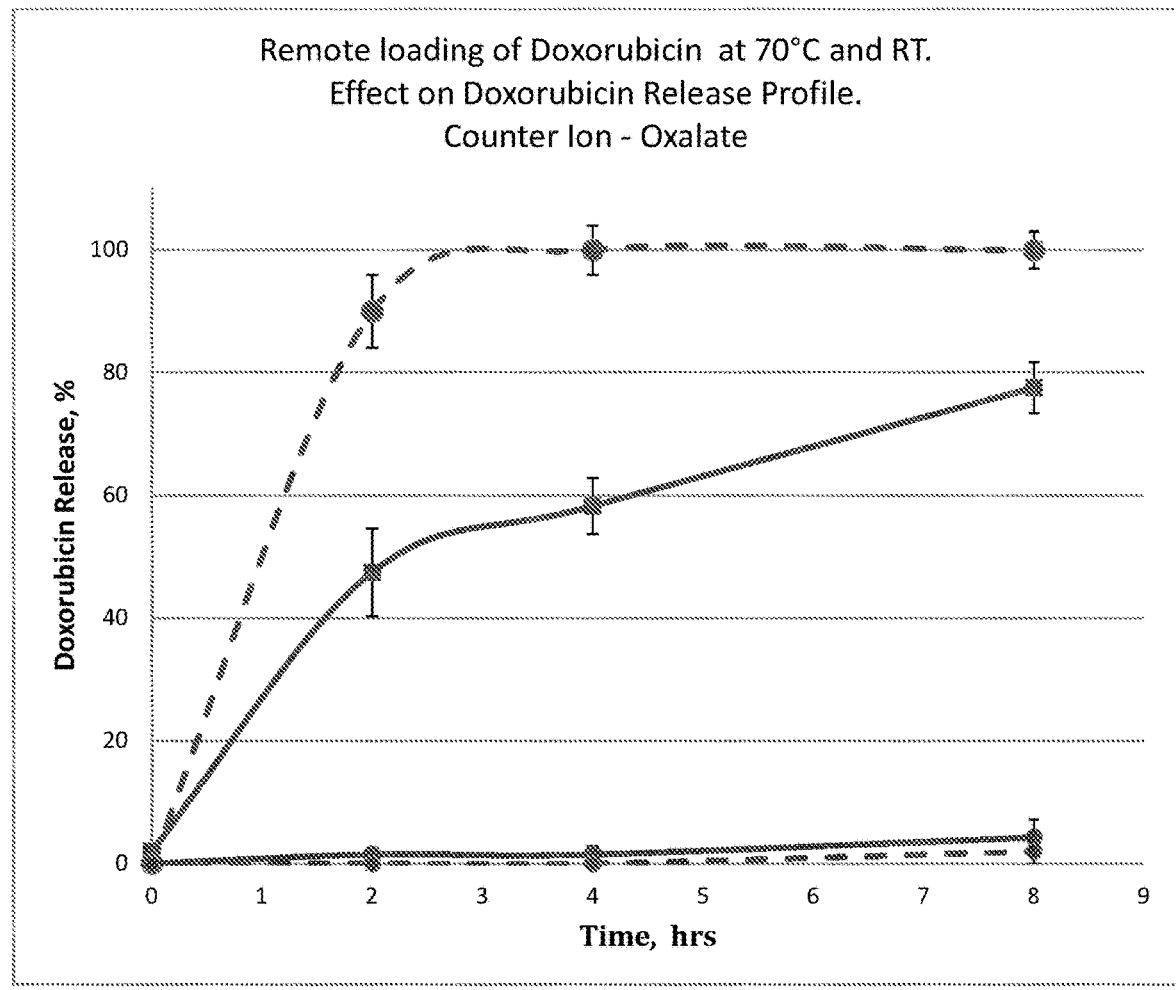
FIG. 13 is a graph showing effect of different loading temperature on percent of intraliposomal doxorubicin release into dissolution media determined at 37° C. Doxorubicin loading into oxalate-containing liposomes was performed at 70° C.: a) Release at pH 5.0 (the top solid line); b) Release at pH 7.4 (the bottom solid line); each point on the curves represents mean±STD of data obtained in four independent experiments. Doxorubicin loading oxalate-containing liposomes was performed at room temperature: c) Release at pH 5.0 (the top dotted line); Release at pH 7.4 (the bottom dotted line); each point on the curves represents mean±STD of data obtained in two independent experiments. For each experiment all the measurements were performed in sixtiplicate.
Figure 14:
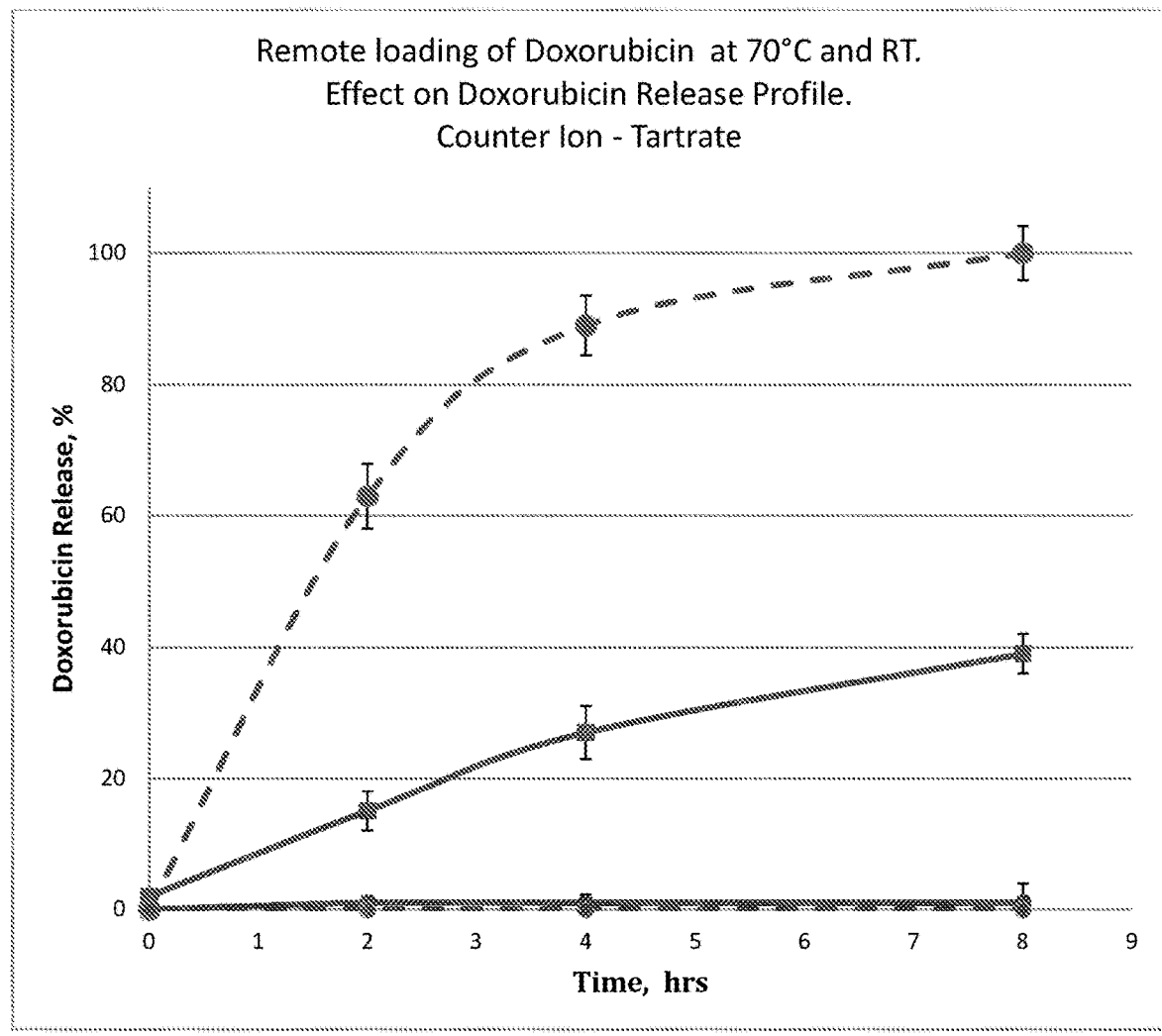
FIG. 14 is a graph showing effect of different loading temperature on percent of intraliposomal doxorubicin release into dissolution media determined at 37° C. Doxorubicin loading into tartrate-containing liposomes was performed at 70° C.: a) Release at pH 5.0 (the top solid line); b) Release at pH 7.4 (the bottom solid line); each point on the curves represents mean±STD of data obtained in two independent experiments. Doxorubicin loading into Tartrate-containing liposomes was performed at room temperature. c) Release at pH 5.0 (the top dotted line); Release at pH 7.4 (the bottom dotted line); each point on the curves represents mean±STD of data obtained in two independent experiments. For each experiment all the measurements were performed in sixtiplicate.

Surprisingly, when oxalate and/or tartrate were used as counter ions, cold loading (e.g. mixing at room temperature) further improved (maximized) ΔpH 7.4/5.0 release differential compared to liposomes loaded at 70° C. by markedly increasing drug release at pH 5 while suppressing its release at pH 7.4 (Table 26e and FIG. 13 and FIG. 14). At acidic pH doxorubicin release from the cold loaded oxalate-containing liposomes achieved ~100% at 2 hrs time point, and was doubled that of liposomes loaded at 70° C. (FIG. 13). Doxorubicin release from the cold loaded tartrate-containing liposomes achieved ~90% at 4 hrs (FIG. 14), and was triple that of the liposomes loaded at 70° C.

Interestingly, doxorubicin-citrate containing liposomes demonstrated low release rate at pH 5, although ΔpH 7.4/5.0 release differential was acceptable due to extremely low release at pH 7.4 (Table 13 and FIG. 3).

Figure 11:
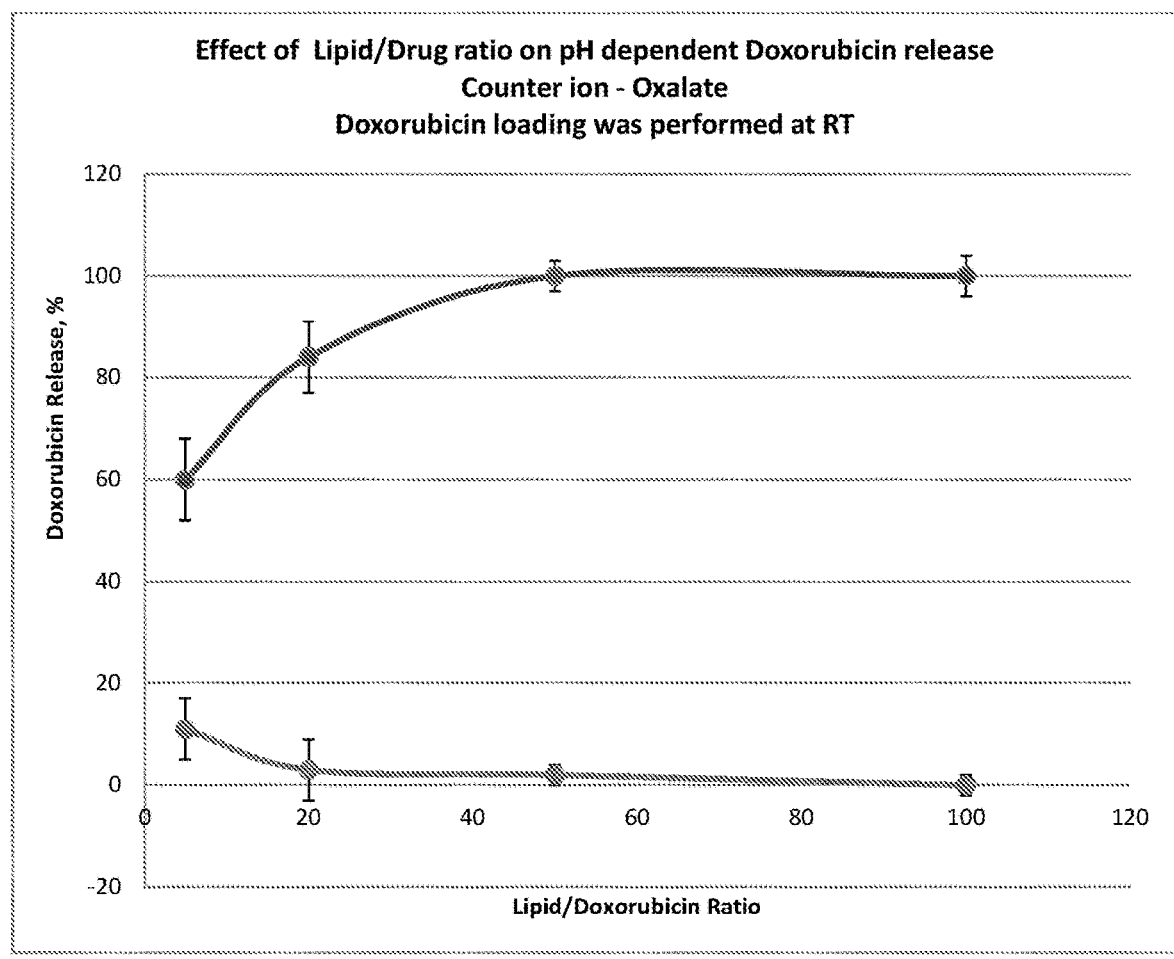
FIG. 11 is a graph showing effect of lipid/drug ratio on percent of release of intraliposomal doxorubicin into dissolution media at 8 hrs. Doxorubicin loading into oxalate-containing liposomes was performed at room temperature. Release experiment was carried out at 37° C. Release at pH 5.0—the top line. Release at pH 7.4—the bottom line. Each point on the curves represents mean±STD of data obtained in two to three independent experiments. For each experiment all the measurements were performed in sixtiplicate.
Figure 12:
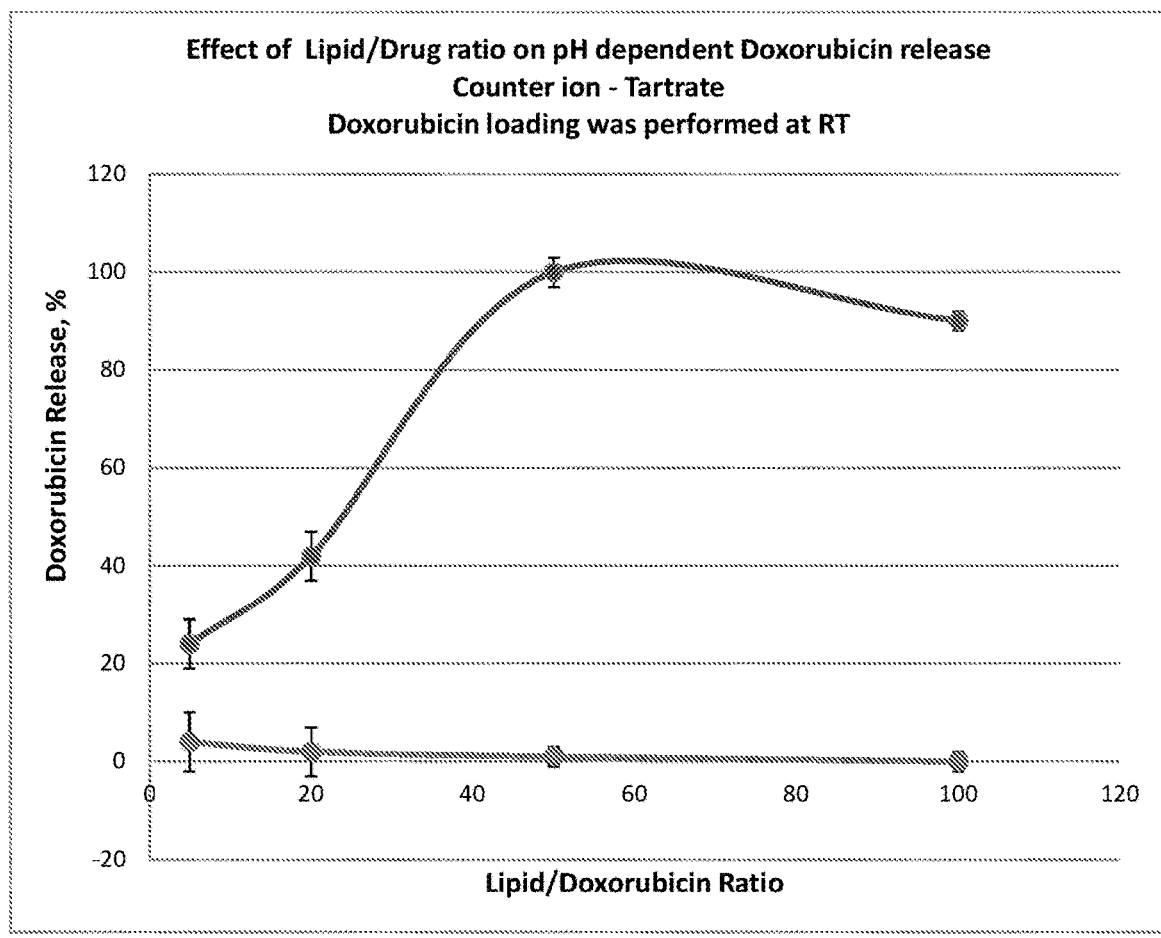
FIG. 12 is a graph showing effect of lipid/drug ratio on percent of release of intraliposomal doxorubicin into dissolution media at 8 hrs. Doxorubicin loading into Tartrate-containing liposomes was performed at room temperature. Release experiment was carried out at 37° C. Release at pH 5.0—the top line. Release at pH 7.4—the bottom line. Each point on the curves represents mean±STD of data obtained in two to three independent experiments. For each experiment all the measurements were performed in sixtiplicate.

In contrast, the formulations with lipid/drug ratios below 5:1 demonstrated poor ΔpH 7.4/5.0 release differential due to lower release at pH 5.0 and leakage of doxorubicin at pH 7.4 (Table 26e and FIGS. 11-12). It is worth mentioning, however, that tartrate containing liposomes at lower than 50:1 lipid/drug ratios demonstrated stronger suppression of doxorubicin leakage at neutral pH compared to oxalate liposomes (Table 26e and FIGS. 11-12).

Thus, in some embodiments, lipid to drug ratio for both counter ions oxalate and tartrate may play a role. Performed studies suggest that in some embodiments, optimal lipid to drug ratios can be in the range from 20:1 to 50:1 at least in some embodiments. Other ratios that can be used include 10:1 to 100:1 in some other embodiments in some other embodiments.

It has been also demonstrated that in some embodiments, cold loading of doxorubicin maximized ΔpH 7.4/5.0 release differential achieved with oxalate and tartrate as counter ions and 50:1 and 100:1 lipid/drug ratios. Other temperatures that can be used for remote doxorubicin loading in oxalate and tartrate include 2-8° C. to 70° C. in some other embodiments.

Example 8.1: Cold Loading of Lyophilized and Reconstituted Doxorubicin into Oxalate and/or Tartrate Containing Liposomes Lyophilization. Doxorubicin-hydrochloride was dissolved to the final concentration of 6 mg/mL in sterile water for injection containing 6% sucrose, or 4% mannitol, or 1% lactose, or 3% lactose, sterile filtered, aseptically filled in 2 mL vials (1 mL fill volume), and lyophilized in VirTis Genesis SQ25EL lyophilizer. Vials containing doxorubicin solution were transferred to a pre-frozen to −40° C. lyophilizer and allowed to freeze overnight (16) hrs. After 16 hrs the vacuum was turned on and the temperature was increased to −32° C. at a temperature rump up rate 1° C./4 min. After 24 hrs of lyophilization at 32° C. the temperature was further increased to 20° C. at a temperature ramp up rate 1° C./20 min. Vials were stoppered under vacuum.

Remote Loading:

Lyophilized material was reconstituted in sterile water for injection to the final concentration 6 mg/mL and 0.4 mL of reconstituted material (~2.24 mg of doxorubicin free base) were added to 2 mL of the liposomal nanosuspension at room temperature to the final concentration 0.936 mg/mL of doxorubicin free base, gently inverted (2-3 times) and incubated at room temperature for 10 min.

Formulation composition is shown in the Table 27.

TABLE 27

Formulation composition.

| Lot # | Counter Ion | Amounts of solids used in formulations, W/W, % | | | | | Ratios Lipid/Drug |
|---|---|---|---|---|---|---|---|
| | | PC | DMPC | FC | P 188 | Doxorubicin Hydrochloride | |
| 647-2-196 | Oxalate | 65.44 | 16.36 | 11.45 | 4.91 | 1.84 | 50 |
| 647-2-198 | Tartrate | 65.44 | 16.36 | 11.45 | 4.91 | 1.84 | 50 |

Coarse suspension was prepared and MF processed at 10 KPSI processing pressure. After 9-15 min of MF processing the particle size (Z-average) reached ~60-70 nm. A sample was collected and sterile filtered into Nalgene flask. The particle size of filtered nanosuspension was determined (Table 27a).

TABLE 27a

Summary of MF processing and resultant emulsion parameters.

| Lot # | Counter Ion | MFD | Lipid/Drug Ratio | Particle size Z avrg, nm |
|---|---|---|---|---|
| 647-2-196 | Oxalate | 5 AUG 16 | 50 | 64 |
| 647-2-198 | Tartrate | 9 AUG 16 | 50 | 65 |

The liposomes were subjected to TFF followed by remote loading with doxorubicin at RT for 10 min. The particle size of doxorubicin loaded liposomes is presented in Table 27b.

TABLE 27b

Particle size of doxorubicin loaded liposomes.

| Lot # | Counter Ion | Cryoprotectant used for doxolubicin lyophilization | MFD | Lipid/Drug | Particle size Z avrg, nm |
|---|---|---|---|---|---|
| 647-2-196 A | Oxalate | Mannitol, 4% | 12 AUG 16 | 50 | 64 |
| 647-2-196 B | Oxalate | Lactose, 1% | 12 AUG 16 | 50 | 64 |
| 647-2-196 C | Oxalate | Lactose, 3% | 12 AUG 16 | 50 | 64 |
| 647-2-198 A | Tartrate | Mannitol, 4% | 12 AUG 16 | 50 | 65 |
| 647-2-198 B | Tartrate | Lactose, 1% | 12 AUG 16 | 50 | 65 |
| 647-2-198 C | Tartrate | Lactose, 3% | 12 AUG 16 | 50 | 65 |

The amount of free (not encapsulated) doxorubicin was determined within one week of manufacturing (Table 27c).

TABLE 27c

Free doxorubicin content.

| Lot # | Counter Ion | Cryoprotectant used for doxolubicin lyophilization | % of Total |
|---|---|---|---|
| 647-2-196 A | Oxalate | Mannitol, 4% | 0.23 |
| 647-2-196 B | Oxalate | Lactose, 1% | 0.24 |
| 647-2-196 C | Oxalate | Lactose, 3% | 0.24 |
| 647-2-198 A | Tartrate | Mannitol, 4% | 0.14 |
| 647-2-198 B | Tartrate | Lactose, 1% | 0.18 |
| 647-2-198 C | Tartrate | Lactose, 3% | 0.17 |

Determination of doxorubicin in liposomal suspension. No second TFF was performed followed the doxorubicin loading step. To determine total doxorubicin concentration at T0 (within one week of MFD) doxorubicin loaded liposomes were diluted with methanol or IPA and subjected to HPLC analysis. Doxorubicin content, percent of recovery (doxorubicin content in liposomal suspension relative to doxorubicin free base concentration used for remote loading), and encapsulation efficiency (%) are presented in the Table 27d. Encapsulation efficiency (%) represents the difference between doxorubicin recovery (%) and free doxorubicin (%).

TABLE 27d

Total doxorubicin content and Encapsulation efficiency.

| | | | | Assay, HPLC | | |
|---|---|---|---|---|---|---|
| Lot # | Counter Ion | Cryoprotectant | Doxorubicin free base used for loading, µg/mL | Doxorubicin content (Liposomal Suspension) µg/mL | Recovery % | Encapsulated doxorubicin, % |
| 647-2-196 A | Oxalate | Mannitol, 4% | 936 | 936 | 100 | 100 |
| 647-2-196 B | Oxalate | Lactose, 1% | 936 | 936 | 100 | 100 |
| 647-2-196 C | Oxalate | Lactose, 3% | 936 | 934 | 97 | 97 |
| 647-2-198 A | Tartrate | Mannitol, 4% | 936 | 934 | 97 | 97 |
| 647-2-198 B | Tartrate | Lactose, 1% | 936 | 936 | 100 | 100 |
| 647-2-198 C | Tartrate | Lactose, 3% | 936 | 936 | 100 | 100 |

Liposomal doxorubicin release studies were carried out at 37° C. within one week after manufacturing (Table 27e). For each sample doxorubicin release was determined at 2, 4 and 8 hrs time points.

TABLE 27e

Doxorubicin release rate determined at 37° C.

| | | | pH 5, Release, % | | | pH 6.7, Release, % | | |
|---|---|---|---|---|---|---|---|---|
| Lot # | Counter Ion | Cryoprotectant used for doxolubicin lyophilization | 2 hrs | 4 hrs | 8 hrs | 2 hrs | 4 hrs | 8 hrs |
| 647-2-196 A | Oxalate | Mannitol, 4% | 92 | 98 | 100 | 0 | 0 | 0 |
| 647-2-196 B | Oxalate | Lactose, 1% | 88 | 100 | 100 | 0 | 0 | 0 |
| 647-2-196 C | Oxalate | Lactose, 3% | 97 | 100 | 100 | 0 | 0 | 0 |
| 647-2-198 A | Tartrate | Mannitol, 4% | 33 | 54 | 74 | 0 | 0 | 0 |
| 647-2-198 B | Tartrate | Lactose, 1% | 28 | 50 | 70 | 0 | 0 | 0 |
| 647-2-198 C | Tartrate | Lactose, 3% | 31 | 53 | 72 | 0 | 0 | 0 |

Lyophilized doxorubicin product. Lyophilized doxorubicin water solution containing Mannitol or Lactose resulted in readily (i.e. instantly) reconstitutable doxorubicin product. In contrast, lyophilization in presence of 6% sucrose yielded not readily reconstitutable material. Therefore, lyophilized doxorubicin product containing 6% sucrose was not considered for further development and was not used in loading experiments.

Particle size. It can be seen from the Tables 27 and 27a that microfluidization of liposomal formulations resulted in similar particle size. Doxorubicin loading did not affect the particle size of the liposomes independent of counter ion and cryoprotectant (Table 27b).

Free (not encapsulated) doxorubicin. Free doxorubicin reflects concentration of the drug that did not get encapsulated into liposomes during loading step or leaked from the liposome during the storage. It can be seen from the Table 27c that free doxorubicin content in Oxalate containing liposomes was ~0.24%. When Tartrate was used as counter ion free doxorubicin content in the liposomal suspension was in the range from 0.14 to 0.18% (Table 27d).

Efficiency of doxorubicin encapsulation. Efficiency of doxorubicin encapsulation was from 97 to 100% (considering the levels of free doxorubicin) independently of counter ion and cryoprotectant (Table 27d).

Liposomal doxorubicin release rate. Cold (room temperature) loading of lyophilized and reconstituted doxorubicin into oxalate and/or tartrate containing liposomes resulted in rapid (within 10 min) encapsulation of the doxorubicin. Liposomal doxorubicin product demonstrated exceptional ΔpH 7.4/5.0 release differential with high release of doxorubicin at pH 5; while doxorubicin release at pH 7.4 was fully suppressed (Table 27e).

Thus, successful lyophilization of the doxorubicin that results in readily reconstitutable at RT in water for injection lyophilized product, unique ability of our novel liposomes to rapidly encapsulate reconstituted doxorubicin product at RT, and provide exceptional ΔpH7.4/5.0 release differential were demonstrated.

Overall, stability of liposomal doxorubicin products depends on both the stability of the liposomes and the stability of the drug product inside the liposomes. Lyophilized and readily reconstitutable at RT doxorubicin, and the capability of oxalate- or tartrate-containing liposomes to rapidly load doxorubicin at RT address these potential stability issues, while also providing superior release profiles. This finding leads to particular product presentation format consisting of two vials: a vial with lyophilized doxorubicin and a vial with liposomal vehicle suspension. Mixing (via simple inversion) the reconstituted content of two vials at room temperature will yield the final ready-for-use product within minutes.

Product Stability. The both suspension of doxorubicin free oxalate- or tartrate-containing liposomes (vehicle) and lyophilized doxorubicin were stable when stored at 2-8° C. and RH for at least 6 months. Six month time point represents last stability testing performed for the formulations described in Section 8.1. The vehicle was loaded with lyophilized and reconstituted doxorubicin and stability testing at included: HPLC assay of lyophilized and reconstituted doxorubicin material (98±2,%), efficiency of doxorubicin encapsulation into liposomes (98±2,%), determination of free (not encapsulated) doxorubicin (0.1-1%), particle size (Zavrg=63-68 nm), pH (7.2-7.4), and ΔpH7.4/5.0 doxorubicin release differential was close to 100%. Moreover, older batch (647-1-190) of oxalate-containing liposomes (vehicle) stored at 2-8° C. and RH showed acceptable stability for at least 18 months with no notable changes observed in above described parameters. Development of lyophilized liposomal vehicle is also considered.

Example 8.2: Comparison of Different Counter Ions at Fixed 50:1 Lipid/Drug Ratio: Cold Loading Hydration media used:
a) 300 mM solution of the following ammonium salts: ammonium-oxalate, or ammonium-sulfate, or ammonium-phosphate, or ammonium-citrate.
b) tartaric acid, ascorbic acid, or N-acetyl L cysteine (NAC) were first titrated with ammonium hydroxide to pH 4.8-5.0 and then used as hydration media.

Formulation composition is shown in Table 27. All formulations were prepared at 50:1 fixed lipid/drug ratio (Table 28)

The data for NAC are not shown since no doxorubicin loading was observed and liposomal material precipitated after overnight storage at 2-8° C.

TABLE 28

Formulation Composition.

Amounts of solids used in formulations, W/W, %

| Lot # | Counter Ion | PC | DMPC | FC | P 188 | Doxorubicin Hydrochloride | Lipid/Drug |
|---|---|---|---|---|---|---|---|
| 647-2-169 B | Sulfate | 65.50 | 16.38 | 11.46 | 4.91 | 1.75 | 50 |
| 647-2-163 B | Oxalate | 65.50 | 16.38 | 11.46 | 4.91 | 1.75 | 50 |
| 647-2-169 C | Phosphate | 65.50 | 16.38 | 11.46 | 4.91 | 1.75 | 50 |
| 647-2-170 B | Tartrate | 65.50 | 16.38 | 11.46 | 4.91 | 1.75 | 50 |
| 647-2-169 D | Citrate | 65.50 | 16.38 | 11.46 | 4.91 | 1.75 | 50 |
| 647-2-164 B | Ascorbate | 65.50 | 16.38 | 11.46 | 4.91 | 1.75 | 50 |

Coarse suspension was prepared and MF processed. After 9-12 min of MF processing the particle size (Z-average) reached ~60-75 nm. A sample was collected and sterile filtered into Nalgene flask. Then liposomes were subjected to TFF followed by remote loading with doxorubicin, and another TFF cycle with PBS sucrose. Particle size of the Microfluidized liposomal material was similar to that shown herein.

Doxorubicin hydrochloride concentration used for remote loading: 1.0 mg/mL (doxorubicin free base concentration: 0.936 mg/mL).

The cold loading of doxorubicin into liposomes was performed as follows: Saline solution of doxorubicin Hydrochloride (6 mg/mL) was added to the liposomal nanosuspension at room temperature to the final concentration 1 mg/mL (i.e. 0.936 mg of doxorubicin free base per mL), gently inverted (2-3 times) and incubated at room temperature for 10-20 min. After 10-20 min of incubation at room temperature the mixture was: a) subjected to another TFF 5× cycle with PBS pH 7.4 containing 6% of Sucrose, and/or b) placed in 2-8° C. refrigerator for 16 hrs, and then subjected to another TFF 5× cycle with PBS pH 7.4 containing 6% of Sucrose. There was no notable difference observed between doxorubicin release profiles of the liposomes loaded at RT, or RT followed by 2-8° C. overnight incubation. Data for RT followed by 2-8° C. overnight incubation are not shown.

The particle size of doxorubicin loaded Liposomes is presented in Table 28a.

TABLE 28a

Particle size of doxorubicin loaded liposomes.

| Lot # | Counter Ion | Loading Date | Particle size Z avrg, nm |
|---|---|---|---|
| 647-2-169 B | Sulfate | 17 JUN 16 | 62 |
| 647-2-163 B | Oxalate | 10 JUN 16 | 67 |
| 647-2-169 C | Phosphate | 17 JUN 16 | 62 |
| 647-2-170 B | Tartrate | 23 JUN 16 | 63 |
| 647-2-169 D | Citrate | 17 JUN 16 | 61 |
| 647-2-164 B | Ascorbate | 15 JUN 16 | 67 |

Determination of doxorubicin in liposomal suspension. Followed doxorubicin loading liposomal suspension was subjected to 5×TFF to majorly remove free (not encapsulated) doxorubicin. To determine total doxorubicin concentration at T0 (within one week of MFD) TFF washed liposomes were diluted with methanol or IPA and subjected to HPLC analysis. Doxorubicin content, percent of recovery (doxorubicin content in liposomal suspension relative to doxorubicin free base concentration used for remote loading), and encapsulation efficiency (%) are presented in the Table 28b. Encapsulation efficiency (%) represents the difference between doxorubicin recovery (%) and free doxorubicin (%).

TABLE 28b

Total doxorubicin content and Encapsulation efficiency.

| Lot # | Counter Ion | Doxorubicin free base used for loading, µg/mL | Assay, HPLC Doxorubicin content (Liposomal Suspesion) µg/mL | Recovery, % | Encapsulated doxorubicin, % [Recovery, %]-[Free, %] |
|---|---|---|---|---|---|
| 647-2-169 B | Sulfate | 936 | 828 | 88 | 88 |
| 647-2-163 B | Oxalate | 936 | 909 | 97 | 97 |
| 647-2-169 C | Phosphate | 936 | 725 | 78 | 78 |
| 647-2-170 B | Tartrate | 936 | 850 | 91 | 91 |
| 647-2-169 D | Citrate | 936 | 853 | 91 | 91 |
| 647-2-164 B | Ascorbate | 936 | 822 | 88 | 86 |

The amount of free doxorubicin was determined within one week of manufacturing (Table 28c).

TABLE 28c

Free doxorubicin content.

| Lot # | Counter Ion | % of Total |
|---|---|---|
| 647-2-169 B | Sulfate | 0.01 |
| 647-2-163 B | Oxalate | 0.08 |
| 647-2-169 C | Phosphate | 0.01 |
| 647-2-170 B | Tartrate | 0.04 |
| 647-2-169 D | Citrate | 0.01 |
| 647-2-164 B | Ascorbate | 1.85 |

Liposomal doxorubicin release studies were carried out at 37° C. (Table 28d). For each sample doxorubicin release was determined at 2, 4 and 8 hrs time points.

TABLE 28d

Doxorubicin release rate determined at 37° C.

| Lot# | Counter Ion | Pka1 | pH 5, Release, % | | | pH 7.4, Release, % | | |
|---|---|---|---|---|---|---|---|---|
| | | | 2 hrs | 4 hrs | 8 hrs | 2 hrs | 4 hrs | 8 hrs |
| 647-2-169 B | Sulfate | −3 | 2 | 1 | 2 | 0 | 0 | 0 |
| 647-2-163 B | Oxalate | 1.27 | 92 | 100 | 100 | 0 | 0 | 2 |
| 647-2-169 C | Phosphate | 1.96 | 2 | 2 | 2 | 0 | 0 | 0 |
| 647-2-170 B | Tartrate | 3.03 | 63 | 89 | 100 | 0 | 0 | 0 |
| 647-2-169 D | Citrate | 3.13 | 19 | 33 | 44 | 0 | 0 | 0 |
| 647-2-164 B | Ascorbate | 4.17 | 97 | 97 | 100 | 58 | 66 | 69 |

Particle size. Microfluidization of different liposomal formulation resulted in similar particle sizes closely resembling to that shown herein. Cold doxorubicin loading resulted in slightly less increase of particle size (except ascorbate-containing liposomes) compared to the liposomes loaded with doxorubicin at 70° C. (Table 28a and Table 8).

Efficiency of doxorubicin encapsulation. Efficiency of doxorubicin encapsulation for the most of the formulas varied from 86 to 97%, except phosphate containing liposomes that showed 78% of doxorubicin recovery (Table 27b). The most efficient encapsulation was observed when oxalate was used as a counter ion, and least efficient with phosphate (Table 28b).

Free (not encapsulated) doxorubicin. Free doxorubicin reflects concentration of not encapsulated drug determined at T0 (within one week after manufacturing). It can be seen from the Table 27c that free doxorubicin content for all formulations (but Ascorbate) was in the range from 0.01-0.08%. Doxorubicin-ascorbate containing liposomes demonstrated markedly higher leakage of free doxorubicin (Table 28c).

Liposomal doxorubicin release rate. Drug release studies were carried out at 37° C.

Cold loading of doxorubicin resulted in some improvement of ΔpH7.4/5.0 release differential for citrate (Table 28d, FIG. 15), marked improvement of ΔpH7.4/5.0 release differential for oxalate, and major improvement for tartrate (Table 28d, FIG. 15) compared to the liposomes loaded with doxorubicin at 70° C. (Table 13, FIG. 3).

Doxorubicin-sulfate and -phosphate containing liposomes retained poor ΔpH 7.4/5.0 release differential (Table 28d, FIG. 15) due to low release at both pH. Although doxorubicin-ascorbate containing liposomes demonstrated high doxorubicin release at pH 5, the ΔpH 7.4/5.0 release differential was very poor due to high release/leakage of the doxorubicin at pH 7.4 (Table 28d, FIG. 15) that defeats the purpose of doxorubicin encapsulation, and will compromise product stability and in vivo performance.

Figure 15:
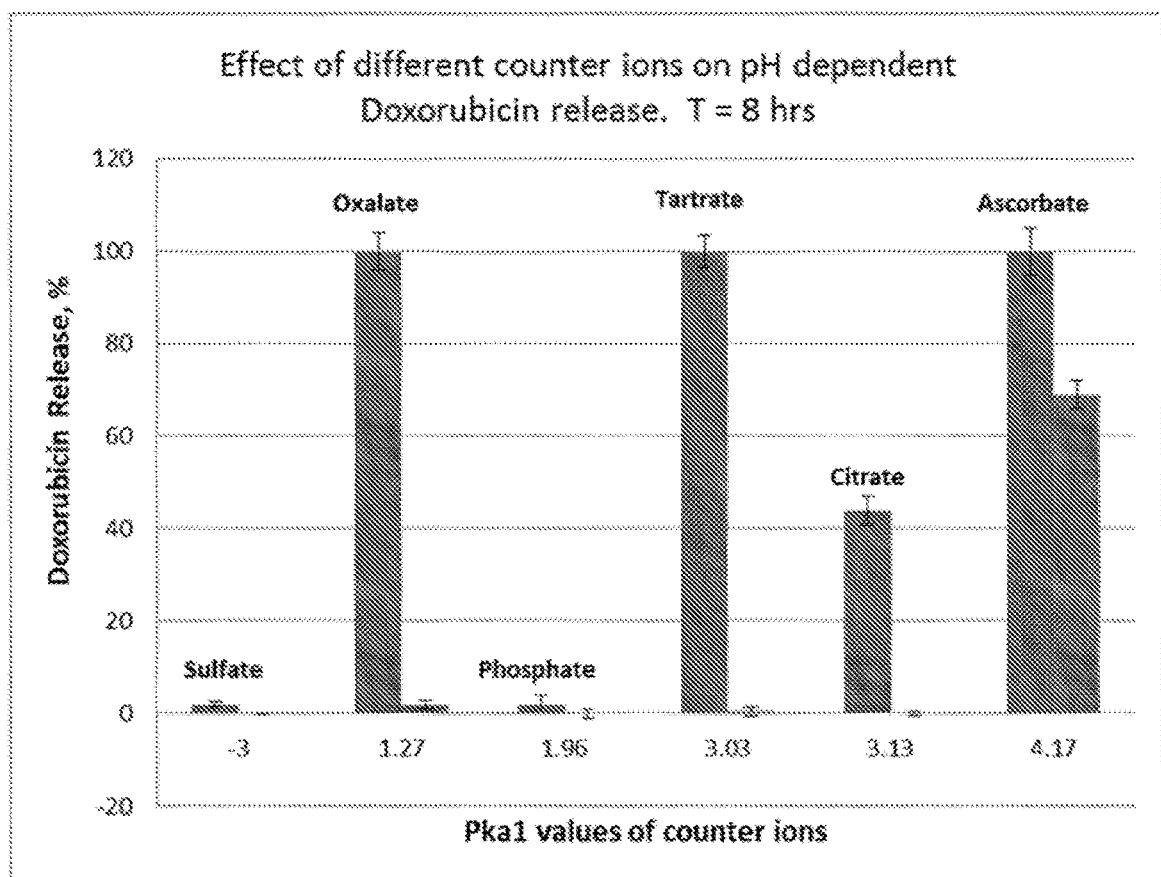
FIG. 15 is a graph showing percent of intraliposomal doxorubicin release into dissolution media after 8 hrs incubation at 37° C. Doxorubicin loading into liposomes was performed at room temperature. Left-side bars of each pair—release at pH 5; right-side bars of each pair—release at pH 7.4. Each point on the curves represents mean±STD of data obtained in 2-3 independent experiments. For each experiment all the measurements were performed in sixtiplicate.

Thus, when oxalate or tartrate were used as a counter ions the difference between doxorubicin release at pH 5 and pH 7.4 was markedly higher compare to other used counter ions regardless of the loading conditions (Table 13, FIG. 3 and Table 28d, FIG. 15). It is worth mentioning, however, that cold loading further improved ΔpH 7.4/5.0 release differential for doxorubicin-oxalate and -tartrate containing liposomes relative to same liposomal formulations that were loaded at 70° C. The observed difference suggests uniqueness of physical state(s) of doxorubicin-oxalate or -tartrate aggregates at 37° C. that may facilitate their dissolution in response to the temperature and pH.

Example 8.3: Cold Loading of Doxorubicin into Oxalate or Tartrate, or Citrate Containing Liposomes This example provides (i) further characterization regarding pH dependent doxorubicin release at pH 7.4, 6.7, 6.0, and 5.0 and (ii) effect of lipid/drug and phospholipid/free cholesterol (PL/FC) ratios on pH dependent doxorubicin release. Comparison was made with Myocet-like formulation ("Myocet", doxorubicin-citrate) and Doxil® (doxorubicin-sulfate).

Oxalate-, tartrate-, and citrate-containing liposomes (vehicle) were prepared and loaded with doxorubicin hydrochloride as described in Methods and section 8.1 to the final concentration of 1 mg/mL. The various lipid/drug and phospholipid/free cholesterol (PL/FC) ratios were achieved by adjusting relative amounts of phospholipid and/or free cholesterol (Table 28e) and/or through respective dilutions of the liposomes before loading with doxorubicin. In the Tables 28e-28h "lipid/drug" represents weight/weight (w/w) ratio of total lipids to doxorubicin free base in final suspension of doxorubicin loaded liposomes. "PL/FC" represents mol/mol ratio of phospholipids (PL) to free cholesterol (FC) in final suspension of doxorubicin loaded liposomes.

Commercial Doxil® and Myocet-like ("Myocet") liposomes were used as comparators. Myocet-like ("Myocet") liposomes were prepared by hydrating lipid film containing 6.9g of PC and 2.84g of FC (55/45 molar ratio) with 100 mL of 0.3M citric Acid pH 4.0 at 65° C. Microfluidization and TFF were performed as described in Methods and section 8.1. The resultant liposomes were sterile filtered. 1.9 mL aliquot was taken and loaded with 50 mg of doxorubicin in total 25 mL of loading media at 70° C. according to the protocol described in Myocet package insert. Detailed formulation composition is presented in the Table 28e.

TABLE 28e

Formulation Composition.

| | | Amounts of solids used in formulations, W/W, % | | | | | | |
|---|---|---|---|---|---|---|---|---|
| Lot # | Counter Ion | PC | DMPC | FC | P 188 | Doxorubicin Hydrochloride | Lipid/Drug w/w | PL/FC, mol/mol |
| 761-1-36 | Oxalate | 65.50 | 16.38 | 11.46 | 4.91 | 1.75 | 50 | 3.68 |
| 761-1-55 | Oxalate | 57.91 | 14.48 | 21.72 | 4.34 | 1.54 | 58 | 1.72 |
| 761-1-63 | Oxalate | 54.01 | 13.50 | 27.00 | 4.05 | 1.44 | 63 | 1.29 |
| 761-1-63-23 | Oxalate | 52.61 | 13.13 | 26.31 | 3.94 | 4.00 | 23 | 1.29 |
| 761-1-63-16 | Oxalate | 51.70 | 12.93 | 25.85 | 3.87 | 5.65 | 16 | 1.29 |
| 761-1-64 | Oxalate | 47.58 | 11.90 | 35.69 | 3.57 | 1.27 | 68 | 0.86 |
| 761-1-37 | Tartrate | 65.50 | 16.38 | 11.46 | 4.91 | 1.75 | 50 | 3.68 |
| 761-1-38 | Citrate | 65.50 | 16.38 | 11.46 | 4.91 | 1.75 | 50 | 3.68 |
| 761-1-69 "Myocet" | Citrate | 54.99 | N/A | 22.63 | N/A | 22.38 | 3.5 | 1.22 |
| | | DSPE-PEG | HSPC | FC | P188 | Doxorubicin | | |
| Doxil ® | Sulfate | 17.76 | 53.34 | 17.76 | N/A | 11.14 | 8.0 | 1.62 |

PL—Phospholipid,
FC—Free Cholesterol.

Doxorubicin release testing was carried out at 20× (Table 28f) and 50× (Table 28g) dilutions in the dissolution media.

TABLE 28f

Doxorubicin release rate determined after 8 hrs of incubation in dissolution medias pH 6.7, 6.7, 6.0, and 5.0 at 37° C. Dilution in the dissolution media = 20X.

| | | Lipid/ | | | Doxorubicin Release, % | | |
|---|---|---|---|---|---|---|---|
| Lot # | Counter Ion | Drug w/w | PL/FC, mol/mol | pH 6.7 | pH 6.7 | pH 6.0 | pH 5.0 |
| 761-1-36 | Oxalate | 50 | 3.68 | 0 | 35 | 88 | 100 |
| 761-1-55 | Oxalate | 58 | 1.72 | 0 | 35 | 64 | 100 |

TABLE 28f-continued

Doxorubicin release rate determined after 8 hrs of incubation in dissolution medias pH 6.7, 6.7, 6.0, and 5.0 at 37° C. Dilution in the dissolution media = 20X.

| Lot # | Counter Ion | Drug w/w | Lipid/ PL/FC, mol/mol | pH 6.7 | Doxorubicin Release, % pH 6.7 | pH 6.0 | pH 5.0 |
|---|---|---|---|---|---|---|---|
| 761-1-63 | Oxalate | 63 | 1.29 | 0 | 25 | 64 | 100 |
| 761-1-63-23 | Oxalate | 23 | 1.29 | 0 | 15 | 50 | 80 |
| 761-1-63-16 | Oxalate | 16 | 1.29 | 0 | 10 | 40 | 70 |
| 761-1-64 | Oxalate | 68 | 0.86 | 0 | 5 | 54 | 100 |
| 761-1-37 | Tartrate | 50 | 3.68 | 0 | 7 | 40 | 81 |
| 761-1-38 | Citrate | 50 | 3.68 | 0 | 3 | 12 | 44 |
| 761-1-69 "Myocet" | Citrate | 3.5 | 1.22 | 0 | 0 | 5 | 15 |
| Doxil ® | Sulfate | 8.0 | 1.62 | 0 | 0 | 2 | 3 |

TABLE 28g

Doxorubicin release rate determined after 8 hrs of incubation in dissolution medias pH 6.7, 6.7, 6.0, and 5.0 at 37° C. Dilution in the dissolution media = 50X.

| Lot # | Counter Ion | Drug w/w | Lipid/ PL/FC, mol/mol | pH 6.7 | Doxorubicin Release, % pH 6.7 | pH 6.0 | pH 5.0 |
|---|---|---|---|---|---|---|---|
| 761-1-36 | Oxalate | 50 | 3.68 | 0 | 40 | 93 | 100 |
| 761-1-55 | Oxalate | 58 | 1.72 | 0 | 39 | 95 | 100 |
| 761-1-63 | Oxalate | 63 | 1.29 | 0 | 36 | 95 | 100 |
| 761-1-63-23 | Oxalate | 23 | 1.29 | 4 | 30 | 80 | 100 |
| 761-1-63-16 | Oxalate | 16 | 1.29 | 6 | 25 | 70 | 100 |
| 761-1-64 | Oxalate | 68 | 0.86 | 0 | 19 | 77 | 100 |
| 761-1-37 | Tartrate | 50 | 3.68 | 0 | 14 | 60 | 100 |
| 761-1-38 | Citrate | 50 | 3.68 | 0 | 7 | 25 | 68 |
| 761-1-69 "Myocet" | Citrate | 3.5 | 1.22 | 0 | 5 | 13 | 23 |
| Doxil ® | Sulfate | 8.0 | 1.62 | 0 | 0 | 3 | 6 |

Effect of counter ions. It can be seen from the Tables 28f, 28g, and FIGS. 16-17 that doxorubicin-Oxalate containing liposomes demonstrated the highest ΔpH (7.4/6.7/6.0/5.0) doxorubicin release differential at both 20× and 50× dilutions when compared with doxorubicin-tartrate and doxorubicin-citrate containing liposomes made with the same (50/1) lipid/drug ratio. It is worth mentioning that pH dependent doxorubicin release from doxorubicin-oxalate containing liposomes (Table 28f, 28g, FIGS. 16, and 17) and in slightly lesser extent of doxorubicin-tartrate liposomes is in line with physiological pH gradient that occurs in vivo (FIG. 1) indicating pH targeting capability of our liposomal delivery system. Markedly lower ΔpH (7.4/6.7/6.0/5.0) doxorubicin release differential was observed for the "Myocet" at both 20× and 50× dilutions (Table 28f, 28g, FIGS. 16-17). ΔpH (7.4/6.7/6.0/5.0) doxorubicin release differential of Doxil® was close to zero (Table 28f, 28g, FIGS. 16-17).

Figure 18:
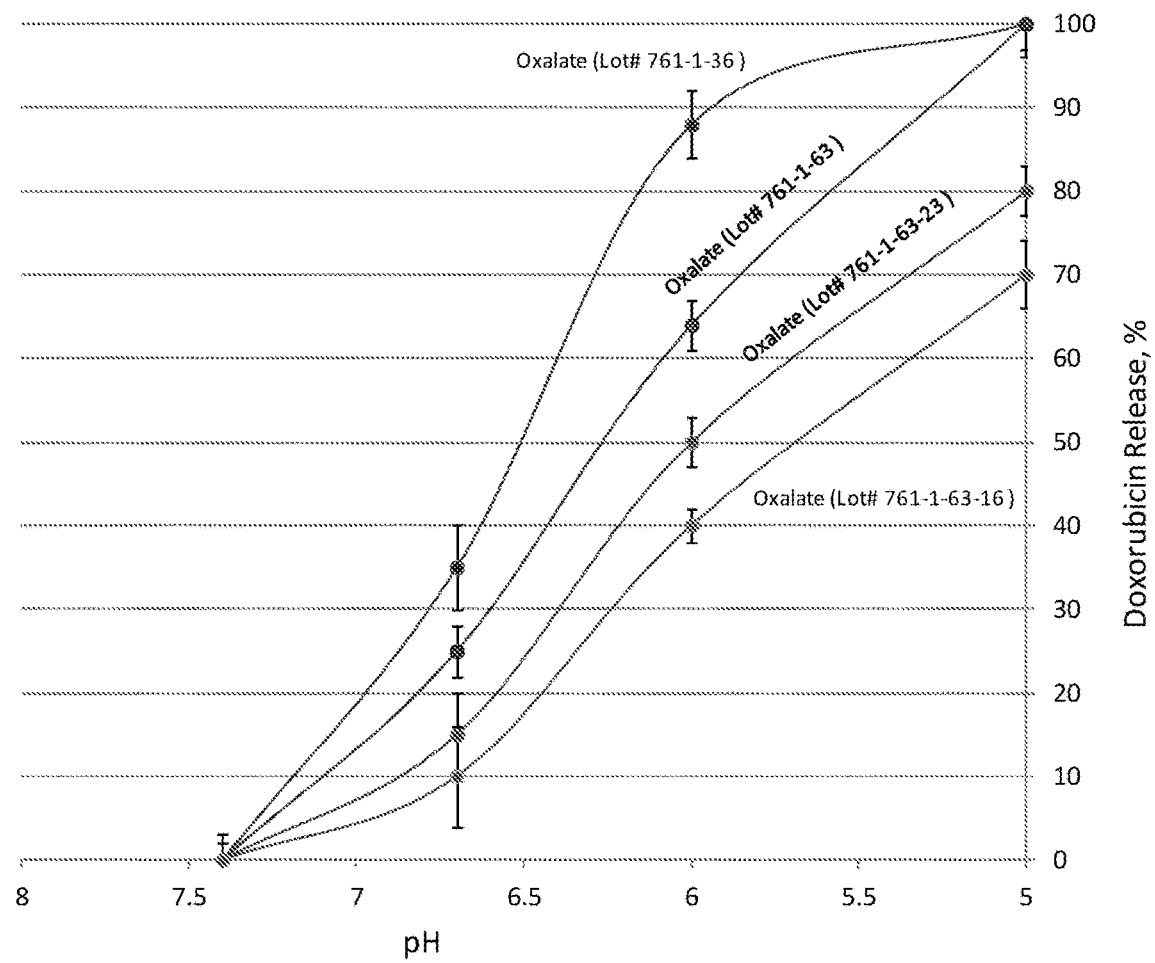
FIG. 18 is a graph showing the effect of lipid/drug and phospholipid/free cholesterol (PL/FC) ratios on pH dependent doxorubicin release from liposomes. Comparison with Doxil® and "Myocet". Liposomal material was diluted in dissolution media 20× and release experiments were carried out at 37° C. for 8 hrs at pH 7.4, 6.7, 6.0, and 5.0. Each point on the curves represents mean±STD of data obtained in 2-3 independent experiments. For each experiment all the measurements were performed in sixtiplicate. Formulation composition, lipid/drug and phospholipid/free cholesterol (PL/FC) ratios are shown in the Tables 28e-28g.
Figure 19:
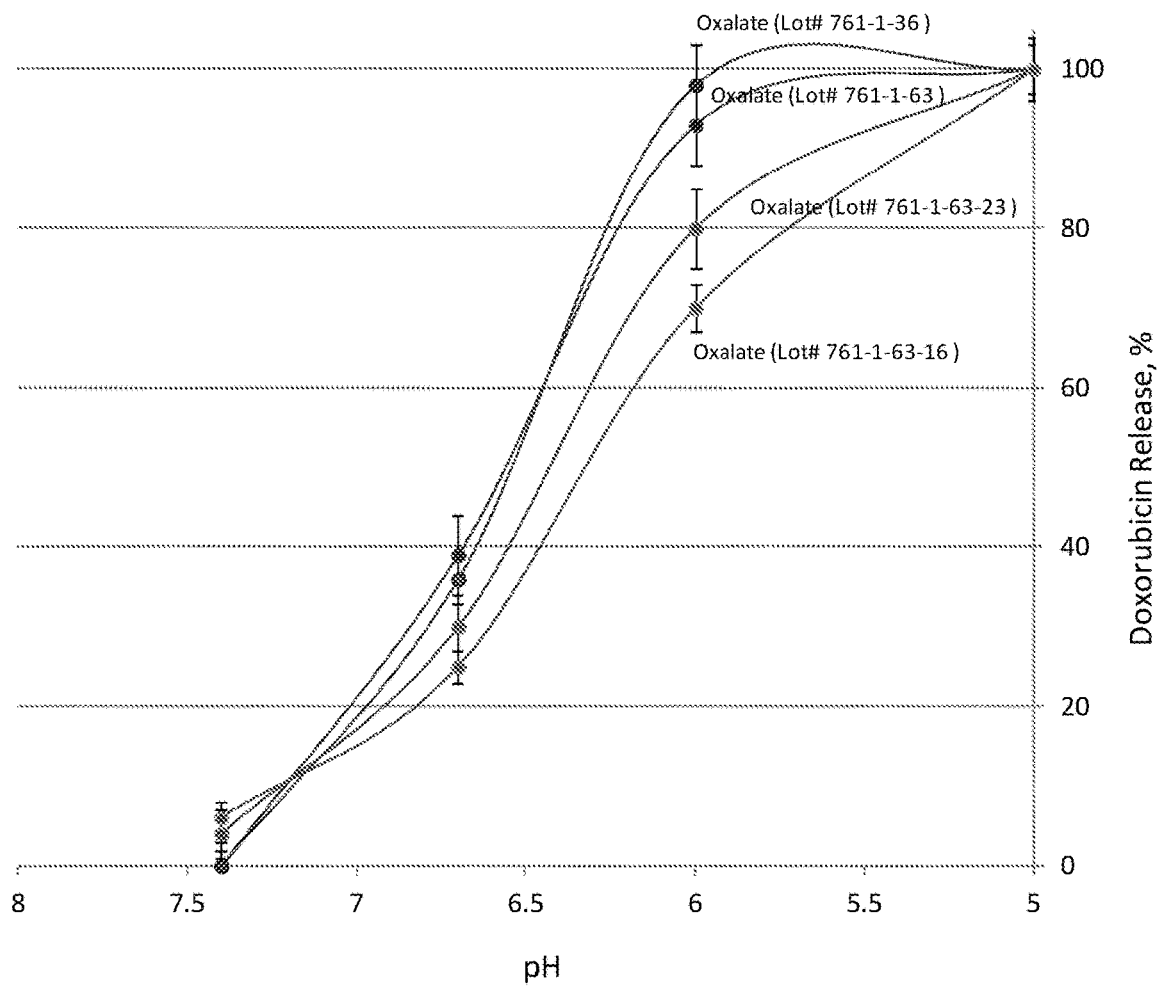
FIG. 19 is a graph showing the effect of lipid/drug and phospholipid/free cholesterol (PL/FC) ratios on pH dependent doxorubicin release from liposomes. Comparison with Doxil® and "Myocet". Liposomal material was diluted in dissolution media 20× and release experiments were carried out at 37° C. for 8 hrs at pH 7.4, 6.7, 6.0, and 5.0. Each point on the curves represents mean±STD of data obtained in 2-3 independent experiments. For each experiment all the measurements were performed in sixtiplicate. Formulation composition, lipid/drug and phospholipid/free cholesterol (PL/FC) ratios are shown in the Tables 28e-28g.

Effect of Lipid/Drug ratio. The dependence of ΔpH (7.4/6.7/6.0/5.0) doxorubicin release differential on the lipid/drug ratio can be clearly seen when ΔpH release differential of doxorubicin-Oxalate liposomes (50/1 lipid/drug ratio) compared to that of doxorubicin-oxalate liposomes made at 23/1 and/or 16/1 lipid/drug ratio (Table 28f and FIG. 18; 20X dilution of liposomes in the dissolution media). Similar dependence but in a lesser extent was observed at 50× dilution of liposomal material in the dissolution media (Table 28g and FIG. 19). It is worth mentioning that liposomes made at low (23/1 and 16/1) lipid/drug ratios showed marked dependence on dilution factor (i.e. 20× or 50×), whereas liposomes with higher (50/1) lipid/drug ratio demonstrated essentially similar drug release at both conditions (Table 28f, 28g, and FIGS. 16-19). Some leakage of doxorubicin from the liposomes prepared at low (23/1 and 16/1) lipid to drug ratio was observed at 50× dilution (Table 28g and FIG. 19).

Marked dependence of ΔpH (7.4/6.7/6.0/5.0) doxorubicin release differential on the lipid/drug ratio can be seen from comparison of doxorubicin-citrate liposomes made at 50/1 and 3.5/1 lipid/drug ratios (Table 28f, 28g, and FIGS. 16-17) at both 20× and 50 dilutions.

Thus, obtained data demonstrate that in some embodiments, higher lipid/drug ratios achieve higher ΔpH 7.4/6.7, 7.4/6.0, and 7.4/5.0 doxorubicin release differentials. In some embodiments, at lower lipid/drug ratios doxorubicin-oxalate, or -tartrate, or possibly citrate aggregates may be forced to form denser fibril like structures that would negatively impact dissolution of aggregates. These data also indicate that in some embodiments, higher lipid/drug ratios accommodate/support the pH sensitive, possibly disorganized, physical state of doxorubicin aggregates. The leakage of doxorubicin at neutral pH observed for lower lipid/drug ratio formulations could be due to the lower lipid content resulting in increased surface tension and compromised integrity of the lipid bilayer of doxorubicin loaded liposomes at least in some embodiments.

Effect of PL/FC (Phospholipid/Free Cholesterol) ratio. Free cholesterol content can affect unilamellar liposomes lipid bilayer rigidity that may potentially translate in serum/blood stability of the liposomes [52, 53], and may also lay a path to further development of lyophilized product. To test whether or not increased FC content will negatively affect ΔpH (7.4/6.7/6.0/5.0) doxorubicin release differential the experiments on effect of FC content, and therefore PL/FC ratio on ΔpH release differential were carried out. It can be seen in the Table 28f and FIG. 18 (20× dilution in dissolution media) that increase of FC content and respective decrease of PL/FC ratio from 3.68 to 0.86 in the doxorubicin-oxalate liposomes resulted in notable decrease of drug release at pH 6.7, while release at pH 6.0 and 5.0 was not significantly affected.

No notable effect of FC on ΔpH (7.4/6.7/6.0/5.0) doxorubicin release differential was observed when release experiments were performed at 50× dilution (Table 28g and FIG. 19) using liposomes with 3.68 to 1.29 PL/FC ratios. It is worth mentioning that PL/FC ratio <1.0 resulted in notable changes of doxorubicin release at both 20× and 50× dilutions (Table 28f and 28g).

Thus, overall data demonstrate that in some embodiments, ΔpH (7.4/6.7/6.0/5.0) doxorubicin release differential of doxorubicin-oxalate liposomes can highly tolerate decrease of PL/FC molar ratio from 3.68 to 1.29 when release experiments are performed at 50× dilution. At 20× dilution the decrease of PL/FC molar ratio from 3.68 to 1.29 mostly affected ΔpH (7.4/6.7) release differential while no significant changes of doxorubicin release rate were observed at pH 6.0 and 5.0. In contrast, decrease of PL/FC molar ratio of doxorubicin-citrate liposomes from 3.68 to 1.22 resulted in decrease of ΔpH release differential across of entire pH range (Table 28f, 28g, and FIGS. 16-17).

Example 8.4: Cold Loading of Doxorubicin into Oxalate or Tartrate, or Citrate Containing Liposomes This examples provides (i) further characterization regarding the stability of doxorubicin-oxalate, doxorubicin-tartrate and (ii) doxorubicin-citrate containing liposomes in human serum. Effect of lipid/drug and phospholipid/free cholesterol (PL/FC) ratios is demonstrated.

Oxalate-, tartrate-, and citrate-containing liposomes (vehicle) were prepared and loaded with doxorubicin hydrochloride as described in Methods and section 8.1 to the final concentration of 1 mg/mL. The various lipid/drug and phospholipid/free cholesterol (PL/FC) ratios were achieved by manipulating of relative amounts of phospholipid and/or free cholesterol (Table 28e), and/or through appropriate dilution of the liposomes before loading with doxorubicin.

Commercial Doxil® and Myocet-like ("Myocet") liposomes were used as comparators. Myocet-like ("Myocet") liposomes were prepared by hydrating lipid film containing 6.9 g of PC and 2.84 g of FC (55/45 molar ratio) with 100 mL of 0.3M Citric Acid pH 4.0 at 65° C. Microfluidization and TFF were performed as described in Methods and section 8.1. The resultant liposomes were sterile filtered. 1.9 mL aliquot was taken and loaded with 50 mg of doxorubicin in total 25 mL of loading media at 70° C. according to the protocol described in Myocet package insert. Detailed formulation composition is presented in the Table 28e.

Serum stability studies were conducted at 50× dilution (simulates administration of 60 mg/m$^2$ or 110 mg/70 kg human dose of doxorubicin) of the liposomal material in human serum by adding of 50 uL of the doxorubicin loaded liposomes to 2.45 mL (50× dilution) of the human serum. T0 samples were analyzed immediately and other samples were incubated at 37° C. for 2, 4, and 8 hrs. At each time point fluorescence of intact liposomes (Fi) and total fluorescence of liposomes ruptured with Triton X-100 (Ft) was measured. The data are presented in the Table 28h.

TABLE 28h

Doxorubicin release determined after 2, 4, and 8 hrs of incubation of the doxorubicin loaded liposomes in human serum at 37° C. and 50X dilution.

| Lot# | Counter Ion | Lipid/Drug w/w | PL/FC, mol/mol | Doxorubicin Release, % 2 hrs | 4 hrs | 8 hrs |
|---|---|---|---|---|---|---|
| 761-1-36 | Oxalate | 50 | 3.68 | 45 | 50 | 52 |
| 761-1-55 | Oxalate | 58 | 1.72 | 42 | 45 | 52 |
| 761-1-63 | Oxalate | 63 | 1.29 | 25 | 27 | 33 |
| 761-1-63-23 | Oxalate | 23 | 1.29 | 46 | 65 | 77 |
| 761-1-63-16 | Oxalate | 16 | 1.29 | 60 | 92 | 100 |
| 761-1-64 | Oxalate | 68 | 0.86 | 12 | 14 | 20 |
| 761-1-37 | Tartrate | 50 | 3.68 | 48 | 49 | 53 |
| 761-1-38 | Citrate | 50 | 3.68 | 40 | 43 | 46 |
| 761-1-69 "Myocet" | Citrate | 3.5 | 1.22 | 100 | 100 | 100 |
| Doxil ® | Sulfate | 8.0 | 1.62 | 4 | 6 | 8 |

Effect of counter ions. Similar stability in human serum was observed for doxorubicin-Oxalate, -Tartrate, and -Citrate liposomes made at the same (50/1) lipid/drug ratio (Table 28h). This data indicate that counter ions do not determine stability of the tested articles in human serum. It is worth mentioning that marked stability of Doxil® liposomes in serum is achieved via using pegylated lipids [2-5, 7-8].

Figure 20:
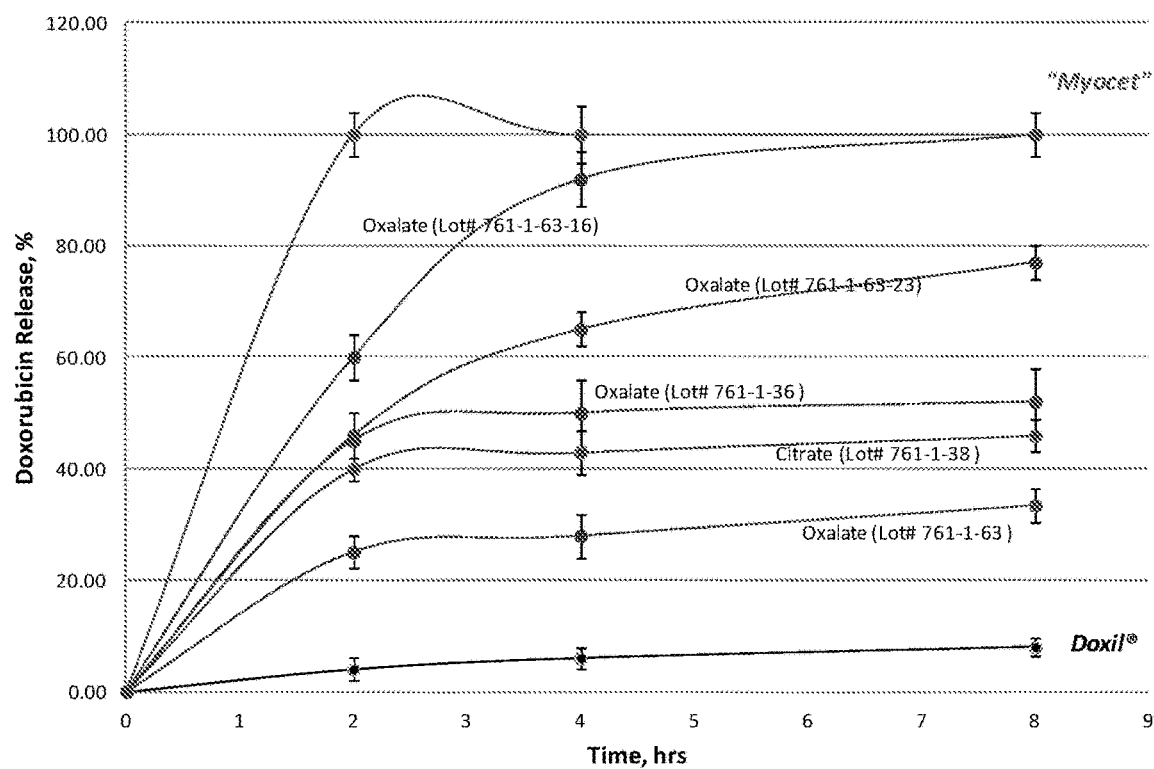
FIG. 20 is a graph showing the effect of lipid/drug ratio on serum stability of liposomes. Comparison with Doxil® and "Myocet". Liposomal material was diluted 50× in human serum and stability of the liposomes was monitored at 37° C. for 2, 4, and 8 hrs. Each point on the curves represents mean±STD of data obtained in 2-3 independent experiments. For each experiment all the measurements were performed in sixtiplicate. Formulation composition, lipid/drug and phospholipid/free cholesterol (PL/FC) ratios are shown in the Tables 28e and 28h.

Effect of lipid/drug ratio. It can be seen in the Table 28h and FIG. 20 that serum stability of the doxorubicin-oxalate liposomes decreases with decrease of the lipid/drug ratio. Stability of doxorubicin-oxalate liposomes made at ≥50/1 lipid/drug ratios is markedly higher compared to doxorubicin-oxalate liposomes made with 23/1 and 16/1 lipid/drug ratios. Same trend was observed upon comparison of doxorubicin-citrate liposomes made at 50/1 and 3.5/1 lipid/drug ratios (Table 28h and FIG. 20). These data clearly demonstrate that lipid/drug ratio may contribute to serum stability of the liposomes. The effect of lipid/drug ratio on serum stability of the liposomes as well as its effect on ΔpH (7.4/6.7/6.0/5.0) doxorubicin release differential demonstrates advantage of using higher lipid/drug ratios for optimal performance of liposomal delivery system in some embodiments.

Figure 21:
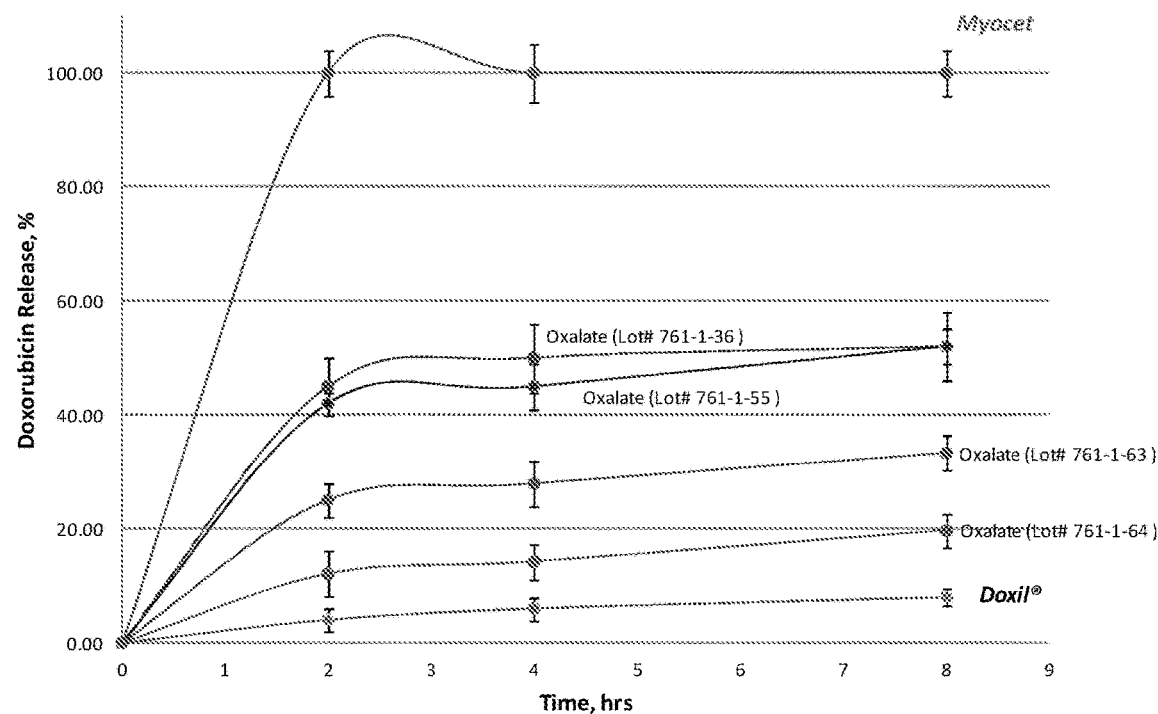
FIG. 21 is a graph showing the effect of phospholipid/free cholesterol (PL/FC) ratios on serum stability of liposomes. Comparison with Doxil® and "Myocet". Liposomal material was diluted 50× in human serum and stability of the liposomes was monitored at 37° C. for 2, 4, and 8 hrs. Each point on the curves represents mean±STD of data obtained in 2-3 independent experiments. For each experiment all the measurements were performed in sixtiplicate. Formulation composition, lipid/drug and phospholipid/free cholesterol (PL/FC) ratios are shown in the Tables 28e and 28h.

Effect of PL/FC (phospholipid/free cholesterol) ratio. Further increase of serum stability of doxorubicin-oxalate liposomes was observed with increase of FC content and subsequent decrease of PL/FC ratio (Table 28h and FIG. 21). PL/FC ratio 0.86 demonstrated the highest protection of the liposomes in human serum, although notable negative impact of 0.86 PL/FC ratio on ΔpH (7.4/6.7/6.0/5.0) doxorubicin release differential was observed (Table 28f and 28g). The obtained data suggest that the optimal PL/FC ratio for doxorubicin-oxalate liposomes would lie between 3.68 and 1 (Table 28f-28h, and FIGS. 20-21). It is worth mentioning however, that doxorubicin-oxalate liposomes with near optimal PL/FC ratio (1.29) but lower than 50/1 lipid/drug ratio (i.e. 23/1 and 16/1) demonstrated lower serum stability (Table 28h and FIG. 20). These data demonstrate contribution of both lipid/drug and PL/FC ratio to liposomal serum stability. Similar relationships between lipid/drug and PL/FC ratios were observed for doxorubicin-citrate liposomes ((Table 28h, and FIG. 20). It is also worth mentioning that human blood as well as mouse serum showed less deleterious effect on the liposomes compared to human serum (data not shown).

Obtained data clearly demonstrate impact of lipid/drug ratio and PL/FC ratio on both serum stability of the liposomes and ΔpH (7.4/6.7/6.0/5.0) doxorubicin release differential emphasizing beneficial effect of higher lipid/drug ratios and lower than 3.68 but higher than 1.0 PL/FC ratios in some embodiments.

Figure 16:
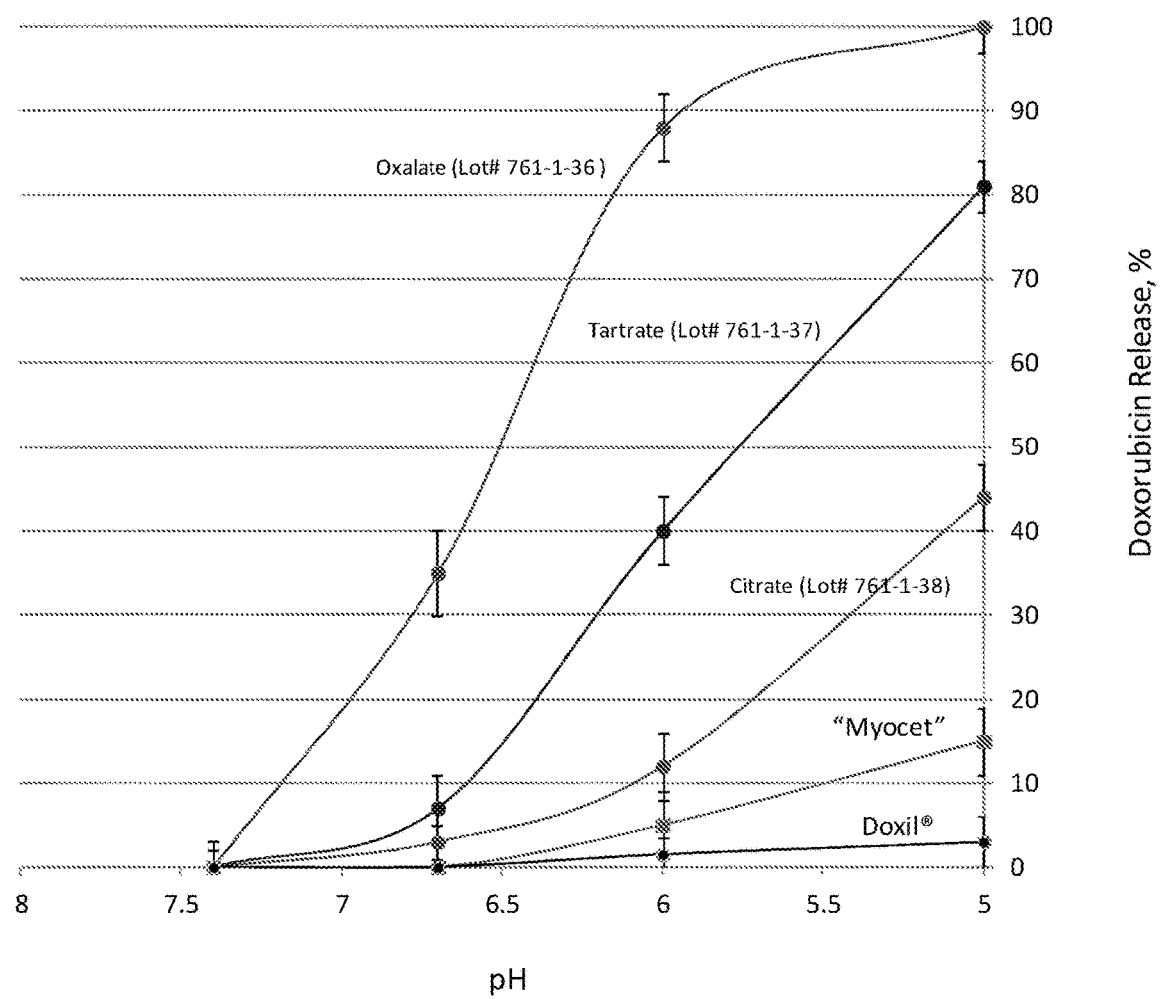
FIG. 16 is a graph showing the effect of various counter ions on pH dependent doxorubicin release from liposomes. Comparison with Doxil® and "Myocet". Liposomal material was diluted in dissolution media 20× and release experiments were carried out at 37° C. for 8 hrs at pH 7.4, 6.7, 6.0, and 5.0. Each point on the curves represents mean±STD of data obtained in 2-3 independent experiments. For each experiment all the measurements were performed in sixtiplicate. Formulation composition, lipid to drug (i.e. lipid/drug) and phospholipid to free cholesterol (i.e. phospholipid/free cholesterol or PL/FC) ratios are shown in the Tables 28e-28g.
Figure 17:
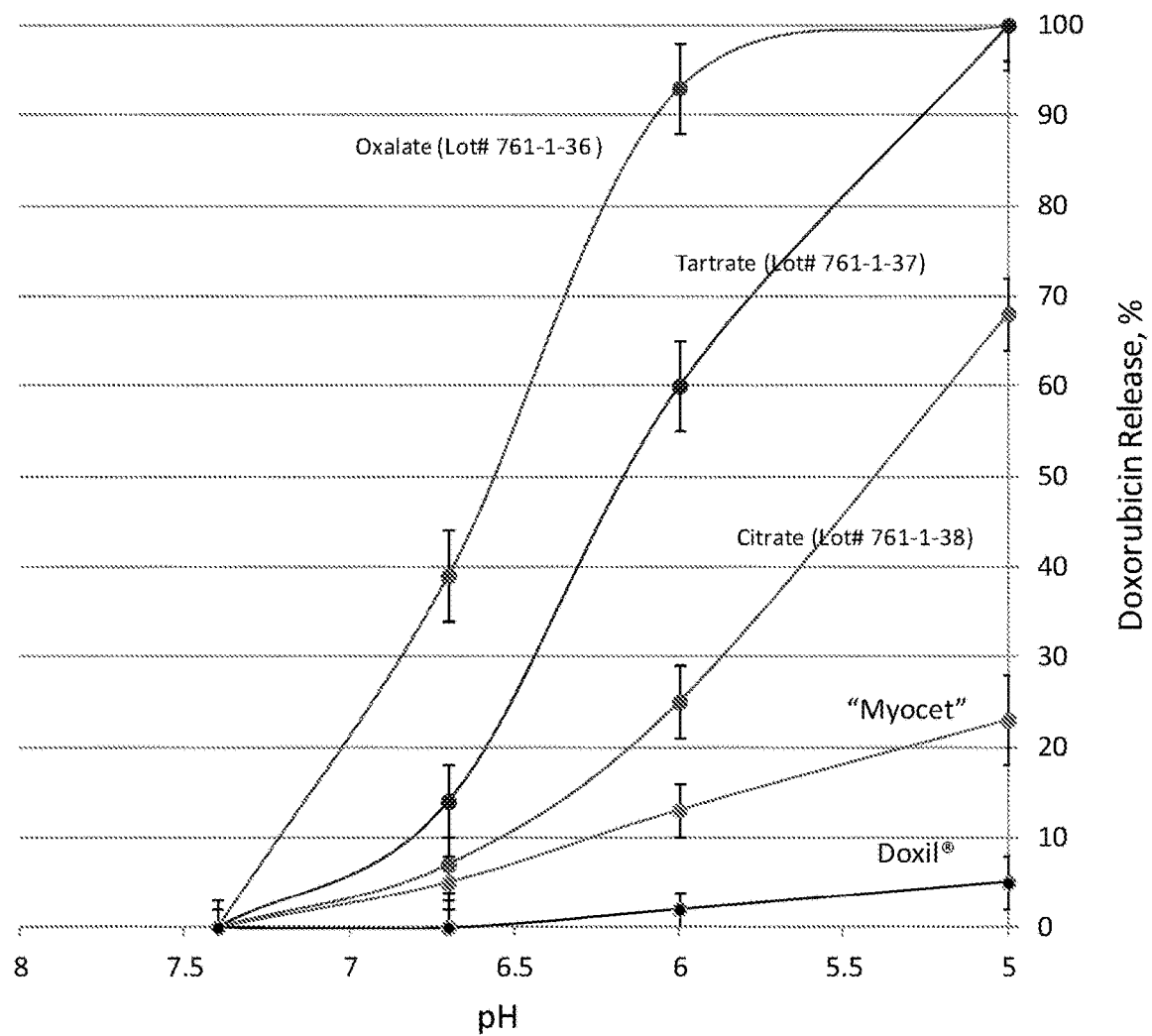
FIG. 17 is a graph showing the effect of various counter ions on pH dependent doxorubicin release from liposomes. Comparison with Doxil® and "Myocet". Liposomal material was diluted in dissolution media 50× and release experiments were carried out at 37° C. for 8 hrs at pH 7.4, 6.7, 6.0, and 5.0. Each point on the curves represents mean±STD of data obtained in 2-3 independent experiments. For each experiment all the measurements were performed in sixtiplicate. Formulation composition, lipid/drug and phospholipid/free cholesterol (PL/FC) ratios are shown in the Tables 28e-28g.

Overall, obtained data demonstrate that doxorubicin-oxalate liposomes exhibit markedly higher ΔpH (7.4/6.7/6.0/5.0) doxorubicin release differential compared to "Myocet" and Doxil® (Table 28e-28g and FIGS. 16-17). The serum stability of doxorubicin-oxalate liposomes is markedly higher than that of "Myocet" but lower then Doxil®, although lowering of PL/FC ratio while keeping the lipid/drug ratio ≥50/1 further improves serum stability of doxorubicin-oxalate liposomes and makes it somewhat comparable to Doxil® (Table 28e. 28h, and FIG. 21). Several physical and chemical properties of liposomes, such as size, lipid composition, charge, and surface coatings, are known to determine their interaction with plasma proteins that influence the clearance pharmacokinetics of the vesicles [53]. Therefore, if in vivo pharmacokinetics of the liposomal delivery system in accordance with the disclosure herewith (i.e. area under the plasma concentration-time curve, elimination half-life . . . etc) is reflective of serum performance (i.e. between Myocet and Doxil®) that would be highly desirable outcome.

Example 9: Cold Loading of Doxorubicin into Fixed (50:1) Lipid/Drug Ratio Liposomes: Addition of Ascorbic Acid (AA), or N-Acetylcysteine (NAC), Ascorbil Palmitate (AP), Ubiquinone (CoQ10), or Ethylenediaminetetraacetic Acid (EDTA) to Ammonium-Oxalate and/or -Tartrate Hydration Media Hydration medias used: 300 mM solution of ammonium-oxalate; tartaric acid was first titrated with ammonium hydroxide to pH 4.8-5.0 and then used as hydration media.

Liposomes were prepared as described in the methods section, except that NAC, or AA, or AP, or CoQ10, or EDTA were added to 300 mM Ammonium-Oxalate hydration media to the final concentrations 100 mM (NAC), or 36 and 100 mM (AA), 2 mM or 20 mM (AP), 1 mM (CoQ10), 2 mM or 20 mM (EDTA).

The cold loading of doxorubicin into liposomes was performed as follows: saline solution of doxorubicin hydrochloride (6 mg/mL) was added to the liposomal nanosuspension at room temperature to the final concentration 1 mg/mL (i.e. 0.936 mg of doxorubicin free base per mL), gently inverted (2-3 times) and incubated at room temperature for 10-20 min. After 10-20 min of incubation at room temperature the mixture was: a) subjected to another TFF 5× cycle with PBS pH 7.4 containing 6% of sucrose, and/or b) placed in 2-8° C. refrigerator for 16 hrs, and then subjected to another TFF 5× cycle with PBS pH 7.4 containing 6% of sucrose. There was no notable difference observed between doxorubicin release profiles of the liposomes loaded at RT, or RT followed by 2-8° C. overnight incubation. Data for RT followed by 2-8° C. overnight incubation are not shown.

Formulation composition is shown in Table 29.

TABLE 29

Formulation composition.

| Lot # | Hydration Media | PC | DMPC | FC | P 188 | Doxorubicin Hydrochloride | Ratios Lipid/Drug |
|---|---|---|---|---|---|---|---|
| | | \multicolumn{5}{c}{Amounts of solids used in formulations, W/W, %} | | |
| 647-2-163 B | Ammonium Oxalate | 65.50 | 16.38 | 11.46 | 4.91 | 1.75 | 50 |
| 647-2-170 B | Ammonium Tartrate | 65.50 | 16.38 | 11.46 | 4.91 | 1.75 | 50 |
| 647-2-153 C | Ammonium Oxalate Ascorbic acid (36 mM) | 65.50 | 16.38 | 11.46 | 4.91 | 1.75 | 50 |
| 647-2-161 B | Ammonium Oxalate Ascorbic acid (100 mM) | 65.50 | 16.38 | 11.46 | 4.91 | 1.75 | 50 |
| 647-2-165 B | Ammonium Oxalate NAC (100 mM) | 65.50 | 16.38 | 11.46 | 4.91 | 1.75 | 50 |
| 647-2-172 B | Ammonium Oxalate Ascorbil Palmitate (2 mM) | 65.50 | 16.38 | 11.46 | 4.91 | 1.75 | 50 |
| 647-2-173 B | Ammonium Oxalate Ascorbil Palmitate (20 mM) | 65.50 | 16.38 | 11.46 | 4.91 | 1.75 | 50 |
| 647-2-175 B | Ammonium Oxalate Ubiquinone (1 mM) | 65.50 | 16.38 | 11.46 | 4.91 | 1.75 | 50 |
| 647-2-190 B | Ammonium Oxalate EDTA (2 mM) | 65.50 | 16.38 | 11.46 | 4.91 | 1.75 | 50 |
| 647-2-192 B | Ammonium Oxalate EDTA (20 mM) | 65.50 | 16.38 | 11.46 | 4.91 | 1.75 | 50 |
| 647-2-193 B | Ammonium Tartrate EDTA (2 mM) | 65.50 | 16.38 | 11.46 | 4.91 | 1.75 | 50 |
| 647-2-194 B | Ammonium Tartrate EDTA (20 mM) | 65.50 | 16.38 | 11.46 | 4.91 | 1.75 | 50 |

Coarse suspension was prepared and MF processed at 10 KPSI processing pressure. After 9-15 min of MF processing the particle size (Z-average) reached ~60-75 nm. A sample was collected and sterile filtered into Nalgene flask. The particle size of filtered nanosuspension was determined (Table 29a).

TABLE 29a

Summary of MF processing and resultant emulsion parameters.

| Lot # | MFD | Particle size Z avrg, nm |
|---|---|---|
| 647-2-163 B | 24 MAY 16 | 66 |
| 647-2-170 B | 23 JUN 16 | 63 |
| 647-2-153 C | 19 MAY16 | 62 |
| 647-2-161 B | 3 JUN 16 | 62 |
| 647-2-165 B | 16 JUN 16 | 65 |
| 647-2-172 B | 5 JUL 16 | 63 |
| 647-2-173 B | 6 JUL 16 | 67 |
| 647-2-175 B | 7 JUL 16 | 62 |
| 647-2-190 B | 28 JUL 16 | 62 |
| 647-2-192 B | 29 JUL 16 | 62 |
| 647-2-193 B | 1 AUG 16 | 62 |
| 647-2-194 B | 2 AUG 16 | 62 |

The liposomes were subjected to TFF followed by remote loading with doxorubicin, and another TFF cycle with PBS sucrose.

The particle size of doxorubicin loaded liposomes is presented in Table 29b.

TABLE 29b

Particle size of doxorubicin loaded liposomes.

| Lot # | Loading Date | Particle size Z avrg, nm |
|---|---|---|
| 647-2-163 B | 10 JUN 16 | 67 |
| 647-2-170 B | 23 JUN 16 | 63 |
| 647-2-153 C | 3 JUN 16 | 63 |
| 647-2-161 B | 3 JUN 16 | 66 |
| 647-2-165 B | 16 JUN 16 | 69 |
| 647-2-172 B | 5 JUL 16 | 64 |
| 647-2-173 B | 6 JUL 16 | 67 |
| 647-2-175 B | 7 JUL 16 | 62 |
| 647-2-190 B | 28 JUL 16 | 62 |
| 647-2-192 B | 29 JUL 16 | 62 |

TABLE 29b-continued

Particle size of doxorubicin loaded liposomes.

| Lot # | Loading Date | Particle size Z avrg, nm |
|---|---|---|
| 647-2-193 B | 1 AUG 16 | 62 |
| 647-2-194 B | 2 AUG 16 | 62 |

The amount of free (not encapsulated) doxorubicin was determined within one week of manufacturing (Table 29c).

TABLE 29c

Free doxorubicin content.

| Lot # | % of Total |
|---|---|
| 647-2-163 B | 0.08 |
| 647-2-170 B | 0.04 |
| 647-2-153 C | 0.07 |
| 647-2-161 B | 0.03 |
| 647-2-165 B | 0.01 |
| 647-2-172 B | 0.08 |
| 647-2-173 B | 0.09 |
| 647-2-175 B | 0.16 |
| 647-2-190 B | 0.1 |
| 647-2-192 B | 0.07 |
| 647-2-193 B | 0.02 |
| 647-2-194 B | 0.01 |

Determination of doxorubicin in liposomal suspension. Followed doxorubicin loading liposomal suspension was subjected to 5× TFF to majorly remove free (not encapsulated) doxorubicin. To determine total doxorubicin concentration at T0 (within one week of MFD) TFF washed liposomes were diluted with methanol or IPA and subjected to HPLC analysis. Doxorubicin content, percent of recovery (doxorubicin content in liposomal suspension relative to doxorubicin free base concentration used for remote loading), and encapsulation efficiency (%) are presented in the Table 29d. Encapsulation efficiency (%) represents the difference between doxorubicin recovery (%) and free doxorubicin (%).

TABLE 29d

Total doxorubicin content and Encapsulation efficiency.

| Lot # | Doxorubicin free base used for loading, µg/mL | Assay, HPLC Doxorubicin content (Liposomal Suspesion) µg/mL | Recovery, % | Encapsulated doxorubicin, % [Recovery, %] - [Free, %] |
|---|---|---|---|---|
| 647-2-163 B | 936 | 909 | 97 | 97 |
| 647-2-170 B | 936 | 850 | 91 | 91 |
| 647-2-153 C | 936 | 750 | 80 | 80 |
| 647-2-161 B | 936 | 745 | 80 | 80 |
| 647-2-165 B | 936 | 910 | 97 | 97 |
| 647-2-172 B | 936 | 936 | 100 | 100 |
| 647-2-173 B | 936 | 936 | 100 | 100 |
| 647-2-175 B | 936 | 912 | 97 | 97 |
| 647-2-190 B | 936 | 936 | 100 | 100 |
| 647-2-192 B | 936 | 926 | 99 | 99 |
| 647-2-193 B | 936 | 926 | 99 | 99 |
| 647-2-194 B | 936 | 926 | 99 | 99 |

Liposomal doxorubicin release studies were carried out at 37° C. within one week after manufacturing (Table 29e). For each sample doxorubicin release was determined at 2, 4 and 8 hrs time points.

TABLE 29e

Doxorubicin release rate determined at 37° C.

| | pH 5, Release, % | | | pH 7.4, Release, % | | |
|---|---|---|---|---|---|---|
| Lot # | 2 hrs | 4 hrs | 8 hrs | 2 hrs | 4 hrs | 8 hrs |
| 647-2-163 B | 92 | 100 | 100 | 0 | 0 | 2 |
| 647-2-170 B | 63 | 89 | 100 | 0 | 0 | 0 |
| 647-2-153 C | 90 | 97 | 100 | 0 | 3 | 3 |
| 647-2-161 B | 92 | 100 | 100 | 0 | 1 | 4 |
| 647-2-165 B | 82 | 90 | 100 | 1 | 5 | 13 |
| 647-2-172 B | 80 | 87 | 94 | 0 | 0 | 0 |
| 647-2-173 B | 69 | 71 | 75 | 0 | 0 | 0 |
| 647-2-175 B | 80 | 94 | 94 | 0 | 0 | 0 |
| 647-2-190 B | 77 | 88 | 94 | 0 | 0 | 0 |
| 647-2-192 B | 6 | 9 | 18 | 0 | 0 | 0 |
| 647-2-193 B | 33 | 50 | 64 | 0 | 0 | 0 |
| 647-2-194 B | 3 | 5 | 12 | 0 | 0 | 0 |

Efficiency of doxorubicin encapsulation in presence or absence of ascorbic acid or NAC was in the range 80-97% (Table 29d). Addition of ascorbic acid or NAC to ammonium-oxalate hydration media did not have significant impact on the particle size of the liposomes doxorubicin (Tables 289 and 29b), free (not encapsulated or leaked) doxorubicin (Tables 29c), and more importantly doxorubicin release profile (Table 29e) compared to liposomes formed with oxalate or tartrate alone (Tables 29a-e).

Addition of 2 mM or 20 mM of EDTA, 2 mM or 20 mM of AP, or 1 mM of CoQ10 did not have any significant effect on particles size of empty or doxorubicin loaded liposomes (Tables 29a and 29b), free doxorubicin (29c), and encapsulation efficiency (Table 29d).

Complementing oxalate with 2 mM of AP (AP/Oxalate—1:150) or 1 mM of CoQ10 (CoQ10/Oxalate—1:300) did not affect the doxorubicin release profile (Table 29e). Although some decrease of doxorubicin release was observed upon addition of 20 mM AP (AP/Oxalate-1:15), the ΔpH7.4/5.0 release differential was sufficiently high (Table 29e).

Complementing oxalate with 2 mM of EDTA (Oxalate/EDTA at 1:150 ratio) did not affect the doxorubicin release profile (Table 28e). Although notable decrease of doxorubicin release was observed when 2 mM EDTA was added to 300 mM of tartrate (tartrate/EDTA—1:150) hydration media (Table 29e), the ΔpH7.4/5.0 release differential was sufficiently high. In contrast, very low doxorubicin release was observed when 20 mM of EDTA were added to 300 mM of either oxalate or tartrate hydration media (Table 29e).

These findings enable use of ascorbic acid, and/or NAC, and/or ascorbil palmitate, and/or CoQ10, and/or EDTA in combination with oxalate or tartrate (preferred counter ions in some embodiments) or citrate to alleviate oxidative stress during processing and may result in more stable product with a longer shelf life. Moreover, ascorbic acid can exert cardioprotective effect to prevent or alleviate doxorubicin induced cardiac toxicity [28-29, and 33]. In embodiments, this may result from unrestrained, drug induced, cardiac reactive oxygen metabolism [28-29]. Investigations have shown that electron transfer after treatment with doxorubicin is markedly enhanced in the heart, and leads to a substantial increase in superoxide anion and hydrogen peroxide formation in mitochondria and sarcoplasmic reticulum, two major sites of cardiac damage from doxorubicin [28, 30-31]. Vitamin C (ascorbic acid) is an antioxidant vitamin that has been shown to antagonize the effects of reactive oxygen species-generating antineoplastic drugs [29, 32-33]. It has been also demonstrated that treatment of experimental animals with pharmacologic dosages of the NAC selectively rescues the heart from the toxicity of doxorubicin [28, 29, 34]. Chelating agents such as EDTA can reduce generation of reactive oxygen species (ROS) by chelating transition metal ions, therefore decrease damage to the cardiomyocyte membrane and the risk of doxorubicin-related cardiomyopathy [36, 37]. Besides EDTA can increase the stability of liposomal formulations by inhibiting metal catalyzed lipid oxidation.

Thus, complementing oxalate or tartrate (preferred counter ion in some embodiments) or citrate with ascorbic acid (AA/oxalate—1:8 or 1:3), and/or NAC (NAC/oxalate 1:3), and/or AP (AP/oxalate—1:150 or 1:15), and/or CoQ10 (CoQ10/Oxalate—1:300), and/or EDTA (EDTA/oxalate 1:150) did not have considerable negative effect on $\Delta$pH7.4/5.0 doxorubicin release differential. Therefore this powerful combination of optimized $\Delta$pH7.4/5.0 release differential and antioxidant(s)/chelators maybe efficacious for the cancer patients and advantageous for alleviation of cardiotoxic effect of free doxorubicin. Other ratios of ascorbic acid or NAC to oxalate or tartrate or citrate that can be used include 1:10 to 1:1. Other ratios of AP to oxalate or tartrate or citrate that can be used include 1:300 to 1:10. Other ratios of CoQ10 to oxalate or tartrate or citrate that can be used include 1:300 to 1:10. Other ratios of EDTA to oxalate or tartrate or citrate that can be used include 1:300 to 1:5.

The ratios of a chelator (e.g. ascorbic acid (AA), or N-Acetylcysteine (NAC), ascorbil palmitate (AP), ubiquinone (CoQ10), or ethylenediaminetetraacetic acid (EDTA)) to a counter ion (e.g. oxalate, tartrate or citrate), i.e. a chelator/counter ion ration can be about 1:1 to about 1:10,000.

Thus, in embodiments, the ratio of AA/oxalate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of NAC/oxalate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of AP/oxalate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of CoQ10/oxalate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of EDTA/oxalate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more.

In embodiments, the ratio of AA/tartrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of NAC/tartrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of AP/tartrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of CoQ10/tartrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of EDTA/tartrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more.

In embodiments, the ratio of AA/citrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of NAC/citrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of AP/citrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of CoQ10/citrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more. In embodiments, the ratio of EDTA/citrate can be about 1:1, about 1:2, about 1:3, about 1:5, about 1:8, about 1:10, about 1:15, about 1:20, about 1:50, about 1:100, about 1:200, about 1:300, about 1:500, about 1:1000, about 1:2000, about 1:5000, about 1:10,000 or more.

Other counter ions and/or antioxidants, and/or chelators that can be advantageous and/or used in combination with oxalate and/or tartrate include citrate, and/or phytate and/or glutathione, and/or vitamin e, and/or dexrazoxane, and/or deferoxamine.

Overall, obtained data demonstrated the effect of:
a) proper counter ions such as oxalate and tartrate that determine physical state of intraliposomal doxorubicin aggregates and optimal ΔpH7.4/5.0 and ΔpH7.4/6.7/6.0/5.0 release differential;
b) lipid/drug ratio (preferred range is 20:-50:1 in some embodiments) for selective response to pH change;
c) doxorubicin loading temperature (advantage of cold loading for maximizing ΔpH7.4/5.0 and ΔpH7.4/6.7/6.0/5.0 release differential);
for optimal pH dependent drug release profile and stable performance of doxorubicin loaded liposomes.

Moreover, complementing of preferred counter ion(s) with other counter ions, and/or antioxidants, and/or chelators may be beneficial for the final product stability and its biological performance.

Example 10: Irinotecan

Methods:
Fluorometry

All analyses were performed using a Molecular Devices SpectraMax Gemini EM Fluorescence Plate Reader. SoftMax Pro software controlled the device and was used for analysis and reporting of values.

Standard stock solution of Irinotecan hydrochloride was prepared in a 6% sucrose solution in sterile water for injection (e.g., 6.0 mg Irinotecan hydrochloride powder in 1 mL water containing 6% of Sucrose). Calibration standards were prepared by diluting the stock solution in phosphate buffered saline, pH 7.4 and 5.0 to bracket the target concentration for analysis. The plate reader temperature was set to 25° C., and excitation and emission wavelengths were set at 370 nm and 470 nm, respectively. The linear response range was determined to be 0.5-4 µg/mL of Irinotecan hydrochloride. To remain in the linear response range, the Irinotecan hydrochloride calibration standards and samples were diluted accordingly.

To determine fluorescence of total Irinotecan in liposomal formulation (Ft), the liposomes were ruptured by addition of Triton X-100 to the final concentration 1%, mixed by inversion, and incubated for 5-10 min prior to quantification.

To determine fluorescence of intraliposomal Irinotecan (Fi) the liposomal formulation was subjected to fluorometric analysis without pretreatment with Triton X-100.

Quantification of Irinotecan Release from Liposomal Formulations

The method which employs a fluorescence dequenching technique and relays it to fluorescence (liposomes ruptured with Triton X-100) has been used for determination of Irinotecan release. This approach is based on the fact that fluorescence of Irinotecan quenched upon encapsulation into liposomes and markedly increases upon Irinotecan release from liposomes. Therefore, increase of fluorescence of intact liposomes (Fi) during the incubation of sample in dissolution media represents release of Irinotecan into the media. The difference between Fi values at different time points and T0 relayed to Ft (fluorescence of ruptured liposomes), and represents percent of released drug.

The study was carried out for the following time points: T0, T2 hrs, T4 hrs, and T8 hrs. Individual samples were diluted in 2 separate diluents/dissolution medias; PBS pH 7.4 and PBS pH. 5 by a factor of 20 times (e.g. 100 µL of sample+1.9 mL of diluent) to simulate intravenous injection into mouse. For T0 time point determination, liposomal formulations were diluted in PBS pH 7.4 and pH 5 buffers at ~25° C. The fluorescence of intact liposomes (Fi) and total fluorescence of liposomes ruptured with Triton X-100 (Ft) were measured immediately (within 10 min). The plate reader temperature was set to 25° C. and excitation and emission wavelengths were set at 370 nm and 470 nm, respectively.

Other liposomal samples were diluted 20× in PBS pH 7.4 and pH 5 buffers pre-warmed to 37° C. (to simulate in vivo temperature) and incubated for 2, 4, and 8 hrs at 37° C. At each time point fluorescence of intact liposomes (Fi) and total fluorescence of liposomes ruptured with Triton X-100 (Ft) was measured. The percent of drug release was quantified as $[(Fi\_n-Fi\_t0)/Ft\_avrg)]*100\%$, where $Fi\_n$—Fi measured at 2, 4, or 8 hrs, $Fi\_t0$—Fi measured at T0, and $Ft\_avrg$—average of Ft values determined for T0 time point.

It is worth mentioning that total fluorescence (Ft) increased significantly over 8 hrs of incubation of the liposomes at pH 7.4. This observation was in agreement with reported conversion of Irinotecan to carboxylate form in neutral medium [26-27].

Particle Size Determination

All analyses were performed using a Malvern Zetasizer Nano ZS with 4 mW He—Ne laser operating at a wavelength of 633 nm and a detection angle of 173°. Zetasizer software controlled the device and was used for analysis and reporting of values.

The intensity-averaged particle diameters (Z-average) were calculated from the cumulants analysis as defined in ISO 13321 (International Organization for Standardization 1996).

Samples are prepared using 30 µL of liposomal formulation in 1.5 mL of phosphate buffered saline (pH 7.4) and were equilibrated to 25° C. prior to analysis. Size measurements were done in triplicates for each sample.

pH Measurements

All analyses were performed using a Mettler Toledo SevenCompact pH meter with a Mettler Toledo InLab pH microelectrode.

Preparation of Liposomes: Coarse Suspension Preparation.

Coarse suspension was prepared by dissolving PC, DMPC, FC, and P188 in 10 mL of DCM at the ratios indicated in Table 29. The mixture was dried under the stream of Nitrogen until viscous film was formed. The film was further dried in vacuum oven overnight. Next day dried lipid film was hydrated with 300 mM Ammonium-Oxalate, or Ammonium-Sulfate, or Ammonium-Phosphate, or Ammonium-Citrate buffer pre-warmed to 65° C., and immediately homogenized with a hand-held homogenizer for 2-3 min. Tartaric acid was first titrated to pH 4.8-5.0 with $NH_4OH$ and then used as hydration media. Particle size of coarse suspension was determined and always was in the range of 800-1200 nm.

MF Processing

MF processing volume was always 100 ml unless specified differently. MF processing pressure was always 10 KPSI. Microfluidization of coarse suspension was performed in recycling mode (return of the material into the feed reservoir) at controlled (≤65° C.) temperature. Processing time was in 9-12 min range. The target particle size was 60-70 nm (Z-average).

Tangential Flow Filtration

Translucent nanosuspension was harvested from Microfluidizer and subjected to tangential flow filtration (TFF) with 15-20×volumes of PBS, pH 7.4. The purpose of TFF was to replace ammonium-oxalate, or ammonium-sulfate, or ammonium-phosphate, ammonium-citrate Or ammonium-tartrate external, buffer by PBS and to majorly remove ammonium from intraliposomal space. Ammonium in external buffer was measured by using ammonium specific electrode. TFF was stopped when ammonium concentration in external buffer was <3 mM.

Remote Loading of Irinotecan

Irinotecan hydrochloride was dissolved in sterile water for injection containing 6% sucrose to the final concentration 6 mg/mL. Solution of irinotecan hydrochloride was added to the liposomal nanosuspension at room temperature to the final concentration 1 mg/mL (e.g. 0.94 mg of irinotecan free base per mL), and incubated at room temperature for 10-30 min with or without overnight incubation at 2-8° C., and then subjected to another TFF 5× cycle with PBS pH 7.4 containing 6% of sucrose. The purpose of this TFF cycle was to wash out free (not encapsulated) Irinotecan. There was no notable difference observed between Irinotecan release profiles of the liposomes loaded at RT, or RT followed by 2-8° C. overnight incubation. Data for RT followed by 2-8° C. overnight incubation not shown.

Then liposomal nanosuspension was sterile filtered into sterile Nalgene flask via 0.22 um filter. Particle size, pH, Fi, Ft, and Irinotecan release profile were determined. The sterile nanosuspension was aseptically dispensed into 2 mL pre-sterilized vials, stoppered, and sealed. The vials were stored at 2-8° C.

Example 11: Cold Loading of Irinotecan into Fixed (50:1) Lipid/Drug Ratio Liposomes The counter ions that demonstrated ability to facilitate loading of doxorubicin into 50:1 lipid/drug ratio liposomes were used in this example.

Hydration media used: 300 mM ammonium-sulfate, ammonium-oxalate, ammonium-phosphate, ammonium-citrate.

Tartaric acid, was first titrated with ammonium hydroxide to pH 5 and then used as hydration media.

Cold remote loading was carried out with 1 mg/mL (i.e. 0.94 mg of irinotecan free base per mL) of irinotecan hydrochloride. Formulation composition is shown in Table 30. All formulations were prepared at 50:1 fixed lipid/drug ratio (Table 30).

TABLE 30

Formulation Composition.

Amounts of solids used in formulations, W/W, %

| Lot # | Hydration Media | PC | DMPC | FC | P 188 | Irinotecan Hydrochloride | Lipid/Drug |
|---|---|---|---|---|---|---|---|
| 647-2-142 A | Ammonium-Sulfate | 65.50 | 16.38 | 11.46 | 4.91 | 1.75 | 50 |
| 647-2-91 | Ammonium-Oxalate | 65.50 | 16.38 | 11.46 | 4.91 | 1.75 | 50 |
| 647-2-142 B | Ammonium-Phosphate | 65.50 | 16.38 | 11.46 | 4.91 | 1.75 | 50 |
| 647-2-161 A | Ammonium-Tartrate | 65.50 | 16.38 | 11.46 | 4.91 | 1.75 | 50 |
| 647-2-142 C | Ammonium-Citrate | 65.50 | 16.38 | 11.46 | 4.91 | 1.75 | 50 |

Coarse suspension was prepared and MF processed at 10 KPSI processing pressure. After 9-12 min of MF processing the particle size (Z-average) reached ~60-65 nm. A sample was collected and sterile filtered into Nalgene flask. The particle size of filtered nanosuspension was determined (Table 31).

TABLE 31

Summary of MF processing and resultant emulsion parameters.

| Lot # | Counter Ion | MFD | Particle size Z avrg, nm |
|---|---|---|---|
| 647-2-142 A | Sulfate | 28 MAR 16 | 60 |
| 647-2-91 | Oxalate | 11 MAR 16 | 65 |
| 647-2-142 B | Phosphate | 28 APR 16 | 64 |
| 647-2-161 A | Tartrate | 17 MAY 16 | 65 |
| 647-2-142 C | Citrate | 3 MAY 16 | 62 |

The liposomes were subjected to TFF followed by remote loading with Irinotecan, and another TFF cycle of Irinotecan loaded liposomes with PBS containing 6% sucrose. Irinotecan hydrochloride concentration used for remote loading: 1.0 mg/mL (Irinotecan free base concentration: 0.94 mg/mL).

The particle size of Irinotecan loaded liposomes is presented in Table 32.

TABLE 32

Particle size of irinotecan loaded liposomes.

| Lot # | Counter Ion | Loading Date | Particle size Z avrg, nm |
|---|---|---|---|
| 647-2-142 A | Sulfate | 28 MAR 16 | 64 |
| 647-2-91 | Oxalate | 11 MAR 16 | 65 |
| 647-2-142 B | Phosphate | 28 APR 16 | 65 |
| 647-2-161 A | Tartrate | 17 MAY 16 | 65 |
| 647-2-142 C | Citrate | 3 MAY 16 | 63 |

Followed irinotecan loading liposomal suspension was subjected to 5× TFF to majorly remove free (not encapsulated) irinotecan. To determine liposomal irinotecan concentration at T0 (within one week of MFD) TFF washed liposomes were ruptured by addition of Triton X-100 to the final concentration 1%, mixed by inversion, and incubated for 5-10 min prior to quantification via fluorometric analysis. Irinotecan content and percent of recovery (Irinotecan content in liposomal suspension relative to irinotecan free base concentration used for remote loading) are presented in the Table 33.

TABLE 33

Liposomal irinotecan content.

| Lot # | Counter Ion | Irinitecan free base used for loading, µg/mL | Assay, HPLC Irinotecan content (Liposomal Suspesion) µg/mL | Recovery, % |
|---|---|---|---|---|
| 647-2-142 A | Sulfate | 0.94 | 870 | 100 |
| 647-2-91 | Oxalate | 0.94 | 850 | 98 |
| 647-2-142 B | Phosphate | 0.94 | 850 | 98 |
| 647-2-161 A | Tartrate | 0.94 | 869 | 100 |
| 647-2-142 C | Citrate | 0.94 | 800 | 93 |

Liposomal irinotecan release studies were carried out at 37° C. within one week after manufacturing (Table 34). For each sample irinotecan release was determined at 2, 4 and 8 hrs time points.

TABLE 34

Irinotecan release rate determined at T0 (within one week after MFD).

| | | | | pH 5, Release, % | |
|---|---|---|---|---|---|
| Lot# | Counter Ion | Pka1 | 2 hrs | 4 hrs | 8 hrs |
| 647-2-142 A | Sulfate | −3 | 0 | 3 | 3 |
| 647-2-91 | Oxalate | 1.27 | 95 | 95 | 95 |
| 647-2-142 B | Phosphate | 1.96 | 9 | 11 | 7 |
| 647-2-161 A | Tartrate | 3.03 | 76 | 93 | 100 |
| 647-2-142 C | Citrate | 3.13 | 25 | 67 | 70 |

Particle size. It can be seen from the Tables 31 that microfluidization of different liposomal formulation resulted in similar particle sizes. Irinotecan loading did not result in any significant increase of particle size for any of prepared formulations (Tables 31-32).

Liposomal Irinotecan Content. The 100% recovery was observed when sulfate was used as a counter ion (Table 33). Interestingly, similar trend was observed for doxorubicin containing liposomes (Table 9). The ~100% recovery of liposomal Irinotecan after 5× TFF with PBS (pH 7.4) strongly suggest no leakage of encapsulated irinotecan.

Figure 22:
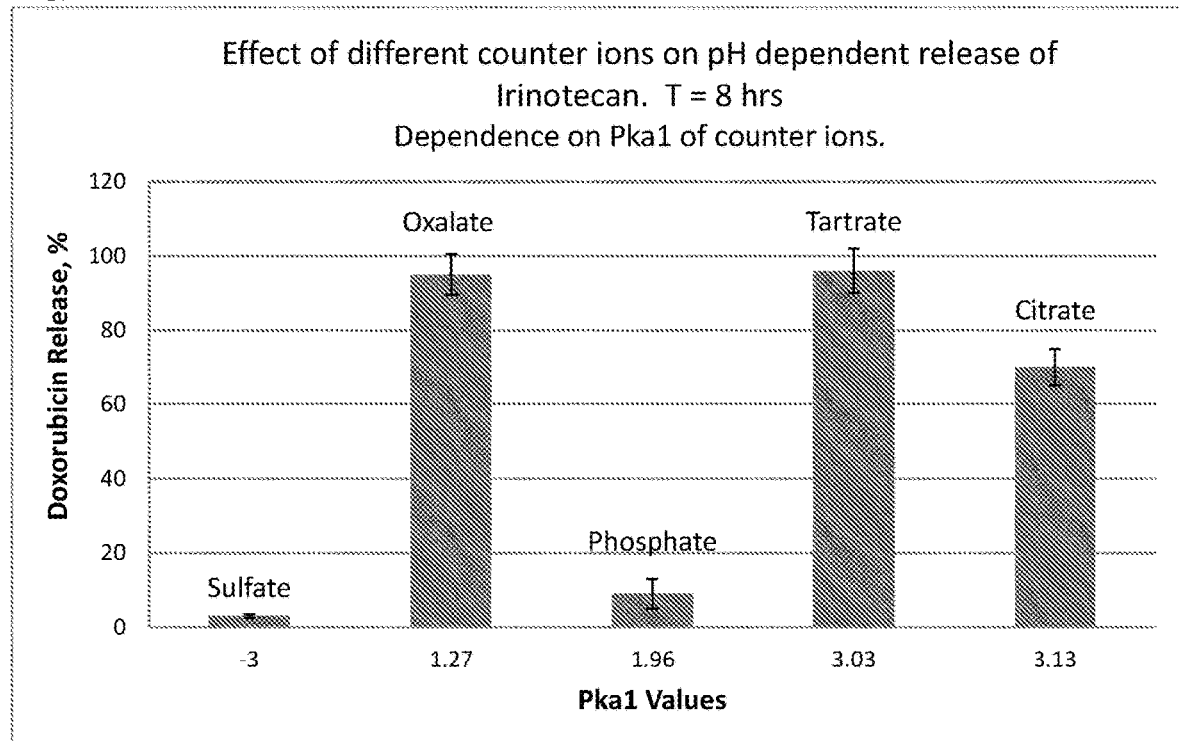
FIG. 22 is a graph showing percent of intraliposomal Irinotecan release into dissolution media (pH 5) after 2 hrs of incubation at 37° C. Each point on the curves represents mean±STD of data obtained in 2-6 independent experiments. For each experiment all the measurements were performed in sixtiplicate.

Liposomal Irinotecan release rate. Drug release studies were carried out within one week after MFD. Since Irinotecan is highly unstable at neutral pH and rapidly converts to carboxylate form in neutral medium [26-27], the release experiments were carried out at pH 5 only. It can be seen from the Table 34 that when oxalate or tartrate were used as a counter ions, irinotecan release rate at pH 5 reached ~100% and plateaued at 2-4 hrs time points. When citrate was used as a counter ion the release at acidic pH was more modest and reached 70% at 4-8 hrs. Formulations with sulfate and phosphate- showed very low release at pH 5 (Table 34 and FIG. 22). Overall, the obtained data on liposomal Irinotecan content and its release at pH 5 indicate high ΔpH7.4/5.0 release differential achieved when oxalate, or tartrate, or citrate were used as a counter ions.

Interestingly, that release of either doxorubicin or irinotecan from sulfate, phosphate, or citrate containing liposomes showed dependence on pKa1 value of corresponding counter ion (FIGS. 15 and 16). However, release of either doxorubicin or irinotecan from oxalate or tartrate (preferred counter ions in some embodiments) containing liposomes did not line up with pKa1 values of tested counter ions (FIGS. 15 and 16). These data strongly suggest contribution of unique physical state of doxorubicin-oxalate and/or -tartrate as well as irinotecan-oxalate and/or -tartrate intraliposomal aggregates into doxorubicin or irinotecan release profiles, and are in agreement with c_TEM analysis of doxorubicin-oxalate containing liposomes.

Overall, obtained data on irinotecan liposomes are in a good agreement with results obtained for doxorubicin and support the effect of oxalate and tartrate counter ions at preferred lipid/drug ratio. Thus, in some embodiments, oxalate or tartrate counter ion can be used for delivery of irinotecan. The data also suggest the use of citrate as a counter ion for irinotecan in some embodiments.

Example 12: Mitoxantrone

Methods.
Mitoxantrone Release from Liposomal Formulations

The study was carried out at 37° C. for the following time points: T0 and T24 hrs. Individual samples were diluted in 2 separate diluents/dissolution medias; PBS pH 7.4 and PBS pH 5 by a factor of 20 times (e.g. 100 µL of sample+1.9 mL of diluent) to simulate intravenous injection into mouse. For T0 time point, liposomal formulations were diluted in PBS pH 7.4 and pH 5 buffers at ~25° C.

Other liposomal samples were diluted 20× in PBS pH 7.4 and pH 5 buffers pre-warmed to 37° C. (to simulate in vivo temperature) and incubated for 0 and T24 hrs at 37° C. At each time point the release of mitoxantrone from the liposomes was assessed by visual observation: PBS/saline solution of mitoxantrone has intense blue color and it turns purple upon encapsulation into liposomes. Release of mitoxantrone from the liposomes results in changing the color from purple to blue.

Particle Size Determination

All analyses were performed using a Malvern Zetasizer Nano ZS with 4 mW He—Ne laser operating at a wavelength of 633 nm and a detection angle of 173°. Zetasizer software controlled the device and was used for analysis and reporting of values.

The intensity-averaged particle diameters (Z-average) were calculated from the cumulants analysis as defined in ISO 13321 (International Organization for Standardization 1996).

Samples are prepared using 30 µL of liposomal formulation in 1.5 mL of phosphate buffered saline (pH 7.4) and were equilibrated to 25° C. prior to analysis. Size measurements were done in triplicates for each sample.

pH Measurements

All analyses were performed using a Mettler Toledo SevenCompact pH meter with a Mettler Toledo InLab pH microelectrode.

Coarse Suspension Preparation.

Coarse suspension was prepared by dissolving PC, DMPC, FC, and P188 in 10 mL of DCM at the ratios indicated in Table 34. The mixture was dried under the stream of Nitrogen until viscous film was formed. The film was further dried in vacuum oven overnight. Next day dried lipid film was hydrated with 300 mM ammonium-oxalate buffer pre-warmed to 65° C., and immediately homogenized with a hand-held homogenizer for 2-3 min. Particle size of coarse suspension was determined and always was in the range of 800-1200 nm.

MF Processing

MF processing volume was always 100 ml unless specified differently. MF processing pressure was always 10 KPSI. Microfluidization of coarse suspension was performed in recycling mode (return of the material into the feed reservoir) at controlled (≤65° C.) temperature. Processing time was in 9-12 min range. The target particle size was 60-70 nm (Z-average).

Tangential Flow Filtration

Translucent nanosuspension was harvested from Microfluidizer and subjected to tangential flow filtration (TFF) with 15-20×volumes of PBS, pH 7.4. The purpose of TFF was to replace ammonium-oxalate, external buffer by PBS and to primarily remove ammonium from intraliposomal and external space. Ammonium in external buffer was measured by using ammonium specific electrode. TFF was stopped when ammonium concentration in external buffer was ≤3 mM.

Remote Loading of Mitoxantrone

Mitoxantrone hydrochloride was dissolved in saline to the final concentration 6 mg/mL. Saline solution of mitoxantrone hydrochloride was added to the liposomal nanosuspension in PBS, pH 7.4 to the final concentration 1 mg/mL, incubated at room temperature for 30 minutes, and placed at 2-8° C. After 16 hrs of incubation at 2-8° C. the mixture was subjected to another TFF 5× cycle with PBS pH 7.4 containing 6% of Sucrose. The purpose of this TFF cycle was to remove free (not encapsulated) mitoxantrone.

Then liposomal nanosuspension was sterile filtered into sterile Nalgene flask via 0.22 urn filter. Particle size and pH were determined. The sterile nanosuspension was aseptically dispensed into 2 mL pre-sterilized vials, stoppered, and sealed. The vials were stored at 2-8° C.

Example 13: Cold Loading of Mitoxantrone into Fixed (50:1) Lipid/Drug Ratio Liposomes Oxalate demonstrated ability to facilitate loading of doxorubicin and irinotecan into 50:1 lipid/drug ratio liposomes. Therefore, Oxalate was used in this example (Table 35).

TABLE 35

Formulation Composition.

| | | Amounts of solids used in formulations, W/W, % | | | | | |
|---|---|---|---|---|---|---|---|
| Lot # | Hydration Media | PC | DMPC | FC | P 188 | Mitoxantrone Dihydrochloride | Lipid/Drug |
| 647-2-97 B | Ammonium-Oxalate | 65.50 | 16.38 | 11.46 | 4.91 | 1.75 | 50 |

Coarse suspension was prepared and MF processed at 10 KPSI processing pressure. After 9-12 min of MF processing the particle size (Z-average) reached ~60-70 nm. A sample collected and sterile filtered into Nalgene flask. The particle size of filtered nanosuspension was determined (Table 36).

TABLE 36

Summary of MF processing and resultant emulsion parameters.

| Lot # | Counter Ion | MFD | Processing Pressure, KPSI | Particle size Z avrg, nm |
|---|---|---|---|---|
| 647-2-97 B | Oxalate | 11 MAR 16 | 10 | 65 |

The liposomes were subjected to TFF followed by remote loading with mitoxantrone, and another TFF cycle with PBS sucrose. Mitoxantrone hydrochloride concentration used for remote loading: 1.0 mg/mL The particle size of mitoxantrone loaded liposomes is presented in Table 37.

TABLE 37

Particle size. Mitoxantrone loaded liposomes.

| Lot # | Counter Ion | Loading Date | Particle size Z avrg, nm |
|---|---|---|---|
| 647-2-97 B | Oxalate | 15 MAR 16 | 67 |

Liposomal mitoxantrone release studies were carried out within one week after manufacturing. At each time point (0 and 24 hrs) the release of mitoxantrone from the liposomes was assessed by visual observation. It is worth mentioning that mitoxantrone release from the liposomes was markedly slower compare to doxorubicin and irinotecan.

Since mitoxantrone release study continued for 24 hrs, the particle size of incubated samples was determined at T0 and T24 to prove that integrity of the liposomes was not compromised. It can be seen from the Table 37 that there was no dramatic change of the particle size or aggregation observed after 24 hrs of incubation of 20 fold diluted sample at 37° C.

TABLE 38

Particle size measurements during release study.

| Lot# | Time point | pH | Particle size Z avrg, nm |
|---|---|---|---|
| 647-2-97 B | 0 hrs | 5 | 63 |
| 647-2-97 B | 24 hrs | | 70 |
| 647-2-97 B | 0 hrs | 7 | 63 |
| 647-2-97 B | 24 hrs | | 69 |

DISCUSSION

Particle size. It can be seen from the Tables 36 and 37 that microfluidization and loading of mitoxantrone resulted in similar particle sizes comparable to doxorubicin (Tables 16 and 17) and irinotecan (Tables 31 and 32).

Figure 23:
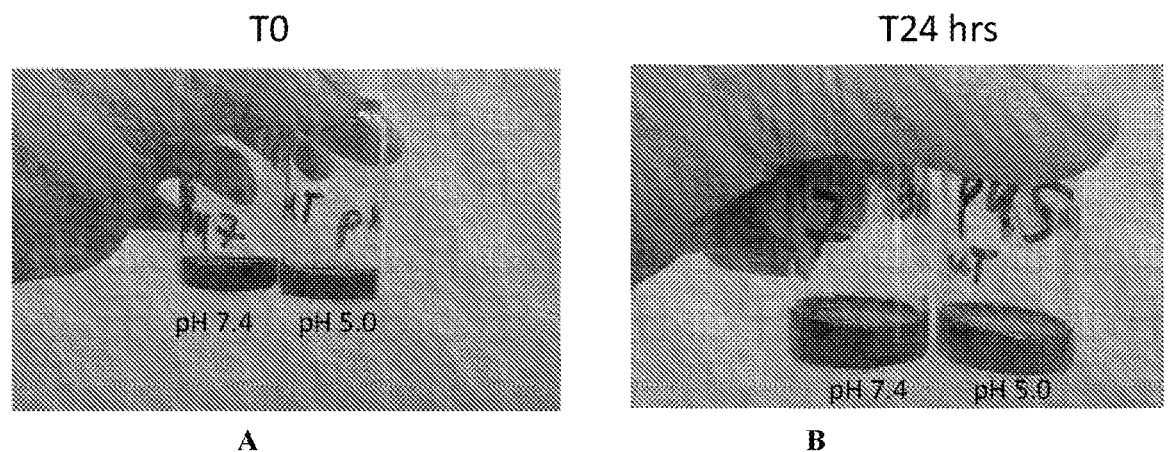
FIG. 23A and FIG. 23B are images of mitoxantrone solutions at pH 7.4 and pH 5.0.

Liposomal Mitoxantrone release. Drug release studies were carried out within one week after MFD. It is worth mentioning that PBS/saline solution of mitoxantrone has intense blue color and it turns purple upon encapsulation into liposomes. It can be seen from FIG. 23A that at T0 the color of mitoxantrone remains purple at both pH 7.4 and 5 that is indicative of encapsulated Mitoxantrone. When oxalate was used as counter ion, the color of the sample turned blue after 24 hrs at pH 5.0, whereas it remained purple at pH 7.4 (FIG. 23B). These data indicate release of mitoxantrone from the liposomes at pH 5.0 and absence of release at pH 7.4.

Thus, overall obtained data demonstrate the effect of oxalate and tartrate counter ions, lipid/drug ratio, and drug loading conditions for preferential physical state of the intraliposomal doxorubicin aggregates that result in optimal ΔpH7.4/5.0 release differential at least in some embodiments. All these factors may contribute to efficient pH targeted delivery of the weak bases chemotherapeutic agents to the tumor sites.

Summary of Experimental Findings

In embodiments, identification of proper counter ions oxalate and tartrate (e.g. preferred counter ions in some embodiments) that can form intraliposomal pharmaceutical salts aggregates with weak bases, proper lipid/drug ratio (e.g. preferred range 20:1 to 65:1 in some embodiments), and PL/FC ratio (e.g. preferred range I/1 to 4/1 in some embodiments) to maximize drug release differential between neutral and acidic pH and to increase liposomal stability in serum/blood for optimal pH targeted delivery of weak bases chemotherapeutic agents (for various molecular targets) to tumor site. The marked difference between in vitro characteristics of oxalate or tartrate containing liposomes, and other tested counter ions strongly suggests uniqueness of physical state(s) of intraliposomal doxorubicin-oxalate or -tartrate aggregates that evidently facilitates their dissolution in response to the temperature and pH.

Only 5 (sulfate, oxalate, phosphate, tartrate, and citrate) from 15 tested counter ions facilitated remote loading of doxorubicin and formation of stable doxorubicin-salt containing liposomes. Other 10 tested counter ions resulted in no loading of doxorubicin into the liposomes and caused precipitation of the liposomal material during overnight storage at 2-8° C.

In embodiments, it was surprising finding that only oxalate and tartrate yielded doxorubicin-containing liposomes with desirable pH dependent drug release profile (ΔpH 7.4/5.0 or ΔpH 7.4/6.7/6.0/5.0 release differential) at 37° C. (body temperature). Therefore, oxalate and tartrate were selected as preferred counter-ions in some embodiments.

Increased cytotoxicity of doxorubicin-oxalate-containing liposomes compared to Doxil® (doxorubicin-sulfate) was observed with two cancerous cell lines (Daudi and Hela cells)

Improved safety and efficacy of doxorubicin-oxalate-containing liposomes compared to Doxil® (doxorubicin-sulfate) was observed in mouse B lymphoma model;

In some embodiments, it was surprising finding that oxalate and tartrate containing liposomes can efficiently and rapidly encapsulate doxorubicin at room temperature. It was also surprising finding that in some embodiments, room temperature (RT) loading of doxorubicin into oxalate and tartrate containing liposomes further improved (maximized) ΔpH 7.4/5.0 release differential compared to oxalate- and/or tartrate-containing liposomes loaded at 70° C. Other temperatures that can be used for remote doxorubicin loading in oxalate containing liposomes include 2-8° C. to 70° C., with or without overnight incubation at 2-8° C.

In some embodiments, citrate was another counter ion that showed notable improvement of ΔpH 7.4/5.0 release differential upon cold loading of doxorubicin. In contrast, room temperature loading did not result in improvement of doxorubicin release profile when sulfate and/or phosphate were used as counter ions. Other temperatures that can be used for remote doxorubicin loading in tartrate and citrate containing liposomes include 2-8° C. to 70° C. with or without overnight incubation at 2-8° C.

In embodiments, successful lyophilization of the doxorubicin in presence of lactose and/or mannitol resulted in lyophilized material that was readily reconstitutable in water for injection at room temperature to the final concentration up to 6 mg/mL. In embodiments, mixing of lyophilized and reconstituted doxorubicin material with the novel oxalate and tartrate (preferred counter ions in some embodiments) containing liposomes resulted in efficient and rapid encapsulation of the doxorubicin at room temperature. The resultant product demonstrated exceptional ΔpH 7.4/5.0 or ΔpH 7.4/6.7/6.0/5.0 release differential in some embodiments. In embodiments, this finding leads to particular product presentation format having or consisting of two vials: a vial with lyophilized doxorubicin and a vial with liposomal vehicle suspension. Mixing (via simple inversion) the reconstituted content of two vials at room temperature will yield the final ready-for-use product within minutes—a very convenient formulation to prepare at the bedside. Development of lyophilized liposomal vehicle is also considered.

In embodiments, the effect of lipid/drug ratio for achieving maximum ΔpH 7.4/5.0 or ΔpH 7.4/6.7/6.0/5.0 release differential and optimal serum/blood stability was demonstrated for both preferred counter ions oxalate and tartrate. In embodiments, it was also surprising finding that liposomes exhibited high ΔpH 7.4/5.0 or ΔpH 7.4/6.7/6.0/5.0 release differential and increased serum/blood stability when lipid to drug ratio was above 20 (preferred range is 20:1-65:1). In embodiments, when lipid/drug ratio was <20, doxorubicin loading was poor and leakage of the doxorubicin from liposomes was evident. Other ratios that can be used include 20:1 to 100:1. Performed studies suggest that in some embodiments, optimal lipid/drug ratios for achieving maximum pH release differential are in the range from 20:1 to 65:1. Other ratios that can be used include 10:1 to 100:1. In embodiments, the effect of specific range of PL/FC ratios (e.g. 1/1 to 4/1) for optimal serum/blood stability and ΔpH 7.4/6.7/6.0/5.0 release differential was demonstrated for preferred counter ion oxalate.

Applicability of specified counter ions and optimized Lipid/Drug ratio to achieving pH discriminative drug release profile was demonstrated for -3 structurally different weak bases cancer therapeutic agents: doxorubicin, irinotecan, and mitoxantrone. Other ratios that can be used include 20:1 to 100:1.

Cryo transmission electron microscopy (cryo-TEM) led to important finding that doxorubicin-oxalate aggregates appeared to have non-crystalline nature and did not form tightly packed bundles observed when sulfate, phosphate, or citrate were used as a counter ions. This finding signifies unique physical state of the intraliposomal doxorubicin-oxalate aggregates compared to doxorubicin-sulfate, phosphate, and citrate aggregates, and is in a good agreement with observed difference in drug release profiles.

In embodiments, the poor ΔpH 7.4/5.0 release differential was observed at 25° C. for all tested counter ions, while at 37° C. dramatic increase of ΔpH7.4/5.0 release differential was observed with oxalate or tartrate, but not with sulfate, phosphate, or citrate. The observed difference in ΔpH 7.4/5.0 release differential determined at 25° C. and 37° C. might also indicates on more profound temperature dependent transition of the physical state of doxorubicin-oxalate or -tartrate intraliposomal aggregates compared to -sulfate, -phosphate, or -citrate at least in some embodiments.

In embodiments, addition of P188 to the liposomal formulation did not have any significant impact on particle size, efficiency of doxorubicin encapsulation, and doxorubicin release profile compared to liposomal formulation prepared with no P188. However, P188 was used in liposomal formulations due to its possible advantageous impact on biological performance of drug-loaded liposomes [10-11, 16-19] in some embodiments.

In embodiments, complementing preferred counter ions oxalate and/or tartrate with ascorbic acid (e.g. AA/oxalate—1:8 or 1:3), and/or NAC (e.g. NAC/oxalate—1:3), and/or ascorbil palmitate (e.g. AP/oxalate—1:150 or 1:15), and/or CoQ10 (e.g. CoQ10/oxalate—1:300), and/or EDTA (e.g. EDTA/oxalate 1:150) did not show considerable negative effect on doxorubicin release profile compared to liposomes containing oxalate or tartrate alone. In embodiments, this finding enables use of ascorbic acid and/or NAC, and/or ascorbil palmitate, and/or CoQ10, and/or EDTA in combination with oxalate or tartrate. In embodiments, citrate can be used with any above-listed chelators in any ratio. In embodiments, addition of antioxidants and/or chelators can alleviate oxidative stress during liposomes processing, and therefore may be beneficial for the final product stability. Moreover, in embodiments, the combination of optimized ΔpH7.4/5.0 release differential and antioxidant(s) and/or chelators may be advantageous for the final product biological performance. It has been shown that ascorbic acid, NAC, and EDTA exert cardioprotective effect alleviating doxorubicin induced cardiac toxicity [28-29, 33, 36-37]. In embodiments, other ratios of PA to oxalate or tartrate that can be used include 1:300 to 1:10. Other ratios of CoQ10 to oxalate or tartrate that can be used include 1:300 to 1:10. Other ratios of EDTA to oxalate or tartrate that can be used include 1:300 to 1:5. Other counter ions and/or antioxidants, and/or chelators that can be advantageous and/or used in combination with oxalate and/or tartrate include citrate, and/or phytate, and/or glutathione, and/or vitamin e, and/or dexrazoxane, and/or deferoxamine.

In embodiments, it was surprising finding that structurally different chemotherapeutic agents irinotecan and mitoxantrone (Table 2) demonstrated similar to doxorubicin pH discriminative release profile when oxalate and/or tartrate were used as a counter ions at 50:1 lipid/drug ratio (other ratios that can be used include 20:1 to 100:1). It is worth mentioning that doxorubicin, irinotecan, and mitoxantrone are weak bases (Table 2). Thus, in embodiments, basicity of chemotherapeutic agents, proper counter ions, optimal lipid/drug ratio, and loading conditions may contribute to pH discriminative drug release and efficient delivery of weak bases chemotherapeutic agents (Table 3) to the tumor.

In embodiments, release of either doxorubicin or irinotecan from sulfate, phosphate, or citrate containing liposomes showed dependence on pKa1 value of corresponding counter ion. However, release of either doxorubicin or irinotecan from oxalate or tartrate (preferred counter ions in some embodiments) containing liposomes did not line up with pKa1 values of tested counter ions. These data may suggest contribution of unique physical state of doxorubicin-oxalate and -tartrate intraliposomal aggregates into doxorubicin release profile, and are in agreement with c_TEM analysis of doxorubicin-oxalate containing liposomes.

EMBODIMENTS

Embodiment 1

A pharmaceutical composition comprising a liposome, the liposome encompassing a weakly basic anticancer compound and an acid or salt thereof, wherein the acid is oxalic acid or tartaric acid.

Embodiment 2

The pharmaceutical composition of Embodiment 1, wherein the weakly basic anticancer compound is doxorubicin, irinotecan, mitoxantrone or a combination thereof.

Embodiment 3

The pharmaceutical composition of Embodiment 1 or 2, wherein the liposome comprises a poloxamer.

Embodiment 4

The pharmaceutical composition of Embodiment 3, wherein the poloxamer is poloxamer 188.

Embodiment 5

The pharmaceutical composition of any one of Embodiments 1-3, wherein the liposome comprises a plurality of lipid compounds and the weight ratio of the plurality of lipids to the weakly basic anticancer agent is at least 20/1.

Embodiment 6

The pharmaceutical composition of any one of Embodiments 1-3, wherein the liposome comprises a plurality of lipid compounds and the weight ratio of the plurality of lipids to the weakly basic anticancer agent is about 20/1 to about 100/1.

Embodiment 7

The pharmaceutical composition of any one of Embodiments 1-3, wherein the liposome comprises a plurality of lipid compounds and the weight ratio of the plurality of lipids to the weakly basic anticancer agent is 20/1 to about 50/1.

Embodiment 8

The pharmaceutical composition of any one of Embodiments 1-7, wherein the weakly basic anticancer compound is substantially released from the liposome only at acidic pH.

Embodiment 9

The pharmaceutical composition of Embodiment 8, wherein at least 40% of the weakly basic anticancer compound is released from the liposome at pH 5 under standard assay conditions and wherein less than 5% of the weakly basic anticancer compound is released from the liposome at pH 7.4 under standard assay conditions.

Embodiment 10

The pharmaceutical composition of Embodiment 8, wherein at least 80% of the weakly basic anticancer compound is released from the liposome at pH 5 under standard assay conditions and wherein less than 5% of the weakly basic anticancer compound is released from the liposome at pH 7.4 under standard assay conditions.

Embodiment 11

The pharmaceutical composition of Embodiment 9, wherein the standard assay conditions comprise 20× dilution in PBS buffer pH 7.4 or pH 5 and incubation at 25° C. or 37° C. for 2, 4, or 8 hours.

Embodiment 12

The pharmaceutical composition of any one of Embodiments 1-11, wherein the liposome is substantially spherical.

Embodiment 13

The pharmaceutical composition of any one of Embodiments 1-12, wherein the pharmaceutical composition comprises a plurality of the liposome having mean longest dimension of about 60-80 nm determined by the intensity-averaged particle diameters (Z-average) measured by Dynamic Light Scattering.

Embodiment 14

The pharmaceutical composition of any one of Embodiments 1-12, wherein the pharmaceutical composition comprises a plurality of the liposome having the mean longest dimension of about 10-30 nm determined by the number-based particle diameters measured by Dynamic Light Scattering.

Embodiment 15

The pharmaceutical composition of any one of Embodiments 1-12, wherein the pharmaceutical composition comprises a plurality of the liposome having a mean longest dimension from 10-30 nm determined by Cryo-Transmission Electron Microscopy.

Embodiment 16

The pharmaceutical composition of any of Embodiments 1-14, wherein the liposome comprises about 500-1000 µg/mL of the weakly basic anticancer compound and an acid or salt thereof.

Embodiment 17

The pharmaceutical composition of any of Embodiments 1-14, wherein the liposome comprises about 700-850 µg/mL of the weakly basic anticancer compound and an acid or salt thereof.

Embodiment 18

The pharmaceutical composition of Embodiment 1-17, wherein the liposome comprises a plurality of the weakly basic anticancer compound forming a disorganized non-crystalline aggregate.

Embodiment 19

The pharmaceutical composition of any of Embodiments 1-18, wherein the liposome comprises a plurality of the weakly basic anticancer compound and retains greater than 90% of the plurality of weakly basic anticancer compound after 40 days when stored at 2-8° C. under standard storage conditions.

Embodiment 20

The pharmaceutical composition of Embodiment 1-2 or 4-19, wherein the liposome does not comprise a cholesterol or a poloxamer 188.

Embodiment 21

The pharmaceutical composition of Embodiment 1, wherein the liposome does not comprise an acidic organic compound other than oxalic acid, tartaric acid, or salts thereof.

Embodiment 22

The pharmaceutical composition of any one of Embodiments 1-21, wherein the drug loaded liposome is formed by loading the weakly basic anticancer compound into an unloaded liposome containing an encapsulated acid or salt thereof, followed by incubation at a room temperature.

Embodiment 23

A method for preparing a liposome encompassing a weakly basic anticancer compound and an acid or salt thereof, wherein the acid is oxalic acid or tartaric acid, the method comprising
 mixing a solution of the weakly basic anticancer compound with a suspension comprising the liposomes containing an encapsulated acid or salt thereof; and
 incubating the solution of the weakly basic anticancer compound with the suspension comprising the liposomes containing an encapsulated acid or salt thereof.

Embodiment 24

The method of Embodiment 23, wherein about 85-100% of the weakly basic anticancer compound used in mixing with a suspension comprising the liposomes containing an encapsulated acid or salt thereof is retained within the liposomes.

Embodiment 25

The method of Embodiment 23, wherein about 95-100% of the weakly basic anticancer compound used in mixing with a suspension comprising the liposomes containing an encapsulated acid or salt thereof is retained within the liposomes.

Embodiment 26

The method of any of Embodiments 23-26, wherein the incubating step occurs at room temperature.

Embodiment 27

The method of Embodiment 25, wherein the incubating step is about 10-30 minutes.

Embodiment 28

The method of Embodiment 25, wherein the incubating step is about 5-25 minutes.

Embodiment 29

A kit comprising a first vial comprising a weakly basic anticancer compound, and a second vial with a suspension comprising the liposomes containing an encapsulated acid or salt thereof.

Embodiment 30

The kit of Embodiment 29, wherein the weakly basic anticancer compound of the first vial is a lyophilized weakly basic anticancer.

Embodiment 31

The kit of Embodiment 29, wherein the liposome suspension of the second vial is an aqueous suspension of liposomes containing an encapsulated acid or salt thereof.

Embodiment 32

A method of using the kit of any one of Embodiments 28-31, comprising mixing the contents of the first vial with the contents of the second vial.

Embodiment 33

The method of Embodiment 32, wherein the mixing is at room temperature.

Embodiment 34

The method of any of Embodiments 23-25, wherein the incubating step occurs at Room temperature followed by incubation at 2-8° C.

Embodiment 35

The method of Embodiment 34, wherein the incubating step at RT is about 10-30 minutes.

Embodiment 36

The method of any of Embodiments 34, wherein the incubating step at 2-8° C. is about 60-960 minutes.

Embodiment 37

The method of any of Embodiments 23-35, wherein the incubating step occurs at 70° C.

Embodiment 38

The method of Embodiment 37, wherein the incubating step is about 10-30 minutes.

Embodiment 39

A method for preparing a liposome encompassing a weakly basic anticancer compound and an acid or salt thereof, wherein the acid is citric acid, the method comprising
  mixing a solution of the weakly basic anticancer compound with a suspension comprising the liposomes containing an encapsulated acid or salt thereof; and
  incubating the solution of the weakly basic anticancer compound with the suspension comprising the liposomes containing an encapsulated acid or salt thereof.

Embodiment 40

A pharmaceutical composition comprising a liposome, the liposome encompassing a weakly basic anticancer compound and an acid or salt thereof, wherein the acid is citric acid and wherein the liposome comprises a plurality of lipid compounds and the weight ratio of the plurality of lipids to the weakly basic anticancer agent is at least 20/1.

Embodiment 41

A pharmaceutical composition comprising a liposome, the liposome encompassing a weakly basic anticancer compound and an acid or salt thereof, wherein the acid is oxalic acid or tartaric acid.

Embodiment 42

The pharmaceutical composition of Embodiment 41, wherein the weakly basic anticancer compound is doxorubicin, irinotecan, mitoxantrone or a combination thereof.

Embodiment 43

The pharmaceutical composition of Embodiment 41, wherein the liposome comprises a poloxamer.

Embodiment 44

The pharmaceutical composition of Embodiment 43, wherein the poloxamer is poloxamer 188.

Embodiment 45

The pharmaceutical composition of Embodiment 41, wherein the liposome comprises a plurality of lipids and the weight ratio of the lipids to the weakly basic anticancer compound and an acid or salt thereof is at least 10/1.

Embodiment 46

The pharmaceutical composition of Embodiment 41, wherein the liposome comprises a plurality of lipids and the weight ratio of the lipids to the weakly basic anticancer compound and an acid or salt thereof is about 10/1 to about 100/1.

Embodiment 47

The pharmaceutical composition of Embodiment 41, wherein the liposome comprises a plurality of lipids and the weight ratio of the lipids to the weakly basic anticancer compound and an acid or salt thereof is 20/1 to about 50/1.

Embodiment 48

The pharmaceutical composition of Embodiment 41, wherein the liposome comprises a plurality of free cholesterols.

Embodiment 49

The pharmaceutical composition of Embodiment 41, wherein the liposome comprises a plurality of phospholipids.

Embodiment 50

The pharmaceutical composition of Embodiment 48, wherein said pharmaceutical composition comprises phospholipids and a molar ratio of the phospholipids to the free cholesterols is at least 0.5/1.

Embodiment 51

The pharmaceutical composition of Embodiment 48, wherein said pharmaceutical composition comprises phospholipids and a molar ratio of the phospholipids to the free cholesterols is at least 0.5/1 to about 4/1.

Embodiment 52

The pharmaceutical composition of Embodiment 48, wherein said pharmaceutical composition comprises phospholipids and a molar ratio of the phospholipids to the free cholesterols is in the range of about 0.86/1 to about 3.68/1.

Embodiment 53

The pharmaceutical composition of Embodiment 41, wherein the weakly basic anticancer compound is substantially released from the liposome at pH<7.4.

Embodiment 54

The pharmaceutical composition of Embodiment 41, wherein at least 40% of the weakly basic anticancer compound is released from the liposome at pH 5 under standard assay conditions.

Embodiment 55

The pharmaceutical composition of Embodiment 41, wherein less than 5% of the weakly basic anticancer compound is released from the liposome at pH 7.4 under standard assay conditions.

Embodiment 56

The pharmaceutical composition of Embodiment 41, wherein at least 80% of the weakly basic anticancer compound is released from the liposome at pH 5 under standard assay conditions.

Embodiment 57

The pharmaceutical composition of Embodiment 41, wherein at least 10% of the weakly basic anticancer compound is released from the liposome at about pH 6.0 under standard assay conditions.

Embodiment 58

The pharmaceutical composition of Embodiment 41, wherein at least 50% of the weakly basic anticancer compound is released from the liposome at pH 6.0 under standard assay condition's.

Embodiment 59

The pharmaceutical composition of Embodiment 41, wherein at least 7% of the weakly basic anticancer compound is released from the liposome at pH 6.7 under standard assay conditions.

Embodiment 60

The pharmaceutical composition of Embodiment 41, wherein at least 30% of the weakly basic anticancer compound is released from the liposome at pH 6.7 under standard assay conditions.

Embodiment 61

The pharmaceutical composition of Embodiment 41, wherein the liposome comprises a plurality of weakly basic anticancer compounds and retains greater than 35-50% of the plurality of weakly basic anticancer compound for up to about 8 hrs of incubation in serum or blood when tested under standard assay conditions.

Embodiment 62

The pharmaceutical composition of any one of Embodiments 54-61, wherein the standard assay conditions comprise 20× or 50× dilution of the liposomes in PBS buffer.

Embodiment 63

The pharmaceutical composition of any one of Embodiments 54-61, wherein the standard assay conditions comprise incubation at pH 7.4, pH 6.7, pH 6.0 or pH 5.0.

Embodiment 64

The pharmaceutical composition of any one of Embodiments 54-61, wherein the standard assay conditions comprise incubation at about 25° C. or about 37° C.

Embodiment 65

The pharmaceutical composition of any one of Embodiments 14-21, wherein the standard assay conditions comprise incubation for about 2, about 4 or about 8 hours.

Embodiment 66

The pharmaceutical composition of any one of Embodiments 54-61, wherein the standard assay conditions comprise 50× dilution of the liposomes in serum or blood and incubation at 37° C. for 2, 4, or 8 hours at a physiological pH (pH 7.4).

Embodiment 67

The pharmaceutical composition of Embodiment 41, wherein the liposome is substantially spherical.

Embodiment 68

The pharmaceutical composition of Embodiment 41, wherein the pharmaceutical composition comprises a plurality of the liposome having a mean longest dimension of about 60-80 nm determined by the intensity-averaged particle diameters (Z-average) measured by Dynamic Light Scattering.

Embodiment 69

The pharmaceutical composition of Embodiment 41, wherein the pharmaceutical composition comprises a plurality of the liposome having a mean longest dimension of about 10-30 nm determined by the number-based particle diameters measured by Dynamic Light Scattering.

Embodiment 70

The pharmaceutical composition of Embodiment 41, wherein the pharmaceutical composition comprises a plurality of the liposome having a mean longest dimension from 10-30 nm determined by Cryo-Transmission Electron Microscopy.

Embodiment 71

The pharmaceutical composition of Embodiment 41, wherein the liposome comprises about 500-1000 µg/mL of the weakly basic anticancer compound and an acid or salt thereof.

Embodiment 72

The pharmaceutical composition of Embodiment 41, wherein the liposome comprises about 700-850 µg/mL of the weakly basic anticancer compound and an acid or salt thereof.

Embodiment 73

The pharmaceutical composition of Embodiment 41, wherein the liposome comprises a plurality of the weakly basic anticancer compound forming a disorganized non-crystalline aggregate.

Embodiment 74

The pharmaceutical composition of Embodiment 41, wherein the liposome comprises a plurality of the weakly basic anticancer compound and retains greater than 90% of the plurality of weakly basic anticancer compound after 40 days when stored at 2-8° C. under standard storage conditions.

Embodiment 75

The pharmaceutical composition of Embodiment 41, wherein the liposome does not comprise a cholesterol or a poloxamer 188.

Embodiment 76

The pharmaceutical composition of Embodiment 41, wherein the liposome does not comprise an acidic organic compound other than oxalic acid, tartaric acid, or salts thereof.

Embodiment 77

The pharmaceutical composition of Embodiment 41, wherein the liposome does not comprise the weakly basic anticancer compound and an acid or salt thereof other than oxalic acid, tartaric acid or salts thereof.

Embodiment 78

The pharmaceutical composition of Embodiment 41, wherein the liposome encompassing the weakly basic anticancer compound and an acid or salt thereof is formed by loading the weakly basic anticancer compound into an unloaded liposome containing an encapsulated acid or salt thereof, followed by incubation at a room temperature.

Embodiment 79

The pharmaceutical composition of Embodiment 38, wherein the unloaded liposome after 180 and/or 540 days of storage at 2-8° C. under standard storage conditions retains greater than 90% of the weakly basic anticancer compound and an acid or salt thereof upon loading.

Embodiment 80

The pharmaceutical composition of Embodiment 39, wherein about 40-80% of the loaded weakly basic anticancer compound and an acid or salt thereof is released from the liposome at pH 5.0 under standard assay, conditions.

Embodiment 81

The pharmaceutical composition of Embodiment 39, wherein about 20-60% of the loaded weakly basic anticancer compound and an acid or salt thereof is released from the liposome at pH 6.0 under standard assay conditions.

Embodiment 82

The pharmaceutical composition of Embodiment 39, wherein about 7-30% of the loaded weakly basic anticancer compound and an acid or salt thereof is released from the liposome at pH 6.7 under standard assay conditions.

Embodiment 83

The pharmaceutical composition of Embodiment 39, wherein less than 5% of the weakly basic anticancer compound and an acid or salt thereof is released from the liposome at pH 7.4 under standard assay conditions.

Embodiment 84

The pharmaceutical composition of claim 41 further comprising a compound selected from the group consisting of ascorbic acid (AA), or N-Acetylcysteine (NAC), ascorbil palmitate (AP), ubiquinone (CoQ10), and ethylenediaminetetraacetic acid (EDTA).

Embodiment 85

A method for preparing a liposome encompassing a weakly basic anticancer compound and an acid or salt thereof, wherein the acid is oxalic acid or tartaric acid, the method comprising
mixing a solution comprising a weakly basic anticancer compound with a suspension comprising a plurality of liposomes, wherein each of the liposomes comprise an oxalic acid or tartaric acid or salts thereof.

Embodiment 86

The method of Embodiment 85, wherein further comprising incubating the solution and the suspension.

Embodiment 87

The method of Embodiment 85, wherein about 85-100% of the weakly basic anticancer compound is incorporated within the plurality of liposomes subsequent to said mixing.

Embodiment 88

The method of Embodiment 85, wherein about 95-100% of the weakly basic anticancer compound is incorporated within the plurality of liposomes subsequent to said mixing.

Embodiment 89

The method of Embodiment 86, wherein the incubating step occurs at room temperature (RT).

Embodiment 90

The method of Embodiment 89, wherein the incubating step is about 10-30 minutes.

Embodiment 91

The method of Embodiment 89, wherein the incubating step is about 5-25 minutes.

Embodiment 92

The method of Embodiment 85, wherein the incubating step occurs at room temperature (RT) followed by incubation at 2-8° C.

Embodiment 93

The method of Embodiment 92, wherein the incubating step at RT is about 10-30 minutes.

Embodiment 94

The method of Embodiment 92, wherein the incubating step at 2-8° C. is about 60-960 minutes.

Embodiment 95

The method of Embodiment 86, wherein the incubating step occurs at 70° C.

Embodiment 96

The method of Embodiment 95, wherein the incubating step is about 10-30 minutes.

Embodiment 97

A kit comprising a first container comprising a weakly basic anticancer compound, and a second container comprising a suspension, said suspension comprising a plurality of liposomes, wherein each of said plurality of liposome comprise an acid or salt of said weakly basic anticancer compound, wherein the acid is oxalic acid or tartaric acid.

Embodiment 98

The kit of Embodiment 97, wherein the weakly basic anticancer compound is a lyophilized weakly basic anticancer compound.

Embodiment 99

The kit of Embodiment 97, wherein the suspension is an aqueous suspension.

Embodiment 100

A method of using the kit of Embodiment 97, comprising mixing the contents of the first container with the contents of the second container.

Embodiment 101

The method of Embodiment 100, wherein the mixing is at room temperature.

Embodiment 102

A method for preparing a liposome comprising a weakly basic anticancer compound and an acid or salt thereof, wherein the acid is citric acid, the method comprising
mixing a solution comprising the weakly basic anticancer compound with a suspension comprising a plurality of liposomes, wherein each of aid plurality of liposome comprise an acid or salt thereof.

Embodiment 103

The method of Embodiment 102 further comprising incubating the solution with the suspension.

Embodiment 104

The method of Embodiment 102, wherein the incubating step occurs at room temperature (RT).

Embodiment 105

The method of Embodiment 104, wherein the incubating step is about 10-30 minutes.

Embodiment 106

The method of Embodiment 104, wherein the incubating step is about 5-25 minutes.

Embodiment 107

The method of Embodiment 103, wherein the incubating step occurs at room temperature (RT) followed by incubation at 2-8° C.

Embodiment 108

The method of Embodiment 107, wherein the incubating step at RT is about 10-30 minutes.

Embodiment 109

The method of Embodiment 107, wherein the incubating step at 2-8° C. is about 60-960 minutes.

Embodiment 110

The method of Embodiment 103, wherein the incubating step occurs at 70° C.

Embodiment 111

The method of Embodiment 110, wherein the incubating step is about 10-30 minutes.

Embodiment 112

A pharmaceutical composition comprising a liposome, the liposome comprising a weakly basic anticancer compound and an acid or salt thereof, wherein the acid is citric acid.

Embodiment 113

The pharmaceutical composition of Embodiment 112, wherein the liposome comprises a plurality of lipids and the weight ratio of the plurality of lipids to the weakly basic anticancer compound and an acid or salt thereof is at least 10 to 1.

Embodiment 114

The pharmaceutical composition of Embodiment 112, wherein the liposome comprises a plurality of free cholesterols.

Embodiment 115

The pharmaceutical composition of Embodiment 114, wherein the liposome comprises phospholipids, wherein the molar ratio of the phospholipid to the free cholesterols is at least 1 to 1.

Embodiment 116

The pharmaceutical composition of Embodiment 112 further comprising a compound selected from the group consisting of ascorbic acid (AA), or N-Acetylcysteine (NAC), ascorbil palmitate (AP), ubiquinone (CoQ10), and ethylenediaminetetraacetic acid (EDTA).

Embodiment 117

A method of treating a cancer in a subject, the method comprising:
administering an effective amount of the pharmaceutical composition of Embodiment 40 to the subject in need of the treatment.

Embodiment 118

The method of Embodiment 117, wherein the weakly basic anticancer compound is doxorubicin, irinotecan, mitoxantrone or a combination thereof.

Embodiment 119

The method of Embodiment 117, wherein the liposome comprises a poloxamer.

Embodiment 120

The method of Embodiment 117, wherein the poloxamer is poloxamer 188.

Embodiment 121

The method of Embodiment 117, wherein the liposome comprises lipids and the weight ratio of the lipids to the weakly basic anticancer compound is at least 10 to 1.

Embodiment 122

The method of Embodiment 117, wherein the liposome comprises a lipids and the weight ratio of the lipids to the weakly basic anticancer compound is about 10 to 1 to about 100 to 1.

Embodiment 123

The method of Embodiment 117, wherein the liposome comprises a plurality of lipids and the weight ratio of the lipids to the weakly basic anticancer compound is about 20 to 1 to about 50 to 1.

Embodiment 124

The method of Embodiment 117, wherein the liposome comprises a plurality of free cholesterols.

Embodiment 125

The method of Embodiment 117, wherein the liposome comprises a plurality of phospholipids.

Embodiment 126

The method of Embodiment 125, wherein said liposome comprises phospholipids and a molar ratio of the phospholipids to the free cholesterols is at least 0.5 to 1.

Embodiment 127

The method of Embodiment 125, wherein said liposome comprises phospholipids and a molar ratio of the phospholipids to the free cholesterols is at least 0.5 to 1 to about 4 to 1.

Embodiment 128

The method of Embodiment 125, wherein said liposome comprises phospholipids and a molar ratio of the phospholipids to the free cholesterols is in the range of about 0.86 to 1 to about 3.68 to 1.

Embodiment 129

The method of Embodiment 117, wherein the weakly basic anticancer compound is substantially released from the liposome at pH<7.4.

Embodiment 130

The method of Embodiment 117, wherein at least 40% of the weakly basic anticancer compound is released from the liposome at pH 5 under standard assay conditions.

Embodiment 131

The method of Embodiment 117, wherein less than 5% of the weakly basic anticancer compound is released from the liposome at pH 7.4 under standard assay conditions.

Embodiment 132

The method of Embodiment 117, wherein at least 80% of the weakly basic anticancer compound is released from the liposome at pH 5 under standard assay conditions.

Embodiment 132

The method of Embodiment 117, wherein at least 10% of the weakly basic anticancer compound is released from the liposome at about pH 6.0 under standard assay conditions.

Embodiment 134

The method of Embodiment 117, wherein at least 50% of the weakly basic anticancer compound is released from the liposome at pH 6.0 under standard assay conditions.

Embodiment 135

The method of Embodiment 117, wherein at least 7% of the weakly basic anticancer compound is released from the liposome at pH 6.7 under standard assay conditions.

Embodiment 136

The method of Embodiment 117, wherein at least 30% of the weakly basic anticancer compound is released from the liposome at pH 6.7 under standard assay conditions.

Embodiment 137

The method of Embodiment 117, wherein the liposome comprises a plurality of weakly basic anticancer compounds and retains greater than 35-50% of the plurality of weakly basic anticancer compound for up to about 8 hrs of incubation in serum or blood when tested under standard assay conditions.

Embodiment 138

The method of any one of Embodiments 130-137, wherein the standard assay conditions comprise 20× or 50× dilution of the liposomes in PBS buffer.

Embodiment 139

The method of any one of Embodiments 130-137, wherein the standard assay conditions comprise incubation at pH 7.4, pH 6.7, pH 6.0 or pH 5.0.

Embodiment 140

The method of any one of Embodiments 130-137, wherein the standard assay conditions comprise incubation at about 25° C. or about 37° C.

Embodiment 141

The method of any one of Embodiments 130-137, wherein the standard assay conditions comprise incubation for about 2, about 4 or about 8 hours.

Embodiment 142

The method of any one of Embodiments 130-137, wherein the standard assay conditions comprise 50× dilution of the liposomes in serum or blood and incubation at 37° C. for 2, 4, or 8 hours at a physiological pH (pH 7.4).

Embodiment 143

The method of Embodiment 117, wherein the liposome is substantially spherical.

Embodiment 144

The method of Embodiment 117, wherein the liposome comprises about 500-1000 μg/mL of the weakly basic anticancer compound and an acid or salt thereof.

Embodiment 145

The method of Embodiment 117, wherein the liposome comprises about 700-850 μg/mL of the weakly basic anticancer compound and an acid or salt thereof.

Embodiment 146

The method of Embodiment 117, wherein the liposome comprises a plurality of the weakly basic anticancer compound forming a disorganized non-crystalline aggregate.

Embodiment 147

The method of Embodiment 117, wherein the liposome does not comprise a cholesterol or a poloxamer 188.

Embodiment 148

The method of Embodiment 117, wherein the liposome does not comprise an acidic organic compound other than oxalic acid, tartaric acid, or salts thereof.

Embodiment 149

The method of Embodiment 117, wherein the liposome does not comprise the weakly basic anticancer compound and an acid or salt thereof other than oxalic acid, tartaric acid or salts thereof.

REFERENCES

1. Robert J. Lee, Susan Wang, Mary Jo Turk, and Philip S. Low. The Effects of pH and Intraliposomal Buffer Strength on the Rate of Liposome Content Release and Intracellular Drug Delivery. 1998. Bioscience Reports, Vol. 18, No. 2, 69-78.
2. A. Gabizon, R. Catane, B. Uziely, B. Kaufman, T. Safra, R. Cohen, F. Martin, A. Huang, Y. Barenholz, Prolonged circulation time and enhanced accumulation in malignant exudates of doxorubicin encapsulated in polyethyleneglycol coated liposomes. 1994. Cancer Res. 54, 987-992.
3. H. Maeda, J. Wu, T. Sawa, Y. Matsumura, K. Hori, Tumor vascular permeability and the EPR effect in macromolecular therapeutics: a review. 2000. J. Control. Release 65, 271-284.
4. A. A. Gabizon, O. Lyass, G. J. Berry, M. Wildgust, Cardiac safety of pegylated liposomal doxorubicin (Doxil/Caelyx) demonstrated by endomyocardial biopsy in patients with advanced malignancies. 2004. Cancer Invest. 22, 663-669.
5. Gabizon, Cardiac safety of liposomal anthracyclines, Semin. Oncol. 2004. 31, 161-181.
6. E. Rivera, V. Valero, F. J. Esteva, L. Syrewicz, M. Cristofanilli, Z. Rahman, D. J. Booser, G. N. Hortobagyi, Lack of activity of stealth liposomal doxorubicin in the treatment of patients with anthracycline-resistant breast cancer. 2002. Cancer Chemother. Pharmacol. 49, 299-302.
7. M. E. O'Brien, N. Wigler, M. Inbar, R. Rosso, E. Grischke, A. Santoro, R. Catane, D. G. Kieback, P. Tomczak, S. P. Ackland, F. Orlandi, L. Mellars, L. Alland, C. Tendler, C. B. C. S. Group, Reduced cardiotoxicity and comparable efficacy in a phase III trial of pegylated liposomal doxorubicin HCl (CAELYX/Doxil) versus conventional doxorubicin for first-line treatment of metastatic breast cancer. 2004. Ann. Oncol. 15, 440-449.
8. Judson, J. A. Radford, M. Harris, J. Y. Blay, Q. van Hoesel, A. le Cesne, A. T. van Oosterom, M. J. Clemons, C. Kamby, C. Hermans, J. Whittaker, E. Donato di Paola, J. Verweij, S. Nielsen, Randomised phase II trial of pegylated liposomal doxorubicin (DOXIL/CAELYX) versus doxorubicin in the treatment of advanced or metastatic soft tissue sarcoma: a study by the EORTC Soft Tissue and Bone Sarcoma Group. 2001. Eur. J. Cancer 37, 870-877.
9. K. M. Laginha, S. Verwoert, G. J. Charrois, T. M. Allen, Determination of doxorubicin levels in whole tumor and tumor nuclei in murine breast cancer tumors. 2005. Clin. Cancer Res. 11, 6944-6949.

10. Roberto Angioli, Michela Angelucci, Francesco Plotti, Corrado Terranova, Roberto Montera, Patrizio Damiani, Ester Valentina Cafa, Pierluigi Benedetti Panici and Angiolo Gadducci. Liposome Encapsulated Doxorubicin Citrate (Ledc) as an Alternative Therapeutic Option for Patients with Recurrent Ovarian Cancer Suffering from Doxorubicin-Related Cutaneous Toxicity. 2013. Chemotherapy, Volume 2, Issue 1, 1-5.

11. Yi Zhao, Dania Y. Alakhova, Jong Oh Kim, Tatiana K. Bronich, Alexander V. Kabanov. A simple way to enhance Doxil® therapy: Drug release from liposomes at the tumor site by amphiphilic block copolymer. 2013. Journal of Controlled Release 168, 61-69

12. Ann L. B. Seynhaeve, Bilyana M. Dicheva, Saske Hoving, Gerben A. Koning, Timo L. M. ten Hagen. Intact Doxil is taken up intracellularly and released doxorubicin sequesters in the lysosome: Evaluated by in vitro/in vivo live cell imaging. 2013. Journal of Controlled Release 172, 330-340

13. Andreas Fritze, Felicitas Hens, Andrea Kimpf ler, Rolf Schubert, Regine Peschka-Süss. Remote loading of doxorubicin into liposomes driven by a transmembrane phosphate gradient. 2006. Biochim. Biophys. Acta. 1758, 1633-1640

14. Lei Zhang, Hong Pan, Min Liu, Weiyue Lu. In vitro and in vivo stabilities of doxorubicin aggregates with various salts inside liposomes. (http://www.paper.edu.cn)

15. Li, Xingong, Hirsh, Donald J., Cabral-Lilly, Donna., Zirkel, Achim., Gruner, Sol M., Janoff, Andrew S., Perkins Walter R. Doxorubicin physical state in solution and inside liposomes loaded via a pH gradient. 1998. Biochim. Biophys. Acta. 1415, 23-40

16. Hitesh R. Patel, Rakesh P. Patel, M. M. Patel. "Poloxamers: A pharmaceutical excipient with therapeutic behaviors". 2009. International Journal of PharmTech Research, Vol. 1, No. 2, pp 299-303.

17. Guohui Wu, Jaroslaw Majewski, Canay Ege, Kristian Kjaer, Markus Jan Weygand, and Ka Yee C. Lee. "Interaction between Lipid Monolayers and Poloxamer 188: An X-Ray Reflectivity and Diffraction Study". 2005. Biophysical Journal Volume 89, 3159-3173.

18. Zhang, Wen-li, Liu Jian-ping, Liu Xiao-xu, Chen Zhiqiang. "Stealth tanshinone IIA-loaded solid lipid nanoparticles: effects of poloxamer 188 coating on in vitro phagocytosis and in vivo pharmacokinetics in rats". 2009. Acta Pharm Sin, 44: 1421-1428.

19. Parag Aggarwal, Jennifer B. Hall, Christopher B. McLeland, Marina A. Dobrovolskaia, Scott E. McNeil. "Nanoparticle interaction with plasma proteins as it relates to particle biodistribution, biocompatibility and therapeutic efficacy". 2009. Advanced Drug Delivery Reviews 61, 428-437.

20. Lee, R. J., Wang, S., Turk, M. J., and Low, P. S. "The effects of pH and intraliposomal buffer strength on the rate of liposome content release and intracellular drug delivery". 1998. Bioscience Reports 18(2):69-78.

21. Ghetie M A, Tucker K, Richardson J, Uhr J W, Vitetta E S. Eradication of minimal disease in severe combined immunodeficient mice with disseminated Daudi lymphoma using chemotherapy and an immunotoxin cocktail. 1994. Blood. 84(3):702-707.

22. Newton D L, Hansen H J, Mikulski S M, Goldenberg D M, Rybak S M. Potent and specific antitumor effects of an anti-CD22-targeted cytotoxic ribonuclease: potential for the treatment of non-Hodgkin lymphoma. 2001. Blood; 97(2):528-535.

23. Lasic, D. D. Doxorubicin in sterically stabilized liposomes. 1996. Nature 380, 561-562.

24. Lasic, D. D., Frederik, P. M., Stuart, M. C., Barenholz, Y., and McIntosh, T. J. Gelation of liposome interior. A novel method for drug encapsulation. 1992. FEBS Lett. 312, 255-258.

25. Sheela A. Abraham, Dawn N. Waterhouse, Lawrence D. Mayer, Pieter R. Cullis, Thomas D. Madden, and Marcel B. Bally. The Liposomal Formulation of Doxorubicin. 2005. Methods in Enzymology, Vol. 391: 71-97.

26. Hongyan Wei, Juan Song, Hao Li, Yang Li, Shanshan Zhu, Xiaodan Zhou, Xiwen Zhang, Li Yang. Active loading liposomal irinotecan hydrochloride: Preparation, in vitro and in vivo evaluation. 2013. Asian Journal of Pharmaceutical Sciences, 8, 303-311.

27. Daryl C. Drummond, Charles O. Noble, Zexiong Guo, Keelung Hong, John W. Park, and Dmitri B. Kirpotin. Development of a Highly Active Nanoliposomal Irinotecan Using a Novel Intraliposomal Stabilization Strategy. 2006. Cancer research, 66: (6), 3271-7.

28. James H. Doroshow, Gershon Y. Locker, Ina Ifrim, And Charles E. Myers. Prevention of Doxorubicin Cardiac Toxicity in the Mouse by N-Acetylcysteine. 1981. J. Clin. Invest. Volume 68, 1053-1064.

29. Sakthibalan M, Sawadkar M S, Asmathulla S, Ivan E A, Muthu G. Study of cardio protective effect of NAcetylcysteine, Vitamin C, and Enalapril given in combination to prevent doxorubicin induced cardio toxicity in Wistar rats. 2013. J Pharm Biomed Sci. 36(36): 1902-1908

30. Myers, C. E., W. P. McGuire, R. H. Liss, I. Ifrim, K. Grotzinger, and R. C. Young. Adriainycin: the role of lipid peroxidation in cardiac toxicity and tumor response. 1977. Science (Wash. D. C.). 197: 165-167.

31. Doroshow, J. H., and J. Reeves. Anthracycline enhanced oxygen radical formation in the heart. 1980. Proc. Am. Assoc. Cancer Res. 21: 266.

32. Heaney M L, Gardner J R, Karasavvas N, Golde D W, Scheinberg D A, Smith E A, O'Connor O A. Vitamin C antagonizes the cytotoxic effects of antineoplastic drugs. 2008. Cancer Res. 68(19): 8031-803.

33. Viswanatha Swamy A H, Wangikar U, Koti B C, et al. Cardioprotective effect of ascorbic acid on doxorubicin-induced myocardial toxicity in rats. 2011. Indian J Pharmacol 43: 507-511.

34. Villani F, Galimberti M, Monti E, Piccinini F, Lanza E, Rozza A, Favalli L, Poggi P, Zunino F. Effect of glutathione and N-acetylcysteine on in vitro and in vivo cardiac toxicity of doxorubicin. 1990. Free Radic Res Commun. 11(1-3): 145-51.

35. Guidelines for Dynamic Light Scattering Measurement and Analysis. Nanocomposix's guide to dynamic light scattering measurement and analysis. 2015. V. 1.4.

36. Song Y, Huang Z, Song Y, Tian Q, Liu X, She Z, Jiao J, Lu E, Deng Y. The application of EDTA in drug delivery systems: doxorubicin liposomes loaded via NH4EDTA gradient. 2014. Int J Nanomedicine. 9:3611-21.

37. Cranton E M, Frackelton J P. Free oxygen radical pathology and EDTA chelation therapy: mechanisms of action. 1988. Journal of Advancement in Medicine. 11(4): 277-310

38. Hong R L, Tseng Y L. Phase I and pharmacokinetic study of a stable, polyethylene-glycolated liposomal doxorubicin in patients with solid tumors: the relation between pharmacokinetic property and toxicity. 2001. Cancer; 91:1826-1833.

39. Chao T C, Wang W S, Yen C C, et al. A dose-escalating pilot study of sterically stabilized, pegylated liposomal doxorubicin (Lipo-Dox) in patients with metastatic breast cancer. 2003. Cancer Invest; 21:837-847.
40. Ian F. Tannock and Daniela Rotin. Acid pH in Tumors and Its Potential for Therapeutic Exploitation. 1989. Cancer Research 49, 4173-4384.
41. 36. Wike-Hooley, J. L., Haveman, J., and Reinhold, J. S. The relevance of tumour pH to the treatment of malignant disease. 1984. Radiother. Oncol., 2: 343-366.
42. Yuan F, Leunig M, Huang S K, Berk D A, Papahadjopoulos D, Jain R K. Microvascular permeability and interstitial penetration of sterically stabilized (Stealth) liposomes in a human tumor xenograft. 1994. Cancer Res 54: 3352-3356.
43. Vitols S: Uptake of low-density lipoprotein by malignant cells—possible therapeutic applications. 1991. Cancer Cells 3, 488-495.
44. Muller C P, Trilling B, Steinke B: The prognostic significance of total serum cholesterol in patients with Hodgkin's disease. 1992. Cancer 69, 1042-1046.
45. Parag Aggarwal, Jennifer B. Hall, Christopher B. McLeland, Marina A. Dobrovolskaia, Scott E. McNeil. "Nanoparticle interaction with plasma proteins as it relates to particle biodistribution, biocompatibility and therapeutic efficacy". 2009. Advanced Drug Delivery Reviews 61, 428-437.
46. Innerarity T L and Mahley R W Enhanced binding by cultured human fibroblasts of apo-E-containing lipoproteins as compared with low density lipoproteins. 1978. Biochemistry 17: 1440-1447.
47. Innerarity T L Pitas R E and Mahley R W (1979) Binding of arginine-rich (E) apoprotein after recombination with phospholipid vesicles to the low density lipoprotein receptors of fibroblasts. 1979. J Biol Chem 254: 4186-4190.
48. A J Versluis, P C N Rensen, E T Rump, T J C Van Berkel and M K Bijsterbosch. Low-density lipoprotein receptor-mediated delivery of a lipophilic daunorubicin derivative to B16 tumours in mice using apolipoprotein E-enriched liposomes. 1998. British Journal of Cancer 78(12): 1607-1614.
49. Zensi A, Begley D, Pontikis C, et al. Albumin nanoparticles targeted with Apo E enter the CNS by transcytosis and are delivered to neurones. 2009. J Control Release; 137(1):78-86.
50. Pillay, C. S., E. Elliott, and C. Dennison. 2002. Endolysosomal proteolysis and its regulation. Biochem. J. 363:417-429.
51. Joseph A. Mindell. Lysosomal Acidification Mechanisms. 2012. Annual Review of Physiology Vol. 74: 69-86.
52. Guo L S, Hamilton R L, Goerke J, Weinstein J N, Havel R J. Interaction of unilamellar liposomes with serum lipoproteins and apolipoproteins. 1980. J Lipid Res. Vol. 21(8):993-1003.
53. Sean C. Semple, Arcadio Chonn, Pieter R. Cullis. Interactions of liposomes and lipid-based carrier systems with blood proteins: Relation to clearance behaviour in vivo. 1998. Advanced Drug Delivery Reviews. Vol. 32: 3-17.

What is claimed is:

1. A pharmaceutical composition comprising a liposome, wherein the liposome comprises a plurality of lipids; a weakly basic anticancer compound; and oxalic acid or a salt of oxalic acid; wherein the weight ratio of the lipids to the weakly basic anticancer compound is from about 50:1 to about 100:1.

2. The pharmaceutical composition of claim 1, wherein the weakly basic anticancer compound is doxorubicin, irinotecan, mitoxantrone, or a combination of two or more thereof.

3. The pharmaceutical composition of claim 1, wherein the plurality of lipids comprise a poloxamer.

4. The pharmaceutical composition of claim 1, wherein the plurality of lipids comprise a plurality of free cholesterols; a plurality of phospholipids; or a combination thereof.

5. The pharmaceutical composition of claim 4, wherein the plurality of lipids comprise a plurality of free cholesterols and a plurality of phospholipids, and wherein the molar ratio of the phospholipids to the free cholesterols is at least 0.5 to 1 to about 4 to 1.

6. The pharmaceutical composition of claim 1, wherein the weakly basic anticancer compound is substantially released from the liposome at pH<7.4.

7. The pharmaceutical composition of claim 1, wherein at least 40-80% of the weakly basic anticancer compound is released from the liposome at pH 5 under standard assay conditions; wherein at least 10-50% of the weakly basic anticancer compound is released from the liposome at pH 6.0 under standard assay conditions; wherein at least 7-30% of the weakly basic anticancer compound is released from the liposome at pH 6.7 under standard assay conditions; or wherein less than 5% of the weakly basic anticancer compound is released from the liposome at pH 7.4 under standard assay conditions.

8. The pharmaceutical composition of claim 1, wherein the liposome comprises a plurality of weakly basic anticancer compounds and retains greater than 50% of the plurality of weakly basic anticancer compound for up to about 8 hours of incubation in serum or blood when tested under standard assay conditions.

9. The pharmaceutical composition of claim 7, wherein the standard assay conditions comprise 50 times dilution of the liposomes in serum or blood and incubation at 37° C. for 2, 4, or 8 hours at pH 7.4.

10. The pharmaceutical composition of claim 1, wherein the pharmaceutical composition comprises a plurality of the liposome having a mean longest dimension of about 40 nm to about 100 nm determined by the intensity-averaged particle diameters measured by dynamic light scattering; or wherein the pharmaceutical composition comprises a plurality of the liposome having a mean longest dimension from about 1 nm to about 50 nm determined by cryo-transmission electron microscopy.

11. The pharmaceutical composition of claim 1, wherein the liposome comprises about 500 µg/mL to about 1,000 µg/mL of the weakly basic anticancer compound.

12. The pharmaceutical composition of claim 1, wherein the liposome comprises about 750 µg/mL to about 850 µg/mL of the weakly basic anticancer compound.

13. The pharmaceutical composition of claim 1, wherein the liposome comprises a plurality of the weakly basic anticancer compound and retains greater than 90% of the plurality of weakly basic anticancer compound after 40 days when stored at 2-8° C. under standard storage conditions.

14. The pharmaceutical composition of claim 1, further comprising a compound selected from the group consisting of ascorbic acid, N-acetylcysteine, ascorbyl palmitate, ubiquinone, and ethylenediaminetetraacetic acid.

15. The pharmaceutical composition of claim 1, wherein the weakly basic anticancer compound has a pKa from about 7.5 to about 9.0.

16. The pharmaceutical composition of claim 5, wherein the molar ratio of the phospholipids to the free cholesterols is from about 1 to 1 to about 4 to 1.

17. A pharmaceutical composition comprising a liposome, wherein the liposome comprises a plurality of lipids; a weakly basic anticancer compound; and tartaric acid or a salt of tartaric acid; wherein the weight ratio of the lipids to the weakly basic anticancer compound is from about 20:1 to about 100:1.

18. The pharmaceutical composition of claim 17, wherein the weakly basic anticancer compound is doxorubicin, irinotecan, mitoxantrone, or a combination of two or more thereof.

19. The pharmaceutical composition of claim 17, wherein the plurality of lipids comprise a poloxamer.

20. The pharmaceutical composition of claim 17, wherein the plurality of lipids comprise a plurality of free cholesterols; a plurality of phospholipids; or a combination thereof.

21. The pharmaceutical composition of claim 20, wherein the plurality of lipids comprise a plurality of free cholesterols and a plurality of phospholipids, and wherein the molar ratio of the phospholipids to the free cholesterols is at least 0.5 to 1 to about 4 to 1.

22. The pharmaceutical composition of claim 17, wherein the weakly basic anticancer compound is substantially released from the liposome at pH<7.4.

23. The pharmaceutical composition of claim 17, wherein at least 40-80% of the weakly basic anticancer compound is released from the liposome at pH 5 under standard assay conditions; wherein at least 10-50% of the weakly basic anticancer compound is released from the liposome at pH 6.0 under standard assay conditions; wherein at least 7-30% of the weakly basic anticancer compound is released from the liposome at pH 6.7 under standard assay conditions; or wherein less than 5% of the weakly basic anticancer compound is released from the liposome at pH 7.4 under standard assay conditions.

24. The pharmaceutical composition of claim 17, wherein the liposome comprises a plurality of weakly basic anticancer compounds and retains greater than 50% of the plurality of weakly basic anticancer compound for up to about 8 hours of incubation in serum or blood when tested under standard assay conditions.

25. The pharmaceutical composition of claim 23, wherein the standard assay conditions comprise 50 times dilution of the liposomes in serum or blood and incubation at 37° C. for 2, 4, or 8 hours at pH 7.4.

26. The pharmaceutical composition of claim 17, wherein the pharmaceutical composition comprises a plurality of the liposome having a mean longest dimension of about 40 nm to about 100 nm determined by the intensity-averaged particle diameters measured by dynamic light scattering; or wherein the pharmaceutical composition comprises a plurality of the liposome having a mean longest dimension from about 1 nm to about 50 nm determined by cryo-transmission electron microscopy.

27. The pharmaceutical composition of claim 17, wherein the liposome comprises about 500 µg/mL to about 1,000 µg/mL of the weakly basic anticancer compound.

28. The pharmaceutical composition of claim 17, wherein the liposome comprises about 750 µg/mL to about 850 µg/mL of the weakly basic anticancer compound.

29. The pharmaceutical composition of claim 17, wherein the liposome comprises a plurality of the weakly basic anticancer compound and retains greater than 90% of the plurality of weakly basic anticancer compound after 40 days when stored at 2-8° C. under standard storage conditions.

30. The pharmaceutical composition of claim 17, further comprising a compound selected from the group consisting of ascorbic acid, N-acetylcysteine, ascorbyl palmitate, ubiquinone, and ethylenediaminetetraacetic acid.

31. The pharmaceutical composition of claim 17, wherein the weakly basic anticancer compound has a pKa from about 7.5 to about 9.0.

32. The pharmaceutical composition of claim 21, wherein the molar ratio of the phospholipids to the free cholesterols is from about 1 to 1 to about 4 to 1.

* * * * *

UNITED STATES PATENT AND TRADEMARK OFFICE
CERTIFICATE OF CORRECTION

PATENT NO. : 11,033,520 B2
APPLICATION NO. : 16/331258
DATED : June 15, 2021
INVENTOR(S) : Igor Nikoulin et al.

Page 1 of 1

It is certified that error appears in the above-identified patent and that said Letters Patent is hereby corrected as shown below:

In the Claims

At Column 125, at the 5th Line in Claim 17, delete "20:1" and replace it with "50:1"

Signed and Sealed this
Ninth Day of August, 2022

Katherine Kelly Vidal
*Director of the United States Patent and Trademark Office*